US011208439B2

(12) United States Patent
Comstedt et al.

(10) Patent No.: US 11,208,439 B2
(45) **Date of Patent: *Dec. 28, 2021**

(54) MUTANT FRAGMENTS OF OSPA AND METHODS AND USES RELATING THERETO

(71) Applicant: Valneva Austria GmbH, Vienna (AT)

(72) Inventors: Pär Comstedt, Vienna (AT); Markus Hanner, Pressbaum (AT); Urban Lundberg, Pressbaum (AT); Andreas Meinke, Pressbaum (AT); Wolfgang Schüler, Vienna (AT); Benjamin Wizel, Hoeilaart (BE)

(73) Assignee: Valneva Austria GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,618

(22) Filed: Feb. 27, 2018

(65) Prior Publication Data

US 2018/0327460 A1 Nov. 15, 2018

Related U.S. Application Data

(63) Continuation of application No. 15/267,372, filed on Sep. 16, 2016, now Pat. No. 9,926,343, which is a continuation of application No. 14/623,681, filed on Feb. 17, 2015, now abandoned, which is a continuation of application No. 13/802,991, filed on Mar. 14, 2013, now Pat. No. 8,986,704.

(60) Provisional application No. 61/668,627, filed on Jul. 6, 2012.

(51) Int. Cl.

| | |
|---|---|
| ***A61K 38/00*** | (2006.01) |
| ***C07K 14/20*** | (2006.01) |
| ***C07K 16/12*** | (2006.01) |
| ***C12P 21/02*** | (2006.01) |
| ***A61K 39/02*** | (2006.01) |
| ***C12N 5/07*** | (2010.01) |
| ***C12N 15/70*** | (2006.01) |
| ***C12P 21/00*** | (2006.01) |
| *A61K 39/00* | (2006.01) |

(52) U.S. Cl.

CPC .............. *C07K 14/20* (2013.01); *A61K 39/02* (2013.01); *A61K 39/0225* (2013.01); *C07K 16/12* (2013.01); *C07K 16/1207* (2013.01); *C12N 5/06* (2013.01); *C12N 15/70* (2013.01); *C12P 21/00* (2013.01); *C12P 21/02* (2013.01); *A61K 38/00* (2013.01); *A61K 2039/55505* (2013.01); *A61K 2039/6018* (2013.01); *A61K 2039/6031* (2013.01); *C07K 2317/24* (2013.01); *C07K 2317/54* (2013.01); *C07K 2317/55* (2013.01); *C07K 2319/00* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 6,248,562 | B1 | 6/2001 | Dunn et al. | |
| 7,008,625 | B2 | 3/2006 | Dattwyler et al. | |
| 8,986,704 | B2 * | 3/2015 | Comstedt | C07K 14/20 424/190.1 |
| 9,926,343 | B2 | 3/2018 | Comstedt et al. | |
| 9,975,927 | B2 * | 5/2018 | Lundberg | C07K 16/1207 |
| 10,544,194 | B2 | 1/2020 | Comstedt et al. | |
| 10,766,931 | B2 * | 9/2020 | Lundberg | C07K 14/20 |
| 2004/0023325 | A1 | 2/2004 | Luft et al. | |
| 2011/0293652 | A1 * | 12/2011 | Crowe | A61K 39/0225 424/190.1 |
| 2014/0010835 | A1 | 1/2014 | Comstedt et al. | |
| 2015/0232517 | A1 | 8/2015 | Comstedt et al. | |
| 2015/0250865 | A1 | 9/2015 | Comstedt et al. | |
| 2016/0333056 | A1 | 11/2016 | Lundberg et al. | |
| 2017/0101446 | A1 | 4/2017 | Comstedt et al. | |
| 2017/0107263 | A1 | 4/2017 | Comstedt et al. | |
| 2018/0362593 | A1 | 12/2018 | Lundberg et al. | |
| 2020/0239525 | A1 | 7/2020 | Comstedt et al. | |

FOREIGN PATENT DOCUMENTS

| | | | |
|---|---|---|---|
| CN | 103118701 | A | 5/2013 |
| WO | WO 2002/016421 | A2 | 2/2002 |
| WO | WO 2008/031133 | A2 | 3/2008 |
| WO | WO 2011/143617 | A1 | 11/2011 |
| WO | WO 2011/143623 | A1 | 11/2011 |
| WO | WO 2012/066420 | A1 | 5/2012 |
| WO | WO 2012/066423 | A1 | 5/2012 |
| WO | WO 2014/006226 | A1 | 1/2014 |
| WO | WO 2015/104396 | A1 | 7/2015 |

(Continued)

OTHER PUBLICATIONS

Greenspan et al. 1999 (Defining epitopes: It's not as easy as it seems; Nature Biotechnology, 17:936-937). (Year: 1999).*

Koide et al. 2005 (Structure-based Design of a Second-generation Lyme Disease Vaccine Based on a C-terminal Fragment of Borrelia burgdorferi OspA; J. Mol. Biol. 350:290-299) (Year: 2005).*

Hertadi et al. 2003 (Unfolding Mechanics of Multiple OspA Substructures Investigated with Single Molecular Force Spectroscopy; J. Mol. Biol. 333: 993-1002) (Year: 2003).*

(Continued)

*Primary Examiner* — Mary Maille Lyons

(74) *Attorney, Agent, or Firm* — Wolf, Greenfield & Sacks, P.C.

(57) ABSTRACT

The present invention relates to a polypeptide comprising a mutant fragment of an outer surface protein A (OspA), a nucleic acid coding the same, a pharmaceutical composition (particularly for use as a medicament of in a method of treating or preventing a *Borrelia* infection) comprising the polypeptide and/or the nucleic acid, a method of treating or preventing a *Borrelia* infection and a method of immunizing a subject.

19 Claims, 3 Drawing Sheets

Figure 2:
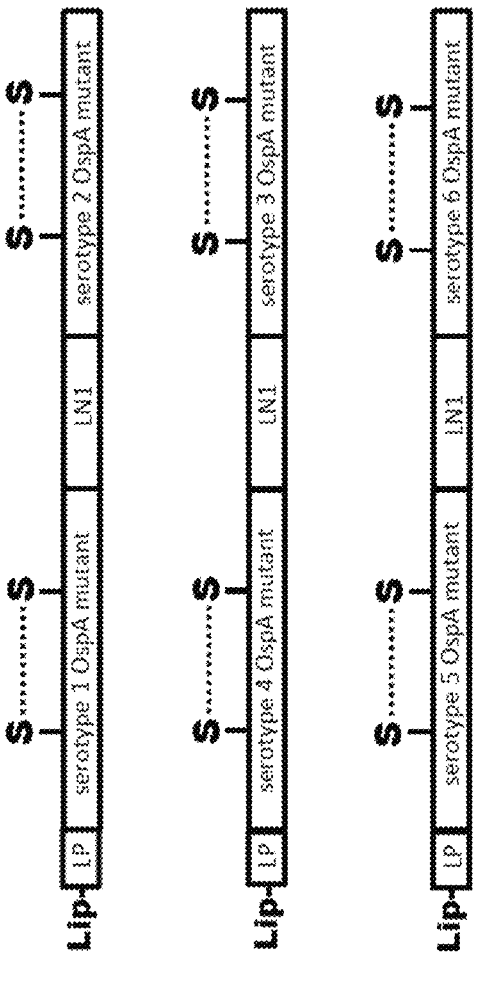

Specification includes a Sequence Listing.

(56) References Cited

FOREIGN PATENT DOCUMENTS

WO WO 2015/169271 A1 11/2015
WO WO 2018/189372 A1 10/2018

OTHER PUBLICATIONS

Li et al. 1997 (Crystal structure of Lyme disease antigen outer surface protein A complexed with an Fab; Proc. Natl. Acad. Sci. 95: 3584-3589) (Year: 1997).*

PCT/EP2015/050365, Apr. 2, 2015, International Search Report and Written Opinion.

PCT/EP2015/050365, Jul. 21, 2016, International Preliminary Report on Patentability.

[No Author Listed] ECDC; Meeting Report: Second expert consultation on tick-borne diseases with emphasis on Lyme borreliosis and tick-borne encephalitis, Stockholm, Sweden, Nov. 22-23, 2011.

[No Author Listed], Press release: Valneva Reports Positive Initial Booster Data and Final Phase 1 Data for its Lyme Disease Vaccine Candidate.

Altschul SF, et al. Basic Local Alignment Search Tool (1990) J. Mol. Biol. 215:403-410.

Bunikis et al. A Surface-Exposed Region of a Novel Outer Membrane Protein (P66) of *Borrelia* spp. is Variable in Size and Sequence (1998) Journal of Bacteriology 180(7):1618-1623.

Chakrabarti and Janin. Dissecting Protein—Protein Recognition Sites; Proteins: Structure. Function, and Genetics (2002) 47:334-343.

Compton et al., Introduction of a Disulfide Bond Leads to Stabilization and Crystallization of a Ricin Immunogen (2011) Proteins 79(4):1048-1060. doi:10.1002/prot.22933.

Comstedt P, et al. Characterization and optimization of a novel vaccine for protection against Lyme borreliosis (2015) Vaccine 33:5982-5988.

Cutler SJ, et al. Emerging borreliae—Expanding beyond Lyme borreliosis (2017) Molecular and Cellular Probes 31:22-27.

Davies and Cohen. Interactions of protein antigens with antibodies (1996) Proc. Natl. Acad. Sci. USA 93:7-12.

De Silva AM, et al. *Borrelia burgdorferi* OspA Is an Arthropod-specific Transmission-blocking Lyme Disease Vaccine (1996) J. Exp. Med. 183:271-275.

Devereaux J, et al. A comprehensive set of sequence analysis programs for the VAX (1984) Nucleic Acids Research 12(1):387-395.

Embers and Narasimhan. Vaccination against Lyme disease: past, present, and future (2013) Frontiers in Cellular and Infection Microbiology www.frontiersin.org 3(6): doi:10.3389/fcimb.2013.00006.

Fingerle V, et al. Epidemiological aspects and molecular characterization of *Borrelia burgdorferi* s.l. from southern Germany with special respect to the new species *Borrelia spielmanii* sp. nov. (2008) International Journal of Medical Microbiology 298:279-290. doi:10.1016/j.ijmm.2007.05.002.

Grygorczuk S, et al. Assessment of the frequency of different *Borrelia burgdorferi sensu lato* species in patients with Lyme borreliosis from north-east Poland by studying preferential serologic response and DNA isolates (2013) Annals of Agricultural and Environmental Medicine 20(1):21-29.

Hinckley AF, et al. Lyme Disease Testing by Large Commercial Laboratories in the United States (2014) Clin Infect Dis. 59(5):676-681. doi:10.1093/cid/ciu397.

Iyer R, et al. Stage-specific global alterations in the transcriptomes of Lyme disease spirochetes during tick feeding and following mammalian host adaptation (2015) Molecular Microbiology 95(3):509-538. doi:10.1111/mmi.12882 First published online Dec. 30, 2014.

Jiang W, et al. Purification of *Borrelia burgdorferi* Outer Surface Protein A (OspA) and Analysis of Antibody Binding Domains (1994) Clinical and Diagnostic Laboratory Immunology 1(4):406-412.

Legros V, et al. Characterization of an anti-*Borrelia burgdorferi* OspA conformational epitope by limited proteolysis of monoclonal antibody-bound antigen and mass spectrometric peptide mapping (2000) Protein Science 9:1002-1010.

Lingelbach. T World Vaccine Congress presentation, Apr. 16, 2019 entitled: "Developing a vaccine against Lyme disease; Phase 1 results and next steps".

Lo Conte L, et al. The Atomic Structure of Protein-Protein Recognition Sites (1999) J. Mol. Biol. 285:2177-2198.

Montgomery RR, et al. Direct Demonstration of Antigenic Substitution of *Borrelia burgdorferi* Ex Vivo: Exploration of the Paradox of the Early Immune Response to Outer Surface Proteins A and C in Lyme Disease(1996) J. Exp. Med. 183:261-269.

Nelson CA, et al. Incidence of Clinician-Diagnosed Lyme Disease, United States, 2005-2010 (2015) Emerging Infectious Diseases 21(9):1625-1631. DOI: http://dx.doi.org/10.3201/eid2109.150417.

Ornstein K, et al. Characterization of Lyme Borreliosis Isolates from Patients with Erythema Migrans and Neuroborreliosis in Southern Sweden (2001) Journal of Clinical Microbiology 39(4):1294 1298. DOI: 10.1128/JCM.39.4.1294-1298.

Ornstein K, et al. Differential Immune Response to the Variable Surface Loop Antigen of P66 of *Borrelia burgdorferi Sensu Lato* Species in Geographically Diverse Populations of Lyme.

Borreliosis Patients (2002) Clinical and Diagnostic Laboratory Immunology 9(6):1382-1384. DOI: 10.1128/CDLI.9.6.1382-1384. 2002.

Pal U, et al. Attachment of *Borrelia burgdorferi* within *Ixodes scapularis* mediated by outer surface protein A (2000) J. Clin. Invest. 106:561-569.

Piesman and Gern. Lyme borreliosis in Europe and North America (2004) Parasitology 129, S191-S220. DOI: 10.1017/S0031182003004694.

Poland GA. Vaccines against Lyme Disease: What Happened and What Lessons Can We Learn? (2011) Clinical Infectious Diseases 52(S3):S253-S258, DOI: 10.1093/cid/ciq116.

Radolf JD, et al. Of ticks, mice and men: understanding the dual-host lifestyle of Lyme disease spirochaetes (2012) Nat Rev Microbiol. 10(2): 87-99. doi:10.1038/nrmicro2714.

Rizzoli A, et al. Lyme borreliosis in Europe (2011) Euro Surveill. 16(27):pii=19906. Available online: http://www.eurosurveillance.org/ViewArticle.aspx?ArticleId=19906.

Scarselli M, et al. Rational Design of a Meningococcal Antigen Inducing Broad Protective Immunity (2011) www.ScienceTranslationalMedicine.org 3(91):91ra62.

Schaible UE, et al. Monoclonal antibodies specific for the outer surface protein A (OspA) of *Borrelia burgdorferi* prevent Lyme borreliosis in severe combined immunodeficiency (scid) mice (1990) Proc. Nati. Acad. Sci. USA 87:3768-3772.

Schubach WH, et al. Mapping Antibody-Binding Domains of the Major Outer Surface Membrane Protein (OspA) of *Borrelia burgdorferi* (1991) Infection and Immunity 59(6):1911-1915.

Schuijt TJ, et al. Lyme borreliosis vaccination: the facts, the challenge, the future (2011) Trends in Parasitology 27(1):40-47. doi:10.1016/j.pt.2010.06.006.

Sears JE, et al. Moleculm Mapping of Osp-A Mediated Immunity Against *Borrelia burgdorferi*, The Agent of Lyme Disease (1991) J of Immunol 147(6):1995-2000.

Sigal LH, et al. A vaccine consisting of recombinant *Borrelia burgdorferi* outer surface protein A to prevent Lyme disease (1998) N Engl J Med 339:216-22.

Stanek G, et al. Lyme borreliosis (2012) Lancet 379:461-73 DOI:10.1016/S0140-6736(11)60103-7. Published Online Sep. 7, 2011.

Stupica D, et al. Correlation of Culture Positivity, PCR Positivity, and Burden of *Borrelia burgdorferi* Sensu Lato in Skin Samples of Erythema Migrans Patients with Clinical Findings (2015) PLoS One 10(9): e0136600. doi:10.1371/journal.pone.0136600.

Wressnig N, et al. Safety and immunogenicity of a novel multivalent OspA vaccine against Lyme borreliosis in healthy adults: a double-blind, randomised, dose-escalation phase ½ trial (2013) The Lancet http://dx.doi.org/10.1016/S1473-3099(13)70110-5.

Zhong W, et al. Plasmid DNA and protein vaccination of mice to the outer surface protein A of *Borrelia burgdorferi* leads to induction of T helper cells with specificity for a major epitope and augmentation of protective IgG antibodies in vivo (1996) Eur. J. Immunol. 26:2749-2757.

(56) References Cited

OTHER PUBLICATIONS

[No Author Listed] pET System Manual. 2006. Novagen.
[No Author Listed] Valneva report positive phase I interim results for its Lyme vaccine candidate VLA15. Valneva. Mar. 19, 2018.
Clinical Trials Identifier: NCT3010228. Study assessing the safety, immunogenicity and dose response of VLA15, a new vaccine candidate against Lyme borreliosis. Jan. 4, 2017. retrieved Mar. 26, 2018 from https://clinicaltrials.gov/ct2/show/study/NCT03010228.
Baker et al., Electrostatics of nanosystems: application to microtubules and the ribosome. Proc Natl Acad Sci U S A. Aug. 28, 2001;98(18):10037-41.
Bessler et al. Synthetic lipopeptides as novel adjuvants. Res Immunol. Jun. 1992;143(5):548-53; discussion 579-80.
Betz, Disulfide bonds and the stability of globular proteins. Protein Sci. Oct. 1993;2(10):1551-8.
Bockenstedt et al., Identification of a Borrelia burgdorferi OspA T cell epitope that promotes anti-OspA IgG in mice. J Immunol. Dec. 15, 1996;157(12):5496-502.
Bockenstedt et al., Inability of truncated recombinant Osp A proteins to elicit protective immunity to Borrelia burgdorferi in mice. J Immunol. Jul. 15, 1993;151(2):900-6.
Bouchon et al., Analysis of the lipidated recombinant outer surface protein A from Borrelia burgdorferi by mass spectrometry. Anal Biochem. Mar. 1, 1997;246(1):52-61.
Caruthers et al., New chemical methods for synthesizing polynucleotides. Nucleic Acids Symp Ser. 1980;(7):215-23.
Comstedt et al., Design and development of a novel vaccine for protection against Lyme borreliosis. PLoS One. Nov. 19, 2014;9(11):e113294. doi: 10.1371/journal.pone.0113294.
Comstedt et al., Efficacy testing of a novel OspA based Lyme borreliosis vaccine. Gordon Research Conference: "Biology of Spirochetes", Ventura, California. Jan. 19-24, 2014. Abstract.
Comstedt et al., Investigation of a vaccine targeting Lyme borreliosis in Europe. Gordon Research Conference: "Biology of Spirochetes". Ventura, California. Jan. 19-24, 2014. Abstract.
Comstedt et al., The novel Lyme borreliosis vaccine VLA15 shows broad protection against *Borrelia* species expressing six different OspA serotypes. PLoS One. Sep. 1, 2017;12(9):e0184357. doi:10.1371/journal.pone.0184357. eCollection 2017.
Creighton et al., Mechanisms and catalysts of disulfide bond formation in proteins. Trends Biotechnol. Jan. 1995;13(1):18-23.
Crowe, A Lyme borreliosis vaccine for Europe and beyond. Climate change impact on ticks and tick-borne diseases. Brussels. Feb. 6, 2009.
Ding et al., Structural identification of a key protective B-cell epitope in Lyme disease antigen OspA. J Mol Biol. Oct. 6, 2000;302(5):1153-64.
Dolinsky et al., PDB2PQR: expanding and upgrading automated preparation of biomolecular structures for molecular simulations. Nucleic Acids Res. Jul. 2007;35(Web Server issue):W522-5.
Dykhuizen et al., Borrelia burgdorferi is clonal: Implications for taxonomy and vaccine development; Proc. Natl. Acad. Sci. Nov. 1, 1993;90: 10163-10167.
Erdile et al., Role of attached lipid in immunogenicity of Borrelia burgdorferi OspA. Infect Immun. Jan. 1993;61(1):81-90.
Fass, Disulfide bonding in protein biophysics. Annu Rev Biophys. 2012;41:63-79. doi: 10.1146/annurev-biophys-050511-102321. Epub Dec. 20, 2011.
Friguet et al., Measurements of the true affinity constant in solution of antigen-antibody complexes by enzyme-linked immunosorbent assay. J Immunol Methods. Mar. 18, 1985;77(2):305-19.
Gern et al., Immunization with a polyvalent OspA vaccine protects mice against Ixodes ricinus tick bites infected by *Borrelia burgdorferi* ss, Borrelia garinii and Borrelia afzelii. Vaccine. Oct. 1997;15(14):1551-7.
Golde et al., Reactivity with a specific epitope of outer surface protein A predicts protection from infection with the Lyme disease spirochete, Borrelia burgdorferi. Infect Immun. Mar. 1997;65(3):882-9.
Greenspan et al., Defining epitopes: It's not as easy as it seems. Nat Biotechnol. Oct. 1999;17(10):936-7.
Hertadi et al., Unfolding mechanics of multiple OspA substructures investigated with single molecule force spectroscopy. J Mol Biol. Nov. 7, 2003;333(5):993-1002.
Horn et al., Synthesis of oligonucleotides on cellulose. Part II: Design and synthetic strategy to the synthesis of 22 oligodeoxynucleotides coding for gastric inhibitory polypeptide (GIP). Nucleic Acids Symp Ser. 1980;(7):225-32.
Kiefer et al., The Swiss-Model Repository and associated resources. Nucleic Acids Res. Jan. 2009;37(Database issue):D387-92. doi: 10.1093/nar/gkn750.
Koide et al., Multistep denaturation of Borrelia burgdorferi OspA, a protein containing a single-layer beta-sheet. Biochemistry. Apr. 13, 1999;38(15):4757-67.
Koide et al., Structure-based design of a second-generation Lyme disease vaccine based on a C-terminal fragment of Borrelia burgdorferi OspA. J Mol Biol. Jul. 8, 2005;350(2):290-9.
Li et al., Crystal structure of Lyme disease antigen outer surface protein A complexed with an Fab. Proc Natl Acad Sci U S A. Apr. 15, 1997;94(8):3584-9.
Liang et al., An immunodominant conserved region within the variable domain of VlsE, the variable surface antigen of Borrelia burgdorferi. J Immunol. Nov. 15, 1999;163(10):5566-73.
Lindgren et al., Lyme borreliosis in Europe: influences of climate and climate change, epidemiology, ecology and adaptation measures. World Health Organization. 2006. 34 pages.
Lingelbach, Developing a vaccine against Lyme disease Progress update post Phase 1 interim results. World Vaccine Congress. Apr. 4, 2018. Valneva.
Livey et al., A new approach to a Lyme disease vaccine. Clin Infect Dis. Feb. 2011;52 Suppl 3:S266-70. doi: 10.1093/cid/ciq118.
Livey et al., Development of a novel Lyme disease vaccine. The International Conference on Lyme Borreliosis and other Tick Borne Diseases. 2010. Poster.
Makabe et al., Atomic-resolution crystal structure of Borrelia burgdorferi outer surface protein A via surface engineering. Protein Sci. Aug. 2006;15(8):1907-14. Epub Jul. 5, 2006.
Marshall et al., Safety and immunogenicity of a meningococcal B bivalent rLP2086 vaccine in healthy toddlers aged 18-36 months: a phase 1 randomized-controlled clinical trial. Pediatr Infect Dis J. Oct. 2012;31(10):1061-8.
Nakagawa et al., Calorimetric dissection of thermal unfolding of OspA, a predominantly beta-sheet protein containing a single-layer beta-sheet. J Mol Biol. Nov. 1, 2002;323(4):751-62.
Nissen et al., A randomized, controlled, phase ½ trial of a Neisseria meningitides serogroup B bivalent rLP2086 vaccine in healthy children and adolescents. Pediatr Infect Dis J. Apr. 2013;32(4):364-71. doi: 10.1097/INF.0b013e31827b0d24.
Pantoliano et al., High-density miniaturized thermal shift assays as a general strategy for drug discovery. J Biomol Screen. Dec. 2001;6(6):429-40.
Parmley, Uptick for Lyme vaccine. Biocentury innovations. Jan. 2015;15-16.
Pawley et al., Backbone dynamics and thermodynamics of Borrelia outer surface protein A. J Mol Biol. Dec. 13, 2002;324(5):991-1002.
Pham et al., NMR studies of Borrelia burgdorferi OspA, a 28 kDa protein containing a single-layer beta-sheet. J Biomol NMR. May 1998;11(4):407-14.
Pronk et al., GROMACS 4.5: a high-throughput and highly parallel open source molecular simulation toolkit. Bioinformatics. Apr. 1, 2013;29(7):845-54. doi: 10.1093/bioinformatics/btt055.
Richmond et al., A bivalent Neisseria meningitidis recombinant lipidated factor H binding protein vaccine in young adults: results of a randomised, controlled, dose-escalation phase 1 trial. Vaccine. Sep. 21, 2012;30(43):6163-74. doi: 10.1016/j.vaccine.2012.07.065. Epub Aug. 5, 2012.
Richmond et al., Safety, immunogenicity, and tolerability of meningococcal serogroup B bivalent recombinant lipoprotein 2086 vaccine in healthy adolescents: a randomised, single-blind, placebo-controlled, phase 2 trial. Lancet Infect Dis. Aug. 2012;12(8):597-607. Epub May 7, 2012.

(56) References Cited

OTHER PUBLICATIONS

Roberge et al., A strategy for a convergent synthesis of N-linked glycopeptides on a solid support. Science. Jul. 14, 1995;269(5221):202-4.

Schwendinger et al., Evaluation of OspA vaccination-induced serological correlates of protection against Lyme borreliosis in a mouse model. PLoS One. Nov. 18, 2013;8(11):e79022. doi: 10.1371/journal.pone.0079022.

Steere et al., Vaccination against Lyme disease with recombinant Borrelia burgdorferi outer-surface lipoprotein A with adjuvant. Lyme Disease Vaccine Study Group. N Engl J Med. Jul. 23, 1998;339(4):209-15.

Van Hoecke et al., Evaluation of the safety, reactogenicity and immunogenicity of three recombinant outer surface protein (OspA) Lyme vaccines in healthy adults. Vaccine. Dec. 1996;14(17-18):1620-6.

Wilske et al., An OspA serotyping system for Borrelia burgdorferi based on reactivity with monoclonal antibodies and OspA sequence analysis. J Clin Microbiol. Feb. 1993;31(2):340-50.

Yoder et al., Tripalmitoyl-S-glyceryl-cysteine-dependent OspA vaccination of toll-like receptor 2-deficient mice results in effective protection from Borrelia burgdorferi challenge. Infect Immun. Jul. 2003;71(7):3894-900.

[No Author Listed] Valneva Completes Recruitment for Phase 2 Studies of its Lyme Disease Vaccine Candidate VLA15. Valneva SE. 3 pages.

Ulbrandt et al., Conformational Nature of the *Borrelia burgdorferi* Decorin Binding Protein A Epitopes That Elicit Protective Antibodies. Infection and Immunity (2001) 69(8)4799-4807. doi: 10.1128/IAI.69.8.4799-4807.

U.S. Appl. No. 16/702,885, filed Dec. 4, 2019, Comstedt et al.

U.S. Appl. No. 16/990,023, filed Aug. 11, 2020, Lundberg et al.

EP20158277, Jul. 2, 2020, Extended European Search Report.

* cited by examiner

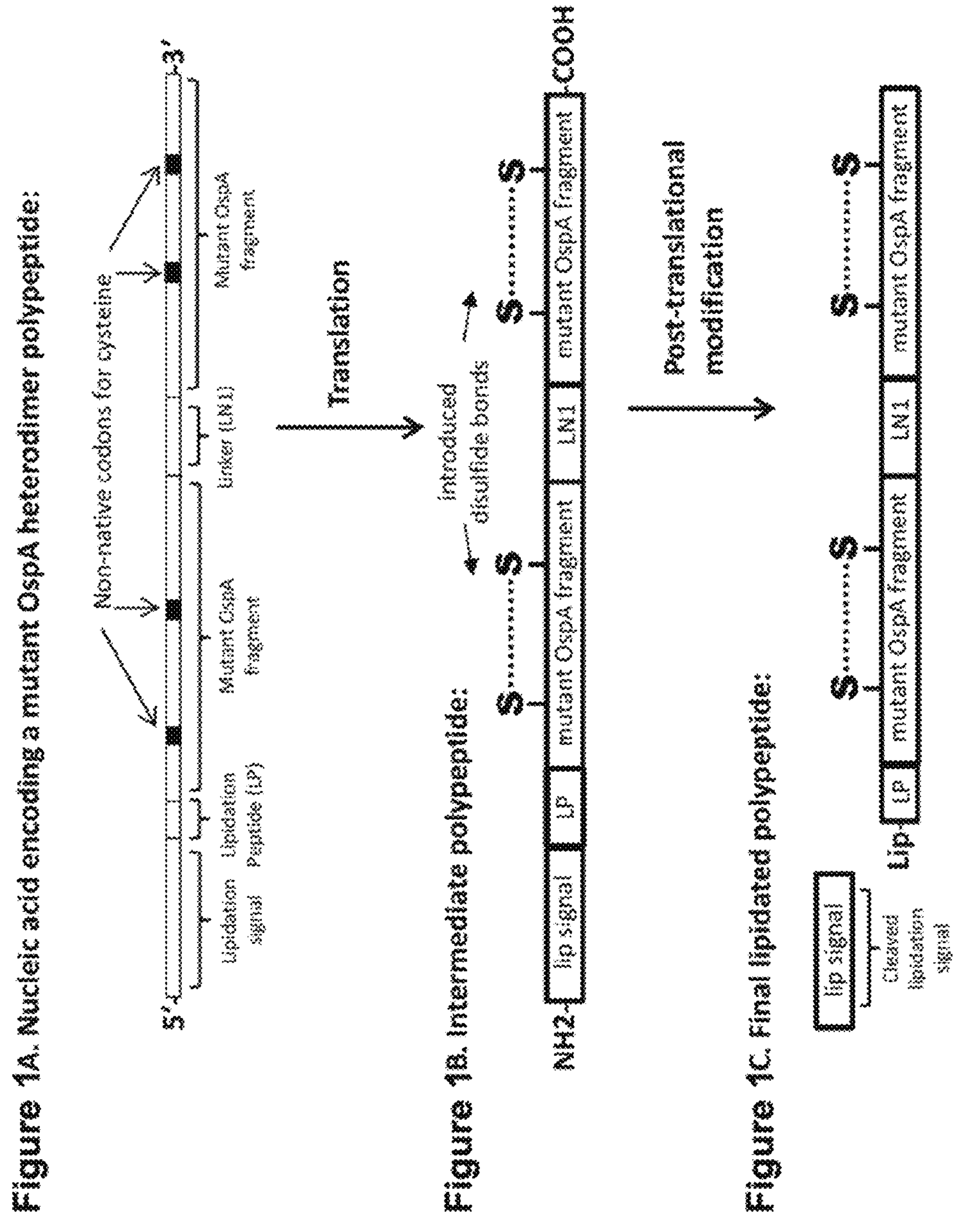
Figure 1A. Nucleic acid encoding a mutant OspA heterodimer polypeptide:
5'
3'
Non-native codons for cysteine
Lipidation signal
Lipidation Peptide (LP)
Mutant OspA fragment
Linker (LN1)
Mutant OspA fragment
Translation
Figure 1B. Intermediate polypeptide:
NH2-
lip signal
LP
mutant OspA fragment
LN1
mutant OspA fragment
-COOH
S
S
S
S
introduced disulfide bonds
Post-translational modification
Figure 1C. Final lipidated polypeptide:
lip signal
Cleaved lipidation signal
Lip
LP
mutant OspA fragment
LN1
mutant OspA fragment
S
S
S
S

MUTANT FRAGMENTS OF OSPA AND METHODS AND USES RELATING THERETO

RELATED APPLICATIONS

This application is a continuation of U.S. patent application Ser. No. 15/267,372, filed Sep. 16, 2016, which is a continuation of U.S. patent application Ser. No. 14/623,681, filed Feb. 17, 2015, now abandoned, which is a continuation of U.S. patent application Ser. No. 13/802,991, filed Mar. 14, 2013 and now issued as U.S. Pat. No. 8,986,704, which claims the benefit under 35 U.S.C. § 119(e) of U.S. provisional application Ser. No. 61/668,627, filed Jul. 6, 2012, the disclosures of which are incorporated by reference herein in their entirety.

FIELD OF THE INVENTION

The present invention relates to compositions and methods for the prevention and treatment of *Borrelia* infection.

BACKGROUND OF THE INVENTION

Lyme borreliosis, or Lyme disease, is the most commonly reported tick-borne disease in Europe and North America. The disease is caused by the arthropod-borne gram-negative-like spirochete, *Borrelia burgdorferi* sensu lato (*B. burgdorferi* s.l.), and is an infection that can involve multiple organs or tissues, resulting in skin, cardiac, musculoskeletal and neurological disorders. In most countries, Lyme borreliosis is not a notifiable disease and no exact data regarding annual incident rates are available. In the United States, the causative agent is *B. burgdorferi* sensu stricto (*B. burgdorferi* s.s.) and Lyme borreliosis is localized to northeastern, mid-Atlantic and upper north-central states. In 2010, a total of about 30,000 cases of Lyme borreliosis were reported for the US to the Centers for Disease Control and Prevention (CDC). In Europe, *B. afzelii* and *B. garinii* are the main causative agents of Lyme borreliosis, as well as *B. burgdorferi* s.s. and *B. bavariensis*, which contribute to a lesser extent depending on the geographic location. The prevalence of Lyme borreliosis varies considerably in different European countries with an overall increased prevalence from west to east. In much of Europe, the number of reported cases of Lyme borreliosis has increased since the early 1990s (e.g., the Czech Republic, Estonia, Lithuania; see Lyme borreliosis in Europe, WHO report of 2006), and the geographic distribution of cases has also expanded.

In some risk groups, such as farmers, forestry workers, hikers, runners or vacationers, seroprevalence and disease incidence rates have increased, as in children under 15 years of age and adults between 39 and 59, without gender preference. This increased incidence of Lyme borreliosis is linked to changes in forest habitats as well as social factors. Environmental changes, such as forest fragmentation, have led to a sharp reduction of rodent predators such as foxes and birds of prey, which in turn has led to an increase in the mouse population, with a subsequent increase in the tick population. More recently, patchy reforestation has increased the number of deer and thus the number of ticks. Suburban sprawl and the increasing use of woodland areas for recreation such as camping and hiking has brought humans into greater contact with the larger number of tick *Borrelia* vectors. All of these factors together have contributed to a wider distribution of *Borrelia* and a higher incidence of Lyme borreliosis.

Antimicrobial agents are the principle method of treatment of *Borrelia* infection. The antibiotic used depends on the stage of the disease, symptoms, and the patient's allergies to medication. The length of the antibiotic course also depends on the stage of the disease and the severity of symptoms. Early Lyme borreliosis is typically treated with oral tetracyclines, such as doxycycline, and semi-synthetic penicillins, such as amoxicillin or penicillin V. Arthritic and neurological disorders are treated with high-dose intravenous penicillin G or ceftriaxone. Up to 30% of Lyme borreliosis patients do not display the early characteristic symptoms of infection with *Borrelia*, making diagnosis and treatment problematic. The antibiotic course can be long (up to several months) and sometimes ineffective and is thus debated in the *Borrelia* field, especially during later-stage disease. Even in the case of effective treatment of *Borrelia*, patients can be left with debilitating fatigue, pain, or neurological symptoms for years afterwards referred to as post-treatment Lyme disease syndrome. In general, the use of antibiotics can have undesirable consequences, such as the development of resistance by the target micro-organisms. Finally, antibiotic therapy may effectively cure Lyme borreliosis, but provides no protection against subsequent infections.

A monovalent OspA-based vaccine (LYMErix™) was approved and marketed in the USA for the prevention of Lyme disease. However, heterogeneity in OspA sequences across different serotypes in Europe and elsewhere precludes efficient protection with a vaccine based on OspA from a single serotype.

Chimeric OspA molecules comprising the proximal portion from one OspA serotype, together with the distal portion form another OspA serotype, while retaining antigenic properties of both of the parent polypeptides, may be used in the prevention and treatment of Lyme disease or borreliosis (WO2011/143617, WO2011/143623).

X-ray crystallography and NMR analysis have been used to identify immunologically important hypervariable domains in OspA and have mapped the LA-2 epitope to amino acids 203-257 (Ding et al., Mol. Biol. 302: 1153-64, 2000).

Currently, there is no preventative medicament for Lyme borreliosis on the market and thus there is a need in the art for the development of such a medicament that can provide effective protection against a variety of species of *Borrelia* that are present in the USA, Europe and elsewhere.

SUMMARY OF THE INVENTION

The present invention relates to a polypeptide comprising a mutant fragment of *Borrelia* outer surface protein A (OspA), a nucleic acid encoding the same, a pharmaceutical composition (particularly for use as a medicament or in a method of treating or preventing a *Borrelia* infection) comprising the polypeptide and/or the nucleic acid, a method of treating or preventing a *Borrelia* infection and a method of immunizing a subject.

Efforts to develop a subunit vaccine for prevention of Lyme borreliosis have been focused in large part on the use of borrelial outer surface protein A (OspA) as an antigen. The OspA protein is expressed by *Borrelia* only when it is in the gut of the tick vector. Thus, OspA antibodies produced by vaccination do not fight infection in the body, but rather enter the gut of the tick when it takes a blood meal. There, the antibodies neutralise the spirochetes and block the migration of bacteria from the midgut to the salivary glands of the tick, the route through which *Borrelia* enters the vertebrate host. Thus, OspA-specific antibodies prevent the transmission of *Borrelia* from the tick vector to the human host.

The lipidated form of OspA from *B. burgdorferi* s.s., strain ZS7, together with aluminium hydroxide was commercially developed as a vaccine against *Borrelia* (LYMErix™) by SmithKline Beecham, now GlaxoSmithKline (GSK) for the US market. Three doses of LYMErix™ over a period of one year were needed for optimal protection. After the first two doses, vaccine efficacy against Lyme borreliosis was 49%, and after the third dose 76%. However, shortly after LYMErix™ was commercially available, it was withdrawn from the market in 2002. Reasons cited were matters of practical application of the vaccine, for example the need for booster injections every year or every other year, as well as the relatively high cost of this preventive approach compared with antibiotic treatment of early infection. In addition, there was a concern that LYMErix™ could trigger autoimmune reactions in a subgroup of the population due to sequence homology with a human protein, though this was never proven. In addition, cross-protection against other clinically important *Borrelia* species was not provided by this vaccine.

Accordingly, in one embodiment, it was an object of the present invention to provide an improved vaccine for the prevention of Lyme borreliosis. Preferably, the vaccine is easily produced while being protective, safe and more effective than existing therapies and/or provides protection against more than one *Borrelia* species.

The problem underlying the present invention is solved by a polypeptide comprising a mutant fragment of an outer surface protein A (OspA), wherein the mutant fragment consists of a C-terminal domain of an OspA protein of *Borrelia* and differs from the corresponding wild-type fragment by the introduction of at least one disulfide bond.

Surprisingly, it was found that the introduction of at least one disulfide bond in a mutant fragment increases the protective capacity of the polypeptide comprising the mutant OspA fragment relative to a polypeptide comprising the wild-type OspA fragment, as shown in an in vivo model of infection. As shown in the Examples, the introduction of at least one disulfide bond into the *B. afzelii* OspA C-terminal fragment increased its protective capacity relative to the wild-type OspA fragment without a disulfide bond. Tables 2 and 3 provide data demonstrating the protective capacity of mutant fragments with an introduced disulfide bond ("S2D1-5") as compared to the wild-type OspA fragment ("S2D0"), as fewer animals were infected after immunization with mutant OspA fragments in comparison to wild-type OspA fragments. Some of the mutant OspA fragments tested provided protection comparable to that conveyed by the positive control antigen, the non-lipidated full-length OspA protein.

DETAILED DESCRIPTION OF THE INVENTION

Accordingly, in a first aspect, the present invention relates to a polypeptide comprising a mutant fragment of an outer surface protein A (OspA), wherein the mutant fragment consists of a C-terminal domain of an OspA of *Borrelia* and differs from the corresponding wild-type fragment by the introduction of at least one disulfide bond.

The term *B. burgdorferi* s.l. encompasses at least 13 *Borrelia* species (Table A-1). These species occur in different geographic regions, and live in nature in enzootic cycles involving ticks of the *Ixodes ricinus* complex (also called *Ixodes persulcatus* complex) and a wide range of animal hosts. Four *Borrelia* species are responsible for the majority of infections in humans: *B. burgdorferi* s.s., *B. afzelii, B. bavariensis* and *B. garinii*. Three other species, *B. lusitaniae, B. bissettii* and *B. spielmanii*, have occasionally been detected in humans, but their role in Lyme borreliosis is uncertain at present. New species of *Borrelia* are still being reported.

TABLE A-1

| | Principal tick vector | Location |
|---|---|---|
| Pathogenic species (4) | | |
| *Borrelia burgdorferi* (*Borrelia burgdorferi* s.s.) | *Ixodes scapularis* | Northeastern/north-central US |
| | *Ixodes pacificus* | Western US |
| | *Ixodes ricinus* | Europe |
| | *Ixodes persulcatus* | Asia |
| *Borrelia garinii* | *Ixodes ricinus* | Europe |
| | *Ixodes persulcatus* | Asia |
| *Borrelia afzelii* | *Ixodes ricinus* | Europe |
| | *Ixodes persulcatus* | Asia |
| *Borrelia bavariensis* | *Ixodes ricinus* | Europe |
| | *Ixodes persulcatus* | Asia |
| Minimally pathogenic or non-pathogenic species (9) | | |
| *Borrelia andersonii* | *Ixodes dentatus* | Eastern US |
| *Borrelia bissettii* | *Ixodes spinipalpis* | Western US |
| | *Ixodes pacificus* | Europe |
| | *Ixodes ricinus* | |
| *Borrelia valaisiana* | *Ixodes ricinus* | Europe and Asia |
| | *Ixodes columnae* | |
| *Borrelia lusitaniae* | *Ixodes ricinus* | Europe |
| *Borrelia spielmanii* | *Ixodes ricinus* | Europe |
| *Borrelia japonica* | *Ixodes ovatus* | Japan |
| *Borrelia tanukii* | *Ixodes tanuki* | Japan |
| *Borrelia turdi* | *Ixodes turdus* | Japan |
| *Borrelia sinica* | *Ixodes persulcatus* | China |

As detailed above, *Borrelia* outer surface protein A (OspA) is an abundant immunogenic lipoprotein of *Borrelia* of particular interest because of its potential as a vaccine candidate. OspA of *B. burgdorferi* s.l. is a basic lipoprotein that has a molecular mass of approximately 30 kDa and is encoded on a linear plasmid. An important aspect of the OspA protein is its N-terminal lipidation; that is, the N-terminal cysteine residue is substituted with fatty acids with a chain length of between C14 and C19 with or without double-bonds, a feature that enhances the immunogenicity of the OspA protein. It has been shown that poorly-immunogenic synthetic peptides induce stronger antibody responses when lipidated; for example, when covalently coupled to $Pam_3Cys$ (Bessler and Jung, Research Immunology (1992) 143:548-552), a fatty acid substitution found at the amino terminus of many bacterial lipoproteins that are synthesized with a signal sequence specifying lipid attachment. Additionally, the $Pam_3Cys$ moiety was shown to enhance immune responses to OspA in mice, partially through its interaction with TLR-2 (Yoder, et al. (2003) Infection and Immunity 71:3894-3900). Therefore, lipidation of a C-terminal fragment of OspA would be expected to enhance the immunogenicity and protective capacity of the fragment.

Analysis of isolates of *B. burgdorferi* s.l. obtained in North America and Europe has revealed that OspA has antigenic variability and that several distinct groups can be defined based on serology. Anti-OspA mAbs which bind to specific N- and C-terminal antigenic determinants have been reported. Previous studies have shown that the production of antibodies against the C-terminal epitope LA-2 correlates with protective immunity after vaccination with OspA (Van Hoecke et al. Vaccine (1996) 14(17-18):1620-6 and Steere et al., N Engl J Med (1998) 339:209-215). Antibodies to LA-2 were shown to block the transmission of *Borrelia* from tick to host (Golde et al., Infect Immun (1997) 65(3):882-889). These studies suggested that the C-terminal portion of the OspA protein may be sufficient for inducing protective immunity. Based on information from these and other studies, truncated forms of OspA comprising the C-terminal portion (also referred to herein as "OspA fragment" or "monomer") were used in the current invention. These truncated forms of OspA proved to be less protective than the full-length OspA protein. Surprisingly, however, it was found in the course of the current invention that the introduction of a disulfide bond in the truncated form (also referred to herein as "mutant OspA fragment" or "mutant fragment") overcomes this disadvantage. While not being limited to a specific mechanism, it is thought that improved protection is due to increased stability of the OspA fragment, as shown in assays measuring thermal stability.

In accordance with the present invention, the mutant OspA fragment may be derived from any *Borrelia* species; however, due to their relevance in the medical field, particularly for humans, *B. burgdorferi* s.s., *B. afzelii, B. bavariensis* and *B. garinii* are preferred. In this regard, these four *Borrelia* species can be further classified according to their OspA serotypes, which have been determined by analysis with monoclonal antibodies specific to the respective OspA protein. Serotypes 1-7, which account for the majority of human *Borrelia* infections, along with their rates of prevalence, are shown in Table A-2 below.

TABLE A-2

Serotype designation and prevalence of *B. burgdorferi* s.s., *B. afzelii*, *B. bavariensis* and *B. garinii*. *Borrelia* isolated from human cerebrospinal fluid or skin or from tick vectors were serotyped by probing whole-cell lysates with mouse monoclonal antibodies, each specific to a particular epitope of OspA (as described by Wilske et al., J. of Clin Microbiol (1993) 31(2): 340-350 and presented by Baxter Bioscience at "Climate change effect on ticks and tick-borne diseases", Brussels, 06 Feb 2009).

| *Borrelia* sp. | OspA serotype defined by mAb testing | Prevalence in human disease | Strain source for sequence | Seq ID No: |
|---|---|---|---|---|
| *B. burgdorferi* s.s. | 1 | 11% | B31 | 20 |
| *B. afzelii* | 2 | 63% | K78 | 19 |
| *B. garinii* | 3 | 1.5% | PBr | 21 |
| *B. bavariensis* | 4 | 4% | PBi | 22 |
| *B. garinii* | 5 | 6% | PHEi | 23 |
| *B. garinii* | 6 | 13% | DK29 | 24 |
| *B. garinii* | 7 | 0.5% | T25 | 25 |

The structure of the OspA protein from *B. burgdorferi* s.s. strain B31 was determined by Li et al. (Proc Natl Acad Sci (1997) 94:3584-3589). It is composed of N-terminal β-strands 1 to 4) and central β-sheets β-strands 5 to 14n [N-terminal part]), barrel sheet 1 (β-strands 14c [C-terminal part] to 16), barrel sheet 2 (β-strands 17 to 21) and a C-terminal α-helix. The term "OspA C-terminal domain" or "C-terminal domain" or "wild-type fragment" with respect to OspA as used throughout the present specification shall mean the C-terminal portion of OspA, i.e., OspA lacking at least the N-terminal β-sheet (including β-strands 1 to 4). In OspA from *B. burgdorferi* s.s. strain B31, the N-terminal sheet consists of amino acids 17 to 70 (following post-translational cleavage of the 16 aa long lipidation signal peptide). The C-terminal OspA fragment of the current invention may also include a lipidation signal sequence at the N-terminus, e.g., the lipidation signal sequence of amino acids 1 to 16 of OspA (SEQ ID NO: 14) or OspB (SEQ ID NO: 15) from *B. burgdorferi* s.s. strain B31, a lipidation signal sequence from *E. coli*, referred to herein as the "lpp lipidation signal" (SEQ ID NO: 16), or any other signal sequence, e.g., as defined below.

Lipidation of a protein with an N-terminal lipidation signal sequence, such as those present on a nascent OspA polypeptide, occurs in the *E. coli* expression vector by the step-wise action of the enzymes diacylglyceryl transferase, signal peptidase II and transacylase, respectively. The first step is the transfer of a diacylglyceride to the cysteine sulphydryl group of the unmodified prolipoprotein, followed by the cleavage of the signal peptide by signal peptidase II and, finally, the acylation of the α-amino group of the N-terminal cysteine of the apolipoprotein. The result is the placement of one lipid and a glycerol group substituted with two further lipids on the N-terminal cysteine residue of the polypeptide. The lipidation signal sequence, which is cleaved off during lipidation, is not present in the final polypeptide sequence.

According to the current invention, the mutant OspA fragment may be a lipidated protein, also lipoprotein, wherein the lipid moieties, along with the glycerol group, is also referred to as "Lip". According to the invention, Lip comprises one to three lipids such as $C_{14-20}$ alkyl and/or $C_{14-20}$ alkenyl attached to a glycerol and the N-terminal cysteine of the polypeptide of the invention, or preferably wherein Lip is a moiety of formula (I) below, Formula (I)

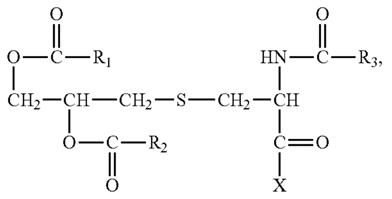

in which one of $R_1$, $R_2$ or $R_3$ is $C_{14}$-$C_{20}$ alkyl or alkenyl, and each of the others, independently is $C_{14}$-$C_{20}$ alkyl or $C_{14}$-$C_{20}$ alkenyl, and X is an amino acid sequence attached to the cysteine residue shown in Formula (I). More preferably, Lip plus the N-terminal cysteine of the polypeptide is N-palmitoyl-S-(2RS)-2,3-bis-(palmitoyloxy) propyl cysteine (referred to herein as "$Pam_3Cys$" (SEQ ID NO: 139)) and is connected via the carbonyl C of the cysteine to said amino acid sequence of the invention. In Formula (I) above $R_1$, $R_2$ and $R_3$ would be palmitoyl moieties and X is an amino acid sequence attached to the cysteine residue.

In accordance with the current invention, the C-terminal domain of an OspA from a strain other than *B. burgdorferi* s.s. B31 is defined by (i) lacking at least amino acids 17 to 70 and/or (ii) by lacking at least the N-terminal domain homologous to amino acids 17 to 70 of OspA from *B. burgdorferi* s.s. B31. Additionally, the OspA C-terminal domain according to the present invention may also lack further portions of the central sheet as defined by Li and co-workers (Li et al., supra), particularly further strands such as the amino acid portions from amino acid 17 to 82, 93, 105, 118 or 119, preferably 17 to 129, more preferably 1 to 125, 1 to 129 or 1 to 130 of any *Borrelia*, particularly *B.*

*burgdorferi* s.s. B31, or homologous portions of an OspA protein from a *Borrelia* sp. other than *B. burgdorferi* s.s. B31.

In the context of the present invention, the OspA C-terminal domain is also referred to as "OspA fragment" or "fragment of OspA".

The "mutant fragment" in the context of the polypeptide of the present invention and as used throughout the present specification shall mean the OspA C-terminal fragment, as defined above, which differs from the wild-type fragment by at least two introduced cysteines that can form a disulfide bond. Without being bound to that theory, it is assumed that the disulfide bond stabilizes the fragment in a conformation conducive to the induction of antibody binding. The fold of the wild-type C-terminal fragment of OspA shows reduced temperature stability in comparison to the full-length protein (Koide et al., Structure-based Design of a Second-generation Lyme Disease Vaccine Based on a C-terminal Fragment of *Borrelia burgdorferi* OspA, J. Mol. Biol. (2005) 350:290-299). For the present invention, the sequence of the C-terminal domain of the *B. burgdorferi* s.s. B31 OspA has been in silico analyzed to determine positions for introduced disulfide bridges that may enhance the stability of the fold of this C-terminal domain. The results of the analysis have been transferred to homologous OspA fragments of other *Borrelia* species with the assumption that the fold is conserved across species.

Typically, the disulfide bond may be introduced by introduction of one or more cysteine residues, wherein a disulfide bond (S—S bridge) is formed between the thiol groups of two cysteine residues. Only one cysteine residue need be introduced if a disulfide bond is formed with a cysteine residue present in the wild-type fragment. The one, or preferably two, cysteine(s) may be introduced by amino acid addition or, preferably, substitution.

The OspA mutant fragment may also comprise further mutations relative to the wild-type. As detailed above, the structure and surface domain of OspA are known in the art. Accordingly, the mutant fragment may comprise further mutations, particularly at sites not on the surface of the protein and/or not involved in the immune response and, therefore not impacting antigenic capacity. These can include one or more amino acid deletion(s), particularly small (e.g., up to 10 amino acids) deletions, one or more amino acid addition(s) (particularly C- or N-terminally), one or more amino acid substitution(s), particularly one or more conservative amino acid substitutions. Examples of conservative amino acid substitutions include, but are not limited to, those listed below:

| | |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Preferred mutations include changes in selected portions of the fragment, for example, wherein the sequence with sequence similarity to human leukocyte function-associated antigen (hLFA-1), which exists in *B. burgdorferi* s.s., is modified, for example, replaced by a homologous sequence from an OspA protein from another *Borrelia* sp. The rationale for this modification is to reduce the risk for inducing immunological cross-reaction with human proteins. Also possible is the addition of a signal sequence for lipidation in the final, or an intermediate, fragment, or the addition of a marker protein (e.g., for identification or purification).

In some embodiments, the mutant OspA fragment has an amino acid sequence that has 60%, preferably at least 70%, more preferably at least 80%, more preferably 85%, more preferably 90%, even more preferably 95% sequence identity to the wild-type fragment.

Identity, as known in the art and as used herein, is the relationship between two or more polypeptide sequences, as determined by comparing the sequences. In the art, identity also means the degree of sequence relatedness between polypeptide or polynucleotide sequences, as the case may be, as determined by the match between strings of such sequences. Identity can be readily calculated. While a number of methods exist to measure identity between two polynucleotides or two polypeptide sequences, the term is well known to skilled artisans (e.g. Sequence Analysis in Molecular Biology, von Heinje, G., Academic Press, 1987). Preferred methods to determine identity are designed to give the largest match between the sequences tested. Methods to determine identity are codified in computer programs. Preferred computer program methods to determine identity between two sequences include, but are not limited to, the GCG program package (Devereux, J. et al., 1984), BLASTP, BLASTN, and FASTA (Altschul, S. et al., 1990).

In contrast to the mutant OspA fragment, the "wild-type fragment" in the context of the present invention relates to a fragment of a naturally-occurring OspA of *Borrelia*. The wild-type fragment is obtained by N-terminal deletions, but it does not comprise internal deletions (except from signal sequences as detailed herein) or mutations. In relation to the mutant OspA fragment, the wild-type fragment consists of an identical part of the OspA (identical length and same strain of OspA, etc.) and differs only in the mutation(s) detailed above, particularly in the introduction of at least one disulfide bond or the replacement of a sequence with human homology.

In one embodiment of the present invention, the mutant OspA fragment may differ from the respective wild-type fragment only by the introduction of at least one, preferably exactly one, disulfide bond.

A polypeptide is a single linear polymer of amino acids linked by peptide bonds. In accordance with the present invention, the polypeptide may also compromise one or more posttranslational modifications; i.e., an attached biochemical functional group, such as an attached acetate, phosphate, lipid or carbohydrate, preferably a lipid or lipids attached to the N-terminal cysteine along with a glycerol, more preferably 1 to 3 $C_{14}$-$C_{20}$ alkyl or alkenyl moieties, even more preferably 1 to 3 palmitoyl groups, most preferably three palmitoyl groups ($Pam_3$).

In accordance with the present invention, the polypeptide of the present invention comprises the above-described mutant OspA fragment. According to the present invention, it does not comprise (i) the N-terminal sheet as defined above and (ii) optionally further strands of the central sheet as defined above. However, the polypeptide may comprise one or more functional sequences such as a signal sequence, e.g., a lipidation signal sequence or a posttranslational modification, such as lipidation.

In a further embodiment of the present invention, the polypeptide of the present invention consists of (i) one or more mutant OspA fragments, optionally joined by linkers, e.g., as defined below and (ii) optionally one or more amino acids heterologous to OspA, particularly a signal sequence and (iii) optionally a posttranslational modification, such as lipidation.

The polypeptide of the present invention has protective capacity. As detailed above, the introduction of a disulfide bond into the mutant OspA fragment increases the protective capacity of the polypeptide relative to a polypeptide comprising the respective fragment without the disulfide bond(s). In some embodiments, the protective capacity is increased by at least 10%, more preferably by at least 20%, more preferably by at least 30%, more preferably by at least 40%, more preferably by at least 50%, more preferably by at least 60%, more preferably by at least 70%, more preferably by at least 80%, even more preferably by at least 90%.

The term protective capacity describes the ability to protect a subject against a *Borrelia* infection. With respect to the polypeptide of the invention, protective capacity relates to the ability of the polypeptide to induce an immune response that protects a subject against a *Borrelia* infection. Protective capacity can be tested by administering to a subject the polypeptide in a manner to induce an immune reaction against the polypeptide. Thereafter, the subject may be challenged with *Borrelia*. The subject's reaction to the infection is monitored. Particularly, the presence of *Borrelia* in the subject may be determined. For example, the polypeptide is protective if *Borrelia* cannot be detected in the subject. The presence of *Borrelia* can be determined by detecting *Borrelia*-specific nucleic acids (e.g., by PCR) or *Borrelia*-specific antibodies (e.g., by ELISA or Western blot) or by detecting *Borrelia* itself (e.g., culturing organs or tissues in growth medium and verifying the presence of *Borrelia* by microscopy). In particular, the protective capacity ("pc"), reported as a percentage, for a particular dose is defined as follows:

$$pc(\%)=[(\text{number of total tested subjects}-\text{number of } \textit{Borrelia}\text{-infected subjects})/\text{number of total tested subjects}]\times 100$$

Differences in protective capacity (Δpc) may be determined by, e.g. comparing the protective capacity (pc) of a mutant OspA fragment with a disulfide bond(s) (pc [with bond]) to the protective capacity of an OspA fragment without a disulfide bond(s) (pc [w/o bond]). In accordance with the present invention, the polypeptides to be compared differ only in the introduction of at least one disulfide bond. The change in protective capacity (Δpc) by the introduction of the disulfide bond(s) is determined as follows:

$$\Delta pc=(pc[\text{sample}]-pc[\text{control}])$$

e.g.

$$\Delta pc=(pc[\text{with bond}]-pcz[\text{w/o bond}])$$

If Δpc is greater than zero (>0), assuming all other parameters (e.g., dose and assay) are the same, then the protective capacity of the sample (e.g. the mutant OspA fragment with a disulfide bond(s)) is better than the protective capacity of the control (e.g. the OspA fragment without a disulfide bond(s)). Conversely, if Δpc is less than zero (<0) and assuming all other parameters (e.g., dose and assay) are the same, then the protective capacity of the sample (e.g. the mutant OspA fragment with a disulfide bond(s)) is less than the protective capacity of the comparison (e.g., the OspA fragment without a disulfide bond(s)).

Preferably, the polypeptide of the present invention is assessed for its protective capacity by an in vivo animal assay wherein mice immunized with the polypeptide of the invention or with a control inoculate are challenged with *Borrelia* introduced into the immunized subjects with a hypodermic needle. More preferably, the polypeptide of the present invention is assessed for its protective capacity by an in vivo animal assay comprising the steps of a) applying at least one *I. ricinus* nymph infected with *Borrelia*, e.g., *B. afzelii*, strain IS1, to a mouse that is immunized with said first polypeptide of the first aspect; and b) applying at least one *I. ricinus* nymph infected with *Borrelia*, e.g., *B. afzelii*, strain IS1, to a second mouse that is immunized with said second polypeptide of the first aspect; and c) comparing the rates of infection in the two mice. Preferably, the assay or test is done with a group of mice per polypeptide to be tested. A suitable test is also described and illustrated in the Examples.

In a preferred embodiment of the present invention, the products of the invention such as, e.g. the polypeptides of the invention comprising the mutant OspA fragment with a disulfide bond(s) administered 3 times at a dose of 5.0 μg, preferably 1.0 μg, preferably 0.3 μg or lower have a protective capacity of 80% or more, preferably 90% or more, even more preferably 95% or more, most preferred 99% or more. It has been surprisingly observed that immunization with an OspA mutant fragment of one *Borrelia* serotype can provide cross-protection against other another serotype (Example 4, Table 4). Based on this finding, it might be anticipated that the dose of polypeptide of the present invention could be even further reduced.

In a preferred embodiment of the present invention, the C-terminal domain of an OspA protein of *Borrelia* consists of (i) the amino acids from position 126, 131 or 130 to position 273 of the OspA of *B. afzelii*, strain K78 or (ii) the homologous domain to amino acids of OspA from a *Borrelia* strain other than *B. afzelii*, strain K78. Accordingly, the polypeptide of the present invention comprises or consists of (i) one or more of these mutant fragments, optionally joined by linkers, e.g., as defined below and (ii) optionally one or more amino acids heterologous to OspA, particularly a signal sequence or site for a post-translational modification such as lipidation and (iii) optionally a posttranslational modification, such as lipidation.

In accordance with the present invention, a disulfide bond is introduced into an OspA fragment. This may preferably be achieved by introducing into the fragment at least 1 or 2 cysteine(s), particularly 2 cysteines, in order to allow for the formation of the at least one disulfide bond. Only one cysteine may be introduced, if another cysteine in the fragment is available for a disulfide bond. However, preferably two cysteines are introduced. The cysteine(s) is/are introduced by amino acid addition or substitution, preferably substitution. In case of addition, the cysteine is inserted into the amino acid sequence between two amino acids, whereas in case of substitution one amino acid is replaced with the cysteine.

In accordance with the present invention, the OspA may be from any *Borrelia* strain, particularly from those specified herein such as *B. burgdorferi* s.s., *B. garinii, B. afzelii, B. andersonii, B. bissettii, B. valaisiana, B. lusitaniae, B. spielmanii, B. japonica, B. tanukii, B. turdi* or *B. sinica, B. bavariensis*, preferably from *B. burgdorferi* s.s., *B. afzelii, B. bavariensis* or *B. garinii*. Preferably, the OspA is from *B. afzelii*, particularly strain K78, OspA serotype 2 (SEQ ID NO: 19); *B. burgdorferi* s.s., particularly strain B31, OspA serotype 1 (SEQ ID NO: 20); *B. garinii*, particularly strain PBr, OspA serotype 3 (SEQ ID NO: 21); *B. bavariensis*, particularly strain PBi, OspA serotype 4 (SEQ ID NO: 22); *B. garinii*, particularly strain PHei, OspA serotype 5 (SEQ ID NO: 23); *B. garinii*, particularly strain DK29, OspA serotype 6 (SEQ ID NO: 24) or *B. garinii*, particularly strain T25, OspA serotype 7 (SEQ ID NO: 25). The amino acid sequences of these OspA proteins (full-length) are given below.

TABLE A-3

Accession numbers of OspA sequences from selected strains of *Borrelia* species.

| Organism_Strain | db\|accession.version | Organism_Strain | db\|accession.version | Organism_Strain | db\|accession.version |
|---|---|---|---|---|---|
| Bbu_156a (serotype 1) | gb\|ACL33776.1 | Bbu_K48 | emb\|CAA44492.1 | Bga_Mng4702 | gb\|ABF29559.1 |
| Baf_K78 (serotype 2) | emb\|CAA49828.1 | Bbu_N40 | gb\|ACS94765.1 | Bga_N34 | emb\|CAB64763.1 |
| Bga_PBr (serotype 3) | emb\|CAA56549.1 | Bbu_P0A3N6.1 | sp\|P0A3N6.1 | Bga_Nov1006 | gb\|ACD02016.1 |
| Bga_PBi (serotype 4) | emb\|CAA56550.1 | Bbu_PBo | emb\|CAA56468.1 | Bga_Nov105 | gb\|ABF29551.1 |
| Bbu_PHei (serotype 5) | tr\|Q06228 | Bbu_PBre | emb\|CAA59742.1 | Bga_Nov14506 | gb\|ACD02013.1 |
| Bbu_DK29 (serotype 6) | emb\|CAA45010.1 | Bbu_PHei | emb\|CAA56544.1 | Bga_Nov14606 | gb\|ACD02017.1 |
| Bga_T25 (serotype 7) | emb\|CAA56547.1 | Bbu_PKa | emb\|CAA56467.1 | Bga_Nov2005 | gb\|ABF29553.1 |
| Baf_ACA-1 | gb\|ACJ73559.1 | Bbu_PKo | emb\|CAA46550.1 | Bga_Nov2006 | gb\|ACD02018.1 |
| Baf_K78 | (sequenced) | Bbu_Poti_B1 | emb\|CAB64754.1 | Bga_Nov3305 | gb\|ABF29554.1 |
| Baf_Khab_625 | gb\|AAR96311.1 | Bbu_Poti_B2 | emb\|CAB64755.1 | Bga_Nov405 | gb\|ABF29552.1 |
| Baf_Khab2-Sakh | gb\|AAP94134.1 | Bbu_Poti_B3 | emb\|CAB64756.1 | Bga_Nov7006 | gb\|ACD02014.1 |
| Baf_Khab470 | gb\|AAO91923.1 | Bbu_PTro | emb\|CAA56471.1 | Bga_Nov9906 | gb\|ACD02015.1 |
| Baf_Khab505 | gb\|AAO91925.1 | Bbu_PWudI | emb\|CAA56469.1 | Bga_PBi | gb\|AAT93773.1 |
| Baf_LU192 | (sequenced, partial) | Bbu_PWudI/6 | emb\|CAA56470.1 | Bga_PBr | emb\|CAA56549.1 |
| Baf_Mng3602 | gb\|ABF29573.1 | Bbu_PWudII | emb\|CAA56546.1 | Bga_Q1HLH6 | gb\|ABF29564.1 |
| Baf_Mng4302 | gb\|ABF29574.1 | Bbu_Q04851.1 | sp\|Q04851.1 | Bga_T25 | emb\|CAA56547.1 |
| Baf_Mng6702 | gb\|ABF29578.1 | Bbu_Q04968.1 | sp\|Q04968.1 | Bga_TlsI | emb\|CAA59727.1 |
| Baf_Mng702 | gb\|ABF29572.1 | Bbu_Q09086.1 | sp\|Q09086.1 | Bga_TN | emb\|CAA56545.1 |
| Baf_Nov1105 | gb\|ABF29569.1 | Bbu_Q09087.1 | sp\|Q09087.1 | Bga_Tom1003 | gb\|ABF29564.1 |
| Baf_Nov11506 | gb\|ACD02019.1 | Bbu_Q44738 | tr\|Q44738 | Bga_Tom1805 | gb\|ABF29567.1 |
| Baf_Nov3005 | gb\|ABF29570.1 | Bbu_Q44956 | emb\|CAA56937.1 | Bga_Tom203 | gb\|ABF29562.1 |
| Baf_P0A3N7.1 | sp\|P0A3N7.1 | Bbu_Q44962 | dbj\|BAA06133.1 | Bga_Tom2903 | gb\|ABF29565.1 |
| Baf_PHo | emb\|CAA59724.1 | Bbu_Q45039 | emb\|CAR95556.1 | Bga_Tom3005 | gb\|ABF29568.1 |
| Baf_PKo | gb\|ABH02138.1 | Bbu_Q45040 | tr\|Q45040 | Bga_Tom303 | gb\|ABF29563.1 |
| Baf_PLe | emb\|CAA59970.1 | Bbu_S-1-10 | gb\|AAB96354.1 | Bga_Tom3101 | gb\|ABF29557.1 |
| Baf_PLj7 | emb\|CAA59725.1 | Bbu_T.R.O. | emb\|CAA46549.1 | Bga_Tom3803 | gb\|ABF29566.1 |
| Baf_PLud | emb\|CAA59726.1 | Bbu_T255 | emb\|CAA59730.1 | Bga_Tom5102 | gb\|ABF29560.1 |
| Baf_Tom1103 | gb\|ABF29581.1 | Bbu_UK | emb\|CAB64758.1 | Bga_Tom5202 | gb\|ABF29561.1 |
| Baf_Tom1303 | gb\|ABF29582.1 | Bbu_VS116 | emb\|CAB64757.1 | Bga_Tom7105 | gb\|ABF29556.1 |
| Baf_Tom1503 | gb\|ABF29583.1 | Bbu_VS461 | emb\|CAA82329.1 | Bga_VS100 | emb\|CAB64765.1 |
| Baf_Tom2303 | gb\|ABF29584.1 | Bbu_WI91-23 | ref\|ZP_03091138.1 | Bga_VS307 | emb\|CAB64764.1 |
| Baf_Tom2403 | gb\|ABF29585.1 | Bbu_ZQ1 | emb\|CAA01704.1 | Bga_WABSou | emb\|CAA59728.1 |
| Baf_Tom2504 | gb\|ABF29577.1 | Bbu_ZS7 | gb\|ACK74228.1 | Bja_Cow611 | emb\|CAB64759.1 |
| Baf_Tom2803 | gb\|ABF29586.1 | Bga_BgVir-1 | gb\|ABF29555.1 | Bja_F63 | emb\|CAB64760.1 |
| Baf_Tom3401 | gb\|ABF29571.1 | Bga_Far04 | ref\|ZP_03328706.1 | Bja_HO14 | emb\|CAB64762.1 |
| Baf_Tom3703 | gb\|ABF29587.1 | Bga_FujiP2 | gb\|AAA92301.1 | Bja_IKA2 | emb\|CAB64761.1 |
| Baf_Tom4703 | gb\|ABF29588.1 | Bga_IP90 | emb\|CAJ75754.1 | Blu_A8D057 | gb\|ABR22627.1 |
| Baf_Tom5403 | gb\|ABF29575.1 | Bga_Ip90 | emb\|CAJ75754.1 | Blu_A8D060 | gb\|ABR22625.1 |
| Baf_Tom603 | gb\|ABF29579.1 | Bga_JEM1 | gb\|AAB81567.1 | Blu_A8D075 | gb\|ABR22628.1 |
| Baf_Tom6303 | gb\|ABF29576.1 | Bga_JEM2 | gb\|AAB81569.1 | Blu_A8D079 | gb\|ABR22629.1 |
| Baf_Tom703 | gb\|ABF29580.1 | Bga_JEM3 | gb\|AAB81571.1 | Blu_ABR22624.1 | gb\|ABR22624.1 |
| Baf_XJ23 | gb\|AAB95225.1 | Bga_JEM4 | dbj\|BAA19222.1 | Blu_ABR22626.1 | gb\|ABR22626.1 |
| Bbu_118a | ref\|ZP_02720644.1 | Bga_JEM5 | gb\|AAB81573.1 | Bsp_A14S | gb\|AAD16455.1 |
| Bbu_156a | gb\|ACL33776.1 | Bga_JEM6 | gb\|AAB81575.1 | Btu_Ya501 | dbj\|BAA32513.1 |
| Bbu_19857 | emb\|CAA48196.1 | Bga_JEM7 | gb\|AAB81577.1 | Bva_AR-2 | gb\|AAF00571.1 |
| Bbu_2005348A | prf\|2005348A | Bga_JEM8 | gb\|AAB81579.1 | Bva_M19 | gb\|AAF00573.1 |
| Bbu_2005348B | prf\|2005348B | Bga_Khab3155 | gb\|AAR96310.1 | Bva_M49 | gb\|AAF00574.1 |
| Bbu_297 | emb\|CAA59729.1 | Bga_Khab550 | gb\|AAR96306.1 | Bva_M52 | gb\|AAF00575.1 |
| Bbu_29805 | ref\|ZP_03092996.1 | Bga_Khab616 | gb\|AAR96307.1 | Bva_M53 | gb\|AAF00576.1 |
| Bbu_64b | ref\|ZP_03097520.1 | Bga_Khab648 | gb\|AAR96308.1 | Bva_M7 | gb\|AAF00572.1 |
| Bbu_72a | ref\|ZP_02724465.1 | Bga_Khab722 | gb\|AAR96309.1 | Bva_Q9RM88 | emb\|CAB56150.1 |
| Bbu_80a | ref\|ZP_03088001.1 | Bga_Khab23 | gb\|AAP94125.1 | Bva_QLZSP1 | gb\|ACA13516.1 |
| Bbu_94a | ref\|ZP_02725946.1 | Bga_Khab24 | gb\|AAP94126.1 | Bva_QSDS4 | gb\|ACA13517.1 |
| Bbu_AAB23809.1 | gb\|AAB23809.1 | Bga_Khab31 | gb\|AAP94127.1 | Bva_QSYSP3 | gb\|ACA13518.1 |
| Bbu_AAB23810.1 | gb\|AAB23810.1 | Bga_Khab31a | gb\|AAP94128.1 | Bva_QSYSP4 | gb\|ACA13519.1 |
| Bbu_B29 | gb\|AAA18508.1 | Bga_Khab-466 | gb\|AAP94129.1 | Bva_QTMP2 | gb\|ACA13520.1 |
| Bbu_B31 | gb\|AAC66260.1 | Bga_Khab489 | gb\|AAP94130.1 | Bva_QX-S13 | gb\|ACA13521.1 |
| Bbu_Bol26 | ref\|ZP_02531917.1 | Bga_Khab5-Sakh | gb\|AAO91932.1 | Bva_UK | gb\|AAF00570.1 |
| Bbu_C-1-11 | gb\|AAB96351.1 | Bga_Khab506 | gb\|AAP94132.1 | Bva_VS116 | gb\|AAF00569.1 |
| Bbu_CA-11.2a_1 | ref\|ZP_03094587.1 | Bga_Khab516 | gb\|AAP94133.1 | Bsp_10MT | dbj\|BAA32516.1 |
| Bbu_CA-11.2a_2 | ref\|ZP_03094587.1 | Bga_Khab721 | gb\|AAP94131.1 | Bsp_5MT | dbj\|BAA32515.1 |
| Bbu_CA-11.2a_CA-112a | ref\|ZP_03094587.1 | Bga_Khab2119 | gb\|AAO91928.1 | Bsp_Am501 | dbj\|BAA32514.1 |
| Bbu_CAA00316.1 | emb\|CAA00316.1 | Bga_Khab2559 | gb\|AAO91929.1 | Bsp_LV5 | gb\|AAB96353.1 |
| Bbu_CAA42842.1 | emb\|CAA42842.1 | Bga_Khab2560 | gb\|AAO91930.1 | Bsp_PAnz | emb\|CAJ43585.1 |
| Bbu_CAA44258.1 | emb\|CAA44258.1 | Bga_Khab2594 | gb\|AAO91931.1 | Bsp_PHaP_PHap | emb\|CAJ43582.1 |
| Bbu_CAR95597.1 | emb\|CAR95597.1 | Bga_Khab430 | gb\|AAO91919.1 | Bsp_PJes | emb\|CAJ43586.1 |
| Bbu_DK1 | gb\|AAA22955.1 | Bga_Khab448 | gb\|AAO91920.1 | Bsp_PMai | emb\|CAJ43584.1 |
| Bbu_DK29 | emb\|CAA45010.1 | Bga_Khab457 | gb\|AAO91921.1 | Bsp_PMew | emb\|CAJ43583.1 |
| Bbu_DK6_Danish_isolate | emb\|CAA58601.1 | Bga_Khab468 | gb\|AAO91922.1 | Bsp_PSigII | emb\|CAJ43581.1 |

TABLE A-3-continued

Accession numbers of OspA sequences from selected strains of *Borrelia* species.

| Organism_Strain | db\|accession.version | Organism_Strain | db\|accession.version | Organism_Strain | db\|accession.version |
|---|---|---|---|---|---|
| Bbu_G2 | gb\|AAA88846.1 | Bga_Khab492 | gb\|AAO91924.1 | Bsp_SV1 | ref\|ZP_03095680.1 |
| Bbu_G25 | emb\|CAA82328.1 | Bga_Khab511 | gb\|AAO91926.1 | Bbi_25015 | gb\|AAB21761.1 |
| Bbu_H.E. | emb\|CAA46551.1 | Bga_Khab560 | gb\|AAO91927.1 | Bbi_DN127 | emb\|CAB64766.1 |
| Bbu_HB19 | gb\|AAC18776.1 | Bga_LV4 | gb\|AAB96352.1 | Bbi_Q09087.1 | gb\|AAB21761.1 |

Abbreviations:
Baf = *Borrelia afzelii*,
Bbu = *Borrelia burgdorferi* s.s.,
Bga = *Borrelia garinii*,
Bsp = *Borrelia spielmanii*,
Bbi = *Borrelia bissettii*,
Bva = *Borrelia valaisiana*,
Btu = *Borrelia turicatae*,
Bdu = *Borrelia duttonii*,
Blu = *Borrelia lusitaniae*,
Bja = *Borrelia japonica*,
gb = GenBank,
emb = EMBL,
tr = UniProt/tremble,
sp = UniProt/Swissprot,
prf = Protein Research Foundation,
dbj = DNA Databank of Japan (DDBJ),
pdb = Protein Data Bank,
db = database In accordance with the present invention, the disulfide bond may be formed between cysteines that have been introduced at any position of the OspA fragment allowing or supporting appropriate folding of the fragment. The positions may be selected, as detailed above, based on the known structure of the OspA. In a preferred embodiment, the polypeptide of the current invention contains at least one disulfide bond between any of positions 182+/−3 and any of positions 269+/−3 (disulfide bond type 1); any of positions 182+/−3 and any of positions 272+/−3 (disulfide bond type 2); any of positions 244+/−3 and any of positions 259+/−3 (disulfide bond type 3); any of positions 141+/−3 and any of positions 241+/−3 (disulfide bond type 4); any of positions 165+/−3 and any of positions 265+/−3 (disulfide bond type 5); any of positions 185+/−3 and any of positions 272+/−3 (disulfide bond type 6); any of positions 199+/−3 and any of positions 223+/−3 (disulfide bond type 7); any of positions 243+/−3 and any of positions 262+/−3 (disulfide bond type 8); any of positions 184+/−3 and any of positions 204+/−3 (disulfide bond type 9); any of positions 201+/−3 and any of positions 214+/−3 (disulfide bond type 10); any of positions 246+/−3 and any of positions 259+/−3 (disulfide bond type 11); and/or any of positions 167+/−3 and any of positions 178+/−3 (disulfide bond type 12) of a *B. afzelii*, particularly *B. afzelii* K78 serotype 2 OspA, or the homologous amino acids of an OspA from a *Borrelia* sp. other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

More particularly, the polypeptide of the current invention contains the at least one disulfide bond between any of positions 182 and 269 (disulfide bond type 1); positions 182 and 272 (disulfide bond type 2); positions 244 and 259 (disulfide bond type 3); positions 141 and 241 (disulfide bond type 4); positions 165 and 265 (disulfide bond type 5); positions 185 and 272 (disulfide bond type 6); positions 199 and 223 (disulfide bond type 7); positions 243 and 262 (disulfide bond type 8); positions 184 and 204 (disulfide bond type 9); positions 201 and 214 (disulfide bond type 10); positions 246 and 259 (disulfide bond type 11); and/or positions 167 and 178 (disulfide bond type 12) of a *B. afzelii*, particularly *B. afzelii* K78 serotype 2 OspA, or the homologous amino acids of an OspA from a *Borrelia* other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

TABLE A-4

Disulfide bond types with nomenclature and the position of the cysteine substitutions in the serotype 2 OspA protein.

| Disulfide bond type | Nomenclature | Position of cysteines in *B. afzelii* K78 serotype 2 OspA |
|---|---|---|
| wild-type sequence | D0 | No cysteine substitutions |
| 1 | D1 | 182 and 269 |
| 2 | D2 | 182 and 272 |
| 3 | D3 | 244 and 259 |
| 4 | D4 | 141 and 241 |
| 5 | D5 | 165 and 265 |
| 6 | D6 | 185 and 272 |
| 7 | D7 | 199 and 223 |
| 8 | D8 | 243 and 262 |
| 9 | D9 | 184 and 204 |
| 10 | D10 | 201 and 214 |
| 11 | D11 | 246 and 259 |
| 12 | D12 | 167 and 178 |

Even more preferred are disulfide bond types 1 to 5, especially disulfide bond types 1 to 4.

It is noted that:

Position 182+/−3 is an abbreviation for position 179, 180, 181, 182, 183, 184 or 185, preferably 182.

Position 269+/−3 is an abbreviation for position 266, 267, 268, 269, 270, 271 or 272, preferably 269.

Position 272+/−3 is an abbreviation for position 269, 270, 271, 272, 273, 274 or 275, preferably 272.

Position 244+/−3 is an abbreviation for position 241243, 242, 243, 244, 245, 246 or 247, preferably 244.

Position 259+/−3 is an abbreviation for position 256, 257, 258, 259, 260, 261 or 262, preferably 259.

Position 141+/−3 is an abbreviation for position 138, 139, 140, 141, 142, 143 or 144, preferably 141.

Position 241+/−3 is an abbreviation for position 238, 239, 240, 241, 242, 243 or 244, preferably 241.

Position 165+/−3 is an abbreviation for position 162, 163, 164, 165, 166, 167 or 168, preferably 165.

Position 265+/−3 is an abbreviation for position 262, 263, 264, 265, 266, 267 or 268, preferably 265.

Position 185+/−3 is an abbreviation for position 182, 183, 184, 185, 186, 187 or 188, preferably 185.

Position 199+/−3 is an abbreviation for position 196, 197, 198, 199, 200, 201 or 202, preferably 199.

Position 223+/−3 is an abbreviation for position 220, 221, 222, 223, 224, 225 or 226, preferably 223.

Position 243+/−3 is an abbreviation for position 240, 241, 242, 243, 244, 245 or 246, preferably 143.

Position 262+/−3 is an abbreviation for position 259, 260, 261, 262, 263, 264 or 265, preferably 262.

Position 184+/−3 is an abbreviation for position 181, 182, 183, 184, 185, 186 or 187, preferably 184.

Position 204+/−3 is an abbreviation for position 201, 202, 203, 204, 205, 206 or 207, preferably 204.

Position 201+/−3 is an abbreviation for position 198, 199, 200, 201, 202, 203 or 204, preferably 201.

Position 214+/−3 is an abbreviation for position 211, 212, 213, 214, 215, 216 or 217, preferably 214.

Position 246+/−3 is an abbreviation for position 243, 244, 245, 246, 247, 248 or 249, preferably 246.

Position 167+/−3 is an abbreviation for position 164, 165, 166, 167, 168, 169 or 170, preferably 167.

Position 178+/−2+/−3 is an abbreviation for position 175, 176, 177, 178, 179, 180 or 181, preferably 178.

In a preferred embodiment, the mutant fragment is derived from the amino acids from position 126, 130 or 131 to position 273 of the wild-type sequence of the OspA of *B. afzelii* strain K78, serotype 2 (SEQ ID NO: 19) and differs only by the introduction of at least one disulfide bond, particularly wherein the at least one disulfide bond is between positions 182 and 269 (disulfide bond type 1); positions 182 and 272 (disulfide bond type 2); positions 244 and 259 (disulfide bond type 3); positions 141 and 241 (disulfide bond type 4); positions 165 and 265 (disulfide bond type 5); positions 185 and 272 (disulfide bond type 6); positions 199 and 223 (disulfide bond type 7); positions 243 and 262 (disulfide bond type 8); positions 184 and 204 (disulfide bond type 9); positions 201 and 214 (disulfide bond type 10); positions 246 and 259 (disulfide bond type 11); and/or positions 167 and 178 (disulfide bond type 12), or the homologous fragments and positions of an OspA from a *Borrelia* sp. other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

In a still more preferred embodiment, the mutant fragment has an amino acid sequence selected from the group consisting of SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178 and an amino acid sequence that has 80%, more preferably 85%, more preferably 90%, even more preferably 95% sequence identity to at least one of sequences with SEQ ID NOs: 2 to 13, wherein the cysteines are not replaced. Further details on mutations and sequence identity are given above.

As detailed above, the polypeptide of the present invention may comprise signal sequences. It has been shown that lipidation confers adjuvant properties on OspA. Accordingly, lipidated forms of the polypeptide of the invention or polypeptides comprising a lipidation signal are preferred. In a preferred embodiment, the polypeptide of the current invention comprises a lipidation signal, preferably a lipidation signal of a *Borrelia* outer surface protein, OspA or OspB (SEQ ID NOs: 14 and 15, respectively) or more preferably an *E. coli* lpp lipidation signal sequence (SEQ ID NO: 16). The OspA fragment of the invention comprising a lipidation signal is lipidated during processing and the lipidation signal peptide is cleaved off. Therefore the signal peptide is no longer present in the mature lipidated protein.

Figure 3:
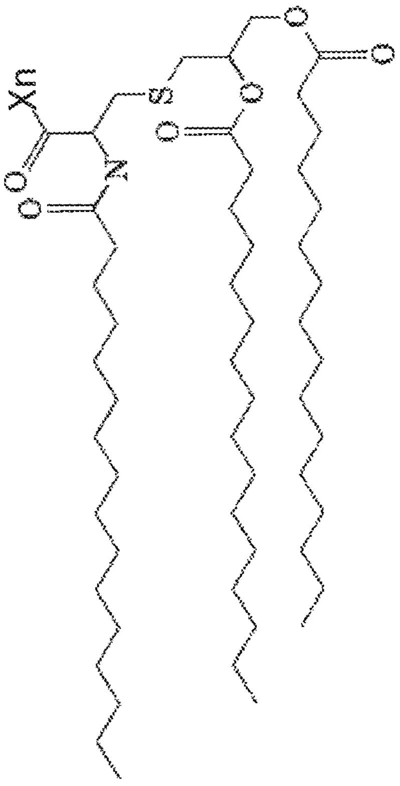

Lipidated proteins according to the current invention are labeled with "Lip" at the N-terminus to indicate the addition of 3 fatty acid groups and a glycerol to the polypeptide (see FIG. 3). Suitable lipidation signals as described above include MKKYLLGIGLILALIA (SEQ ID NO: 14), MRLLIGFALALALIG (SEQ ID NO: 15) and MKATKLVLGAVILGSTLLAG (SEQ ID NO: 16). Because lipid moieties and a glycerol are attached to the N-terminal cysteine residue which is present in the full-length wild-type OspA protein, OspA C-terminal fragments for lipidation may additionally comprise a peptide comprising a cysteine residue followed by additional amino acids, herein referred to as "Lipidation Peptide" or "LP" (see FIGS. 1 and 2). For example, sequences such as CSS (SEQ ID NO: 210) or CKQN (SEQ ID NO: 211) immediately C-terminal to the lipidation signal sequence provide an N-terminal cysteine residue for lipidation upon cleavage of the lipidation signal peptide. The lipidated cysteine-containing peptides are present in the final lipidated polypeptide of the invention.

It has been found that the OspA protein of *B. burgdorferi* s.s. comprises a sequence with the capacity to bind to a T-cell receptor that also has the capacity to bind to human leukocyte function-associated antigen (hLFA-1) (herein referred to also as "hLFA-1-like sequence"). The similarity of this OspA region to hLFA-1 may result in an immune response with cross-reactivity upon administration of *B. burgdorferi* s.s. OspA to a human subject and may induce autoimmune diseases, particularly autoimmune arthritis, in susceptible individuals. Accordingly, in a preferred embodiment, the polypeptide of the current invention does not comprise a sequence with binding capacity to the T-cell receptor that has a binding capacity to the human leukocyte function-associated antigen (hLFA-1), and particularly does not comprise the amino acid sequence GYVLEGTLTAE (SEQ ID NO: 17). To this end, the hLFA-1-like sequence, particularly the amino acid sequence GYVLEGTLTAE (SEQ ID NO: 17), may be replaced with a homologous sequence from an OspA protein of another *Borrelia* sp., particularly with NFTLEGKVAND (SEQ ID NO: 18).

In a preferred embodiment, the polypeptide of the current invention comprising at least one disulfide bond essentially establishes the same protective capacity with said polypeptide against a *Borrelia* infection relative to at least one of the wild-type full-length OspA proteins derived from at least one *Borrelia* strain, particularly *B. afzelii* K78, OspA serotype 2 (SEQ ID NO: 19); *B. burgdorferi* s.s., particularly strain B31, serotype 1 (SEQ ID NO: 20); *B. garinii*, particularly strain PBr, serotype 3 (SEQ ID NO: 21); *B. bavariensis*, particularly strain PBi, serotype 4 (SEQ ID NO: 22); *B. garinii*, particularly strain PHei, serotype 5 (SEQ ID NO: 23); *B. garinii*, particularly strain DK29, serotype 6

(SEQ ID NO: 24) or *B. garinii*, particularly strain T25, serotype 7 (SEQ ID NO: 25).

In order to provide cross-protection against different *Borrelia* species or OspA serotypes, the development of a multivalent vaccine is desirable. Accordingly, in another preferred embodiment, the polypeptide of the first aspect comprises at least two mutant fragments from two different *Borrelia* serotypes as defined above. In a preferred embodiment, the polypeptide of the first aspect comprises at least two mutant OspA fragments which are selected from the group consisting of fragment with disulfide bond type 1 and fragment with disulfide bond type 2;
fragment with disulfide bond type 1 and fragment with disulfide bond type 3;
fragment with disulfide bond type 1 and fragment with disulfide bond type 4;
fragment with disulfide bond type 1 and fragment with disulfide bond type 5;
fragment with disulfide bond type 1 and fragment with disulfide bond type 6;
fragment with disulfide bond type 1 and fragment with disulfide bond type 7;
fragment with disulfide bond type 1 and fragment with disulfide bond type 8;
fragment with disulfide bond type 1 and fragment with disulfide bond type 9;
fragment with disulfide bond type 1 and fragment with disulfide bond type 10;
fragment with disulfide bond type 1 and fragment with disulfide bond type 11;
fragment with disulfide bond type 1 and fragment with disulfide bond type 12;
fragment with disulfide bond type 2 and fragment with disulfide bond type 3;
fragment with disulfide bond type 2 and fragment with disulfide bond type 4;
fragment with disulfide bond type 2 and fragment with disulfide bond type 5;
fragment with disulfide bond type 2 and fragment with disulfide bond type 6;
fragment with disulfide bond type 2 and fragment with disulfide bond type 7;
fragment with disulfide bond type 2 and fragment with disulfide bond type 8;
fragment with disulfide bond type 2 and fragment with disulfide bond type 9;
fragment with disulfide bond type 2 and fragment with disulfide bond type 10;
fragment with disulfide bond type 2 and fragment with disulfide bond type 11;
fragment with disulfide bond type 2 and fragment with disulfide bond type 12;
fragment with disulfide bond type 3 and fragment with disulfide bond type 4;
fragment with disulfide bond type 3 and fragment with disulfide bond type 5;
fragment with disulfide bond type 3 and fragment with disulfide bond type 6;
fragment with disulfide bond type 3 and fragment with disulfide bond type 7;
fragment with disulfide bond type 3 and fragment with disulfide bond type 8;
fragment with disulfide bond type 3 and fragment with disulfide bond type 9;
fragment with disulfide bond type 3 and fragment with disulfide bond type 10;
fragment with disulfide bond type 3 and fragment with disulfide bond type 11;
fragment with disulfide bond type 3 and fragment with disulfide bond type 12;
fragment with disulfide bond type 4 and fragment with disulfide bond type 5;
fragment with disulfide bond type 4 and fragment with disulfide bond type 6;
fragment with disulfide bond type 4 and fragment with disulfide bond type 7;
fragment with disulfide bond type 4 and fragment with disulfide bond type 8;
fragment with disulfide bond type 4 and fragment with disulfide bond type 9;
fragment with disulfide bond type 4 and fragment with disulfide bond type 10;
fragment with disulfide bond type 4 and fragment with disulfide bond type 11;
fragment with disulfide bond type 4 and fragment with disulfide bond type 12;
fragment with disulfide bond type 5 and fragment with disulfide bond type 6;
fragment with disulfide bond type 5 and fragment with disulfide bond type 7;
fragment with disulfide bond type 5 and fragment with disulfide bond type 8;
fragment with disulfide bond type 5 and fragment with disulfide bond type 9;
fragment with disulfide bond type 5 and fragment with disulfide bond type 10;
fragment with disulfide bond type 5 and fragment with disulfide bond type 11;
fragment with disulfide bond type 5 and fragment with disulfide bond type 12;
fragment with disulfide bond type 6 and fragment with disulfide bond type 7;
fragment with disulfide bond type 6 and fragment with disulfide bond type 8;
fragment with disulfide bond type 6 and fragment with disulfide bond type 9;
fragment with disulfide bond type 6 and fragment with disulfide bond type 10;
fragment with disulfide bond type 6 and fragment with disulfide bond type 11;
fragment with disulfide bond type 6 and fragment with disulfide bond type 12;
fragment with disulfide bond type 7 and fragment with disulfide bond type 8;
fragment with disulfide bond type 7 and fragment with disulfide bond type 9;
fragment with disulfide bond type 7 and fragment with disulfide bond type 10;
fragment with disulfide bond type 7 and fragment with disulfide bond type 11;
fragment with disulfide bond type 7 and fragment with disulfide bond type 12;
fragment with disulfide bond type 8 and fragment with disulfide bond type 9;
fragment with disulfide bond type 8 and fragment with disulfide bond type 10;
fragment with disulfide bond type 8 and fragment with disulfide bond type 11;
fragment with disulfide bond type 8 and fragment with disulfide bond type 12;
fragment with disulfide bond type 9 and fragment with disulfide bond type 10;

fragment with disulfide bond type 9 and fragment with disulfide bond type 11;

fragment with disulfide bond type 9 and fragment with disulfide bond type 12;

fragment with disulfide bond type 10 and fragment with disulfide bond type 11;

fragment with disulfide bond type 10 and fragment with disulfide bond type 12;

fragment with disulfide bond type 11 and fragment with disulfide bond type 12; and particularly wherein the fragment with disulfide bond type 1 has the amino acid sequence of SEQ ID NO: 2 or an amino acid sequence that has at least 80%, more preferably 85%, more preferably 90%, even more preferably 95% sequence identity to SEQ ID NO: 2, wherein the cysteines are not replaced;

the fragment with disulfide bond type 2 has the amino acid sequence of SEQ ID NO: 3 or an amino acid sequence that has at least 80%, more preferably 85%, more preferably 90%, even more preferably 95% sequence identity to SEQ ID NO: 3, wherein the cysteines are not replaced;

the fragment with disulfide bond type 3 has the amino acid sequence of SEQ ID NO: 4 or an amino acid sequence that has at least 80%, more preferably 85%, more preferably 90%, even more preferably 95% sequence identity to SEQ ID NO: 4, wherein the cysteines are not replaced;

the fragment with disulfide bond type 4 has the amino acid sequence of SEQ ID NO: 5 or an amino acid sequence that has at least 80%, more preferably 85%, more preferably 90%, even more preferably 95% sequence identity to SEQ ID NO: 5, wherein the cysteines are not replaced;

the fragment with disulfide bond type 5 has the amino acid sequence of SEQ ID NO: 6 or an amino acid sequence that has at least 80%, more preferably 85%, more preferably 90%, even more preferably 95% sequence identity to SEQ ID NO: 6, wherein the cysteines are not replaced;

the fragment with disulfide bond type 6 has the amino acid sequence of SEQ ID NO: 7 or an amino acid sequence that has at least 80%, more preferably 85%, more preferably 90%, even more preferably 95% sequence identity to SEQ ID NO: 7, wherein the cysteines are not replaced;

the fragment with disulfide bond type 7 has the amino acid sequence of SEQ ID NO: 8 or an amino acid sequence that has at least 80%, more preferably 85%, more preferably 90%, even more preferably 95% sequence identity to SEQ ID NO: 8, wherein the cysteines are not replaced;

the fragment with disulfide bond type 8 has the amino acid sequence of SEQ ID NO: 9 or an amino acid sequence that has at least 80%, more preferably 85%, more preferably 90%, even more preferably 95% sequence identity to SEQ ID NO: 9, wherein the cysteines are not replaced;

the fragment with disulfide bond type 9 has the amino acid sequence of SEQ ID NO: 10 or an amino acid sequence that has at least 80%, more preferably 85%, more preferably 90%, even more preferably 95% sequence identity to SEQ ID NO: 10, wherein the cysteines are not replaced;

the fragment with disulfide bond type 10 has the amino acid sequence of SEQ ID NO: 11 or an amino acid sequence that has at least 80%, more preferably 85%, more preferably 90%, even more preferably 95% sequence identity to SEQ ID NO: 11, wherein the cysteines are not replaced;

the fragment with disulfide bond type 11 has the amino acid sequence of SEQ ID NO: 12 or an amino acid sequence that has at least 80%, more preferably 85%, more preferably 90%, even more preferably 95% sequence identity to SEQ ID NO: 12, wherein the cysteines are not replaced; and/or the fragment with disulfide bond type 12 has the amino acid sequence of SEQ ID NO: 13 or an amino acid sequence that has at least 80%, more preferably 85%, more preferably 90%, even more preferably 95% sequence identity to SEQ ID NO: 13, wherein the cysteines are not replaced.

Please note that further details on mutations and sequence identity are given above.

TABLE A-5

Nomenclature and SEQ ID NOs. of mutant OspA fragment heterodimers, non-lipidated and lipidated, described in the current invention.

| Mutant OspA fragment heterodimer* | SEQ ID NO: | Lipidated mutant OspA fragment heterodimer* | SEQ ID NO: |
|---|---|---|---|
| S1D4-S2D4 | 43 | Lip-S1D4-S2D4 | 185 |
| S1D1-S2D1 | 47 | Lip-S1D1-S2D1 | 186 |
| S3D4-S4D4 | 51 | Lip-S3D4-S4D4 | 187 |
| S3D1-S4D1 | 55 | Lip-S3D1-S4D1 | 188 |
| S5D4-S6D4 | 59 | Lip-S5D4-S6D4 | 189 |
| S5D1-S6D1 | 63 | Lip-S5D1-S6D1 | 190 |
| S2D4-S1D4 | 67 | Lip-S2D4-S1D4 | 191 |
| S2D1-S1D1 | 71 | Lip-S2D1-S1D1 | 192 |
| S4D4-S3D4 | 75 | Lip-S4D4-S3D4 | 193 |
| S4D1-S3D1 | 79 | Lip-S4D1-S3D1 | 194 |
| S6D4-S5D4 | 83 | Lip-S6D4-S5D4 | 195 |
| S6D1-S5D1 | 87 | Lip-S6D1-S5D1 | 196 |
| S1D4-S2D1 | 91 | Lip-S1D4-S2D1 | 197 |
| S1D1-S2D4 | 95 | Lip-S1D1-S2D4 | 198 |
| S3D4-S4D1 | 99 | Lip-S3D4-S4D1 | 199 |
| S3D1-S4D4 | 103 | Lip-S3D1-S4D4 | 200 |
| S5D4-S6D1 | 107 | Lip-S5D4-S6D1 | 201 |
| S5D1-S6D4 | 111 | Lip-S5D1-S6D4 | 202 |
| S2D4-S1D1 | 115 | Lip-S2D4-S1D1 | 203 |
| S2D1-S1D4 | 119 | Lip-S2D1-S1D4 | 204 |
| S4D4-S3D1 | 123 | Lip-S4D4-S3D1 | 205 |
| S4D1-S3D4 | 127 | Lip-S4D1-S3D4 | 206 |
| S6D4-S5D1 | 131 | Lip-S6D4-S5D1 | 207 |
| S6D1-S5D4 | 135 | Lip-S6D1-S5D4 | 208 |

*S = Serotype (1-6) (see Table A-2);
D = Disulfide Bond Type (see Table A-4);
Lip = lipidation: the N-terminal addition of glycerol and fatty acid residues.

In another preferred embodiment, the polypeptide according to the first aspect comprises at least two or three mutant fragments which are connected via one or more linkers. A linker is a rather short amino acid sequence employed to connect two fragments. It should be designed in order to avoid any negative impact on the fragments, their interaction in subjects to be treated or vaccinated or upon their protective capacity. Preferred are short linkers of at most 21 amino acids, particularly at most 15 amino acids, especially at most 12 or 8 amino acids. More preferably, the one or more linkers is/are composed of small amino acids in order to reduce or minimize interactions with the fragments, such as glycine, serine and alanine. Examples or preferred linkers include linkers comprising or consisting of polyG, such as $(G)_8$ (SEQ ID NO: 36), $(G)_{12}$ (SEQ ID NO: 37), GAGA (SEQ ID NO: 38), $(GAGA)_2$ (SEQ ID NO: 39), $(GAGA)_3$ (SEQ ID NO: 40), $(GGGS)_2$ (SEQ ID NO: 41), or $(GGGS)_3$ (SEQ ID NO: 42). A more preferred linker is the "LN1 peptide linker", a fusion of two separate loop regions of the N-terminal half of OspA from *B. burgdorferi* s.s., strain B31 (aa 65-74 and aa 42-53, with an amino acid exchange at position 53 of D53S) which has the following sequence: GTSDKNNGSGSKEKNKDGKYS (SEQ ID NO: 184).

In another preferred embodiment, the polypeptide according to the first aspect comprises a polypeptide with a total size of at most 500 amino acids, comprising two or three different mutant fragments as defined in preferred embodiments of the first aspect; or a polypeptide which consists of essentially two or three different mutant fragments, one or two linkers and, optionally, an N-terminal cysteine; and/or a polypeptide which consists of essentially two or three different mutant fragments, an N-terminal extension of the fragment consisting of at most 24, 23, 22, 21, 20, 19, 18, 17, 16, 15, 14, 13, 12 or 11 amino acids, preferably at most 10, 9, 8, 7 or 6 amino acids, still more preferably at most 5, 4, 3, 2 or 1 amino acid(s), wherein the N-terminal extension is located directly N-terminally from the fragment in the respective *Borrelia* OspA and, optionally, an N-terminal cysteine. The N-terminal cysteine may optionally be followed by a short peptide linker from 1-10 amino acids long, and preferably takes the form of an N-terminal CSS peptide (SEQ ID NO: 210) or CKQN peptide (SEQ ID NO: 211).

In a second aspect, the present invention relates to a nucleic acid encoding for the polypeptide according to the first aspect.

Nucleic acid molecule as used herein generally refers to any ribonucleic acid molecule or deoxyribonucleic acid molecule, which may be unmodified RNA or DNA or modified RNA or DNA. Thus, for instance, nucleic acid molecule as used herein refers to at least single- and double-stranded DNA, hybrid molecules comprising DNA and RNA that may be single-stranded or, more typically, double-stranded, or a mixture of single- and double-stranded regions. As used herein, the term nucleic acid molecule includes DNA or RNA molecules as described above that contain one or more modified bases. Thus, DNA or RNA molecules with backbones modified for stability or for other reasons are "nucleic acid molecule" as that term is intended herein. Moreover, DNA or RNA species comprising unusual bases, such as inosine, or modified bases, such as tritylated bases, to name just two examples, are also nucleic acid molecules as defined herein. It will be appreciated that a great variety of modifications have been made to DNA and RNA molecules that serve many useful purposes known to those of skill in the art. The term nucleic acid molecule as used herein embraces such chemically, enzymatically or metabolically modified forms of nucleic acid molecules, as well as the chemical forms of DNA and RNA characteristic of viruses and cells, including simple and complex cells, inter alia. The term nucleic acid molecule also encompasses short nucleic acid molecules often referred to as oligonucleotide(s). The terms "polynucleotide" and "nucleic acid" or "nucleic acid molecule" are used interchangeably herein.

The nucleic acids according to the present invention may be chemically synthesized. Alternatively, the nucleic acids can be isolated from *Borrelia* and modified by methods known to one skilled in the art. The same applies to the polypeptides according to the present invention.

Furthermore, the nucleic acid of the present invention can be functionally linked, using standard techniques such as cloning, to any desired sequence(s), whether a *Borrelia* regulatory sequence or a heterologous regulatory sequence, heterologous leader sequence, heterologous marker sequence or a heterologous coding sequence to create a fusion gene.

Nucleic acid molecules of the present invention may be in the form of RNA, such as mRNA or cRNA, or in the form of DNA, including, for instance, cDNA and genomic DNA obtained by cloning or produced by chemical synthesis techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The nucleic acid of the present invention may be comprised in a vector or in a cell. The vector may comprise the above-mentioned nucleic acid in such a manner that the vector is replicable and can express the protein encoded by the nucleotide sequence in a host cell.

A great variety of expression vectors can be used to express the polypeptides according to the present invention. Generally, any vector suitable to maintain, propagate or express nucleic acids to express a polypeptide in a host may be used for expression in this regard. In accordance with this aspect of the invention the vector may be, for example, a plasmid vector, a single- or double-stranded phage vector or a single- or double-stranded RNA or DNA viral vector. Starting plasmids disclosed herein are either commercially available, publicly available, or can be constructed from available plasmids by routine application of well-known, published procedures. Preferred among vectors, in certain respects, are those for expression of nucleic acid molecules and the polypeptides according to the present invention. Nucleic acid constructs in host cells can be used in a conventional manner to produce the gene product encoded by the recombinant sequence. Alternatively, the polypeptides according to the present invention can be synthetically produced by conventional peptide synthesizers.

In addition, the present invention relates to a host cell comprising this vector. Representative examples of appropriate host cells include bacteria, such as streptococci, staphylococci, *E. coli, Streptomyces* and *Bacillus subtilis*; fungi, such as yeast and *Aspergillus*; insect cells such as *Drosophila* S2 and *Spodoptera* Sf9 cells; mammalian cells such as CHO, COS, HeLa, C127, 3T3, BHK, 293 or Bowes melanoma cells; and plant cells. Cell-free translation systems can also be employed to produce such proteins using RNA derived from the DNA construct of the present invention.

In order to express the desired amino acid sequence practically by introducing the vector according to the present invention into a host cell, the vector may contain, in addition to the nucleic acid sequence according to the present invention, other sequences for controlling the expression (e.g., promoter sequences, terminator sequences and enhancer sequences) and gene markers for selecting microorganisms, insect cells, animal culture cells, or the like (e.g., neomycin resistance genes and kanamycin resistance genes). Furthermore, the vector may contain the nucleic acid sequence according to the present invention in a repeated form (e.g., in tandem). The vector may be constructed based on procedures and manners which are conventionally used in the field of genetic engineering.

The host cells may be cultured in an appropriate medium, and the protein according to the present invention may be obtained from the culture product. The protein according to the present invention may be recovered from the culture medium and purified in the conventional manner.

In a third aspect the present invention relates to a pharmaceutical composition comprising the polypeptide according to the first aspect and/or the nucleic acid according to the second aspect and, optionally, a pharmaceutically acceptable carrier or excipient. Preferably, the pharmaceutical composition is used as a medicament, particularly as a vaccine or for preventing or treating an infection caused by *Borrelia* species, more preferably pathogenic *Borrelia* species as disclosed herein more preferably comprising *B. burgdorferi* s.s., *B. afzelii, B. bavariensis* and *B. garinii*, and/or other pathogens against which the antigens have been included in the vaccine.

The pharmaceutical composition may contain any pharmaceutically acceptable carrier or excipient, such as buffer substances, stabilisers or further active ingredients, especially ingredients known in connection with pharmaceutical compositions and/or vaccine production.

The invention also includes immunogenic compositions. In some aspects, an immunogenic composition of the invention comprises any of the compositions discussed herein and a pharmaceutically acceptable carrier. In various aspects, the immunogenic composition has the property of inducing production of an antibody that specifically binds an outer surface protein A (OspA) protein. In certain aspects, the immunogenic composition has the property of inducing production of an antibody that specifically binds *Borrelia*. In particular aspects, the immunogenic composition has the property of inducing production of an antibody that neutralizes *Borrelia*. In some aspects, the antibody is produced by an animal. In further aspects, the animal is a mammal. In even further aspects, the mammal is human.

The invention further includes vaccine compositions. In some aspects, a vaccine composition of the invention comprises any immunogenic composition discussed herein and a pharmaceutically acceptable carrier. In various aspects, the invention includes a combination vaccine. In certain aspects, a combination vaccine of the invention comprises any vaccine composition discussed herein in combination with at least a second vaccine composition. In some aspects, the second vaccine composition protects against a tick-borne disease. In various aspects, the tick-borne disease is Rocky Mountain Spotted Fever, Babesiosis, Relapsing Fever, Colorado tick fever, Human monocytic ehrlichiosis (HME), Human granulocytic ehrlichiosis (HGE), Southern Tick-Associated Rash Illness (STARI), Tularemia, Tick paralysis, Powassan encephalitis, Q fever, Crimean-Congo hemorrhagic fever, Cytauxzoonosis, boutonneuse fever, or tick-borne encephalitis. In other aspects, the second vaccine composition is a vaccine selected from the group consisting of a tick-borne encephalitis vaccine, a Japanese encephalitis vaccine, and a Rocky Mountain Spotted Fever vaccine. In various aspects, the second vaccine composition has a seasonal immunization schedule compatible with immunization against *Borrelia* infection or Lyme disease.

The invention also includes methods for inducing an immunological response in a subject. In various aspects, such methods comprise the step of administering any of the immunogenic compositions or vaccine compositions discussed herein to the subject in an amount effective to induce an immunological response. In certain aspects, the immunological response comprises production of an anti-OspA antibody.

The invention includes methods for preventing or treating a *Borrelia* infection or Lyme disease in a subject. In various aspects, such methods comprise the step of administering any of the vaccine compositions discussed herein or any of the combination vaccines discussed herein to the subject in an amount effective to prevent or treat the *Borrelia* infection or Lyme disease.

The invention includes uses of compositions of the invention for the preparation of medicaments. Other related aspects are also provided in the instant invention.

A preferable carrier or excipient for the polypeptides according to the present invention in their diverse embodiments, or a nucleic acid molecule according to the present invention is an immunostimulatory compound such as an adjuvant for further stimulating the immune response to the polypeptide according to the present invention or a coding nucleic acid molecule thereof.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g., oxyhydroxides), phosphates (e.g., hydroxyphosphates, orthophosphates), sulphates, etc., or mixtures of different mineral compounds, with the compounds taking any suitable form (e.g., gel, crystalline, amorphous, etc.), and with adsorption being preferred. The mineral containing compositions may also be formulated as a particle of metal salt.

A useful aluminium phosphate adjuvant is amorphous aluminium hydroxyphosphate with $PO_4$/Al molar ratio between 0.84 and 0.92. Another useful aluminium-based adjuvant is AS04, a combination of aluminium hydroxide+monophosphoryl lipid A (MPL).

B. Oil Emulsions

Oil emulsion compositions suitable for use as adjuvants in the invention include squalene-in-water emulsions, such as MF59 (5% Squalene, 0.5% Tween 80, and 0.5% Span 85, formulated into submicron particles using a microfluidizer), AS03 (squalene, DL-α-tocopherol and Tween 80) and AF03 (squalene, Montane® 80 and Eumulgon® B1 PH). Complete Freund's adjuvant (CFA) and incomplete Freund's adjuvant (WA) may also be used.

Useful oil-in-water emulsions typically include at least one oil and at least one surfactant, with the oil(s) and surfactant(s) being biodegradable (metabolizable) and biocompatible. The oil droplets in the emulsion are generally less than 1 μm in diameter, with these small sizes being achieved with a microfluidizer to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWF AX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g., Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferably, substantially all (e.g. at least 90% by number) of the oil droplets have a diameter of less than 1 μm, e.g. <750 nm, <500 nm, <400 nm, <300 nm, <250 nm, <220 nm, <200 nm, or smaller. One specific useful submicron emulsion consists of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. The MF59 emulsion advantageously includes citrate ions e.g. 10 mM sodium citrate buffer.

C. Saponin Formulations

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree has been widely studied as adjuvant. Saponin can also be commercially obtained from *Smilax ornata* (sarsaprilla), *Gypsophilla paniculata* (brideal veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS 17, QS 18, QS21, QH-A, QH-B and QH-C. Preferably, the saponin is QS21. Saponin formulations may also comprise a sterol, such as cholesterol.

Combinations of saponins and cholesterols can be used to form unique particles called immunostimulating complexes (ISCOMs). ISCOMs typically also include a phospholipid such as phosphatidylethanolamine or phosphatidylcholine. Any known saponin can be used in ISCOMs. Preferably, the ISCOM includes one or more of QS7, QS 17, QS 18, QS21, QH-A, QH-B and QH-C. Optionally, the ISCOMS may be devoid of additional detergent.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retroviruses, Norwalk virus, Human Papilloma virus, HIV, RNA-phages, Qβ-phage (such as coat proteins), GA-phage, fr-phage, AP205 phage, and Ty (such as retrotransposon Ty protein pi).

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. Such "small particles" of 3dMPL are small enough to be sterile filtered through a 0.22 μm membrane. Other non-toxic LPS derivatives include monophosphoryl lipid A mimics, such as aminoalkyl glucosaminide phosphate derivatives e.g. RC-529 and the synthetic phospholipid dimer, E6020.

Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. The CpG sequence may be directed to TLR9, such as the motif GTCGTT or TTCGTT. The CpG sequence may be specific for inducing a Th1 immune response, such as a CpG-A ODN, or it may be more specific for inducing a B cell response, such a CpG-B ODN. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". A particularly useful adjuvant based around immunostimulatory oligonucleotides is known as IC31 ®. Thus an adjuvant used with the invention may comprise a mixture of (i) an oligonucleotide {e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising the 26-mer sequence 5'-$(dIdC)_{13}$-3' (SEQ ID NO: 32). The polycationic polymer may be a peptide comprising the 11-mer amino acid sequence KLKLLLLLKLK (SEQ ID NO: 33).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide, which has the amino acid sequence $NH_2$—RLAGLLRKGGEKIGEKLKKIGQKIKNFFQKLVPQPE-COOH (SEQ ID NO: 31). Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen. These cathelin molecules surprisingly have turned out to be also effective as an adjuvant for an antigen without the addition of further adjuvants. It is therefore possible to use such cathelin molecules as efficient adjuvants in vaccine formulations with or without further immune activating substances.

Bacterial ADP-ribosylating toxins and detoxified derivatives thereof may be used as adjuvants in the invention. Preferably, the protein is derived from *E. coli* (*E. coli* heat labile enterotoxin "LT"), *Vibrio cholerae* (Cholera toxin "CT"), or *Bordetella pertussis* (Pertussis toxin "PT"). The use of detoxified ADP-ribosylating toxins as mucosal adjuvants and as parenteral adjuvants is known. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, LT-G192 or dmLT. A useful CT mutant is CT-E29H.

F. Human Immunomodulators

Human immunomodulators suitable for use as adjuvants in the invention include cytokines such as interleukins (e.g. IL-1, IL-2, IL-4, IL-5, IL-6, IL-7, IL-12, etc.), interferons (e.g. interferon-γ), macrophage colony stimulating factor and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention.

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, a poly(lactide-co-glycolide) etc.), wherein poly (lactide-co-glycolide) are preferred, optionally treated to have a negatively-charged surface (e.g. with SDS) or a positively-charged surface (e.g., with a cationic detergent, such as CTAB).

I. Liposomes

Examples of liposome formulations suitable for use as adjuvants are known.

J. Polyoxyethylene Ether and Polyoxyethylene Ester Formulations

Adjuvants suitable for use in the invention include polyoxyethylene ethers and polyoxyethylene esters. Such formulations further include polyoxyethylene sorbitan ester surfactants in combination with an octoxynol as well as polyoxyethylene alkyl ethers or ester surfactants in combination with at least one additional non-ionic surfactant such as an octoxynol. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-5n-glycero-3-hydroxyphosphoryloxy)-ethylamine MTP-PE).

L. Imidazoquinolone Compounds.

Examples of imidazoquinolone compounds suitable for use as adjuvants in the invention include Imiquimod and its homologues (e.g., "Resiquimod 3M").

The invention may also comprise combinations of aspects of one or more of the adjuvants identified above.

Preferably, the immunostimulatory compound in the pharmaceutical preparation according to the present invention is selected from the group of polycationic substances, especially polycationic peptides, immunostimulatory nucleic acids molecules, preferably immunostimulatory deoxynucleotides, oil-in-water or water-in-oil emulsions, MF59, alum, alum salts, Freund's complete adjuvant, Freund's incomplete adjuvant, neuroactive compounds, especially human growth hormone, or combinations thereof.

The use of an aluminium hydroxide and/or aluminium phosphate adjuvant is particularly preferred, and antigens are generally adsorbed to these salts.

Also, the pharmaceutical composition in accordance with the present invention is a pharmaceutical composition which comprises at least any of the following compounds or combinations thereof: the nucleic acid molecules according to the present invention, the polypeptides according to the present invention in their diverse embodiments, the vector according to the present invention, the cells according to the present invention, the antibody according to the present invention, the functional nucleic acids according to the present invention and the binding peptides such as the anticalines and high-affinity binding peptides and peptide aptamers, respectively, according to the present invention, any agonists and antagonists according to the present invention, preferably screened as described herein. In connection therewith, any of these compounds may be employed in combination with a non-sterile or sterile carrier or carriers for use with cells, tissues or organisms, such as a pharmaceutical carrier suitable for administration to a subject. Such carriers may include, but are not limited to, saline, buffered saline, dextrose, water, glycerol, ethanol and combinations thereof. The formulation should suit the mode of administration.

The pharmaceutical compositions of the present invention may be administered in any effective, convenient manner including, for instance, administration by topical, oral, anal, vaginal, intravenous, intraperitoneal, intramuscular, subcutaneous, intranasal, intratracheal or intradermal routes, among others.

In therapy or as a prophylactic, the active agent of the pharmaceutical composition of the present invention may be administered to an individual as an injectable composition, for example as a sterile aqueous dispersion, preferably isotonic.

Alternatively the composition, preferably the pharmaceutical composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

In a preferred embodiment the pharmaceutical composition is a vaccine composition. Preferably, such vaccine composition is conveniently in injectable form. Conventional adjuvants may be employed to enhance the immune response. A suitable unit dose for vaccination with a protein antigen is for adults between 0.02 μg and 3 μg antigen per kg body weight and for children between 0.2 μg and 10 μg antigen per kg body weight, and such dose is preferably administered 1 to 3 times at intervals of 2 to 24 weeks.

At the indicated dose range, no adverse toxicological effects are expected with the compounds of the invention, which would preclude their administration to suitable individuals.

The pharmaceutical composition can contain a range of different antigens. Examples of antigens are whole-killed or attenuated organisms, subfractions of these organisms, proteins, or, in their most simple form, peptides. Antigens can also be recognized by the immune system in the form of glycosylated proteins or peptides and may also be or contain polysaccharides or lipids. Short peptides can be used, since cytotoxic T-cells (CTL) recognize antigens in the form of short, usually 8-11 amino acids long, peptides in conjunction with major histocompatibility complex (MHC). B cells can recognize linear epitopes as short as 4 to 5 amino acids, as well as three-dimensional structures (conformational epitopes).

In a preferred embodiment, the pharmaceutical composition of the third aspect additionally comprises a hyperimmune serum-reactive antigen against a *Borrelia* protein or an active fragment or variant thereof, such as, e.g., the antigens, fragments and variants as described in WO 2008/031133.

According to the invention, the pharmaceutical composition according to the third aspect may be used as a medicament, particularly as a vaccine, particularly in connection with particularly a disease or diseased condition which is caused by, linked or associated with *Borrelia.*

*Borrelia* belongs to the family Spirochaetaceae, which is subdivided into the medically important genera *Treponema, Leptospira* and *Borrelia. B. burgdorferi* s.l. is a spiral-shaped, vigorously motile gram-negative bacterium, about 10-20 μm long and 0.2-0.5 μm wide, that grows under microaerophilic conditions. The spirochetal cell wall consists of a cytoplasmic membrane surrounded by peptidoglycan and several flagella and then by a loosely-associated outer membrane.

Lyme borreliosis generally occurs in stages characterized by different clinical manifestations, with remissions and exacerbations. Stage 1, early infection, consists of a localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis. Different clinical syndromes of Lyme borreliosis are also caused by infection with diverse *B. burgdorferi* s.l. species. *B. burgdorferi* s.s. more often causes joint manifestations (arthritis) and heart problems, *B. afzelii* causes mainly dermal symptoms (erythema migrans; EM and acrodermatitis chronica atrophicans; ACA), whereas *B. garinii* is implicated in most cases of neuroborreliosis.

Localized infection—The most common symptom of stage 1 of an infection is erythema migrans, which occurs in 70-80% of infected people. This skin lesion is often followed by flu-like symptoms, such as myalgia, arthralgia, headache and fever. These non-specific symptoms occur in 50% of patients with erythema migrans.

Disseminated infection—During stage 2, the bacteria move into the blood stream from the site of infection to distal tissues and organs. Neurological, cardiovascular and arthritic symptoms that occur in this stage include meningitis, cranial neuropathy and intermittent inflammatory arthritis.

Persistent infection—Stage 3 of the infection is chronic and occurs from months to years after the tick bite. The most common symptom in North America is rheumatoid arthritis, caused by an infection with *B. burgdorferi* s.s. Persistent infection of the central nervous system with *B. garinii* causes more severe neurological symptoms during stage 3, and a persistent infection of the skin with *B. afzelii* results in acrodermatitis chronica atrophicans.

The pharmaceutical composition of the present invention may be used as a medicament, particularly as a vaccine, particularly in connection with a disease or disease condition which is caused by, linked with or associated with *Borrelia*, more preferably any pathogenic *Borrelia* species and more preferably in a method for treating or preventing a *Borrelia* infection, particularly a *B. burgdorferi* s.s., *B. garinii, B. afzelii, B. andersonii, B. bavariensis, B. bissettii, B. valaisiana, B. lusitaniae, B. spielmanii, B. japonica, B. tanukii, B. turdi* or *B. sinica* infection, preferably a *B. burgdorferi* s.s., *B. afzelii* or *B. garinii* infection.

In connection therewith, it should be noted that the various *Borrelia* species, including *B. burgdorferi* s.l., comprise several species and strains including those disclosed herein. A disease related, caused or associated with the bacterial infection to be prevented and/or treated according to the present invention includes Lyme borreliosis (Lyme disease). Further aspects, symptoms, stages and subgroups of Lyme borreliosis as well as specific groups of patients suffering from such disease as also disclosed herein, including in the introductory part, are incorporated herein by reference. More specifically, Lyme borreliosis generally occurs in stages, with remission and exacerbations with different clinical manifestation at each stage. Early infection stage 1 consists of localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis.

In a fourth aspect, the present invention relates to a method of treating or preventing a *Borrelia* infection in a subject in need thereof, comprising the step of administering to the subject a therapeutically effective amount of a pharmaceutical composition according to the third aspect.

The term "subject" is used throughout the specification to describe an animal, preferably a mammal, more preferably a human, to whom a treatment or a method according to the present invention is provided. For treatment of those infections, conditions or disease states which are specific for a specific animal such as a human patient, the term patient refers to that specific animal. Preferably, the subject is a human; however, the medical use of the composition may also include animals such as poultry including chicken, turkey, duck or goose, livestock such as horse, cow or sheep, or companion animals such as dogs or cats.

The term "effective amount" is used throughout the specification to describe an amount of the present pharmaceutical composition which may be used to induce an intended result when used in the method of the present invention. In numerous aspects of the present invention, the term effective amount is used in conjunction with the treatment or prevention. In other aspects, the term effective amount simply refers to an amount of an agent which produces a result which is seen as being beneficial or useful, including in methods according to the present invention where the treatment or prevention of a *Borrelia* infection is sought.

The term effective amount with respect to the presently described compounds and compositions is used throughout the specification to describe that amount of the compound according to the present invention which is administered to a mammalian patient, especially including a human patient, suffering from a *Borrelia*-associated disease, to reduce or inhibit a *Borrelia* infection.

In a preferred embodiment, the method of immunizing a subject according to the fourth aspect comprises the step of administering to the subject a therapeutically effective amount of a pharmaceutical composition of the third aspect of the current invention.

The method comprises inducing an immunological response in an individual through gene therapy or otherwise, by administering a polypeptide or nucleic acid according to the present invention in vivo in order to stimulate an immunological response to produce antibodies or a cell-mediated T cell response, either cytokine-producing T cells or cytotoxic T cells, to protect said individual from disease, whether or not that disease is already established within the individual.

The products of the present invention, particularly the polypeptides and nucleic acids, are preferably provided in isolated form, and may be purified to homogeneity. The term "isolated" as used herein means separated "by the hand of man" from its natural state; i.e., if it occurs in nature, it has been changed or removed from its original environment, or both. For example, a naturally-occurring nucleic acid molecule or a polypeptide naturally present in a living organism in its natural state is not "isolated", but the same nucleic acid molecule or polypeptide separated from the coexisting materials of its natural state is "isolated", as the term is employed herein. As part of or following isolation, such nucleic acid molecules can be joined to other nucleic acid molecules, such as DNA molecules, for mutagenesis, to form fusion genes, and for propagation or expression in a host, for instance. The isolated nucleic acid molecules, alone or joined to other nucleic acid molecules such as vectors, can be introduced into host cells, in culture or in whole organisms. Introduced into host cells in culture or in whole organisms, such DNA molecules still would be isolated, as the term is used herein, because they would not be in their naturally-occurring form or environment. Similarly, the nucleic acid molecules and polypeptides may occur in a composition, such as medium formulations, solutions for introduction of nucleic acid molecules or polypeptides, for example, into cells, compositions or solutions for chemical or enzymatic reactions, for instance, which are not naturally occurring compositions, and, therein remain isolated nucleic acid molecules or polypeptides within the meaning of that term as it is employed herein.

The invention is not limited to the particular methodology, protocols and reagents described herein because they may vary. Furthermore, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The present invention is further illustrated by the following Figures, Tables, Examples and the Sequence listing, from which further features, embodiments and advantages may be taken. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

In connection with the present invention

FIGS. 1A-1C schematically shows the production of mutant OspA fragment heterodimers according to the current invention.

FIG. 2 schematically represents the polypeptide components of one possible pharmaceutical composition of the current invention comprising three different mutant OspA heterodimers.

FIG. 3 shows the chemical structure of $Pam_3Cys$, an example of a fatty acid substituted cysteine, such as would be found at the N-terminus of lipidated polypeptides of the current invention.

Table 1 shows the thermal stability of the folding of mutant serotype 2 OspA fragments with disulfide bond types from D1 to D5 (see Table A-4) compared to the wild-type serotype 2 OspA fragment without disulfide bonds (D0).

Table 2 shows the protection of mice from *B. afzelii* infection by the Tick Challenge Method following immunization with mutant serotype 2 OspA fragments with disulfide bond types D1 to D5, including control groups of mice immunized with PBS, full-length OspA or the wild-type serotype 2 OspA fragment.

Table 3 shows the protection of mice from *B. afzelii* infection by the Tick Challenge Method following immunization with lipidated mutant serotype 2 OspA fragments with disulfide bond types D2, D3 and D4, including control groups of mice immunized with PBS or full-length OspA protein.

Table 4 shows the protection of mice from *B. burgdorferi* s.s. delivered by needle challenge or from *B. afzelii* delivered by tick challenge by immunization with lipidated His-tagged mutant OspA serotype 1/serotype 2 fragment heterodimer (Lip-S1D1-S2D1-His). Control groups included mice immunized with lipidated His-tagged mutant OspA serotype 1 (Lip-M1B-His) or serotype 2 (Lip-M2B-His) fragment monomers individually or with adjuvant alone.

The figures and tables which may be referred to in the specification are described below in more detail.

FIGS. 1A-1C Production of a mutant OspA heterodimer of the invention comprising mutant OspA C-terminal fragments from two different serotypes of *Borrelia* sp. (FIG. 1A) Schematic representation of a nucleic acid encoding a lipidated mutant OspA heterodimer. The components, from 5' to 3' comprise the coding sequences for a lipidation signal sequence (Lip signal), a small cysteine-containing peptide for N-terminal lipidation (Lipidation peptide=LP), a mutant C-terminal fragment of OspA with two non-native cysteines, a short linker peptide, LN1, followed by a second mutant OspA C-terminal fragment with two non-native cysteines. (FIG. 1B) The intermediate mutant OspA heterodimer polypeptide comprises the nascent product directly following translation of the nucleic acid construct. From the N- to the C-terminus, this polypeptide consists of a lipidation signal sequence (Lip signal), a cysteine-containing peptide for lipidation (LP), a mutant OspA fragment with a non-native disulfide bond, a short linker peptide, LN1, followed by a second mutant OspA fragment with a non-native disulfide bond. (FIG. 1C) The final lipidated mutant OspA heterodimer polypeptide after post-translational modification. The heterodimer, from the N- to the C-terminus, consists of a short cysteine-containing peptide with the N-terminal cysteine lipidated (indicated by "Lip"), a mutant OspA fragment stabilized by a disulfide bond, a linker peptide, LN1, and a second mutant OspA fragment stabilized by a disulfide bond. The lipidation signal sequence is cleaved off during post-translational modification of the polypeptide as shown.

FIG. 2 An example of a preferred pharmaceutical composition according to the current invention. Three mutant OspA heterodimers, each comprising mutated OspA fragments from two different *Borrelia* serotypes are present in the composition, together providing OspA antigens from six different *Borrelia* serotypes. Such a pharmaceutical composition enables simultaneous immunization against six of the most prevalent serotypes of *Borrelia.*

FIG. 3 Diagram of the chemical structure of $Pam_3Cys$, an example of a fatty acid substitution of the N-terminal cysteine of full-length wild-type OspA protein as well as of lipidated mutant OspA fragment monomers and heterodimers of the invention. During post-translational modification of a full-length OspA protein or polypeptides of the invention, the N-terminal lipidation signal sequence is cleaved off and fatty acids, most commonly three palmitoyl moieties ("$Pam_3$"), are enzymatically covalently attached to the N-terminal cysteine residue (the S atom of which is indicated by an arrow). The remaining residues of the polypeptide chain, which are located C-terminally from the $Pam_3Cys$ residue, are represented by "Xn". (Modified from Bouchon, et al. (1997) Analytical Biochemistry 246: 52-61.)

TABLE 1

Thermal stability of non-lipidated, His-tagged *B. afzelii* K78 mutant serotype 2 OspA fragments with different placement of disulfide bonds. Mutant serotype 2 OspA fragments with different cysteine bond types (see Table A-4) were solubilized in 50 mM Tris-HCl, 150 mM NaCl (pH 8.0) and tested for thermal stability compared with the wild-type serotype 2 OspA fragment (S2D0). The presence of a disulfide bond resulted in an increased melting temperature compared to the wild-type serotype 2 OspA fragment.

| Serotype 2 OspA mutant fragment | SEQ ID NO: | Melting temperature (° C.) |
|---|---|---|
| S2D0-His* | 1 | 47.6 |
| S2D1-His | 2 | 70.4 |
| S2D2-His | 3 | 54.6 |
| S2D3-His | 4 | 58.6 |
| S2D4-His | 5 | 58.4 |
| S2D5-His | 6 | 53.8 |

*see Tables A-4 and A-5 for nomenclature.

TABLE 2

Protection of mice from *B. afzelii* infection by the tick challenge method by immunization with non-lipidated mutant serotype 2 OspA fragments. Five non-lipidated mutant serotype 2 OspA fragments were tested for protective capacity at two different doses (30 μg and 5 μg) and compared with the wild-type serotype 2 fragment. Groups of mice immunized with adjuvant alone or with non-lipidated full-length serotype 2 OspA served as negative and positive controls, respectively. All antigens were His-tagged and non-lipidated. The data presented combine the results of several experiments performed under identical conditions.

| | 3 × 30 μg (data from 11 experiments) (all groups include $Al(OH)_3$) | | | 3 × 5 μg (data from 4 experiments) (all groups include $Al(OH)_3$) | | |
|---|---|---|---|---|---|---|
| Immunogen | Infected mice | total mice | p-value | Infected mice | total mice | p-value |
| Adjuvant alone | 67 | 73 | n/a | 20 | 23 | n/a |
| Full-length OspA K78-His (SEQ ID NO: 209) | 15 | 87 | <0.001*** | 0 | 25 | <0.001*** |
| S2D0-His (SEQ ID NO: 1) | 20 | 27 | 0.045* | 5 | 16 | 0.001*** |
| S2D1-His (SEQ ID NO: 2) | 7 | 32 | <0.001*** | 1 | 25 | <0.001*** |
| S2D2-His (SEQ ID NO: 3) | 2 | 29 | <0.001*** | 3 | 26 | <0.001*** |
| S2D3-His (SEQ ID NO: 4) | 10 | 44 | <0.001*** | 0 | 21 | <0.001*** |
| S2D4-His (SEQ ID NO: 5) | 6 | 35 | <0.001*** | 3 | 27 | <0.001*** |
| S2D5-His (SEQ ID NO: 6) | 6 | 37 | <0.001*** | 2 | 11 | <0.001*** |

*significant (≤0.05),
**highly significant (≤0.01),
***extremely significant (≤0.001), Fisher's exact test, two-tailed.

TABLE 3

Protection of mice from *B. afzelii* infection by the Tick Challenge Method by immunization with decreasing doses of lipidated mutant serotype 2 OspA fragments.
Three lipidated mutant serotype 2 OspA fragments with different disulfide bond types were tested for protective capacity. Groups of mice immunized with adjuvant alone or with non-lipidated full-length serotype 2 OspA served as negative and positive controls, respectively. All antigens were His-tagged.

| | 3 × 3 μg (data from 3 experiments) (all groups included $Al(OH)_3$) | | | 3 × 1 μg (data from 5 experiments) (all groups included $Al(OH)_3$) | | | 3 × 0.3 μg (data from 4 experiments) (all groups included $Al(OH)_3$) | | |
|---|---|---|---|---|---|---|---|---|---|
| Immunogen | Infected mice | Total mice | p-value | Infected mice | Total mice | p-value | Infected mice | Total mice | p-value |
| Adjuvant alone | 22 | 24 | n/a | 33 | 37 | n/a | 28 | 30 | n/a |
| Full-length OspA K78-His (SEQ ID NO: 209) | 0 | 14 | <0.001*** | 0 | 21 | <0.001*** | n/a | n/a | n/a |
| Lip-S2D2-His (SEQ ID NO: 142) | 0 | 17 | <0.001*** | 0 | 15 | <0.001*** | 0 | 21 | <0.001*** |
| Lip-S2D3-His (SEQ ID NO: 143) | 1 | 15 | <0.001*** | 1 | 12 | <0.001*** | 5 | 19 | <0.001*** |
| Lip-52D4-His (SEQ ID NO: 144) | 0 | 8 | <0.001*** | 0 | 14 | <0.001*** | 0 | 19 | <0.001*** |

*significant (<0.05),
**highly significant (<0.01),
***extremely significant ≤0.001), Fisher's exact test, two-tailed.

TABLE 4

Protection of mice from *Borrelia* infection by both needle challenge (*B. burgdorferi* s.s.) and Tick Challenge Method (*B. afzelii*) by immunization with lipidated His-tagged mutant serotype1/serotype 2 OspA fragment heterodimers. The lipidated His-tagged mutant serotype 1/serotype 2 OspA fragment heterodimer protein (Lip-S1D1-S2D1-His) was tested for protective capacity. Groups of mice immunized three times at two week intervals with adjuvant alone or with lipidated His-tagged mutant serotype 1 (Lip-S1D1-His) or serotype 2 (Lip-S2D1-His) OspA fragment monomers individually served as negative and positive controls, respectively. Immunized mice were challenged two weeks after the last immunization with either *B. burgdorferi* s.s. via needle challenge (Experiments 1-3) or with *B. afzelii* via infected ticks (Experiments 4-6). All antigens were lipidated and His-tagged.

| Immunogen | Dose | Needle challenge (serotype 1: *B. burgdorferi* s.s.) | Infected/ Total Exp. 1 | Infected/ Total Exp. 2 | Infected/ Total Exp. 3 |
|---|---|---|---|---|---|
| Lip-S1D1-S2D1-His | 3 × 5.0 μg | N40 (ST1) | 0/10*** | 0/9*** | 4/10** |
| Lip-S1D1-His | 3 × 2.5 μg | N40 (ST1) | 2/10*** | 1/10* | 4/10** |
| Lip-S2D1-His | 3 × 2.5 μg | N40 (ST1) | 1/10*** | 3/10 | 5/10* |
| Adjuvant alone | — | N40 (ST1) | 10/10 | 8/10 | 10/10 |
| Immunogen | Dose | Tick challenge (Serotype 2: *B. afzelii*) | Exp. 4 | Exp. 5 | Exp. 6 |
| Lip-S1D1-S2D1-His | 3 × 2.0 μg | Tick (ST2) | 0/10*** | 0/9*** | 0/6*** |
| Lip-S1D1-His | 3 × 1.0 μg | Tick (ST2) | 2/10*** | 2/8** | 2/4 |
| Lip-S2D1-His | 3 × 1.0 μg | Tick (ST2) | 1/8*** | 0/4** | 0/4** |
| Adjuvant alone | — | Tick (ST2) | 9/9 | 8/8 | 7/7 |

P-value; Fisher's exact test, two tailed.
*significant (<0.05),
**highly significant (<0.01),
***extremely significant (<0.001)

EXAMPLES

Example 1. Assessment of Thermal Stability of Mutant Serotype 2 OspA Fragments Experimental Procedures Thermal Stability The melting temperatures ($T_m$) of non-lipidated mutant serotype 2 OspA fragment monomers were determined by the fluorescence-based thermal shift assay described by Pantoliano, et al. (J. Biomol Screen 6:429-440 (2001)). The fluorescent dye SYPRO® Orange protein gel stain (supplied as a 5000× concentrate in DMSO by Sigma, U.S.A) was used to monitor protein unfolding. In each well, 7.5 μl of SYPRO® Orange (diluted 1:1000 from the stock solution) and 17.5 μl of a solution of protein (1 μg or 2 μg) in buffer were combined. The protein samples were heated from 25° C. to 95° C. at a rate of 0.2° C./10 sec in the CFX96 Real-time Detection System (Bio-Rad, USA) and fluorescent changes were monitored. Fluorescence intensity was measured with excitation and emission wavelengths of 490 and 575 nm, respectively. The Tm was determined using the Bio-Rad CFX Manager 2.0 program. The Tm values of non-lipidated His-tagged serotype 2 OspA mutant fragments were measured in four different buffer systems: 50 mM Tris-HCl, 150 mM NaCl (pH 9.0); 50 mM Tris-HCl, 150 mM NaCl (pH 8.0); PBS (pH 7.4); and 25 mM HEPES, 150 mM NaCl (pH 6.5), using the non-lipidated serotype 2 OspA wild-type fragment (S2D0) as a control.

Results

In all cases, mutant serotype 2 OspA fragments with an introduced cysteine bond had higher melting temperatures than the wild-type serotype 2 OspA fragment (S2D0) (see Table 1). The melting temperatures were tested in four different buffer systems with similar results (data for proteins dissolved in 50 mM Tris-HCl, 150 mM NaCl (pH 8.0) is shown in Table 1), indicating that the stability of the proteins is similar over a wide pH range. This result lends credence to the hypothesis that the introduced disulfide bond stabilizes the OspA fragment.

Example 2. Protection of Mice from Infection with *B. afzelii* in the Tick Challenge Method by Immunization with Non-Lipidated His-Tagged Mutant Serotype 2 OspA Fragment Monomers Experimental Procedures Cloning and Expression of Recombinant Proteins The wild-type serotype 2 OspA fragment as well as the serotype 2 mutant OspA fragments with cysteine bond types 1-5 (SEQ ID NOs: 1, 2, 3, 4, 5 and 6, respectively), were codon-optimized for *E. coli* expression by GenScript, USA. The non-lipidated serotype 2 mutant OspA fragments were C-terminally histidine-tagged for purification purposes. Gene fragments were cloned into the pET28b(+) vector (Novagen, USA), a vector containing a Kanamycin resistance cassette as well as a T7 promoter. The monomers were expressed in BL21 Star™ (DE3) cells (Invitrogen, USA) at 37° C. by the addition of IPTG. Cells were collected after 4 h by centrifugation and the pellet was stored at −70° C. for up to 12 months prior to further processing.

Purification of Non-Lipidated His-Tagged Wild-Type and Mutant OspA Fragment Monomer Proteins Cells were disrupted mechanically by high-pressure homogenization and the soluble fraction containing the His-tagged OspA fragments was applied to a Ni-sepharose column (Ni Sepharose™ 6 Fast Flow; GE Healthcare, United Kingdom) and the His-tagged OspA fragments were eluted on an Imidazole gradient (0-250 mM). Pooled fractions were further purified over a gel filtration column (Superdex 200, GE Healthcare) followed by a buffer exchange column (Sephadex G-25, GE Healthcare). His-tagged OspA fragment peaks were pooled on the basis of the analytical size exclusion column and reversed phase chromatography. After sterile filtration, the purified proteins were stored at −20° C. until formulation.

Immunization of Mice

Female C3H/HeN (H-$2^k$) mice were used for all studies (Harlan, Italy). Prior to each challenge, groups of five 8-week-old mice were bled via the tail vein and pre-immune sera were prepared and pooled. Five non-lipidated mutant serotype 2 OspA fragment proteins (S2D1-5, SEQ ID NOs: 2, 3, 4, 5 and 6, respectively), were tested in fifteen separate experiments. Three subcutaneous (s.c.) immunizations of 100 μL, were administered at two week intervals. Doses used were 30 and 5 μg of the respective protein, tested in 11 and 4 experiments respectively. All formulations included aluminium hydroxide ($Al(OH)_3$) at a final concentration of 0.15%. One week after the third immunization, blood was collected and hyper-immune sera were prepared. In each experiment, one group injected with PBS formulated with $Al(OH)_3$ was included as a negative control and one group of mice was immunized with S2D0, the wild-type C-terminal OspA fragment from *B. afzelii* strain K78 (SEQ ID NO: 1). Another group immunized with a non-lipidated full-length wild-type OspA protein from *B. afzelii*, strain K78 (SEQ ID NO: 209), also formulated with 0.15% $Al(OH)_3$, was included as positive control in each animal study. All animal experiments were conducted in accordance with Austrian law (BGB1 Nr. 501/1989) and approved by "Magistratsabteilung 58".

Tick Challenge of Immunized Mice and Collection of Sera and Tissues (Herein Referred to Also as "Tick Challenge Method")

Tick challenge of immunized mice was done two weeks after the last immunization. In order to challenge the immunized mice with *B. afzelii*, the hair of the back of each mouse was removed with Veet® Cream (Reckitt Benckiser, United Kingdom) and a small ventilated container was glued to the skin with super glue (Pattex, Germany). Thereafter, one or two *I. ricinus* nymphs infected with *B. afzelii*, strain IS1, were applied per mouse, allowed to attach and feed to depletion. The feeding status was monitored for each individual tick and only mice where at least one fully-fed tick was collected were included in the final readout. No distinction was made between mice where one or two fully-fed ticks were collected.

Six weeks after the tick application, blood was collected by orbital bleeding and final sera were prepared and used for VlsE ELISA analysis to determine infection status. The mice were then sacrificed by cervical dislocation and one ear from each mouse was collected, DNA extracted and subjected to nested PCR analysis to identify *Borrelia* in tissue.

Infection Readout

Only mice where the applied tick(s) fed to completion and could be collected were included in the final readout of the experiment. The mice were sacrificed 6 weeks after tick application and organs as well as final sera were collected. The final infection readout was based on two different analyses (nested PCR targeting the 16S-23S intergenic spacer and VlsE (IR6) ELISA as described in detail below).

Nested PCR Targeting the 16S-23S Intergenic Spacer

One ear from each mouse was subjected to DNA extraction and purification using the DNeasy Blood and Tissue Kit (Qiagen, Germany) according to the manufacturer's instructions, with the following modification. Each ear was digested over night at 60° C. in recombinant Proteinase K, PCR grade (Roche, 14-22 mg/mL). The DNA was eluted in 50 μL deionized sterile water and stored at −20° C. until further analysis. As a negative control, one empty purification column was included in each DNA extraction and purification and the eluate subjected to nested PCR. All DNA extracts were screened for the presence of *Borrelia* DNA by a nested PCR procedure, comprising 40 cycles of 94° C. for 30 s, 56° C. for 30 s and 72° C. for 60 s using the primers; Forward 5'-GTATGTTTAGTGAGGGGGGTG-3' (SEQ ID NO: 26) and Reverse 5'-GGATCATAGCTCAGGTGGTTAG-3' (SEQ ID NO: 27). From the reaction volume of 10 μL, 1 μL was used as template for the nested PCR reaction. The nested PCR step comprised 25 cycles of 94° C. for 30 s, 60° C. for 30 s and 72° C. for 60 s using the primers; Forward nested 5'-AGGGGGGTGAAGTCGTAACAAG-3' (SEQ ID NO: 28) and Reversed nested 5'-GTCTGATAAACCTGAGGTCGGA-3' (SEQ ID NO: 29). Of the final reaction volume, 5 μL was separated on a 1% agarose gel containing ethidium bromide and bands were visualized in UV-light.

In each PCR analysis, DNA purified from an in vitro grown culture of *B. afzelii* strain K78 was used as a positive control template. In addition, PBS was used instead of extracted DNA as negative control. Five microliters of the final product was separated on a 1% agarose gel containing ethidium bromide and bands were visualized in UV-light.

ELISA with the Invariable Region 6 (IR6) of the Variable Major Protein-Like Sequence E Protein (VlsE)

A biotinylated 25-mer peptide (MKKDDQIAAAMVLRGMAKDGQFALK) (SEQ ID NO: 30) derived from the sequence of *B. garinii* strain IP90 was used for analysis (Liang F T, et al. (1999) J Immunol. 163:5566-73). Streptavidin pre-coated 96-well ELISA plates (Nunc, Denmark) were coated with 100 μL/well (1 μg/mL) biotinylated peptide in PBS supplemented with 0.1% Tween 20 (PBS/0.1T). The plates were incubated overnight at 4° C. After coating with the peptide, the plates were washed once with PBS/0.1T. The plates were then blocked for one hour at room temperature (RT) with 100 μL/well of PBS+2% BSA, before being washed again with PBS/0.1T. Reactivity of post-challenge sera to the peptide was tested at 1:200, 1:400 and 1:800 dilutions in PBS+1% BSA. Plates were incubated for 90 min at RT before being washed three times with PBS/0.1T. Each well then received 50 μL of 1.3 μg/mL polyclonal rabbit anti-mouse IgG conjugated to HRP (Dako, Denmark) in PBS+1% BSA. The plates were then incubated for 1 h at RT. After three washes with PBS/0.1T, ABTS (50 μl/well) was added as substrate (Sigma-Aldrich, USA) and color was allowed to develop for 30 min. Absorbance was measured at 405 nm. All sera were tested in duplicate; negative controls included PBS instead of sera, as well as plates not coated with the peptide. Sera from mice shown to be culture positive for *B. afzelii* infection were used as positive controls.

Results

Levels of Protection in the Tick Challenge Method

Extremely significant levels of protection (p-value ≤001) were seen for all five stabilized OspA *B. afzelii* fragments at both of the doses tested (30 μg and 5 μg, see Table 2). The high infection rates in the PBS control group indicate that the ticks were infected with high frequency. Additionally, the positive control, non-lipidated full-length OspA from *B. afzelii* strain K78, was very protective. Together these control groups indicate the high reliability of the experimental readout.

Protection data from the seven experiments are combined and summarized in Table 2. The two methods employed to verify infection, namely ELISA and PCR, gave virtually identical results (not shown), demonstrating the robustness of these methods for assessment of infection in the tick challenge method.

Example 3. Protection of Mice from Infection with *B. afzelii* by the Tick Challenge Method by Immunization with Lipidated Mutant Serotype 2 OspA Fragments Experimental Procedures Cloning and Expression of Lipidated His-Tagged Mutant OspA Fragment Proteins The serotype 2 mutant OspA fragments with cysteine bond types 2, 3 and 4 (SEQ ID NOs: 142, 143 and 144, respectively) were modified by the addition of a lipidation signal sequence derived from OspA (SEQ ID NO: 14) and followed directly C-terminally by a CKQN peptide (SEQ ID NO: 211) to provide an N-terminal cysteine for lipidation. All mutant OspA fragments were C-terminally histidine-tagged for purification purposes. Gene fragments were cloned into the pET28b(+) vector (Novagen), a vector containing a Kanamycin resistance cassette as well as a T7 promoter. The lipidated monomers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated His-Tagged Wild-Type and Mutant OspA Fragment Monomer Proteins Cells were disrupted mechanically by high-pressure homogenization and the lipidated His-tagged OspA fragment monomer polypeptides were enriched in the lipid phase by phase separation, using Triton X-114 as detergent. Subsequently, the diluted detergent phase (20 to 30 fold) was applied to a Ni-sepharose column (Ni Sepharose™ 6 Fast Flow; GE Healthcare) and the lipidated His-tagged OspA fragments were eluted by Imidazole gradient (0-250 mM) elution. Pooled fractions were further purified over a gel filtration column (Superdex 200, GE Healthcare) followed by a buffer exchange column (Sephadex G-25, GE Healthcare). Lipidated His-tagged OspA fragment peaks were pooled on the basis of the analytical size exclusion column and reversed phase chromatography. After sterile filtration, the purified proteins were stored at −20° C. until formulation.

Immunization of Mice

Three lipidated mutant OspA proteins (Lip-S2D2-His, Lip-S2D3-His and Lip-S2D4-His) were expressed and purified as described above. In vivo protection studies were performed also as above using PBS and non-lipidated full-length serotype 2 OspA as negative and positive controls, respectively. All immunogens were formulated with 0.15% $Al(OH)_3$. Mice were injected subcutaneously three times at two week intervals with formulations containing 3.0 μg, 1.0 μg or 0.3 μg antigen and challenged with infected ticks two weeks after the last immunization. Mice were sacrificed six weeks following tick challenge and infection was assessed.

Results

Levels of Protection in the Tick Challenge Method

All three lipidated mutant OspA fragments conferred extremely significant levels of protection (p-value ≤0.001) from *B. afzelii* challenge even at the lowest tested dose (Table 3). Infection rates in the PBS groups were high, indicating that the ticks were infected to a high frequency. The positive control antigen, full-length non-lipidated OspA from *B. afzelii* strain K78, was also very protective. Together, these control groups indicate the high reliability of the method of infection and thus give high credibility to the results observed following immunization with the lipidated mutant OspA fragments.

Example 4. Protection of Mice from *Borrelia* Infection by Immunization with Lipidated His-Tagged Mutant OspA Fragment Heterodimers of Different Serotypes Experimental Procedures Cloning and Expression of Lipidated His-Tagged Mutant OspA Fragment Heterodimers The mutant OspA fragment monomers from *B. burgdorferi* s.s. strain B31, *B. afzelii* strain K78, *B. garinii* strain PBr, *B. bavariensis* strain PBi, *B. garinii* strain PHEi and *B. garinii* strain DK29 were codon-optimized for *E. coli* expression by GenScript, USA. The hLFA-1-like epitope (aa 164-174, SEQ ID NO: 17) of the OspA from *B. burgdorferi* s.s. strain B31 was replaced by a non-hLFA-1-like sequence NFTLEGKVAND from *B. afzelii* strain K78 (SEQ ID NO: 18). The lipidation signal sequence added to the mutant OspA fragment heterodimers was derived from the *E. coli* major outer membrane lipoprotein, Lpp, and was followed directly C-terminally by a CSS peptide (SEQ ID NO: 210) to provide an N-terminal cysteine for lipidation. The mutant OspA fragment heterodimers were generated by fusing different mutant OspA fragment monomers as described above via a 21 amino acid linker sequence, originating from two separate loop regions of the N-terminal half of OspA from *B. burgdorferi* s.s. strain B31 ("LN1"; aa 65-74 and aa 42-53 with an amino acid exchange of D53S, SEQ ID NO: 184). The heterodimers were constructed with a His-tag for purification purposes. Gene fragments were cloned into the pET28b(+) vector (Novagen), a vector containing a Kanamycin resistance cassette as well as a T7 promoter. The lipoproteins of the stabilized heterodimers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated His-Tagged Mutant OspA Fragment Heterodimers

Cells were disrupted mechanically by high-pressure homogenization and the lipidated His-tagged mutant OspA fragment heterodimers were enriched in the lipid phase by phase separation, using Triton X-114 as detergent. Subsequently, the diluted detergent phase (20 to 30 fold) was applied to a Ni-sepharose column (Ni Sepharose™ 6 Fast Flow; GE Healthcare) and the lipidated His-tagged OspA heterodimers were eluted by Imidazole gradient (0-250 mM) elution. Pooled fractions were further purified over a gel filtration column (Superdex 200, GE Healthcare) followed by a buffer exchange column (Sephadex G-25, GE Healthcare). The lipidated His-tagged mutant OspA heterodimer peaks were pooled on the basis of the analytical size exclusion column and reversed phase chromatography. After sterile filtration, the purified heterodimers were stored at −20° C. until formulation.

Immunization of Mice

Female C3H/HeN mice (Janvier, France) were used for all studies. Prior to each challenge, groups of ten 8-week-old mice were bled via the facial vein and pre-immune sera were prepared and pooled. Three subcutaneous (s.c.) immunizations of 100 μL each were administered at two week intervals. Each dose contained either 2 μg or 5 μg of the heterodimer protein Lip-S1D1-S2D1-His (SEQ ID NO: 49), or 1.0 μg or 2.5 μg of the respective monomer proteins, formulated with aluminium hydroxide ($Al(OH)_3$) at a final concentration of 0.15%. One week after the third immunization, blood was collected from the facial vein and hyperimmune sera were prepared. In each experiment, one group immunized with $Al(OH)_3$ alone was included as a negative control. All animal experiments were conducted in accordance with Austrian law (BGB1 Nr. 501/1989) and approved by "Magistratsabteilung 58".

Tick Challenge of Immunized Mice and Collection of Sera and Tissues (Herein Referred to Also as "Tick Challenge Method")

In order to challenge the immunized mice with *B. afzelii*, the hair of the back of each mouse was removed with Veet® Cream (Reckitt Benckiser) and a small ventilated container was glued to the skin with super glue (Pattex). Thereafter, one or two *I. ricinus* nymphs infected with *B. afzelii*, strain IS1, were applied per mouse, allowed to attach and feed until they were fully engorged and dropped off. The feeding status was monitored for each individual tick and only mice from which at least one fully fed tick was collected were included in the final readout.

Needle Challenge of Immunized Mice with In Vitro Grown *Borrelia*

Two weeks after the last immunization, the mice were challenged s.c. with *Borrelia* diluted in 100 μL *Borrelia* growth medium (BSK II). The challenge doses were strain-dependent, the virulence of the individual strains being assessed by challenge experiments for determination of $ID_{50}$. Doses employed for needle challenge experiments ranged from 20 to 50 times the $ID_{50}$.

Sacrifice of Mice and Collection of Material

Four weeks after needle challenge with *B. burgdorferi* s.s. or six weeks after tick challenge with *B. afzelii*, mice were sacrificed by cervical dislocation. The blood was collected by orbital bleeding and final sera were prepared and used for VlsE ELISA to determine infection status. In addition, one ear from each mouse was collected, and DNA was extracted and subjected to qPCR for identification of *Borrelia*. The final infection readout was based on two different analyses (qPCR targeting recA and VlsE ELISA).

ELISA with the Invariable Region 6 (IR6) of VlsE

A biotinylated 25-mer peptide (MKKDDQIAAAMVLRGMAKDGQFALK) (SEQ ID NO: 30) derived from the sequence of *B. garinii* strain IP90 was used for the analysis (Liang F T, Alvarez A L, Gu Y, Nowling J M, Ramamoorthy R, Philipp M T. An immunodominant conserved region within the variable domain of VlsE, the variable surface antigen of *Borrelia burgdorferi*. J Immunol. 1999; 163:5566-73). Streptavidin pre-coated 96-well ELISA plates (Nunc), were coated with 100 μL/well (1 μg/mL) peptide in PBS supplemented with 0.1% Tween (PBS/0.1T). The plates were incubated overnight at 4° C. After coating with the peptide, the plates were washed once with PBS/0.1T. The plates were then blocked for one hour at room temperature (RT) with 100 μL/well of PBS+2% BSA, before being washed again with PBS/0.1T. Reactivity of post-challenge sera to the peptide was tested at 1:200, 1:400 and 1:800 dilutions in PBS+1% BSA. Plates were incubated for 90 min at RT before being washed three times with PBS/0.1T. Each well then received 50 μL of 1.3 μg/mL polyclonal rabbit anti-mouse IgG conjugated to HRP (Dako) in PBS+1% BSA. The plates were then incubated for 1 h at RT. After three washes with PBS/0.1T, ABTS (50 μL/well) was added as substrate (Sigma-Aldrich) and color was allowed to develop for 30 min. Absorbance was measured at 405 nm. All sera were tested in duplicate. Negative controls included PBS instead of sera as well as plates not coated with the peptide. Sera from mice shown to be culture positive for *B. afzelii* infection were used as positive controls.

qPCR Targeting recA

Oligonucleotide primers were designed for the recA gene in a manner that they could be used in qPCR for identification of all relevant *Borrelia* species causing Lyme borreliosis (forward: CATGCTCTTGATCCTGTTTA, SEQ ID NO: 213 reverse: CCCATTTCTCCATCTATCTC, SEQ ID NO: 215). The recA fragment was cloned from the *B. burgdorferi* s.s. strain N40 into pET28b(+), to be used as standard in each reaction. The chromosomal DNA extracted from mouse ears was diluted 1:8 in water in order to reduce matrix effects observed with undiluted DNA. A master mix consisting of 10 μL SSoAdvanced™ SYBR® Green Supermix, 0.3 μL of each primer (10 μM), and 7.4 μL water was prepared for each experiment. Eighteen μL of master mix was mixed with 2 μL of the diluted DNA extracted from either bladder or ear in micro-titer plates and the DNA was amplified using a CFX96 real-time PCR detection system (Bio-Rad, USA). The DNA was denatured for 3 minutes at 95° C., followed by 50 cycles of 15 seconds at 95° C. and 30 seconds at 55° C. After amplification, the DNA was prepared for the melting curve analysis by denaturation for 30 seconds at 95° C. followed by 2 minutes at 55° C. The melting curve analysis was performed by 5 seconds incubation at 55° C., with a 0.5° C. increase per cycle, and 5 seconds at 95° C. On each plate, four no-template controls (NTC) were included as well as a standard curve in duplicate with template copy numbers ranging from 10 to 10,000.

Results

The lipidated His-tagged mutant OspA fragment heterodimer (Lip-S1D1-S2D1-His) was tested for protective capacity in six separate experiments. Mice were challenged with either the *B. burgdorferi* s.s. strain N40 (needle challenge) or the *B. afzelii* strain IS1 (tick challenge) in three experiments each. All experiments included mice immunized with the individual respective lipidated His-tagged mutant OspA monomers as positive control groups (Lip-S1D1-His and Lip-S2D1-His) and mice immunized with adjuvant alone as a negative control group. For challenge with ticks, 1-2 ticks were applied per mouse and only mice from which at least one tick fed until fully engorged were included in the final readout. However, no distinction was made between mice from which one or two fully fed ticks were collected. The protection data from the six experiments are summarized in Table 4.

The lipidated His-tagged OspA heterodimer (Lip-S1D1-S2D1-His) showed highly statistically-significant protection (Fisher's exact test, two-tailed) in all six experiments against both challenge species as compared to the negative control group. The infectious status of each mouse was determined using either VlsE ELISA alone (experiments 1-3) or in combination with recA qPCR (experiments 4-6). In cases where both methods were used, a mouse was regarded as infected when at least one method gave a positive result. The level of protection conferred by the lipidated His-tagged mutant OspA fragment heterodimer (Lip-S1D1-S2D1-His) was equal to or better than the protection conferred by either of the lipidated His-tagged mutant OspA fragment monomers individually.

Example 5. Protection of Mice from Infection with *Borrelia* by Immunization with Lipidated Non-His-Tagged Mutant OspA Fragment Heterodimers of Different Serotypes Cloning and Expression of Lipidated Non-His-Tagged Mutant OspA Fragment Heterodimers The constructs made as described in Example 4 were used for the generation of His-less constructs by the introduction of a stop codon by PCR amplification. Gene fragments were cloned into the pET28b(+) vector (Novagen), a vector containing a Kanamycin resistance cassette as well as a T7 promoter. The lipoproteins of the stabilized heterodimers were expressed in BL21 Star™ (DE3) cells (Invitrogen) and after induction by IPTG, the growth temperature of the cells was lowered from 37° C. to 25° C. to promote efficient post-translational processing of the proteins. Cells were collected after 4 h by centrifugation and the pellet was stored at −70° C. for up to 12 months prior to further processing.

Purification of Lipidated Non-His-Tagged Mutant OspA Fragment Heterodimers

Cells were disrupted mechanically by high-pressure homogenization and the lipidated mutant OspA fragment heterodimers were enriched in the lipid phase by phase separation, using Triton X-114 as detergent. Subsequently, the diluted detergent phase was subjected to anion exchange chromatography. The resulting flow-through was subjected to cation exchange chromatography and the lipidated proteins eluted from the column. The eluate was subjected to further purification over a gel filtration column (Superdex 200, GE Healthcare) followed by a buffer exchange column (Sephadex G-25, GE Healthcare). The lipidated mutant OspA heterodimer peaks were pooled on the basis of the analytical size exclusion column and reversed phase chromatography. After sterile filtration, the purified heterodimers were stored at −20° C. until formulation.

Immunization of Mice

Female C3H/HeN mice will be used for all studies. Prior to each challenge, groups of ten 8-week-old mice will be bled via the facial vein and pre-immune sera will be prepared and pooled. Three s.c. immunizations of 100 μL each will be administered at two week intervals. Each dose will contain 5 μg of the respective heterodimer proteins: Lip-S1D1-S2D1 (SEQ ID NO: 186), Lip-S4D1-S3D1 (SEQ ID NO: 194) and Lip-S5D1-S6D1 (SEQ ID NO: 190) or 2.5 μg of the respective monomer proteins, formulated with aluminium hydroxide ($Al(OH)_3$) at a final concentration of 0.15%. One week after the third immunization, blood will be collected from the facial vein and hyper-immune sera will be prepared. In each experiment, one group immunized with PBS formulated with $Al(OH)_3$ will be included as a negative control. All animal experiments will be conducted in accordance with Austrian law (BGB1 Nr. 501/1989) and approved by “Magistratsabteilung 58”.

Needle Challenge of Immunized Mice with In Vitro Grown *Borrelia*

Two weeks after the last immunization, the mice will be challenged s.c. with *Borrelia* diluted in 100 μL *Borrelia* growth medium (BSKII). The challenge doses are strain-dependent, the virulence of the individual strains will require assessment by challenge experiments for determination of $ID_{50}$. Doses employed for needle challenge experiments will range from 20 to 50 times the $ID_{50}$. Four weeks after needle challenge, mice will be sacrificed and blood and tissues will be collected for readout methods to determine the infection status.

SEQUENCES

S2D0-His amino acids of positions 131-273 of *Borrelia afzelii* strain K78, OspA serotype 2, wild-type sequence, C-terminal His tag (GLEHHHHHH) (SEQ ID NO: 214)

SEQ ID NO: 1

ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

TVQKYDSAGTNLEGTAVEIKTLDELKNALKGLEHHHHHH

S2D1-His aa 131-273 of *Borrelia afzelii* strain K78, OspA serotype 2 with disulfide bond type 1 (aa 182 and 269), C-terminal His tag (GLEHHHHHH) (SEQ ID NO: 214)

SEQ ID NO: 2

ELSAKTMTRENGTKLEYTEMKSDGTGKAKEVLKNFTLEGKVANDKVTLEVKCGTV

TLSKEIAKSGEVTVALNDTNTTQATKKTGAWDSKTSTLTISVNSKKTTQLVFTKQDTI

TVQKYDSAGTNLEGTAVEIKTLDELCNALKGLEHHHHHH

S2D2-His aa 131-273 of *Borrelia afzelii* strain K78, OspA serotype 2 with disulfide bond type 2 (aa 182 and 272), C-terminal His tag (GLEHHHHHH) (SEQ ID NO: 214)

SEQ ID NO: 3

ELSAKTMTRENGTKLEYTEMKSDGTGKAKEVLKNFTLEGKVANDKVTLEVKCGTV

TLSKEIAKSGEVTVALNDTNTTQATKKTGAWDSKTSTLTISVNSKKTTQLVFTKQDTI

TVQKYDSAGTNLEGTAVEIKTLDELKNACKGLEHHHHHH

-continued

S2D3-His
aa 131-273 of *Borrelia afzelii* strain K78, OspA serotype 2 with disulfide bond type 3 (aa 244 and 259), C-terminal His tag (GLEHHHHHH) (SEQ ID NO: 214)

SEQ ID NO: 4
ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

CVQKYDSAGTNLEGTCVEIKTLDELKNALKGLEHHHHHH

S2D4-His
aa 131-273 of *Borrelia afzelii* strain K78, OspA serotype 2 with disulfide bond type 4 (aa 141 and 241), C-terminal His tag (GLEHHHHHH) (SEQ ID NO: 214)

SEQ ID NO: 5
ELSAKTMTRECGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQCTI

TVQKYDSAGTNLEGTAVEIKTLDELKNALKGLEHHHHHH

S2D5-His
aa 131-273 of *Borrelia afzelii* strain K78, OspA serotype 2 with disulfide bond type 5 (aa 165 and 265), C-terminal His tag(GLEHHHHHH) (SEQ ID NO: 214)

SEQ ID NO: 6
ELSAKTMTRENGTKLEYTEMKSDGTGKAKEVLKNCTLEGKVANDKVTLEVKEGTV

TLSKEIAKSGEVTVALNDTNTTQATKKTGAWDSKTSTLTISVNSKKTTQLVFTKQDTI

TVQKYDSAGTNLEGTAVEIKTCDELKNALKGLEHHHHHH

S2D6-His
aa 131-273 of *Borrelia afzelii* strain K78, OspA serotype 2 with disulfide bond type 6 (aa 185 and 272), C-terminal His tag (GLEHHHHHH) (SEQ ID NO: 214)

SEQ ID NO: 7
ELSAKTMTRENGTKLEYTEMKSDGTGKAKEVLKNFTLEGKVANDKVTLEVKEGTC

TLSKEIAKSGEVTVALNDTNTTQATKKTGAWDSKTSTLTISVNSKKTTQLVFTKQDTI

TVQKYDSAGTNLEGTAVEIKTLDELKNACKGLEHHHHHH

S2D7-His
aa 131-273 of *Borrelia afzelii* strain K78, OspA serotype 2 with disulfide bond type 7 (aa 199 and 223), C-terminal His tag (GLEHHHHHH) (SEQ ID NO: 214)

SEQ ID NO: 8
ELSAKTMTRENGTKLEYTEMKSDGTGKAKEVLKNFTLEGKVANDKVTLEVKEGTV

TLSKEIAKSGEVTCALNDTNTTQATKKTGAWDSKTSTCTISVNSKKTTQLVFTKQDT

ITVQKYDSAGTNLEGTAVEIKTLDELKNALKGLEHHHHHH

S2D8-His
aa 131-273 of *Borrelia afzelii* strain K78, OspA serotype 2 with disulfide bond type 8 (aa 243 and 262), C-terminal His tag (GLEHHHHHH) (SEQ ID NO: 214)

SEQ ID NO: 9
ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDT

CTVQKYDSAGTNLEGTAVECKTLDELKNALKGLEHHHHHH

S2D9-His
aa 131-273 of *Borrelia afzelii* strain K78, OspA serotype 2 with disulfide bond type 9 (aa 184 and 204), C-terminal His tag (GLEHHHHHH) (SEQ ID NO: 214)

SEQ ID NO: 10
ELSAKTMTRENGTKLEYTEMKSDGTGKAKEVLKNFTLEGKVANDKVTLEVKEGCV

TLSKEIAKSGEVTVALNDCNTTQATKKTGAWDSKTSTLTISVNSKKTTQLVFTKQDT

ITVQKYDSAGTNLEGTAVEIKTLDELKNALKGLEHHHHHH

-continued

S2D10-His
aa 131-273 of *Borrelia afzelii* strain K78, OspA serotype 2 with disulfide bond type 10 (aa 201 and 214), C-terminal His tag (GLEHHHHHH) (SEQ ID NO: 214)

SEQ ID NO: 11

ELSAKTMTRENGTKLEYTEMKSDGTGKAKEVLKNFTLEGKVANDKVTLEVKEGTV

TLSKEIAKSGEVTVACNDTNTTQATKKTCAWDSKTSTLTISVNSKKTTQLVFTKQDT

ITVQKYDSAGTNLEGTAVEIKTLDELKNALKGLEHHHHHH

S2D11-His
aa 131-273 of *Borrelia afzelii* strain K78, OspA serotype 2 with disulfide bond type 11 (aa 246 and 259), C-terminal His tag (GLEHHHHHH) (SEQ ID NO: 214)

SEQ ID NO: 12

ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

TVCKYDSAGTNLEGTCVEIKTLDELKNALKGLEHHHHHH

S2D12-His
aa 131-273 of *Borrelia afzelii* strain K78, OspA serotype 2 with disulfide bond type 12 (aa 167 and 178), C-terminal His tag (GLEHHHHHH) (SEQ ID NO: 214)

SEQ ID NO: 13

ELSAKTMTRENGTKLEYTEMKSDGTGKAKEVLKNFTCEGKVANDKVTCEVKEGTV

TLSKEIAKSGEVTVALNDTNTTQATKKTGAWDSKTSTLTISVNSKKTTQLVFTKQDTI

TVQKYDSAGTNLEGTAVEIKTLDELKNALKGLEHHHHHH

*Borrelia* OspA lipidation signal

SEQ ID NO: 14

MKKYLLGIGLILALIA

*Borrelia* OspB lipidation signal

SEQ ID NO: 15

MRLLIGFALALALIG

*E. coli* lpp lipidation signal

SEQ ID NO: 16

MKATKLVLGAVILGSTLLAG hLFA-1-like sequence from *B. burgdorferi* s.s. strain B31

SEQ ID NO: 17

GYVLEGTLTAE

Non-hLFA-1-like sequence from *B. afzelii* strain K78

SEQ ID NO: 18

NFTLEGKVAND

*B. afzelii* (strain K78; OspA serotype 2) OspA

SEQ ID NO: 19

MKKYLLGIGLILALIACKQNVSSLDEKNSASVDLPGEMKVLVSKEKDKDGKYSLKA

TVDKIELKGTSDKDNGSGVLEGTKDDKSKAKLTIADDLSKTTFELFKEDGKTLVSRK

VSSKDKTSTDEMFNEKGELSAKTMTRENGTKLEYTEMKSDGTGKAKEVLKNFTLEG

KVANDKVTLEVKEGTVTLSKEIAKSGEVTVALNDTNTTQATKKTGAWDSKTSTLTIS

VNSKKTTQLVFTKQDTITVQKYDSAGTNLEGTAVEIKTLDELKNALK

*B. burgdorferi* s.s. (strain B31, OspA serotype 1) OspA

SEQ ID NO: 20

MKKYLLGIGLILALIACKQNVSSLDEKNSVSVDLPGEMKVLVSKEKNKDGKYDLIAT

VDKLELKGTSDKNNGSGVLEGVKADKSKVKLTISDDLGQTTLEVFKEDGKTLVSKK

VTSKDKSSTEEKFNEKGEVSEKIITRADGTRLEYTGIKSDGSGKAKEVLKGYVLEGTL

TAEKTTLVVKEGTVTLSKNISKSGEVSVELNDTDSSAATKKTAAWNSGTSTLTITVN

SKKTKDLVFTKENTITVQQYDSNGTKLEGSAVEITKLDEIKNALK

-continued

*B. garinii* (strain PBr, OspA serotype 3) OspA

SEQ ID NO: 21

MKKYLLGIGLILALIACKQNVSSLDEKNSVSVDLPGGMKVLVSKEKDKDGKYSLMA

TVEKLELKGTSDKSNGSGVLEGEKADKSKAKLTISQDLNQTTFEIFKEDGKTLVSRK

VNSKDKSSTEEKFNDKGKLSEKVVTRANGTRLEYTEIKNDGSGKAKEVLKGFALEG

TLTDGGETKLTVTEGTVTLSKNISKSGEITVALNDTETTPADKKTGEWKSDTSTLTIS

KNSQKPKQLVFTKENTITVQNYNRAGNALEGSPAEIKDLAELKAALK

*B. bavariensis* (strain PBi, OspA serotype 4) OspA

SEQ ID NO: 22

MKKYLLGIGLILALIACKQNVSSLDEKNSVSVDLPGEMKVLVSKEKDKDGKYSLMA

TVDKLELKGTSDKSNGSGTLEGEKSDKSKAKLTISEDLSKTTFEIFKEDGKTLVSKKV

NSKDKSSIEEKFNAKGELSEKTILRANGTRLEYTEIKSDGTGKAKEVLKDFALEGTLA

ADKTTLKVTEGTVVLSKHIPNSGEITVELNDSNSTQATKKTGKWDSNTSTLTISVNSK

KTKNIVFTKEDTITVQKYDSAGTNLEGNAVEIKTLDELKNALK

*B. garinii* (strain PHei, OspA serotype 5) OspA

SEQ ID NO: 23

MKKYLLGIGLILALIACKQNVSSLDEKNSVSVDLPGGMKVLVSKEKDKDGKYSLMA

TVEKLELKGTSDKNNGSGTLEGEKTDKSKVKLTIAEDLSKTTFEIFKEDGKTLVSKK

VTLKDKSSTEEKFNEKGEISEKTIVRANGTRLEYTDIKSDKTGKAKEVLKDFTLEGTL

AADGKTTLKVTEGTVTLSKNISKSGEITVALDDTDSSGNKKSGTWDSGTSTLTISKNR

TKTKQLVFTKEDTITVQNYDSAGTNLEGKAVEITTLKELKNALK

*B. garinii* (strain DK29, OspA serotype 6) OspA

SEQ ID NO: 24

MKKYLLGIGLILALIACKQNVSSLDEKNSVSVDLPGGMTVLVSKEKDKDGKYSLEAT

VDKLELKGTSDKNNGSGTLEGEKTDKSKVKSTIADDLSQTKFEIFKEDGKTLVSKKV

TLKDKSSTEEKFNGKGETSEKTIVRANGTRLEYTDIKSDGSGKAKEVLKDFTLEGTL

AADGKTTLKVTEGTVVLSKNILKSGEITAALDDSDTTRATKKTGKWDSKTSTLTISV

NSQKTKNLVFTKEDTITVQRYDSAGTNLEGKAVEITTLKELKNALK

*B. garinii* (strain T25, OspA serotype 7) OspA

SEQ ID NO: 25

MKKYLLGIGLILALIACKQNVSSLDEKNSVSVDLPGEMKVLVSKEKDKDGKYSLEAT

VDKLELKGTSDKNNGSGVLEGVKAAKSKAKLTIADDLSQTKFEIFKEDGKTLVSKK

VTLKDKSSTEEKFNDKGKLSEKVVTRANGTRLEYTEIQNDGSGKAKEVLKSLTLEGT

LTADGETKLTVEAGTVTLSKNISESGEITVELKDTETTPADKKSGTWDSKTSTLTISK

NSQKTKQLVFTKENTITVQKYNTAGTKLEGSPAEIKDLEALKAALK

*Borrelia* nested per detection forward primer 1

SEQ ID NO: 26

GTATGTTTAGTGAGGGGGGTG

*Borrelia* nested per detection reverse primer 1

SEQ ID NO: 27

GGATCATAGCTCAGGTGGTTAG

*Borrelia* nested per detection forward primer 2

SEQ ID NO: 28

AGGGGGGTGAAGTCGTAACAAG

*Borrelia* nested per detection reverse primer 2

SEQ ID NO: 29

GTCTGATAAACCTGAGGTCGGA 25-mer peptide

SEQ ID NO: 30

MKKDDQIAAAMVLRGMAKDGQFALK

-continued

Mouse cathelin
SEQ ID NO: 31
RLAGLLRKGGEKIGEKLKKIGQKIKNFFQKLVPQPE

5'-$(dIdC)_{13}$-3'
SEQ ID NO: 32
dIdC dIdC dIdC dIdC dIdC dIdC dIdC dIdC dIdC dIdC dIdC dIdC dIdC

KLK peptide
SEQ ID NO: 33
KLKLLLLLKLK

*B. afzelii* (strain K78, serotype 2), OspA aa 126-273
SEQ ID NO: 34
FNEKGELSAKTMTRENGTKLEYTEMKSDGTGKAKEVLKNFTLEGKVANDKVTLEV

KEGTVTLSKEIAKSGEVTVALNDTNTTQATKKTGAWDSKTSTLTISVNSKKTTQLVF

TKQDTITVQKYDSAGTNLEGTAVEIKTLDELKNALK

*B. afzelii* (strain K78, serotype 2), OspA aa 131-273
SEQ ID NO: 35
ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

TVQKYDSAGTNLEGTAVEIKTLDELKNALK peptide linker
SEQ ID NO: 36
GGGGGGGG peptide linker 2
SEQ ID NO: 37
GGGGGGGGGGGG peptide linker 3
SEQ ID NO: 38
GAGA peptide linker 4
SEQ ID NO: 39
GAGAGAGA peptide linker 5
SEQ ID NO: 40
GAGAGAGAGAGA peptide linker 6
SEQ ID NO: 41
GGGSGGGS peptide linker 7
SEQ ID NO: 42
GGGSGGGSGGGS S1D4-S2D4_aa
Heterodimer fusion protein of OspA serotypes 1 and 2 both with disulfide bond type 4, LN1 peptide linker (SEQ ID NO: 184), aa 164-174 of OspA serotype 1 replaced by non-hLFA-1-like sequence NFTLEGKVAND (SEQ ID NO: 18)
SEQ ID NO: 43
FNEKGEVSEKIITRACGTRLEYTGIKSDGSGKAKEVLKNFTLEGKVANDKTTLVVKE

GTVTLSKNISKSGEVSVELNDTDSSAATKKTAAWNSGTSTLTITVNSKKTKDLVFTK

ECTITVQQYDSNGTKLEGSAVEITKLDEIKNALKGTSDKNNGSGSKEKNKDGKYSFN

EKGELSAKTMTRECGTKLEYTEMKSDGTGKAKEVLKNFTLEGKVANDKVTLEVKE

GTVTLSKEIAKSGEVTVALNDTNTTQATKKTGAWDSKTSTLTISVNSKKTTQLVFTK

QCTITVQKYDSAGTNLEGTAVEIKTLDELKNALK

-continued

Lip-S1D4-S2D4_nt
Coding sequence for fusion proteins of OspA serotypes 1 and 2 both with disulfide bond type 4, *E. coli* lpp lipidation signal, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 44

ATGAAAGCTACTAAACTGGTACTGGGCGCGGTAATCCTGGGTTCTACTCTGCTGG

CAGGTTGCTCAAGCTTCAACGAAAAGGGCGAAGTCTCGGAAAAAATCATTACCC

GTGCTTGCGGCACCCGTCTGGAATACACCGGCATTAAATCGGATGGCAGCGGCA

AAGCGAAGGAAGTTCTGAAAAACTTTACCCTGGAAGGCAAAGTCGCAAATGATA

AGACCACCCTGGTGGTGAAAGAAGGCACCGTTACGCTGAGCAAAAACATTAGTA

AGTCCGGTGAAGTCTCTGTGGAACTGAATGATACCGACAGCTCTGCGGCCACCA

AAAAGACGGCAGCTTGGAACTCAGGCACCTCGACGCTGACCATTACGGTTAATT

CCAAAAAGACCAAAGATCTGGTCTTCACGAAAGAATGCACCATCACGGTGCAGC

AATATGACAGCAACGGTACCAAACTGGAAGGCTCTGCGGTGGAAATCACGAAAC

TGGATGAAATCAAAAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAATGCGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAAGAAGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAACAGCAAGAAAACCACGCAGCTGGTCTTCACCAAA

CAATGTACGATCACCGTGCAGAAATACGATAGTGCGGGTACCAACCTGGAAGGC

ACCGCTGTTGAAATCAAAACCCTGGACGAACTGAAAAACGCCCTGAAA

Lip-S1D4-S2D4_His_aa
Heterodimer fusion protein of OspA serotypes 1 and 2 both with disulfide bond type 4, N-terminal CSS for addition of lipids, N-terminal lipidation, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 45

LipCSSFNEKGEVSEKIITRACGTRLEYTGIKSDGSGKAKEVLKNFTLEGKVANDKTTL

VVKEGTVTLSKNISKSGEVSVELNDTDSSAATKKTAAWNSGTSTLTITVNSKKTKDL

VFTKECTITVQQYDSNGTKLEGSAVEITKLDEIKNALKGTSDKNNGSGSKEKNKDGK

YSFNEKGELSAKTMTRECGTKLEYTEMKSDGTGKAKEVLKNFTLEGKVANDKVTL

EVKEGTVTLSKEIAKSGEVTVALNDTNTTQATKKTGAWDSKTSTLTISVNSKKTTQL

VFTKQCTITVQKYDSAGTNLEGTAVEIKTLDELKNALKGLEHHHHHH

Lip-S1D4-S2D4_His_nt
Coding sequence for heterodimer fusion protein of OspA serotypes 1 and 2 both with disulfide bond type 4, *E. coli* lpp lipidation signal, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 46

ATGAAAGCTACTAAACTGGTACTGGGCGCGGTAATCCTGGGTTCTACTCTGCTGG

CAGGTTGCTCAAGCTTCAACGAAAAGGGCGAAGTCTCGGAAAAAATCATTACCC

GTGCTTGCGGCACCCGTCTGGAATACACCGGCATTAAATCGGATGGCAGCGGCA

-continued

AAGCGAAGGAAGTTCTGAAAAACTTTACCCTGGAAGGCAAAGTCGCAAATGATA

AGACCACCCTGGTGGTGAAAGAAGGCACCGTTACGCTGAGCAAAAACATTAGTA

AGTCCGGTGAAGTCTCTGTGGAACTGAATGATACCGACAGCTCTGCGGCCACCA

AAAAGACGGCAGCTTGGAACTCAGGCACCTCGACGCTGACCATTACGGTTAATT

CCAAAAAGACCAAAGATCTGGTCTTCACGAAAGAATGCACCATCACGGTGCAGC

AATATGACAGCAACGGTACCAAACTGGAAGGCTCTGCGGTGGAAATCACGAAAC

TGGATGAAATCAAAAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAATGCGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAAGAAGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAACAGCAAGAAAACCACGCAGCTGGTCTTCACCAAA

CAATGTACGATCACCGTGCAGAAATACGATAGTGCGGGTACCAACCTGGAAGGC

ACCGCTGTTGAAATCAAAACCCTGGACGAACTGAAAAACGCCCTGAAAGGCCTC

GAGCACCACCACCACCACCAC

S1D1-S2D1_aa
Heterodimer fusion protein of OspA serotype 1 and OspA serotype 2 with disulfide bond type 1, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 47

FNEKGEVSEKIITRADGTRLEYTGIKSDGSGKAKEVLKNFTLEGKVANDKTTLVVKC

GTVTLSKNISKSGEVSVELNDTDSSAATKKTAAWNSGTSTLTITVNSKKTKDLVFTK

ENTITVQQYDSNGTKLEGSAVEITKLDEICNALKGTSDKNNGSGSKEKNKDGKYSFN

EKGELSAKTMTRENGTKLEYTEMKSDGTGKAKEVLKNFTLEGKVANDKVTLEVKC

GTVTLSKEIAKSGEVTVALNDTNTTQATKKTGAWDSKTSTLTISVNSKKTTQLVFTK

QDTITVQKYDSAGTNLEGTAVEIKTLDELCNALK

Lip-S1D1-S2D1_nt
Coding sequence for intermediate and final hetero-dimer fusion proteins of OspA serotype 1 and OspA serotype 2 with disulfide bond type 1, *E. coli* lpp lipidation signal, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 48

ATGAAAGCTACTAAACTGGTACTGGGCGCGGTAATCCTGGGTTCTACTCTGCTGG

CAGGTTGCTCAAGCTTCAACGAAAAGGGCGAAGTCAGCGAAAAAATCATTACCC

GCGCAGACGGCACCCGCCTGGAATACACCGGCATCAAATCGGACGGCAGCGGCA

AAGCGAAAGAAGTTCTGAAAAACTTTACCCTGGAAGGCAAAGTCGCAAATGATA

AAACCACCCTGGTGGTGAAATGCGGCACCGTTACGCTGAGCAAAAACATTAGTA

AATCCGGTGAAGTCTCTGTGGAACTGAATGATACCGACAGCTCTGCGGCCACCA

AGAAAACCGCAGCTTGGAACTCAGGCACCTCGACGCTGACCATTACGGTTAATA

GCAAGAAAACCAAAGATCTGGTCTTCACGAAAGAAAACACCATCACGGTGCAGC

AATATGACAGCAATGGTACCAAACTGGAAGGCTCCGCTGTGGAAATCACGAAAC

TGGATGAAATCTGTAATGCTCTGAAAGGTACTAGTGACAAAAACAATGGCTCTG

-continued

GTAGCAAAGAGAAAAACAAAGATGGCAAGTACTCATTCAACGAAAAAGGCGAA

CTGTCGGCGAAAACGATGACGCGTGAAAACGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAATGCGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAATAGCAAGAAAACCACGCAGCTGGTCTTCACCAAA

CAAGATACGATCACCGTGCAGAAATACGACAGTGCGGGTACCAACCTGGAAGGC

ACGGCTGTTGAAATCAAAACCCTGGACGAACTGTGTAACGCCCTGAAA

Lip-S1D1-S2D1_His_aa
Heterodimer fusion protein of OspA serotype 1 and OspA serotype 2 with disulfide bond type 1, N-terminal CSS for addition of lipids, N-terminal lipidation, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 49

LipCSSFNEKGEVSEKIITRADGTRLEYTGIKSDGSGKAKEVLKNFTLEGKVANDKTTL

VVKCGTVTLSKNISKSGEVSVELNDTDSSAATKKTAAWNSGTSTLTITVNSKKTKDL

VFTKENTITVQQYDSNGTKLEGSAVEITKLDEICNALKGTSDKNNGSGSKEKNKDGK

YSFNEKGELSAKTMTRENGTKLEYTEMKSDGTGKAKEVLKNFTLEGKVANDKVTL

EVKCGTVTLSKEIAKSGEVTVALNDTNTTQATKKTGAWDSKTSTLTISVNSKKTTQL

VFTKQDTITVQKYDSAGTNLEGTAVEIKTLDELCNALKGLEHHHHHH

Lip-S1D1-S2D1_His_nt
Coding sequence for heterodimer fusion protein of OspA serotype 1 and OspA serotype 2 with disulfide bond type 1, *E. coli* lpp lipidation signal, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 50

ATGAAAGCTACTAAACTGGTACTGGGCGCGGTAATCCTGGGTTCTACTCTGCTGG

CAGGTTGCTCAAGCTTCAACGAAAAGGGCGAAGTCAGCGAAAAAATCATTACCC

GCGCAGACGGCACCCGCCTGGAATACACCGGCATCAAATCGGACGGCAGCGGCA

AAGCGAAAGAAGTTCTGAAAAACTTTACCCTGGAAGGCAAAGTCGCAAATGATA

AAACCACCCTGGTGGTGAAATGCGGCACCGTTACGCTGAGCAAAAACATTAGTA

AATCCGGTGAAGTCTCTGTGGAACTGAATGATACCGACAGCTCTGCGGCCACCA

AGAAAACCGCAGCTTGGAACTCAGGCACCTCGACGCTGACCATTACGGTTAATA

GCAAGAAAACCAAAGATCTGGTCTTCACGAAAGAAAACACCATCACGGTGCAGC

AATATGACAGCAATGGTACCAAACTGGAAGGCTCCGCTGTGGAAATCACGAAAC

TGGATGAAATCTGTAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAAAACGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAATGCGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

-continued

ACGCTGACCATTAGTGTTAATAGCAAGAAAACCACGCAGCTGGTCTTCACCAAA

CAAGATACGATCACCGTGCAGAAATACGACAGTGCGGGTACCAACCTGGAAGGC

ACGGCTGTTGAAATCAAAACCCTGGACGAACTGTGTAACGCCCTGAAAGGCCTC

GAGCACCACCACCACCACCAC

S3D4-S4D4_aa
Heterodimer fusion protein of OspA serotype 3 and OspA serotype 4 with disulfide bond type 4. LN1 peptide linker (SEQ ID NO: 184)

SEQ ID NO: 51

FNEKGKLSEKVVTRACGTRLEYTEIKNDGSGKAKEVLKGFALEGTLTDGGETKLTV

TEGTVTLSKNISKSGEITVALNDTETTPADKKTGEWKSDTSTLTISKNSQKPKQLVFT

KECTITVQNYNRAGNALEGSPAEIKDLAELKAALKGTSDKNNGSGSKEKNKDGKYS

FNAKGELSEKTILRACGTRLEYTEIKSDGTGKAKEVLKDFALEGTLAADKTTLKVTE

GTVVLSKHIPNSGEITVELNDSNSTQATKKTGKWDSNTSTLTISVNSKKTKNIVFTKE

CTITVQKYDSAGTNLEGNAVEIKTLDELKNALK

Lip-S3D4-S4D4_nt
Coding sequence for intermediate and final hetero-dimer fusion proteins of OspA serotype 3 and OspA serotype 4 with disulfide bond type 4, *E. coli* lpp lipidation signal, LN1 peptide linker (SEQ ID NO: 184)

SEQ ID NO: 52

ATGAAAGCTACTAAACTGGTACTGGGCGCGGTAATCCTGGGTTCTACTCTGCTGG

CAGGTTGCTCAAGCTTCAACGAAAAGGGCAAACTGTCAGAAAAAGTGGTCACCC

GCGCTTGTGGCACCCGCCTGGAATACACCGAAATCAAAAACGACGGCTCGGGCA

AAGCGAAGGAAGTTCTGAAAGGCTTTGCCCTGGAAGGTACCCTGACGGATGGCG

GTGAAACCAAACTGACCGTGACGGAAGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAATGCACGATCACCGTGC

AGAACTATAATCGTGCCGGTAATGCTCTGGAAGGCTCCCCGGCTGAAATCAAGG

ACCTGGCGGAACTGAAGGCGGCACTGAAAGGCACTAGTGACAAAAACAATGGCT

CTGGTAGCAAAGAGAAAAACAAAGATGGCAAGTACTCATTCAACGCTAAAGGTG

AACTGTCGGAAAAAACCATCCTGCGCGCCTGTGGCACCCGCCTGGAATACACGG

AAATCAAGTCGGACGGCACGGGCAAAGCAAAGGAAGTCCTGAAAGATTTTGCTC

TGGAAGGTACCCTGGCGGCCGACAAAACCACGCTGAAGGTGACGGAAGGCACC

GTGGTTCTGAGCAAACATATTCCGAACTCTGGTGAAATCACCGTTGAACTGAACG

ATAGCAATTCTACGCAGGCGACCAAAAAGACGGGCAAATGGGACAGTAATACCT

CCACGCTGACCATTTCAGTCAACTCGAAAAAGACCAAAAATATTGTGTTCACGA

AGGAATGCACGATCACCGTTCAAAAATATGATTCCGCAGGTACCAACCTGGAAG

GCAACGCTGTGGAAATCAAAACCCTGGACGAACTGAAAAATGCTCTGAAG

Lip-S3D4-S4D4_His_aa
Heterodimer fusion protein of OspA serotype 3 and OspA serotype 4 with disulfide bond type 4, N-terminal CSS for addition of lipids, N-terminal lipidation, LN1 peptide linker (SEQ ID NO: 184), C-terminal His tag (GLEHHHHHH) (SEQ ID NO: 214)

SEQ ID NO: 53

LipCSSFNEKGKLSEKVVTRACGTRLEYTEIKNDGSGKAKEVLKGFALEGTLTDGGET

KLTVTEGTVTLSKNISKSGEITVALNDTETTPADKKTGEWKSDTSTLTISKNSQKPKQ

-continued

LVFTKECTITVQNYNRAGNALEGSPAEIKDLAELKAALKGTSDKNNGSGSKEKNKD

GKYSFNAKGELSEKTILRACGTRLEYTEIKSDGTGKAKEVLKDFALEGTLAADKTTL

KVTEGTVVLSKHIPNSGEITVELNDSNSTQATKKTGKWDSNTSTLTISVNSKKTKNIV

FTKECTITVQKYDSAGTNLEGNAVEIKTLDELKNALKGLEHHHHHH

Lip-S3D4-S4D4_His_nt
Coding sequence for heterodimer fusion protein of OspA serotype 3 and OspA serotype 4 with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 54

ATGAAAGCTACTAAACTGGTACTGGGCGCGGTAATCCTGGGTTCTACTCTGCTGG

CAGGTTGCTCAAGCTTCAACGAAAAGGGCAAACTGTCAGAAAAAGTGGTCACCC

GCGCTTGTGGCACCCGCCTGGAATACACCGAAATCAAAAACGACGGCTCGGGCA

AAGCGAAGGAAGTTCTGAAAGGCTTTGCCCTGGAAGGTACCCTGACGGATGGCG

GTGAAACCAAACTGACCGTGACGGAAGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAATGCACGATCACCGTGC

AGAACTATAATCGTGCCGGTAATGCTCTGGAAGGCTCCCCGGCTGAAATCAAGG

ACCTGGCGGAACTGAAGGCGGCACTGAAAGGCACTAGTGACAAAAACAATGGCT

CTGGTAGCAAAGAGAAAAACAAAGATGGCAAGTACTCATTCAACGCTAAAGGTG

AACTGTCGGAAAAAACCATCCTGCGCGCCTGTGGCACCCGCCTGGAATACACGG

AAATCAAGTCGGACGGCACGGGCAAAGCAAAGGAAGTCCTGAAAGATTTTGCTC

TGGAAGGTACCCTGGCGGCCGACAAAACCACGCTGAAGGTGACGGAAGGCACC

GTGGTTCTGAGCAAACATATTCCGAACTCTGGTGAAATCACCGTTGAACTGAACG

ATAGCAATTCTACGCAGGCGACCAAAAAGACGGGCAAATGGGACAGTAATACCT

CCACGCTGACCATTTCAGTCAACTCGAAAAAGACCAAAAATATTGTGTTCACGA

AGGAATGCACGATCACCGTTCAAAAATATGATTCCGCAGGTACCAACCTGGAAG

GCAACGCTGTGGAAATCAAAACCCTGGACGAACTGAAAAATGCTCTGAAGGGTC

TCGAGCACCACCACCACCACCAC

S3D1-S4D1_aa
Heterodimer fusion protein of OspA serotypes 3 and 4 both with disulfide bond type 1, LN1 peptide linker (SEQ ID NO: 184)

SEQ ID NO: 55

FNEKGKLSEKVVTRANGTRLEYTEIKNDGSGKAKEVLKGFALEGTLTDGGETKLTV

TCGTVTLSKNISKSGEITVALNDTETTPADKKTGEWKSDTSTLTISKNSQKPKQLVFT

KENTITVQNYNRAGNALEGSPAEIKDLAELCAALKGTSDKNNGSGSKEKNKDGKYS

FNAKGELSEKTILRANGTRLEYTEIKSDGTGKAKEVLKDFALEGTLAADKTTLKVTC

GTVVLSKHIPNSGEITVELNDSNSTQATKKTGKWDSNTSTLTISVNSKKTKNIVFTKE

DTITVQKYDSAGTNLEGNAVEIKTLDELCNALK

-continued

Lip-S3D1-S4D1_nt
Coding sequence for intermediate and final hetero-
dimer fusion proteins of OspA serotypes 3 and 4 both
with disulfide bond type 1, *E. coli* lpp lipidation
signal, N-terminal CSS for addition of lipids, LN1
peptide linker (SEQ ID NO: 184)
SEQ ID NO: 56

ATGAAAGCTACTAAACTGGTACTGGGCGCGGTAATCCTGGGTTCTACTCTGCTGG

CAGGTTGCTCAAGCTTCAACGAAAAGGGCAAACTGTCGGAAAAAGTGGTCACCC

GCGCAAATGGCACCCGCCTGGAATACACGGAAATCAAAAACGATGGTAGCGGCA

AAGCGAAGGAAGTTCTGAAAGGCTTTGCCCTGGAAGGTACCCTGACGGATGGCG

GTGAAACCAAACTGACCGTGACGTGCGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAAAACACGATCACCGTGC

AGAACTATAATCGTGCCGGTAATGCTCTGGAAGGCTCACCGGCTGAAATCAAGG

ACCTGGCTGAACTGTGTGCGGCACTGAAAGGCACTAGTGACAAAAACAATGGCT

CTGGTAGCAAAGAGAAAAACAAAGATGGCAAGTACTCATTCAACGCTAAAGGTG

AACTGAGCGAAAAAACGATCCTGCGTGCGAATGGCACCCGTCTGGAATACACCG

AAATCAAATCCGATGGTACGGGCAAAGCAAAGGAAGTCCTGAAAGATTTTGCTC

TGGAAGGTACCCTGGCGGCCGACAAAACCACGCTGAAGGTGACGTGCGGCACCG

TGGTTCTGAGCAAACATATTCCGAACTCTGGTGAAATCACCGTTGAACTGAACGA

TAGCAATTCTACGCAGGCAACCAAAAAGACGGGCAAATGGGACAGTAATACCTC

CACGCTGACCATTTCAGTCAACTCGAAAAAGACCAAAAATATTGTGTTCACGAA

GGAAGATACGATCACCGTTCAAAAATATGACTCCGCGGGCACCAACCTGGAAGG

CAATGCCGTCGAAATCAAAACCCTGGATGAACTGTGTAATGCTCTGAAG

Lip-S3D1-S4D1_His_aa
Heterodimer fusion protein of OspA serotypes 3 and 4 both with disulfide bond type 1, *E. coli* lpp lipidation signal, N-terminal CSS for addition of lipids, N-terminal lipidation, LN1 peptide linker (SEQ ID NO: 184), C-terminal His tag (GLEHHHHHH) (SEQ ID NO: 214)

SEQ ID NO: 57

LipCSSFNEKGKLSEKVVTRANGTRLEYTEIKNDGSGKAKEVLKGFALEGTLTDGGET

KLTVTCGTVTLSKNISKSGEITVALNDTETTPADKKTGEWKSDTSTLTISKNSQKPKQ

LVFTKENTITVQNYNRAGNALEGSPAEIKDLAELCAALKGTSDKNNGSGSKEKNKD

GKYSFNAKGELSEKTILRANGTRLEYTEIKSDGTGKAKEVLKDFALEGTLAADKTTL

KVTCGTVVLSKHIPNSGEITVELNDSNSTQATKKTGKWDSNTSTLTISVNSKKTKNIV

FTKEDTITVQKYDSAGTNLEGNAVEIKTLDELCNALKGLEHHHHHH

Lip-S3D1-S4D1_His_nt
Coding sequence for heterodimer fusion protein of OspA serotypes 3 and 4 both with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 58

ATGAAAGCTACTAAACTGGTACTGGGCGCGGTAATCCTGGGTTCTACTCTGCTGG

CAGGTTGCTCAAGCTTCAACGAAAAGGGCAAACTGTCGGAAAAAGTGGTCACCC

GCGCAAATGGCACCCGCCTGGAATACACGGAAATCAAAAACGATGGTAGCGGCA

AAGCGAAGGAAGTTCTGAAAGGCTTTGCCCTGGAAGGTACCCTGACGGATGGCG

GTGAAACCAAACTGACCGTGACGTGCGGCACCGTTACGCTGTCTAAAAACATTA

-continued

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAAAACACGATCACCGTGC

AGAACTATAATCGTGCCGGTAATGCTCTGGAAGGCTCACCGGCTGAAATCAAGG

ACCTGGCTGAACTGTGTGCGGCACTGAAAGGCACTAGTGACAAAAACAATGGCT

CTGGTAGCAAAGAGAAAAACAAAGATGGCAAGTACTCATTCAACGCTAAAGGTG

AACTGAGCGAAAAAACGATCCTGCGTGCGAATGGCACCCGTCTGGAATACACCG

AAATCAAATCCGATGGTACGGGCAAAGCAAAGGAAGTCCTGAAAGATTTTGCTC

TGGAAGGTACCCTGGCGGCCGACAAAACCACGCTGAAGGTGACGTGCGGCACCG

TGGTTCTGAGCAAACATATTCCGAACTCTGGTGAAATCACCGTTGAACTGAACGA

TAGCAATTCTACGCAGGCAACCAAAAAGACGGGCAAATGGGACAGTAATACCTC

CACGCTGACCATTTCAGTCAACTCGAAAAAGACCAAAAATATTGTGTTCACGAA

GGAAGATACGATCACCGTTCAAAAATATGACTCCGCGGGCACCAACCTGGAAGG

CAATGCCGTCGAAATCAAAACCCTGGATGAACTGTGTAATGCTCTGAAGGGTCTC

GAGCACCACCACCACCACCAC

S5D4-S6D4_aa
Heterodimer fusion protein OspA serotypes 5 and 6 both with disulfide bond type 4, LN1 peptide linker (SEQ ID NO: 184)

SEQ ID NO: 59

FNEKGEISEKTIVRACGTRLEYTDIKSDKTGKAKEVLKDFTLEGTLAADGKTTLKVTE

GTVTLSKNISKSGEITVALDDTDSSGNKKSGTWDSGTSTLTISKNRTKTKQLVFTKEC

TITVQNYDSAGTNLEGKAVEITTLKELKNALKGTSDKNNGSGSKEKNKDGKYSFNG

KGETSEKTIVRACGTRLEYTDIKSDGSGKAKEVLKDFTLEGTLAADGKTTLKVTEGT

VVLSKNILKSGEITAALDDSDTTRATKKTGKWDSKTSTLTISVNSQKTKNLVFTKECT

ITVQRYDSAGTNLEGKAVEITTLKELKNALK

Lip-S5D4-S6D4_nt
Coding sequence for intermediate and final heterodimer fusion proteins OspA serotypes 5 and 6 both with disulfide bond type 4, *E. coli* lpp lipidation signal, N-terminal CSS for addition of lipids, LN1 peptide linker (SEQ ID NO: 184)

SEQ ID NO: 60

ATGAAAGCTACTAAACTGGTACTGGGCGCGGTAATCCTGGGTTCTACTCTGCTGG

CAGGTTGCTCAAGCTTCAACGAAAAGGGCGAAATCAGTGAAAAAACCATTGTGC

GTGCGTGTGGCACCCGTCTGGAATATACCGACATCAAGAGCGATAAAACGGGTA

AAGCGAAGGAAGTTCTGAAAGATTTTACGCTGGAAGGTACCCTGGCAGCAGACG

GTAAAACCACGCTGAAGGTGACCGAAGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGACTCAGGCACCTCGACGCTGACCATTTCTAAAAATC

GTACGAAAACCAAGCAGCTGGTCTTCACGAAAGAATGCACGATCACCGTGCAAA

ACTATGATAGCGCAGGTACCAATCTGGAAGGCAAAGCTGTGGAAATTACCACGC

TGAAAGAACTGAAGAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGTGAAAAAACGATTGTTCGCGCCTGTGGCACCCGCCTGGAATACACGGAT

ATCAAGTCGGATGGTTCGGGCAAAGCAAAGGAAGTCCTGAAAGATTTTACGCTG

-continued

GAAGGTACCCTGGCAGCAGACGGTAAAACCACGCTGAAGGTGACGGAAGGCAC

CGTGGTTCTGTCAAAAAACATTCTGAAGTCGGGTGAAATCACCGCAGCTCTGGAT

GACAGCGATACCACGCGTGCTACGAAAAAGACCGGTAAATGGGACAGCAAGAC

CTCTACGCTGACCATTAGTGTCAACTCCCAGAAAACGAAGAATCTGGTGTTCACC

AAAGAATGCACGATCACCGTTCAACGCTATGATAGTGCGGGCACCAACCTGGAA

GGCAAAGCCGTTGAAATTACCACGCTGAAAGAACTGAAGAATGCTCTGAAA

Lip-S5D4-S6D4_His_aa
Heterodimer fusion protein OspA serotypes 5 and 6 both with disulfide bond type 4, N-terminal CSS for addition of lipids, N-terminal lipidation, LN1 peptide linker (SEQ ID NO: 184), C-terminal His tag (GLEHHHHHH) (SEQ ID NO: 214)

SEQ ID NO: 61

LipCSSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALKGTSDKNNGSGSKEKNKDGK

YSFNGKGETSEKTIVRACGTRLEYTDIKSDGSGKAKEVLKDFTLEGTLAADGKTTLK

VTEGTVVLSKNILKSGEITAALDDSDTTRATKKTGKWDSKTSTLTISVNSQKTKNLVF

TKECTITVQRYDSAGTNLEGKAVEITTLKELKNALKGLEHHHHHH

Lip-S5D4-S6D4_His_nt
Coding sequence for heterodimer fusion protein OspA serotypes 5 and 6 both with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 62

ATGAAAGCTACTAAACTGGTACTGGGCGCGGTAATCCTGGGTTCTACTCTGCTGG

CAGGTTGCTCAAGCTTCAACGAAAAGGGCGAAATCAGTGAAAAAACCATTGTGC

GTGCGTGTGGCACCCGTCTGGAATATACCGACATCAAGAGCGATAAAACGGGTA

AAGCGAAGGAAGTTCTGAAAGATTTTACGCTGGAAGGTACCCTGGCAGCAGACG

GTAAAACCACGCTGAAGGTGACCGAAGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGACTCAGGCACCTCGACGCTGACCATTTCTAAAAATC

GTACGAAAACCAAGCAGCTGGTCTTCACGAAAGAATGCACGATCACCGTGCAAA

ACTATGATAGCGCAGGTACCAATCTGGAAGGCAAAGCTGTGGAAATTACCACGC

TGAAAGAACTGAAGAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGTGAAAAAACGATTGTTCGCGCCTGTGGCACCCGCCTGGAATACACGGAT

ATCAAGTCGGATGGTTCGGGCAAAGCAAAGGAAGTCCTGAAAGATTTTACGCTG

GAAGGTACCCTGGCAGCAGACGGTAAAACCACGCTGAAGGTGACGGAAGGCAC

CGTGGTTCTGTCAAAAAACATTCTGAAGTCGGGTGAAATCACCGCAGCTCTGGAT

GACAGCGATACCACGCGTGCTACGAAAAAGACCGGTAAATGGGACAGCAAGAC

CTCTACGCTGACCATTAGTGTCAACTCCCAGAAAACGAAGAATCTGGTGTTCACC

AAAGAATGCACGATCACCGTTCAACGCTATGATAGTGCGGGCACCAACCTGGAA

GGCAAAGCCGTTGAAATTACCACGCTGAAAGAACTGAAGAATGCTCTGAAAGGT

CTCGAGCACCACCACCACCACCAC

-continued

S5D1-S6D1_aa
Heterodimer fusion protein of OspA serotypes 6 both with disulfide bond type 1, LN1 peptide linker (SEQ ID NO: 184)

SEQ ID NO: 63

FNEKGEISEKTIVRANGTRLEYTDIKSDKTGKAKEVLKDFTLEGTLAADGKTTLKVT

CGTVTLSKNISKSGEITVALDDTDSSGNKKSGTWDSGTSTLTISKNRTKTKQLVFTKE

DTITVQNYDSAGTNLEGKAVEITTLKELCNALKGTSDKNNGSGSKEKNKDGKYSFN

GKGETSEKTIVRANGTRLEYTDIKSDGSGKAKEVLKDFTLEGTLAADGKTTLKVTCG

TVVLSKNILKSGEITAALDDSDTTRATKKTGKWDSKTSTLTISVNSQKTKNLVFTKED

TITVQRYDSAGTNLEGKAVEITTLKELCNALK

Lip-S5D1-S6D1_nt
Coding sequence for intermediate and final hetero-dimer fusion proteins of OspA serotypes 6 both with disulfide bond type 1, *E. coli* lpp lipidation signal, N-terminal CSS for addition of lipids, LN1 peptide linker (SEQ ID NO: 184)

SEQ ID NO: 64

ATGAAAGCTACTAAACTGGTACTGGGCGCGGTAATCCTGGGTTCTACTCTGCTGG

CAGGTTGCTCAAGCTTCAACGAAAAGGGCGAAATCTCAGAAAAAACCATCGTCC

GCGCTAACGGCACCCGCCTGGAATACACCGACATCAAATCAGACAAGACCGGTA

AAGCGAAGGAAGTTCTGAAAGATTTTACGCTGGAAGGTACCCTGGCAGCAGACG

GTAAAACCACGCTGAAGGTGACCTGCGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGATTCAGGCACCTCGACGCTGACCATTTCTAAAAATC

GTACGAAAACCAAGCAGCTGGTCTTCACGAAAGAAGATACGATCACCGTGCAAA

ACTATGACAGCGCAGGTACCAATCTGGAAGGCAAAGCTGTGGAAATTACCACGC

TGAAAGAACTGTGTAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGCGAAAAGACCATCGTGCGTGCGAACGGTACCCGCCTGGAATATACGGAC

ATTAAATCGGACGGCAGCGGCAAAGCAAAGGAAGTCCTGAAAGATTTTACGCTG

GAAGGTACCCTGGCAGCAGACGGTAAAACCACGCTGAAGGTGACGTGCGGCACC

GTGGTTCTGTCAAAAAACATTCTGAAGTCGGGTGAAATCACCGCAGCTCTGGATG

ACAGCGATACCACGCGTGCTACGAAAAAGACCGGTAAATGGGATAGCAAGACCT

CTACGCTGACCATTAGTGTCAACTCCCAGAAAACGAAGAATCTGGTGTTCACCAA

AGAAGATACGATCACCGTTCAACGCTATGACAGTGCGGGCACCAACCTGGAAGG

CAAAGCCGTTGAAATTACCACGCTGAAAGAACTGTGTAATGCTCTGAAA

Lip-S5D1-S6D1_His_aa
Heterodimer fusion protein of OspA serotypes 6 both with disulfide bond type 1, N-terminal CSS for addition of lipids, N-terminal lipidation, LN1 peptide linker (SEQ ID NO: 184), C-terminal His tag (GLEHHHHHH) (SEQ ID NO: 214)

SEQ ID NO: 65

LipCSSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGTSDKNNGSGSKEKNKDGK

YSFNGKGETSEKTIVRANGTRLEYTDIKSDGSGKAKEVLKDFTLEGTLAADGKTTLK

VTCGTVVLSKNILKSGEITAALDDSDTTRATKKTGKWDSKTSTLTISVNSQKTKNLV

FTKEDTITVQRYDSAGTNLEGKAVEITTLKELCNALKGLEHHHHHH

-continued

Lip-S5D1-S6D1_His_nt
Coding sequence for heterodimer fusion protein of OspA serotypes 6 both with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 66

ATGAAAGCTACTAAACTGGTACTGGGCGCGGTAATCCTGGGTTCTACTCTGCTGG

CAGGTTGCTCAAGCTTCAACGAAAAGGGCGAAATCTCAGAAAAAACCATCGTCC

GCGCTAACGGCACCCGCCTGGAATACACCGACATCAAATCAGACAAGACCGGTA

AAGCGAAGGAAGTTCTGAAAGATTTTACGCTGGAAGGTACCCTGGCAGCAGACG

GTAAAACCACGCTGAAGGTGACCTGCGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGATTCAGGCACCTCGACGCTGACCATTTCTAAAAATC

GTACGAAAACCAAGCAGCTGGTCTTCACGAAAGAAGATACGATCACCGTGCAAA

ACTATGACAGCGCAGGTACCAATCTGGAAGGCAAAGCTGTGGAAATTACCACGC

TGAAAGAACTGTGTAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGCGAAAAGACCATCGTGCGTGCGAACGGTACCCGCCTGGAATATACGGAC

ATTAAATCGGACGGCAGCGGCAAAGCAAAGGAAGTCCTGAAAGATTTTACGCTG

GAAGGTACCCTGGCAGCAGACGGTAAAACCACGCTGAAGGTGACGTGCGGCACC

GTGGTTCTGTCAAAAAACATTCTGAAGTCGGGTGAAATCACCGCAGCTCTGGATG

ACAGCGATACCACGCGTGCTACGAAAAAGACCGGTAAATGGGATAGCAAGACCT

CTACGCTGACCATTAGTGTCAACTCCCAGAAAACGAAGAATCTGGTGTTCACCAA

AGAAGATACGATCACCGTTCAACGCTATGACAGTGCGGGCACCAACCTGGAAGG

CAAAGCCGTTGAAATTACCACGCTGAAAGAACTGTGTAATGCTCTGAAAGGTCT

CGAGCACCACCACCACCACCAC

S2D4-S1D4_aa
Heterodimer fusion protein of OspA serotypes 2 and 1 both with disulfide bond type 4, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 67

FNEKGELSAKTMTRECGTKLEYTEMKSDGTGKAKEVLKNFTLEGKVANDKVTLEV

KEGTVTLSKEIAKSGEVTVALNDTNTTQATKKTGAWDSKTSTLTISVNSKKTTQLVF

TKQCTITVQKYDSAGTNLEGTAVEIKTLDELKNALKGTSDKNNGSGSKEKNKDGKY

SFNEKGEVSEKIITRACGTRLEYTGIKSDGSGKAKEVLKNFTLEGKVANDKTTLVVK

EGTVTLSKNISKSGEVSVELNDTDSSAATKKTAAWNSGTSTLTITVNSKKTKDLVFT

KECTITVQQYDSNGTKLEGSAVEITKLDEIKNALK

Lip-S2D4-S1D4_nt
Coding sequence for intermediate and final heterodimer fusion proteins of OspA serotypes 2 and 1 both with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 68

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

-continued
GTGAATGCGGCACCAAACTGGAATATACGGAAATGAAAAGCGATGGCACCGGTA

AAGCGAAAGAAGTTCTGAAAAACTTTACCCTGGAAGGCAAAGTCGCCAATGACA

AAGTCACCCTGGAAGTGAAAGAAGGCACCGTTACGCTGTCAAAAGAAATTGCAA

AATCGGGTGAAGTGACCGTTGCTCTGAACGATACGAATACCACGCAAGCGACCA

AGAAAACCGGCGCCTGGGACAGCAAAACCTCTACGCTGACCATTAGTGTTAACA

GCAAGAAAACCACGCAGCTGGTCTTCACCAAACAATGTACGATCACCGTGCAGA

AATACGATAGTGCGGGTACCAACCTGGAAGGCACCGCTGTTGAAATCAAAACCC

TGGACGAACTGAAAAACGCCCTGAAAGGCACTAGTGACAAAAACAATGGCTCTG

GTAGCAAAGAGAAAAACAAAGATGGCAAGTACTCATTCAACGAAAAAGGCGAA

GTCTCGGAAAAAATCATTACCCGTGCTTGCGGCACCCGTCTGGAATACACCGGCA

TTAAATCGGATGGCAGCGGCAAAGCGAAGGAAGTTCTGAAAAACTTTACCCTGG

AAGGCAAAGTCGCAAATGATAAGACCACCCTGGTGGTGAAAGAAGGCACCGTTA

CGCTGAGCAAAAACATTAGTAAGTCCGGTGAAGTCTCTGTGGAACTGAATGATA

CCGACAGCTCTGCGGCCACCAAAAAGACGGCAGCTTGGAACTCAGGCACCTCGA

CGCTGACCATTACGGTTAATTCCAAAAAGACCAAAGATCTGGTCTTCACGAAAG

AATGCACCATCACGGTGCAGCAATATGACAGCAACGGTACCAAACTGGAAGGCT

CTGCGGTGGAAATCACGAAACTGGATGAAATCAAAAATGCACTGAAA

Lip-S2D4-S1D4_His_aa
Heterodimer fusion protein of OspA serotypes 2 and 1 both with disulfide bond type 4, N-terminal CSS for addition of lipids, N-terminal lipidation, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 69
LipCSSFNEKGELSAKTMTRECGTKLEYTEMKSDGTGKAKEVLKNFTLEGKVANDK

VTLEVKEGTVTLSKEIAKSGEVTVALNDTNTTQATKKTGAWDSKTSTLTISVNSKKT

TQLVFTKQCTITVQKYDSAGTNLEGTAVEIKTLDELKNALKGTSDKNNGSGSKEKN

KDGKYSFNEKGEVSEKIITRACGTRLEYTGIKSDGSGKAKEVLKNFTLEGKVANDKT

TLVVKEGTVTLSKNISKSGEVSVELNDTDSSAATKKTAAWNSGTSTLTITVNSKKTK

DLVFTKECTITVQQYDSNGTKLEGSAVEITKLDEIKNALKGLEHHHHHH

Lip-S2D4-S1D4_His_nt
Coding sequence for heterodimer fusion protein of OspA serotypes 2 and 1 both with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 70
ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAATGCGGCACCAAACTGGAATATACGGAAATGAAAAGCGATGGCACCGGTA

AAGCGAAAGAAGTTCTGAAAAACTTTACCCTGGAAGGCAAAGTCGCCAATGACA

AAGTCACCCTGGAAGTGAAAGAAGGCACCGTTACGCTGTCAAAAGAAATTGCAA

AATCGGGTGAAGTGACCGTTGCTCTGAACGATACGAATACCACGCAAGCGACCA

AGAAAACCGGCGCCTGGGACAGCAAAACCTCTACGCTGACCATTAGTGTTAACA

GCAAGAAAACCACGCAGCTGGTCTTCACCAAACAATGTACGATCACCGTGCAGA

-continued

AATACGATAGTGCGGGTACCAACCTGGAAGGCACCGCTGTTGAAATCAAAACCC

TGGACGAACTGAAAAACGCCCTGAAAGGCACTAGTGACAAAAACAATGGCTCTG

GTAGCAAAGAGAAAAACAAAGATGGCAAGTACTCATTCAACGAAAAAGGCGAA

GTCTCGGAAAAAATCATTACCCGTGCTTGCGGCACCCGTCTGGAATACACCGGCA

TTAAATCGGATGGCAGCGGCAAAGCGAAGGAAGTTCTGAAAAACTTTACCCTGG

AAGGCAAAGTCGCAAATGATAAGACCACCCTGGTGGTGAAAGAAGGCACCGTTA

CGCTGAGCAAAAACATTAGTAAGTCCGGTGAAGTCTCTGTGGAACTGAATGATA

CCGACAGCTCTGCGGCCACCAAAAAGACGGCAGCTTGGAACTCAGGCACCTCGA

CGCTGACCATTACGGTTAATTCCAAAAAGACCAAAGATCTGGTCTTCACGAAAG

AATGCACCATCACGGTGCAGCAATATGACAGCAACGGTACCAAACTGGAAGGCT

CTGCGGTGGAAATCACGAAACTGGATGAAATCAAAAATGCACTGAAAGGTCTCG

AGCACCACCACCACCACCAC

S2D1-S1D1_aa
Heterodimer fusion protein of OspA serotypes 2 and 1 both with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 71

FNEKGELSAKTMTRENGTKLEYTEMKSDGTGKAKEVLKNFTLEGKVANDKVTLEV

KCGTVTLSKEIAKSGEVTVALNDTNTTQATKKTGAWDSKTSTLTISVNSKKTTQLVF

TKQDTITVQKYDSAGTNLEGTAVEIKTLDELCNALKGTSDKNNGSGSKEKNKDGKY

SFNEKGEVSEKIITRADGTRLEYTGIKSDGSGKAKEVLKNFTLEGKVANDKTTLVVK

CGTVTLSKNISKSGEVSVELNDTDSSAATKKTAAWNSGTSTLTITVNSKKTKDLVFT

KENTITVQQYDSNGTKLEGSAVEITKLDEICNALK

Lip-S2D1-S1D1_nt
Coding sequence for intermediate and final heterodimer fusion proteins of OspA serotypes 2 and 1 both with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 72

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAAAACGGCACCAAACTGGAATATACGGAAATGAAAAGCGATGGCACCGGT

AAAGCGAAAGAAGTTCTGAAAAACTTTACCCTGGAAGGCAAAGTCGCCAATGAC

AAAGTCACCCTGGAAGTGAAATGCGGCACCGTTACGCTGTCAAAAGAAATTGCA

AAATCGGGTGAAGTGACCGTTGCTCTGAACGATACGAATACCACGCAAGCGACC

AAGAAAACCGGCGCCTGGGACAGCAAAACCTCTACGCTGACCATTAGTGTTAAT

AGCAAGAAAACCACGCAGCTGGTCTTCACCAAACAAGATACGATCACCGTGCAG

AAATACGACAGTGCGGGTACCAACCTGGAAGGCACGGCTGTTGAAATCAAAACC

CTGGACGAACTGTGTAACGCCCTGAAAGGCACTAGTGACAAAAACAATGGCTCT

GGTAGCAAAGAGAAAAACAAAGATGGCAAGTACTCATTCAACGAAAAAGGCGA

AGTCAGCGAAAAAATCATTACCCGCGCAGACGGCACCCGCCTGGAATACACCGG

CATCAAATCGGACGGCAGCGGCAAAGCGAAAGAAGTTCTGAAAAACTTTACCCT

GGAAGGCAAAGTCGCAAATGATAAAACCACCCTGGTGGTGAAATGCGGCACCGT

TACGCTGAGCAAAAACATTAGTAAATCCGGTGAAGTCTCTGTGGAACTGAATGA

-continued

TACCGACAGCTCTGCGGCCACCAAGAAAACCGCAGCTTGGAACTCAGGCACCTC

GACGCTGACCATTACGGTTAATAGCAAGAAAACCAAAGATCTGGTCTTCACGAA

AGAAAACACCATCACGGTGCAGCAATATGACAGCAATGGTACCAAACTGGAAGG

CTCCGCTGTGGAAATCACGAAACTGGATGAAATCTGTAATGCACTGAAA

Lip-S2D1-S1D1_His_aa
Heterodimer fusion protein of OspA serotypes 2 and 1 both with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation, C-terminal His tag (GLEHHHHHH) (SEQ ID NO: 214)

SEQ ID NO: 73

LipCSSFNEKGELSAKTMTRENGTKLEYTEMKSDGTGKAKEVLKNFTLEGKVANDK

VTLEVKCGTVTLSKEIAKSGEVTVALNDTNTTQATKKTGAWDSKTSTLTISVNSKKT

TQLVFTKQDTITVQKYDSAGTNLEGTAVEIKTLDELCNALKGTSDKNNGSGSKEKN

KDGKYSFNEKGEVSEKIITRADGTRLEYTGIKSDGSGKAKEVLKNFTLEGKVANDKT

TLVVKCGTVTLSKNISKSGEVSVELNDTDSSAATKKTAAWNSGTSTLTITVNSKKTK

DLVFTKENTITVQQYDSNGTKLEGSAVEITKLDEICNALKGLEHHHHHH

Lip-S2D1-S1D1_His_nt
Coding sequence for heterodimer fusion protein of OspA serotypes 2 and 1 both with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 74

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAAAACGGCACCAAACTGGAATATACGGAAATGAAAAGCGATGGCACCGGT

AAAGCGAAAGAAGTTCTGAAAAACTTTACCCTGGAAGGCAAAGTCGCCAATGAC

AAAGTCACCCTGGAAGTGAAATGCGGCACCGTTACGCTGTCAAAAGAAATTGCA

AAATCGGGTGAAGTGACCGTTGCTCTGAACGATACGAATACCACGCAAGCGACC

AAGAAAACCGGCGCCTGGGACAGCAAAACCTCTACGCTGACCATTAGTGTTAAT

AGCAAGAAAACCACGCAGCTGGTCTTCACCAAACAAGATACGATCACCGTGCAG

AAATACGACAGTGCGGGTACCAACCTGGAAGGCACGGCTGTTGAAATCAAAACC

CTGGACGAACTGTGTAACGCCCTGAAAGGCACTAGTGACAAAAACAATGGCTCT

GGTAGCAAAGAGAAAAACAAAGATGGCAAGTACTCATTCAACGAAAAAGGCGA

AGTCAGCGAAAAAATCATTACCCGCGCAGACGGCACCCGCCTGGAATACACCGG

CATCAAATCGGACGGCAGCGGCAAAGCGAAAGAAGTTCTGAAAAACTTTACCCT

GGAAGGCAAAGTCGCAAATGATAAAACCACCCTGGTGGTGAAATGCGGCACCGT

TACGCTGAGCAAAAACATTAGTAAATCCGGTGAAGTCTCTGTGGAACTGAATGA

TACCGACAGCTCTGCGGCCACCAAGAAAACCGCAGCTTGGAACTCAGGCACCTC

GACGCTGACCATTACGGTTAATAGCAAGAAAACCAAAGATCTGGTCTTCACGAA

AGAAAACACCATCACGGTGCAGCAATATGACAGCAATGGTACCAAACTGGAAGG

CTCCGCTGTGGAAATCACGAAACTGGATGAAATCTGTAATGCACTGAAAGGTCT

CGAGCACCACCACCACCACCAC

-continued

S4D4-S3D4_aa
Heterodimer fusion protein of OspA serotypes 4 and 3 both with disulfide bond type 4, N-terminal CSS for addition of lipids, LN1 peptide linker (SEQ ID NO: 184)

SEQ ID NO: 75

FNAKGELSEKTILRACGTRLEYTEIKSDGTGKAKEVLKDFALEGTLAADKTTLKVTE

GTVVLSKHIPNSGEITVELNDSNSTQATKKTGKWDSNTSTLTISVNSKKTKNIVFTKE

CTITVQKYDSAGTNLEGNAVEIKTLDELKNALKGTSDKNNGSGSKEKNKDGKYSFN

DKGKLSEKVVTRACGTRLEYTEIKNDGSGKAKEVLKGFALEGTLTDGGETKLTVTE

GTVTLSKNISKSGEITVALNDTETTPADKKTGEWKSDTSTLTISKNSQKPKQLVFTKE

CTITVQNYNRAGNALEGSPAEIKDLAELKAALK

Lip-S4D4-S3D4_nt
Coding sequence for intermediate and final hetero-dimer fusion proteins of OspA serotypes 4 and 3 both with disulfide bond type 4, *E. coli* lpp lipidation signal, N-terminal CSS for addition of lipids, LN1 peptide linker (SEQ ID NO: 184)

SEQ ID NO: 76

ATGAAAGCTACTAAACTGGTACTGGGCGCGGTAATCCTGGGTTCTACTCTGCTGG

CAGGTTGCTCAAGCTTCAACGCTAAAGGTGAACTGTCGGAAAAAACCATCCTGC

GCGCCTGTGGCACCCGCCTGGAATACACGGAAATCAAGTCGGACGGCACGGGCA

AAGCAAAGGAAGTCCTGAAAGATTTTGCTCTGGAAGGTACCCTGGCGGCCGACA

AAACCACGCTGAAGGTGACGGAAGGCACCGTGGTTCTGAGCAAACATATTCCGA

ACTCTGGTGAAATCACCGTTGAACTGAACGATAGCAATTCTACGCAGGCGACCA

AAAAGACGGGCAAATGGGACAGTAATACCTCCACGCTGACCATTTCAGTCAACT

CGAAAAAGACCAAAAATATTGTGTTCACGAAGGAATGCACGATCACCGTTCAAA

AATATGATTCCGCAGGTACCAACCTGGAAGGCAACGCTGTGGAAATCAAAACCC

TGGACGAACTGAAAAACGCCCTGAAGGGTACTAGTGACAAAAACAATGGCTCTG

GTAGCAAAGAGAAAAACAAAGATGGCAAGTACTCATTTAACGATAAGGGCAAA

CTGTCAGAAAAAGTGGTCACCCGCGCTTGTGGCACCCGCCTGGAATACACCGAA

ATCAAAAACGACGGCTCGGGCAAAGCGAAGGAAGTTCTGAAAGGCTTTGCCCTG

GAAGGTACCCTGACGGATGGCGGTGAAACCAAACTGACCGTGACGGAAGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAATGCACGATCACCGTGCAGAACTATAATCGTGCCGGTAATGCTCTGGAA

GGCTCCCCGGCTGAAATCAAGGACCTGGCGGAACTGAAGGCGGCACTGAAA

Lip-S4D4-S3D4_His_aa
Heterodimer fusion protein of OspA serotypes 4 and 3 both with disulfide bond type 4, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 77

LipCSSFNAKGELSEKTILRACGTRLEYTEIKSDGTGKAKEVLKDFALEGTLAADKTT

LKVTEGTVVLSKHIPNSGEITVELNDSNSTQATKKTGKWDSNTSTLTISVNSKKTKNI

VFTKECTITVQKYDSAGTNLEGNAVEIKTLDELKNALKGTSDKNNGSGSKEKNKDG

KYSFNDKGKLSEKVVTRACGTRLEYTEIKNDGSGKAKEVLKGFALEGTLTDGGETK

-continued

LTVTEGTVTLSKNISKSGEITVALNDTETTPADKKTGEWKSDTSTLTISKNSQKPKQL

VFTKECTITVQNYNRAGNALEGSPAEIKDLAELKAALKGLEHHHHHH

Lip-S4D4-S3D4_His_nt
Coding sequence for heterodimer fusion protein of OspA serotypes 4 and 3 both with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 78

ATGAAAGCTACTAAACTGGTACTGGGCGCGGTAATCCTGGGTTCTACTCTGCTGG

CAGGTTGCTCAAGCTTCAACGCTAAAGGTGAACTGTCGGAAAAAACCATCCTGC

GCGCCTGTGGCACCCGCCTGGAATACACGGAAATCAAGTCGGACGGCACGGGCA

AAGCAAAGGAAGTCCTGAAAGATTTTGCTCTGGAAGGTACCCTGGCGGCCGACA

AAACCACGCTGAAGGTGACGGAAGGCACCGTGGTTCTGAGCAAACATATTCCGA

ACTCTGGTGAAATCACCGTTGAACTGAACGATAGCAATTCTACGCAGGCGACCA

AAAAGACGGGCAAATGGGACAGTAATACCTCCACGCTGACCATTTCAGTCAACT

CGAAAAAGACCAAAAATATTGTGTTCACGAAGGAATGCACGATCACCGTTCAAA

AATATGATTCCGCAGGTACCAACCTGGAAGGCAACGCTGTGGAAATCAAAACCC

TGGACGAACTGAAAAACGCCCTGAAGGGTACTAGTGACAAAAACAATGGCTCTG

GTAGCAAAGAGAAAAACAAAGATGGCAAGTACTCATTTAACGATAAGGGCAAA

CTGTCAGAAAAAGTGGTCACCCGCGCTTGTGGCACCCGCCTGGAATACACCGAA

ATCAAAAACGACGGCTCGGGCAAAGCGAAGGAAGTTCTGAAAGGCTTTGCCCTG

GAAGGTACCCTGACGGATGGCGGTGAAACCAAACTGACCGTGACGGAAGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAATGCACGATCACCGTGCAGAACTATAATCGTGCCGGTAATGCTCTGGAA

GGCTCCCCGGCTGAAATCAAGGACCTGGCGGAACTGAAGGCGGCACTGAAAGGT

CTCGAGCACCACCACCACCACCAC

S4D1-S3D1_aa
Heterodimer fusion protein of OspA serotypes 4 and 3 both with disulfide bond type 1, LN1 peptide linker (SEQ ID NO: 184)

SEQ ID NO: 79

FNAKGELSEKTILRANGTRLEYTEIKSDGTGKAKEVLKDFALEGTLAADKTTLKVTC

GTVVLSKHIPNSGEITVELNDSNSTQATKKTGKWDSNTSTLTISVNSKKTKNIVFTKE

DTITVQKYDSAGTNLEGNAVEIKTLDELCNALKGTSDKNNGSGSKEKNKDGKYSFN

DKGKLSEKVVTRANGTRLEYTEIKNDGSGKAKEVLKGFALEGTLTDGGETKLTVTC

GTVTLSKNISKSGEITVALNDTETTPADKKTGEWKSDTSTLTISKNSQKPKQLVFTKE

NTITVQNYNRAGNALEGSPAEIKDLAELCAALK

Lip-S4D1-S3D1_nt
Coding sequence for intermediate and final hetero-dimer fusion proteins of OspA serotypes 4 and 3 both with disulfide bond type 1, *E. coli* lpp lipidation signal, N-terminal CSS for addition of lipids, LN1 peptide linker (SEQ ID NO: 184)

SEQ ID NO: 80

ATGAAAGCTACTAAACTGGTACTGGGCGCGGTAATCCTGGGTTCTACTCTGCTGG

CAGGTTGCTCAAGCTTCAATGCTAAGGGCGAACTGAGCGAAAAAACGATCCTGC

-continued

GTGCGAATGGCACCCGTCTGGAATACACCGAAATCAAATCCGATGGTACGGGCA

AAGCAAAGGAAGTCCTGAAAGATTTTGCTCTGGAAGGTACCCTGGCGGCCGACA

AAACCACGCTGAAGGTGACGTGCGGCACCGTGGTTCTGAGCAAACATATTCCGA

ACTCTGGTGAAATCACCGTTGAACTGAACGATAGCAATTCTACGCAGGCAACCA

AAAAGACGGGCAAATGGGACAGTAATACCTCCACGCTGACCATTTCAGTCAACT

CGAAAAAGACCAAAAATATTGTGTTCACGAAGGAAGATACGATCACCGTTCAAA

AATATGACTCCGCGGGCACCAACCTGGAAGGCAATGCCGTCGAAATCAAAACCC

TGGATGAACTGTGTAACGCCCTGAAGGGTACTAGTGACAAAAACAATGGCTCTG

GTAGCAAAGAGAAAAACAAAGATGGCAAGTACTCATTTAACGATAAGGGCAAA

CTGTCGGAAAAAGTGGTCACCCGCGCAAATGGCACCCGCCTGGAATACACGGAA

ATCAAAAACGATGGTAGCGGCAAAGCGAAGGAAGTTCTGAAAGGCTTTGCCCTG

GAAGGTACCCTGACGGATGGCGGTGAAACCAAACTGACCGTGACGTGCGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAAAACACGATCACCGTGCAGAACTATAATCGTGCCGGTAATGCTCTGGAA

GGCTCACCGGCTGAAATCAAGGACCTGGCTGAACTGTGTGCGGCACTGAAA

Lip-S4D1-S3D1_His_aa
Heterodimer fusion protein of OspA serotypes 4 and 3 both with disulfide bond type 1, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 81

LipCSSFNAKGELSEKTILRANGTRLEYTEIKSDGTGKAKEVLKDFALEGTLAADKTTL

KVTCGTVVLSKHIPNSGEITVELNDSNSTQATKKTGKWDSNTSTLTISVNSKKTKNIV

FTKEDTITVQKYDSAGTNLEGNAVEIKTLDELCNALKGTSDKNNGSGSKEKNKDGK

YSFNDKGKLSEKVVTRANGTRLEYTEIKNDGSGKAKEVLKGFALEGTLTDGGETKL

TVTCGTVTLSKNISKSGEITVALNDTETTPADKKTGEWKSDTSTLTISKNSQKPKQLV

FTKENTITVQNYNRAGNALEGSPAEIKDLAELCAALKGLEHHHHHH

Lip-S4D1-S3D1_His_nt
Coding sequence for heterodimer fusion protein of OspA serotypes 4 and 3 both with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 82

ATGAAAGCTACTAAACTGGTACTGGGCGCGGTAATCCTGGGTTCTACTCTGCTGG

CAGGTTGCTCAAGCTTCAATGCTAAGGGCGAACTGAGCGAAAAAACGATCCTGC

GTGCGAATGGCACCCGTCTGGAATACACCGAAATCAAATCCGATGGTACGGGCA

AAGCAAAGGAAGTCCTGAAAGATTTTGCTCTGGAAGGTACCCTGGCGGCCGACA

AAACCACGCTGAAGGTGACGTGCGGCACCGTGGTTCTGAGCAAACATATTCCGA

ACTCTGGTGAAATCACCGTTGAACTGAACGATAGCAATTCTACGCAGGCAACCA

AAAAGACGGGCAAATGGGACAGTAATACCTCCACGCTGACCATTTCAGTCAACT

CGAAAAAGACCAAAAATATTGTGTTCACGAAGGAAGATACGATCACCGTTCAAA

AATATGACTCCGCGGGCACCAACCTGGAAGGCAATGCCGTCGAAATCAAAACCC

TGGATGAACTGTGTAACGCCCTGAAGGGTACTAGTGACAAAAACAATGGCTCTG

-continued

GTAGCAAAGAGAAAAACAAAGATGGCAAGTACTCATTTAACGATAAGGGCAAA

CTGTCGGAAAAAGTGGTCACCCGCGCAAATGGCACCCGCCTGGAATACACGGAA

ATCAAAAACGATGGTAGCGGCAAAGCGAAGGAAGTTCTGAAAGGCTTTGCCCTG

GAAGGTACCCTGACGGATGGCGGTGAAACCAAACTGACCGTGACGTGCGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAAAACACGATCACCGTGCAGAACTATAATCGTGCCGGTAATGCTCTGGAA

GGCTCACCGGCTGAAATCAAGGACCTGGCTGAACTGTGTGCGGCACTGAAAGGT

CTCGAGCACCACCACCACCACCAC

S6D4-S5D4_aa
Heterodimer fusion protein of OspA serotypes 6 and 5 both with disulfide bond type 4, LN1 peptide linker (SEQ ID NO: 184)

SEQ ID NO: 83

FNGKGETSEKTIVRACGTRLEYTDIKSDGSGKAKEVLKDFTLEGTLAADGKTTLKVT

EGTVVLSKNILKSGEITAALDDSDTTRATKKTGKWDSKTSTLTISVNSQKTKNLVFTK

ECTITVQRYDSAGTNLEGKAVEITTLKELKNALKGTSDKNNGSGSKEKNKDGKYSF

NEKGEISEKTIVRACGTRLEYTDIKSDKTGKAKEVLKDFTLEGTLAADGKTTLKVTE

GTVTLSKNISKSGEITVALDDTDSSGNKKSGTWDSGTSTLTISKNRTKTKQLVFTKEC

TITVQNYDSAGTNLEGKAVEITTLKELKNALK

Lip-S6D4-S5D4_nt
Coding sequence for intermediate and final heterodimer fusion proteins of OspA serotypes 6 and 5 both with disulfide bond type 4, *E. coli* lpp lipidation signal, N-terminal CSS for addition of lipids, LN1 peptide linker (SEQ ID NO: 184)

SEQ ID NO: 84

ATGAAAGCTACTAAACTGGTACTGGGCGCGGTAATCCTGGGTTCTACTCTGCTGG

CAGGTTGCTCAAGCTTCAACGGCAAAGGTGAAACGAGTGAAAAAACGATTGTTC

GCGCCTGTGGCACCCGCCTGGAATACACGGATATCAAGTCGGATGGTTCGGGCA

AAGCAAAGGAAGTCCTGAAAGATTTTACGCTGGAAGGTACCCTGGCAGCAGACG

GTAAAACCACGCTGAAGGTGACGGAAGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGACAGCAAGACCTCTACGCTGACCATTAGTGTCA

ACTCCCAGAAAACGAAGAATCTGGTGTTCACCAAAGAATGCACGATCACCGTTC

AACGCTATGATAGTGCGGGCACCAACCTGGAAGGCAAAGCCGTTGAAATTACCA

CGCTGAAAGAACTGAAGAATGCTCTGAAAGGTACTAGTGACAAAAACAATGGCT

CTGGTAGCAAAGAGAAAAACAAAGATGGCAAGTACTCATTCAACGAAAAAGGC

GAAATCAGTGAAAAAACCATTGTGCGTGCGTGTGGCACCCGTCTGGAATATACC

GACATCAAGAGCGATAAAACGGGTAAAGCGAAGGAAGTTCTGAAAGATTTTACG

CTGGAAGGTACCCTGGCAGCAGACGGTAAAACCACGCTGAAGGTGACCGAAGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGACTCAGGCACC

TCGACGCTGACCATTTCTAAAAATCGTACGAAAACCAAGCAGCTGGTCTTCACGA

AAGAATGCACGATCACCGTGCAAAACTATGATAGCGCAGGTACCAATCTGGAAG

GCAAAGCTGTGGAAATTACCACGCTGAAAGAACTGAAGAATGCTCTGAAA

-continued

Lip-S6D4-S5D4_His_aa
Heterodimer fusion protein of OspA serotypes 6 and 5 both with disulfide bond type 4, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 85

LipCSSFNGKGETSEKTIVRACGTRLEYTDIKSDGSGKAKEVLKDFTLEGTLAADGKT

TLKVTEGTVVLSKNILKSGEITAALDDSDTTRATKKTGKWDSKTSTLTISVNSQKTK

NLVFTKECTITVQRYDSAGTNLEGKAVEITTLKELKNALKGTSDKNNGSGSKEKNKD

GKYSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALKGLEHHHHHH

Lip-S6D4-S5D4_His_nt
Coding sequence for heterodimer fusion protein of OspA serotypes 6 and 5 both with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 86

ATGAAAGCTACTAAACTGGTACTGGGCGCGGTAATCCTGGGTTCTACTCTGCTGG

CAGGTTGCTCAAGCTTCAACGGCAAAGGTGAAACGAGTGAAAAAACGATTGTTC

GCGCCTGTGGCACCCGCCTGGAATACACGGATATCAAGTCGGATGGTTCGGGCA

AAGCAAAGGAAGTCCTGAAAGATTTTACGCTGGAAGGTACCCTGGCAGCAGACG

GTAAAACCACGCTGAAGGTGACGGAAGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGACAGCAAGACCTCTACGCTGACCATTAGTGTCA

ACTCCCAGAAAACGAAGAATCTGGTGTTCACCAAAGAATGCACGATCACCGTTC

AACGCTATGATAGTGCGGGCACCAACCTGGAAGGCAAAGCCGTTGAAATTACCA

CGCTGAAAGAACTGAAGAATGCTCTGAAAGGTACTAGTGACAAAAACAATGGCT

CTGGTAGCAAAGAGAAAAACAAAGATGGCAAGTACTCATTCAACGAAAAAGGC

GAAATCAGTGAAAAAACCATTGTGCGTGCGTGTGGCACCCGTCTGGAATATACC

GACATCAAGAGCGATAAAACGGGTAAAGCGAAGGAAGTTCTGAAAGATTTTACG

CTGGAAGGTACCCTGGCAGCAGACGGTAAAACCACGCTGAAGGTGACCGAAGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGACTCAGGCACC

TCGACGCTGACCATTTCTAAAAATCGTACGAAAACCAAGCAGCTGGTCTTCACGA

AAGAATGCACGATCACCGTGCAAAACTATGATAGCGCAGGTACCAATCTGGAAG

GCAAAGCTGTGGAAATTACCACGCTGAAAGAACTGAAGAATGCTCTGAAAGGTC

TCGAGCACCACCACCACCACCAC

S6D1-S5D1_aa
Heterodimer fusion protein of OspA serotypes 6 and 5 both with disulfide bond type 1, LN1 peptide linker (SEQ ID NO: 184)

SEQ ID NO: 87

FNGKGETSEKTIVRANGTRLEYTDIKSDGSGKAKEVLKDFTLEGTLAADGKTTLKVT

CGTVVLSKNILKSGEITAALDDSDTTRATKKTGKWDSKTSTLTISVNSQKTKNLVFT

KEDTITVQRYDSAGTNLEGKAVEITTLKELCNALKGTSDKNNGSGSKEKNKDGKYS

FNEKGEISEKTIVRANGTRLEYTDIKSDKTGKAKEVLKDFTLEGTLAADGKTTLKVT

-continued

CGTVTLSKNISKSGEITVALDDTDSSGNKKSGTWDSGTSTLTISKNRTKTKQLVFTKE

DTITVQNYDSAGTNLEGKAVEITTLKELCNALK

Lip-S6D1-S5D1_nt
Coding sequence for intermediate and final hetero-dimer fusion proteins of OspA serotypes 6 and 5 both with disulfide bond type 1, *E. coli* lpp lipidation signal, N-terminal CSS for addition of lipids, LN1 peptide linker (SEQ ID NO: 184)

SEQ ID NO: 88

ATGAAAGCTACTAAACTGGTACTGGGCGCGGTAATCCTGGGTTCTACTCTGCTGG

CAGGTTGCTCAAGCTTCAACGGCAAAGGTGAAACGAGCGAAAAGACCATCGTGC

GTGCGAACGGTACCCGCCTGGAATATACGGACATTAAATCGGACGGCAGCGGCA

AAGCAAAGGAAGTCCTGAAAGATTTTACGCTGGAAGGTACCCTGGCAGCAGACG

GTAAAACCACGCTGAAGGTGACGTGCGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGATAGCAAGACCTCTACGCTGACCATTAGTGTCA

ACTCCCAGAAAACGAAGAATCTGGTGTTCACCAAAGAAGATACGATCACCGTTC

AACGCTATGACAGTGCGGGCACCAACCTGGAAGGCAAAGCCGTTGAAATTACCA

CGCTGAAAGAACTGTGTAATGCTCTGAAAGGTACTAGTGACAAAAACAATGGCT

CTGGTAGCAAAGAGAAAAACAAAGATGGCAAGTACTCATTCAACGAAAAAGGC

GAAATCTCAGAAAAAACCATCGTCCGCGCTAACGGCACCCGCCTGGAATACACC

GACATCAAATCAGACAAGACCGGTAAAGCGAAGGAAGTTCTGAAAGATTTTACG

CTGGAAGGTACCCTGGCAGCAGACGGTAAAACCACGCTGAAGGTGACCTGCGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGATTCAGGCACC

TCGACGCTGACCATTTCTAAAAATCGTACGAAAACCAAGCAGCTGGTCTTCACGA

AAGAAGATACGATCACCGTGCAAAACTATGACAGCGCAGGTACCAATCTGGAAG

GCAAAGCTGTGGAAATTACCACGCTGAAAGAACTGTGTAATGCTCTGAAA

Lip-S6D1-S5D1_His_aa
Heterodimer fusion protein of OspA serotypes 6 and 5 both with disulfide bond type 1, LN1 peptide linker (SEQ ID NO: 184), N-terminal lipidation, C-terminal His tag (GLEHHHHHH) (SEQ ID NO: 214)

SEQ ID NO: 89

LipCSSFNGKGETSEKTIVRANGTRLEYTDIKSDGSGKAKEVLKDFTLEGTLAADGKT

TLKVTCGTVVLSKNILKSGEITAALDDSDTTRATKKTGKWDSKTSTLTISVNSQKTK

NLVFTKEDTITVQRYDSAGTNLEGKAVEITTLKELCNALKGTSDKNNGSGSKEKNKD

GKYSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGLEHHHHHH

Lip-S6D1-S5D1_His_nt
Coding sequence for heterodimer fusion protein of OspA serotypes 6 and 5 both with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 90

ATGAAAGCTACTAAACTGGTACTGGGCGCGGTAATCCTGGGTTCTACTCTGCTGG

CAGGTTGCTCAAGCTTCAACGGCAAAGGTGAAACGAGCGAAAAGACCATCGTGC

GTGCGAACGGTACCCGCCTGGAATATACGGACATTAAATCGGACGGCAGCGGCA

-continued

AAGCAAAGGAAGTCCTGAAAGATTTTACGCTGGAAGGTACCCTGGCAGCAGACG

GTAAAACCACGCTGAAGGTGACGTGCGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGATAGCAAGACCTCTACGCTGACCATTAGTGTCA

ACTCCCAGAAAACGAAGAATCTGGTGTTCACCAAAGAAGATACGATCACCGTTC

AACGCTATGACAGTGCGGGCACCAACCTGGAAGGCAAAGCCGTTGAAATTACCA

CGCTGAAAGAACTGTGTAATGCTCTGAAAGGTACTAGTGACAAAAACAATGGCT

CTGGTAGCAAAGAGAAAAACAAAGATGGCAAGTACTCATTCAACGAAAAAGGC

GAAATCTCAGAAAAAACCATCGTCCGCGCTAACGGCACCCGCCTGGAATACACC

GACATCAAATCAGACAAGACCGGTAAAGCGAAGGAAGTTCTGAAAGATTTTACG

CTGGAAGGTACCCTGGCAGCAGACGGTAAAACCACGCTGAAGGTGACCTGCGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGATTCAGGCACC

TCGACGCTGACCATTTCTAAAAATCGTACGAAAACCAAGCAGCTGGTCTTCACGA

AAGAAGATACGATCACCGTGCAAAACTATGACAGCGCAGGTACCAATCTGGAAG

GCAAAGCTGTGGAAATTACCACGCTGAAAGAACTGTGTAATGCTCTGAAAGGTC

TCGAGCACCACCACCACCACCAC

S1D4-S2D1_aa
Heterodimer fusion protein of OspA serotype 1 with disulfide bond type 4 and OspA serotype 2 with disulfide bond type 1, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 91

FNEKGEVSEKIITRACGTRLEYTGIKSDGSGKAKEVLKNFTLEGKVANDKTTLVVKE

GTVTLSKNISKSGEVSVELNDTDSSAATKKTAAWNSGTSTLTITVNSKKTKDLVFTK

ECTITVQQYDSNGTKLEGSAVEITKLDEIKNALKGTSDKNNGSGSKEKNKDGKYSFN

EKGELSAKTMTRENGTKLEYTEMKSDGTGKAKEVLKNFTLEGKVANDKVTLEVKC

GTVTLSKEIAKSGEVTVALNDTNTTQATKKTGAWDSKTSTLTISVNSKKTTQLVFTK

QDTITVQKYDSAGTNLEGTAVEIKTLDELCNALK

Lip-S1D4-S2D1_nt
Coding sequence for intermediate and final heterodimer fusion proteins of OspA serotype 1 with disulfide bond type 4 and OspA serotype 2 with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 92

ATGAAAGCTACTAAACTGGTACTGGGCGCGGTAATCCTGGGTTCTACTCTGCTGG

CAGGTTGCTCAAGCTTCAACGAAAAGGGCGAAGTCTCGGAAAAAATCATTACCC

GTGCTTGCGGCACCCGTCTGGAATACACCGGCATTAAATCGGATGGCAGCGGCA

AAGCGAAGGAAGTTCTGAAAAACTTTACCCTGGAAGGCAAAGTCGCAAATGATA

AGACCACCCTGGTGGTGAAAGAAGGCACCGTTACGCTGAGCAAAAACATTAGTA

AGTCCGGTGAAGTCTCTGTGGAACTGAATGATACCGACAGCTCTGCGGCCACCA

AAAAGACGGCAGCTTGGAACTCAGGCACCTCGACGCTGACCATTACGGTTAATT

CCAAAAAGACCAAAGATCTGGTCTTCACGAAAGAATGCACCATCACGGTGCAGC

AATATGACAGCAACGGTACCAAACTGGAAGGCTCTGCGGTGGAAATCACGAAAC

-continued

TGGATGAAATCAAAAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAAAACGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAATGCGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAATAGCAAGAAAACCACGCAGCTGGTCTTCACCAAA

CAAGATACGATCACCGTGCAGAAATACGACAGTGCGGGTACCAACCTGGAAGGC

ACGGCTGTTGAAATCAAAACCCTGGACGAACTGTGTAACGCCCTGAAA

Lip-S1D4-S2D1_His_aa
Heterodimer fusion protein of OspA serotype 1 with disulfide bond type 4 and OspA serotype 2 with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation, C-terminal His tag (GLEHHHHHH) (SEQ ID NO: 214)

SEQ ID NO: 93

LipCSSFNEKGEVSEKIITRACGTRLEYTGIKSDGSGKAKEVLKNFTLEGKVANDKTTL

VVKEGTVTLSKNISKSGEVSVELNDTDSSAATKKTAAWNSGTSTLTITVNSKKTKDL

VFTKECTITVQQYDSNGTKLEGSAVEITKLDEIKNALKGTSDKNNGSGSKEKNKDGK

YSFNEKGELSAKTMTRENGTKLEYTEMKSDGTGKAKEVLKNFTLEGKVANDKVTL

EVKCGTVTLSKEIAKSGEVTVALNDTNTTQATKKTGAWDSKTSTLTISVNSKKTTQL

VFTKQDTITVQKYDSAGTNLEGTAVEIKTLDELCNALKGLEHHHHHH

Lip-S1D4-S2D1_His_nt
Coding sequence for heterodimer fusion protein of OspA serotype 1 with disulfide bond type 4 and OspA serotype 2 with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 94

ATGAAAGCTACTAAACTGGTACTGGGCGCGGTAATCCTGGGTTCTACTCTGCTGG

CAGGTTGCTCAAGCTTCAACGAAAAGGGCGAAGTCTCGGAAAAAATCATTACCC

GTGCTTGCGGCACCCGTCTGGAATACACCGGCATTAAATCGGATGGCAGCGGCA

AAGCGAAGGAAGTTCTGAAAAACTTTACCCTGGAAGGCAAAGTCGCAAATGATA

AGACCACCCTGGTGGTGAAAGAAGGCACCGTTACGCTGAGCAAAAACATTAGTA

AGTCCGGTGAAGTCTCTGTGGAACTGAATGATACCGACAGCTCTGCGGCCACCA

AAAAGACGGCAGCTTGGAACTCAGGCACCTCGACGCTGACCATTACGGTTAATT

CCAAAAAGACCAAAGATCTGGTCTTCACGAAAGAATGCACCATCACGGTGCAGC

AATATGACAGCAACGGTACCAAACTGGAAGGCTCTGCGGTGGAAATCACGAAAC

TGGATGAAATCAAAAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAAAACGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAATGCGGCACCGTT

ACGCTGTCAAAAGAAATTGCAAAATCGGGTGAAGTGACCGTTGCTCTGAACGAT

-continued

ACGAATACCACGCAAGCGACCAAGAAAACCGGCGCCTGGGACAGCAAAACCTCT

ACGCTGACCATTAGTGTTAATAGCAAGAAAACCACGCAGCTGGTCTTCACCAAA

CAAGATACGATCACCGTGCAGAAATACGACAGTGCGGGTACCAACCTGGAAGGC

ACGGCTGTTGAAATCAAAACCCTGGACGAACTGTGTAACGCCCTGAAAGGCCTC

GAGCACCACCACCACCACCAC

S1D1-S2D4_aa
Heterodimer fusion protein of OspA serotype 1 with disulfide bond type 1 and OspA serotype 2 with disulfide bond type 4, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 95

FNEKGEVSEKIITRADGTRLEYTGIKSDGSGKAKEVLKNFTLEGKVANDKTTLVVKC

GTVTLSKNISKSGEVSVELNDTDSSAATKKTAAWNSGTSTLTITVNSKKTKDLVFTK

ENTITVQQYDSNGTKLEGSAVEITKLDEICNALKGTSDKNNGSGSKEKNKDGKYSFN

EKGELSAKTMTRECGTKLEYTEMKSDGTGKAKEVLKNFTLEGKVANDKVTLEVKE

GTVTLSKEIAKSGEVTVALNDTNTTQATKKTGAWDSKTSTLTISVNSKKTTQLVFTK

QCTITVQKYDSAGTNLEGTAVEIKTLDELKNALK

Lip-S1D1-S2D4_nt
Coding sequence for intermediate and final heterodimer fusion proteins of OspA serotype 1 with disulfide bond type 1 and OspA serotype 2 with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 96

ATGAAAGCTACTAAACTGGTACTGGGCGCGGTAATCCTGGGTTCTACTCTGCTGG

CAGGTTGCTCAAGCTTCAACGAAAAGGGCGAAGTCAGCGAAAAAATCATTACCC

GCGCAGACGGCACCCGCCTGGAATACACCGGCATCAAATCGGACGGCAGCGGCA

AAGCGAAAGAAGTTCTGAAAAACTTTACCCTGGAAGGCAAAGTCGCAAATGATA

AAACCACCCTGGTGGTGAAATGCGGCACCGTTACGCTGAGCAAAAACATTAGTA

AATCCGGTGAAGTCTCTGTGGAACTGAATGATACCGACAGCTCTGCGGCCACCA

AGAAAACCGCAGCTTGGAACTCAGGCACCTCGACGCTGACCATTACGGTTAATA

GCAAGAAAACCAAAGATCTGGTCTTCACGAAAGAAAACACCATCACGGTGCAGC

AATATGACAGCAATGGTACCAAACTGGAAGGCTCCGCTGTGGAAATCACGAAAC

TGGATGAAATCTGTAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAATGCGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAAGAAGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAACAGCAAGAAAACCACGCAGCTGGTCTTCACCAAA

CAATGTACGATCACCGTGCAGAAATACGATAGTGCGGGTACCAACCTGGAAGGC

ACCGCTGTTGAAATCAAAACCCTGGACGAACTGAAAAACGCCCTGAAA

-continued

Lip-S1D1-S2D4_His_aa
Heterodimer fusion protein of OspA serotype 1 with disulfide bond type 1 and OspA serotype 2 with disulfide bond type 4, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation, C-terminal His tag (GLEHHHHHH) (SEQ ID NO: 214)

SEQ ID NO: 97

LipCSSFNEKGEVSEKIITRADGTRLEYTGIKSDGSGKAKEVLKNFTLEGKVANDKTTL

VVKCGTVTLSKNISKSGEVSVELNDTDSSAATKKTAAWNSGTSTLTITVNSKKTKDL

VFTKENTITVQQYDSNGTKLEGSAVEITKLDEICNALKGTSDKNNGSGSKEKNKDGK

YSFNEKGELSAKTMTRECGTKLEYTEMKSDGTGKAKEVLKNFTLEGKVANDKVTL

EVKEGTVTLSKEIAKSGEVTVALNDTNTTQATKKTGAWDSKTSTLTISVNSKKTTQL

VFTKQCTITVQKYDSAGTNLEGTAVEIKTLDELKNALKGLEHHHHHH

Lip-S1D1-S2D4_His_nt
Coding sequence for heterodimer fusion protein of OspA serotype 1 with disulfide bond type 1 and OspA serotype 2 with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 98

ATGAAAGCTACTAAACTGGTACTGGGCGCGGTAATCCTGGGTTCTACTCTGCTGG

CAGGTTGCTCAAGCTTCAACGAAAAGGGCGAAGTCAGCGAAAAAATCATTACCC

GCGCAGACGGCACCCGCCTGGAATACACCGGCATCAAATCGGACGGCAGCGGCA

AAGCGAAAGAAGTTCTGAAAAACTTTACCCTGGAAGGCAAAGTCGCAAATGATA

AAACCACCCTGGTGGTGAAATGCGGCACCGTTACGCTGAGCAAAAACATTAGTA

AATCCGGTGAAGTCTCTGTGGAACTGAATGATACCGACAGCTCTGCGGCCACCA

AGAAAACCGCAGCTTGGAACTCAGGCACCTCGACGCTGACCATTACGGTTAATA

GCAAGAAAACCAAAGATCTGGTCTTCACGAAAGAAAACACCATCACGGTGCAGC

AATATGACAGCAATGGTACCAAACTGGAAGGCTCCGCTGTGGAAATCACGAAAC

TGGATGAAATCTGTAATGCTCTGAAAGGTACTAGTGACAAAAACAATGGCTCTG

GTAGCAAAGAGAAAAACAAAGATGGCAAGTACTCATTCAACGAAAAAGGCGAA

CTGTCGGCGAAAACGATGACGCGTGAATGCGGCACCAAACTGGAATATACGGAA

ATGAAAAGCGATGGCACCGGTAAAGCGAAAGAAGTTCTGAAAAACTTTACCCTG

GAAGGCAAAGTCGCCAATGACAAAGTCACCCTGGAAGTGAAAGAAGGCACCGTT

ACGCTGTCAAAAGAAATTGCAAAATCGGGTGAAGTGACCGTTGCTCTGAACGAT

ACGAATACCACGCAAGCGACCAAGAAAACCGGCGCCTGGGACAGCAAAACCTCT

ACGCTGACCATTAGTGTTAACAGCAAGAAAACCACGCAGCTGGTCTTCACCAAA

CAATGTACGATCACCGTGCAGAAATACGATAGTGCGGGTACCAACCTGGAAGGC

ACCGCTGTTGAAATCAAAACCCTGGACGAACTGAAAAACGCCCTGAAAGGCCTC

GAGCACCACCACCACCACCAC

S3D4-S4D1_aa
Heterodimer fusion protein of OspA serotype 3 with disulfide bond type 4 and OspA serotype 4 with disulfide bond type 1, LN1 peptide linker (SEQ ID NO: 184)

SEQ ID NO: 99

FNEKGKLSEKVVTRACGTRLEYTEIKNDGSGKAKEVLKGFALEGTLTDGGETKLTV

TEGTVTLSKNISKSGEITVALNDTETTPADKKTGEWKSDTSTLTISKNSQKPKQLVFT

-continued

KECTITVQNYNRAGNALEGSPAEIKDLAELKAALKGTSDKNNGSGSKEKNKDGKYS

FNAKGELSEKTILRANGTRLEYTEIKSDGTGKAKEVLKDFALEGTLAADKTTLKVTC

GTVVLSKHIPNSGEITVELNDSNSTQATKKTGKWDSNTSTLTISVNSKKTKNIVFTKE

DTITVQKYDSAGTNLEGNAVEIKTLDELCNALK

Lip-S3D4-S4D1_nt
Coding sequence for intermediate and final hetero-dimer fusion proteins of OspA serotype 3 with di-sulfide bond type 4 and OspA serotype 4 with di-sulfide bond type 1, *E. coli* lpp lipidation sig-nal, N-terminal CSS for addition of lipids, LN1 peptide linker (SEQ ID NO: 184)

SEQ ID NO: 100

ATGAAAGCTACTAAACTGGTACTGGGCGCGGTAATCCTGGGTTCTACTCTGCTGG

CAGGTTGCTCAAGCTTCAACGAAAAGGGCAAACTGTCAGAAAAAGTGGTCACCC

GCGCTTGTGGCACCCGCCTGGAATACACCGAAATCAAAAACGACGGCTCGGGCA

AAGCGAAGGAAGTTCTGAAAGGCTTTGCCCTGGAAGGTACCCTGACGGATGGCG

GTGAAACCAAACTGACCGTGACGGAAGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAATGCACGATCACCGTGC

AGAACTATAATCGTGCCGGTAATGCTCTGGAAGGCTCCCCGGCTGAAATCAAGG

ACCTGGCGGAACTGAAGGCGGCACTGAAAGGCACTAGTGACAAAAACAATGGCT

CTGGTAGCAAAGAGAAAAACAAAGATGGCAAGTACTCATTCAACGCTAAAGGTG

AACTGAGCGAAAAAACGATCCTGCGTGCGAATGGCACCCGTCTGGAATACACCG

AAATCAAATCCGATGGTACGGGCAAAGCAAAGGAAGTCCTGAAAGATTTTGCTC

TGGAAGGTACCCTGGCGGCCGACAAAACCACGCTGAAGGTGACGTGCGGCACCG

TGGTTCTGAGCAAACATATTCCGAACTCTGGTGAAATCACCGTTGAACTGAACGA

TAGCAATTCTACGCAGGCAACCAAAAAGACGGGCAAATGGGACAGTAATACCTC

CACGCTGACCATTTCAGTCAACTCGAAAAAGACCAAAAATATTGTGTTCACGAA

GGAAGATACGATCACCGTTCAAAAATATGACTCCGCGGGCACCAACCTGGAAGG

CAATGCCGTCGAAATCAAAACCCTGGATGAACTGTGTAATGCTCTGAAG

Lip-S3D4-S4D1_His_aa
Heterodimer fusion protein of OspA serotype 3 with di-sulfide bond type 4 and OspA serotype 4 with disulfide bond type 1, N-terminal CSS for addition of lipids, LN1 peptide linker (SEQ ID NO: 184), N-terminal lipi-dation, C-terminal His tag (GLEHHHHHH) (SEQ ID NO: 214)

SEQ ID NO: 101

LipCSSFNEKGKLSEKVVTRACGTRLEYTEIKNDGSGKAKEVLKGFALEGTLTDGGET

KLTVTEGTVTLSKNISKSGEITVALNDTETTPADKKTGEWKSDTSTLTISKNSQKPKQ

LVFTKECTITVQNYNRAGNALEGSPAEIKDLAELKAALKGTSDKNNGSGSKEKNKD

GKYSFNAKGELSEKTILRANGTRLEYTEIKSDGTGKAKEVLKDFALEGTLAADKTTL

KVTCGTVVLSKHIPNSGEITVELNDSNSTQATKKTGKWDSNTSTLTISVNSKKTKNIV

FTKEDTITVQKYDSAGTNLEGNAVEIKTLDELCNALKGLEHHHHHH

-continued

Lip-S3D4-S4D1_His_nt
Coding sequence for heterodimer fusion protein of OspA serotype 3 with disulfide bond type 4 and OspA serotype 4 with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 102

ATGAAAGCTACTAAACTGGTACTGGGCGCGGTAATCCTGGGTTCTACTCTGCTGG

CAGGTTGCTCAAGCTTCAACGAAAAGGGCAAACTGTCAGAAAAAGTGGTCACCC

GCGCTTGTGGCACCCGCCTGGAATACACCGAAATCAAAAACGACGGCTCGGGCA

AAGCGAAGGAAGTTCTGAAAGGCTTTGCCCTGGAAGGTACCCTGACGGATGGCG

GTGAAACCAAACTGACCGTGACGGAAGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAATGCACGATCACCGTGC

AGAACTATAATCGTGCCGGTAATGCTCTGGAAGGCTCCCCGGCTGAAATCAAGG

ACCTGGCGGAACTGAAGGCGGCACTGAAAGGCACTAGTGACAAAAACAATGGCT

CTGGTAGCAAAGAGAAAAACAAAGATGGCAAGTACTCATTCAACGCTAAAGGTG

AACTGAGCGAAAAAACGATCCTGCGTGCGAATGGCACCCGTCTGGAATACACCG

AAATCAAATCCGATGGTACGGGCAAAGCAAAGGAAGTCCTGAAAGATTTTGCTC

TGGAAGGTACCCTGGCGGCCGACAAAACCACGCTGAAGGTGACGTGCGGCACCG

TGGTTCTGAGCAAACATATTCCGAACTCTGGTGAAATCACCGTTGAACTGAACGA

TAGCAATTCTACGCAGGCAACCAAAAAGACGGGCAAATGGGACAGTAATACCTC

CACGCTGACCATTTCAGTCAACTCGAAAAAGACCAAAAATATTGTGTTCACGAA

GGAAGATACGATCACCGTTCAAAAATATGACTCCGCGGGCACCAACCTGGAAGG

CAATGCCGTCGAAATCAAAACCCTGGATGAACTGTGTAATGCTCTGAAGGGTCTC

GAGCACCACCACCACCACCAC

S3D1-S4D4_aa
Heterodimer fusion protein of OspA serotype 3 with disulfide bond type 1 and OspA serotype 4 with disulfide bond type 1, LN1 peptide linker (SEQ ID NO: 184)

SEQ ID NO: 103

FNEKGKLSEKVVTRANGTRLEYTEIKNDGSGKAKEVLKGFALEGTLTDGGETKLTV

TCGTVTLSKNISKSGEITVALNDTETTPADKKTGEWKSDTSTLTISKNSQKPKQLVFT

KENTITVQNYNRAGNALEGSPAEIKDLAELCAALKGTSDKNNGSGSKEKNKDGKYS

FNAKGELSEKTILRACGTRLEYTEIKSDGTGKAKEVLKDFALEGTLAADKTTLKVTE

GTVVLSKHIPNSGEITVELNDSNSTQATKKTGKWDSNTSTLTISVNSKKTKNIVFTKE

CTITVQKYDSAGTNLEGNAVEIKTLDELKNALK

Lip-S3D1-S4D4_nt
Coding sequence for intermediate and final heterodimer fusion proteins of OspA serotype 3 with disulfide bond type 1 and OspA serotype 4 with disulfide bond type 1, *E. coli* lpp lipidation signal, N-terminal CSS for addition of lipids, LN1 peptide linker (SEQ ID NO: 184)

SEQ ID NO: 104

ATGAAAGCTACTAAACTGGTACTGGGCGCGGTAATCCTGGGTTCTACTCTGCTGG

CAGGTTGCTCAAGCTTCAACGAAAAGGGCAAACTGTCGGAAAAAGTGGTCACCC

GCGCAAATGGCACCCGCCTGGAATACACGGAAATCAAAAACGATGGTAGCGGCA

AAGCGAAGGAAGTTCTGAAAGGCTTTGCCCTGGAAGGTACCCTGACGGATGGCG

-continued

GTGAAACCAAACTGACCGTGACGTGCGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAAAACACGATCACCGTGC

AGAACTATAATCGTGCCGGTAATGCTCTGGAAGGCTCACCGGCTGAAATCAAGG

ACCTGGCTGAACTGTGTGCGGCACTGAAAGGCACTAGTGACAAAAACAATGGCT

CTGGTAGCAAAGAGAAAAACAAAGATGGCAAGTACTCATTCAACGCTAAAGGTG

AACTGTCGGAAAAAAACCATCCTGCGCGCCTGTGGCACCCGCCTGGAATACACGG

AAATCAAGTCGGACGGCACGGGCAAAGCAAAGGAAGTCCTGAAAGATTTTGCTC

TGGAAGGTACCCTGGCGGCCGACAAAACCACGCTGAAGGTGACGGAAGGCACC

GTGGTTCTGAGCAAACATATTCCGAACTCTGGTGAAATCACCGTTGAACTGAACG

ATAGCAATTCTACGCAGGCGACCAAAAAGACGGGCAAATGGGACAGTAATACCT

CCACGCTGACCATTTCAGTCAACTCGAAAAAGACCAAAAATATTGTGTTCACGA

AGGAATGCACGATCACCGTTCAAAAATATGATTCCGCAGGTACCAACCTGGAAG

GCAACGCTGTGGAAATCAAAACCCTGGACGAACTGAAAAATGCTCTGAAG

Lip-S3D1-S4D4_His_aa
Heterodimer fusion protein of OspA serotype 3 with disulfide bond type 1 and OspA serotype 4 with disulfide bond type 1, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 105

LipCSSFNEKGKLSEKVVTRANGTRLEYTEIKNDGSGKAKEVLKGFALEGTLTDGGET

KLTVTCGTVTLSKNISKSGEITVALNDTETTPADKKTGEWKSDTSTLTISKNSQKPKQ

LVFTKENTITVQNYNRAGNALEGSPAEIKDLAELCAALKGTSDKNNGSGSKEKNKD

GKYSFNAKGELSEKTILRACGTRLEYTEIKSDGTGKAKEVLKDFALEGTLAADKTTL

KVTEGTVVLSKHIPNSGEITVELNDSNSTQATKKTGKWDSNTSTLTISVNSKKTKNIV

FTKECTITVQKYDSAGTNLEGNAVEIKTLDELKNALKGLEHHHHHH

Lip-S3D1-S4D4_His_nt
Coding sequence for heterodimer fusion protein of OspA serotype 3 with disulfide bond type 1 and OspA serotype 4 with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 106

ATGAAAGCTACTAAACTGGTACTGGGCGCGGTAATCCTGGGTTCTACTCTGCTGG

CAGGTTGCTCAAGCTTCAACGAAAAGGGCAAACTGTCGGAAAAAGTGGTCACCC

GCGCAAATGGCACCCGCCTGGAATACACGGAAATCAAAAACGATGGTAGCGGCA

AAGCGAAGGAAGTTCTGAAAGGCTTTGCCCTGGAAGGTACCCTGACGGATGGCG

GTGAAACCAAACTGACCGTGACGTGCGGCACCGTTACGCTGTCTAAAAACATTA

GCAAGTCTGGTGAAATCACGGTCGCACTGAATGATACCGAAACCACGCCGGCTG

ACAAAAAGACCGGCGAATGGAAAAGTGACACCTCCACGCTGACCATTTCAAAGA

ACTCGCAGAAACCGAAGCAACTGGTCTTCACCAAAGAAAACACGATCACCGTGC

AGAACTATAATCGTGCCGGTAATGCTCTGGAAGGCTCACCGGCTGAAATCAAGG

ACCTGGCTGAACTGTGTGCGGCACTGAAAGGCACTAGTGACAAAAACAATGGCT

CTGGTAGCAAAGAGAAAAACAAAGATGGCAAGTACTCATTCAACGCTAAAGGTG

AACTGTCGGAAAAAAACCATCCTGCGCGCCTGTGGCACCCGCCTGGAATACACGG

-continued

AAATCAAGTCGGACGGCACGGGCAAAGCAAAGGAAGTCCTGAAAGATTTTGCTC

TGGAAGGTACCCTGGCGGCCGACAAAACCACGCTGAAGGTGACGGAAGGCACC

GTGGTTCTGAGCAAACATATTCCGAACTCTGGTGAAATCACCGTTGAACTGAACG

ATAGCAATTCTACGCAGGCGACCAAAAAGACGGGCAAATGGGACAGTAATACCT

CCACGCTGACCATTTCAGTCAACTCGAAAAAGACCAAAAATATTGTGTTCACGA

AGGAATGCACGATCACCGTTCAAAAATATGATTCCGCAGGTACCAACCTGGAAG

GCAACGCTGTGGAAATCAAAACCCTGGACGAACTGAAAAATGCTCTGAAGGGTC

TCGAGCACCACCACCACCACCAC

S5D4-S6D1_aa
Heterodimer fusion protein of OspA serotype 5 with disulfide bond type 4 and OspA serotype 6 with disulfide bond type 1, LN1 peptide linker (SEQ ID NO: 184)

SEQ ID NO: 107

FNEKGEISEKTIVRACGTRLEYTDIKSDKTGKAKEVLKDFTLEGTLAADGKTTLKVTE

GTVTLSKNISKSGEITVALDDTDSSGNKKSGTWDSGTSTLTISKNRTKTKQLVFTKEC

TITVQNYDSAGTNLEGKAVEITTLKELKNALKGTSDKNNGSGSKEKNKDGKYSFNG

KGETSEKTIVRANGTRLEYTDIKSDGSGKAKEVLKDFTLEGTLAADGKTTLKVTCGT

VVLSKNILKSGEITAALDDSDTTRATKKTGKWDSKTSTLTISVNSQKTKNLVFTKEDT

ITVQRYDSAGTNLEGKAVEITTLKELCNALK

Lip-S5D4-S6D1_nt
Coding sequence for intermediate and final heterodimer fusion proteins of OspA serotype 5 with disulfide bond type 4 and OspA serotype 6 with disulfide bond type 1, *E. coli* lpp lipidation signal, N-terminal CSS for addition of lipids, LN1 peptide linker (SEQ ID NO: 184)

SEQ ID NO: 108

ATGAAAGCTACTAAACTGGTACTGGGCGCGGTAATCCTGGGTTCTACTCTGCTGG

CAGGTTGCTCAAGCTTCAACGAAAAGGGCGAAATCAGTGAAAAAACCATTGTGC

GTGCGTGTGGCACCCGTCTGGAATATACCGACATCAAGAGCGATAAAACGGGTA

AAGCGAAGGAAGTTCTGAAAGATTTTACGCTGGAAGGTACCCTGGCAGCAGACG

GTAAAACCACGCTGAAGGTGACCGAAGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGACTCAGGCACCTCGACGCTGACCATTTCTAAAAATC

GTACGAAAACCAAGCAGCTGGTCTTCACGAAAGAATGCACGATCACCGTGCAAA

ACTATGATAGCGCAGGTACCAATCTGGAAGGCAAAGCTGTGGAAATTACCACGC

TGAAAGAACTGAAGAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGCGAAAAGACCATCGTGCGTGCGAACGGTACCCGCCTGGAATATACGGAC

ATTAAATCGGACGGCAGCGGCAAAGCAAAGGAAGTCCTGAAAGATTTTACGCTG

GAAGGTACCCTGGCAGCAGACGGTAAAACCACGCTGAAGGTGACGTGCGGCACC

GTGGTTCTGTCAAAAAACATTCTGAAGTCGGGTGAAATCACCGCAGCTCTGGATG

ACAGCGATACCACGCGTGCTACGAAAAAGACCGGTAAATGGGATAGCAAGACCT

CTACGCTGACCATTAGTGTCAACTCCCAGAAAACGAAGAATCTGGTGTTCACCAA

AGAAGATACGATCACCGTTCAACGCTATGACAGTGCGGGCACCAACCTGGAAGG

CAAAGCCGTTGAAATTACCACGCTGAAAGAACTGTGTAATGCTCTGAAA

-continued

Lip-S5D4-S6D1_His_aa
Heterodimer fusion protein of OspA serotype 5 with disulfide bond type 4 and OspA serotype 6 with disulfide bond type 1, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 109

LipCSSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALKGTSDKNNGSGSKEKNKDGK

YSFNGKGETSEKTIVRANGTRLEYTDIKSDGSGKAKEVLKDFTLEGTLAADGKTTLK

VTCGTVVLSKNILKSGEITAALDDSDTTRATKKTGKWDSKTSTLTISVNSQKTKNLV

FTKEDTITVQRYDSAGTNLEGKAVEITTLKELCNALKGLEHHHHHH

Lip-S5D4-S6D1_His_nt
Coding sequence for heterodimer fusion protein of OspA serotype 5 with disulfide bond type 4 and OspA serotype 6 with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 110

ATGAAAGCTACTAAACTGGTACTGGGCGCGGTAATCCTGGGTTCTACTCTGCTGG

CAGGTTGCTCAAGCTTCAACGAAAAGGGCGAAATCAGTGAAAAAACCATTGTGC

GTGCGTGTGGCACCCGTCTGGAATATACCGACATCAAGAGCGATAAAACGGGTA

AAGCGAAGGAAGTTCTGAAAGATTTTACGCTGGAAGGTACCCTGGCAGCAGACG

GTAAAACCACGCTGAAGGTGACCGAAGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGACTCAGGCACCTCGACGCTGACCATTTCTAAAAATC

GTACGAAAACCAAGCAGCTGGTCTTCACGAAAGAATGCACGATCACCGTGCAAA

ACTATGATAGCGCAGGTACCAATCTGGAAGGCAAAGCTGTGGAAATTACCACGC

TGAAAGAACTGAAGAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGCGAAAAGACCATCGTGCGTGCGAACGGTACCCGCCTGGAATATACGGAC

ATTAAATCGGACGGCAGCGGCAAAGCAAAGGAAGTCCTGAAAGATTTTACGCTG

GAAGGTACCCTGGCAGCAGACGGTAAAACCACGCTGAAGGTGACGTGCGGCACC

GTGGTTCTGTCAAAAAACATTCTGAAGTCGGGTGAAATCACCGCAGCTCTGGATG

ACAGCGATACCACGCGTGCTACGAAAAAGACCGGTAAATGGGATAGCAAGACCT

CTACGCTGACCATTAGTGTCAACTCCCAGAAAACGAAGAATCTGGTGTTCACCAA

AGAAGATACGATCACCGTTCAACGCTATGACAGTGCGGGCACCAACCTGGAAGG

CAAAGCCGTTGAAATTACCACGCTGAAAGAACTGTGTAATGCTCTGAAAGGTCT

CGAGCACCACCACCACCACCAC

S5D1-S6D4_aa
Heterodimer fusion protein of OspA serotype 5 with disulfide bond type 1 and OspA serotype 6 with disulfide bond type 4, LN1 peptide linker (SEQ ID NO: 184)

SEQ ID NO: 111

FNEKGEISEKTIVRANGTRLEYTDIKSDKTGKAKEVLKDFTLEGTLAADGKTTLKVT

CGTVTLSKNISKSGEITVALDDTDSSGNKKSGTWDSGTSTLTISKNRTKTKQLVFTKE

DTITVQNYDSAGTNLEGKAVEITTLKELCNALKGTSDKNNGSGSKEKNKDGKYSFN

GKGETSEKTIVRACGTRLEYTDIKSDGSGKAKEVLKDFTLEGTLAADGKTTLKVTEG

-continued

TVVLSKNILKSGEITAALDDSDTTRATKKTGKWDSKTSTLTISVNSQKTKNLVFTKEC

TITVQRYDSAGTNLEGKAVEITTLKELKNALK

Lip-S5D1-S6D4_nt
Coding sequence for intermediate and final hetero-dimer fusion proteins of OspA serotype 5 with di-sulfide bond type 1 and OspA serotype 6 with di-sulfide bond type 4, *E. coli* lpp lipidation signal, N-terminal CSS for addition of lipids, LN1 peptide linker (SEQ ID NO: 184)

SEQ ID NO: 112

ATGAAAGCTACTAAACTGGTACTGGGCGCGGTAATCCTGGGTTCTACTCTGCTGG

CAGGTTGCTCAAGCTTCAACGAAAAGGGCGAAATCTCAGAAAAAACCATCGTCC

GCGCTAACGGCACCCGCCTGGAATACACCGACATCAAATCAGACAAGACCGGTA

AAGCGAAGGAAGTTCTGAAAGATTTTACGCTGGAAGGTACCCTGGCAGCAGACG

GTAAAACCACGCTGAAGGTGACCTGCGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGATTCAGGCACCTCGACGCTGACCATTTCTAAAAATC

GTACGAAAACCAAGCAGCTGGTCTTCACGAAAGAAGATACGATCACCGTGCAAA

ACTATGACAGCGCAGGTACCAATCTGGAAGGCAAAGCTGTGGAAATTACCACGC

TGAAAGAACTGTGTAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGTGAAAAAACGATTGTTCGCGCCTGTGGCACCCGCCTGGAATACACGGAT

ATCAAGTCGGATGGTTCGGGCAAAGCAAAGGAAGTCCTGAAAGATTTTACGCTG

GAAGGTACCCTGGCAGCAGACGGTAAAACCACGCTGAAGGTGACGGAAGGCAC

CGTGGTTCTGTCAAAAAACATTCTGAAGTCGGGTGAAATCACCGCAGCTCTGGAT

GACAGCGATACCACGCGTGCTACGAAAAAGACCGGTAAATGGGACAGCAAGAC

CTCTACGCTGACCATTAGTGTCAACTCCCAGAAAACGAAGAATCTGGTGTTCACC

AAAGAATGCACGATCACCGTTCAACGCTATGATAGTGCGGGCACCAACCTGGAA

GGCAAAGCCGTTGAAATTACCACGCTGAAAGAACTGAAGAATGCTCTGAAA

Lip-S5D1-S6D4_His_aa
Heterodimer fusion protein of OspA serotype 5 with di-sulfide bond type 1 and OspA serotype 6 with disulfide bond type 4, N-terminal CSS for addition of lipids, LN1 peptide linker (SEQ ID NO: 184), N-terminal lipi-dation, C-terminal His tag (GLEHHHHHH) (SEQ ID NO: 214)

SEQ ID NO: 113

LipCSSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGTSDKNNGSGSKEKNKDGK

YSFNGKGETSEKTIVRACGTRLEYTDIKSDGSGKAKEVLKDFTLEGTLAADGKTTLK

VTEGTVVLSKNILKSGEITAALDDSDTTRATKKTGKWDSKTSTLTISVNSQKTKNLVF

TKECTITVQRYDSAGTNLEGKAVEITTLKELKNALKGLEHHHHHH

-continued

Lip-S5D1-S6D4_His_nt
Coding sequence for heterodimer fusion protein of OspA serotype 5 with disulfide bond type 1 and OspA serotype 6 with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 114

ATGAAAGCTACTAAACTGGTACTGGGCGCGGTAATCCTGGGTTCTACTCTGCTGG

CAGGTTGCTCAAGCTTCAACGAAAAGGGCGAAATCTCAGAAAAAACCATCGTCC

GCGCTAACGGCACCCGCCTGGAATACACCGACATCAAATCAGACAAGACCGGTA

AAGCGAAGGAAGTTCTGAAAGATTTTACGCTGGAAGGTACCCTGGCAGCAGACG

GTAAAACCACGCTGAAGGTGACCTGCGGTACCGTTACGCTGTCCAAAAACATTA

GTAAGTCCGGCGAAATCACGGTCGCCCTGGATGACACCGATAGCTCTGGCAACA

AAAAGAGCGGTACCTGGGATTCAGGCACCTCGACGCTGACCATTTCTAAAAATC

GTACGAAAACCAAGCAGCTGGTCTTCACGAAAGAAGATACGATCACCGTGCAAA

ACTATGACAGCGCAGGTACCAATCTGGAAGGCAAAGCTGTGGAAATTACCACGC

TGAAAGAACTGTGTAATGCTCTGAAAGGTACTAGTGACAAAAACAATGGCTCTG

GTAGCAAAGAGAAAAACAAAGATGGCAAGTACTCATTCAACGGCAAAGGTGAA

ACGAGTGAAAAAACGATTGTTCGCGCCTGTGGCACCCGCCTGGAATACACGGAT

ATCAAGTCGGATGGTTCGGGCAAAGCAAAGGAAGTCCTGAAAGATTTTACGCTG

GAAGGTACCCTGGCAGCAGACGGTAAAACCACGCTGAAGGTGACGGAAGGCAC

CGTGGTTCTGTCAAAAAACATTCTGAAGTCGGGTGAAATCACCGCAGCTCTGGAT

GACAGCGATACCACGCGTGCTACGAAAAAGACCGGTAAATGGGACAGCAAGAC

CTCTACGCTGACCATTAGTGTCAACTCCCAGAAAACGAAGAATCTGGTGTTCACC

AAAGAATGCACGATCACCGTTCAACGCTATGATAGTGCGGGCACCAACCTGGAA

GGCAAAGCCGTTGAAATTACCACGCTGAAAGAACTGAAGAATGCTCTGAAAGGT

CTCGAGCACCACCACCACCACCAC

S2D4-S1D1_aa
Heterodimer fusion protein of OspA serotype 2 with disulfide bond type 4 and OspA serotype 1 with disulfide bond type 1, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 115

FNEKGELSAKTMTRECGTKLEYTEMKSDGTGKAKEVLKNFTLEGKVANDKVTLEV

KEGTVTLSKEIAKSGEVTVALNDTNTTQATKKTGAWDSKTSTLTISVNSKKTTQLVF

TKQCTITVQKYDSAGTNLEGTAVEIKTLDELKNALKGTSDKNNGSGSKEKNKDGKY

SFNEKGEVSEKIITRADGTRLEYTGIKSDGSGKAKEVLKNFTLEGKVANDKTTLVVK

CGTVTLSKNISKSGEVSVELNDTDSSAATKKTAAWNSGTSTLTITVNSKKTKDLVFT

KENTITVQQYDSNGTKLEGSAVEITKLDEICNALK

Lip-S2D4-S1D1_nt
Coding sequence for intermediate and final heterodimer fusion proteins of OspA serotype 2 with disulfide bond type 4 and OspA serotype 1 with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 116

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

-continued

GTGAATGCGGCACCAAACTGGAATATACGGAAATGAAAAGCGATGGCACCGGTA

AAGCGAAAGAAGTTCTGAAAAACTTTACCCTGGAAGGCAAAGTCGCCAATGACA

AAGTCACCCTGGAAGTGAAAGAAGGCACCGTTACGCTGTCAAAAGAAATTGCAA

AATCGGGTGAAGTGACCGTTGCTCTGAACGATACGAATACCACGCAAGCGACCA

AGAAAACCGGCGCCTGGGACAGCAAAACCTCTACGCTGACCATTAGTGTTAACA

GCAAGAAAACCACGCAGCTGGTCTTCACCAAACAATGTACGATCACCGTGCAGA

AATACGATAGTGCGGGTACCAACCTGGAAGGCACCGCTGTTGAAATCAAAACCC

TGGACGAACTGAAAAACGCCCTGAAAGGCACTAGTGACAAAAACAATGGCTCTG

GTAGCAAAGAGAAAAACAAAGATGGCAAGTACTCATTCAACGAAAAAGGCGAA

GTCAGCGAAAAAATCATTACCCGCGCAGACGGCACCCGCCTGGAATACACCGGC

ATCAAATCGGACGGCAGCGGCAAAGCGAAAGAAGTTCTGAAAAACTTTACCCTG

GAAGGCAAAGTCGCAAATGATAAAACCACCCTGGTGGTGAAATGCGGCACCGTT

ACGCTGAGCAAAAACATTAGTAAATCCGGTGAAGTCTCTGTGGAACTGAATGAT

ACCGACAGCTCTGCGGCCACCAAGAAAACCGCAGCTTGGAACTCAGGCACCTCG

ACGCTGACCATTACGGTTAATAGCAAGAAAACCAAAGATCTGGTCTTCACGAAA

GAAAACACCATCACGGTGCAGCAATATGACAGCAATGGTACCAAACTGGAAGGC

TCCGCTGTGGAAATCACGAAACTGGATGAAATCTGTAATGCACTGAAA

Lip-S2D4-S1D1_His_aa
Heterodimer fusion protein of OspA serotype 2 with disulfide bond type 4 and OspA serotype 1 with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation, C-terminal His tag (GLEHHHHHH) (SEQ ID NO: 214)

SEQ ID NO: 117

LipCSSFNEKGELSAKTMTRECGTKLEYTEMKSDGTGKAKEVLKNFTLEGKVANDK

VTLEVKEGTVTLSKEIAKSGEVTVALNDTNTTQATKKTGAWDSKTSTLTISVNSKKT

TQLVFTKQCTITVQKYDSAGTNLEGTAVEIKTLDELKNALKGTSDKNNGSGSKEKN

KDGKYSFNEKGEVSEKIITRADGTRLEYTGIKSDGSGKAKEVLKNFTLEGKVANDKT

TLVVKCGTVTLSKNISKSGEVSVELNDTDSSAATKKTAAWNSGTSTLTITVNSKKTK

DLVFTKENTITVQQYDSNGTKLEGSAVEITKLDEICNALKGLEHHHHHH

Lip-S2D4-S1D1_His_nt
Coding sequence for heterodimer fusion protein of OspA serotype 2 with disulfide bond type 4 and OspA serotype 1 with disulfide bond type 1, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 118

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAATGCGGCACCAAACTGGAATATACGGAAATGAAAAGCGATGGCACCGGTA

AAGCGAAAGAAGTTCTGAAAAACTTTACCCTGGAAGGCAAAGTCGCCAATGACA

AAGTCACCCTGGAAGTGAAAGAAGGCACCGTTACGCTGTCAAAAGAAATTGCAA

AATCGGGTGAAGTGACCGTTGCTCTGAACGATACGAATACCACGCAAGCGACCA

AGAAAACCGGCGCCTGGGACAGCAAAACCTCTACGCTGACCATTAGTGTTAACA

-continued

GCAAGAAAACCACGCAGCTGGTCTTCACCAAACAATGTACGATCACCGTGCAGA

AATACGATAGTGCGGGTACCAACCTGGAAGGCACCGCTGTTGAAATCAAAACCC

TGGACGAACTGAAAAACGCCCTGAAAGGCACTAGTGACAAAAACAATGGCTCTG

GTAGCAAAGAGAAAAACAAAGATGGCAAGTACTCATTCAACGAAAAAGGCGAA

GTCAGCGAAAAAATCATTACCCGCGCAGACGGCACCCGCCTGGAATACACCGGC

ATCAAATCGGACGGCAGCGGCAAAGCGAAAGAAGTTCTGAAAAACTTTACCCTG

GAAGGCAAAGTCGCAAATGATAAAACCACCCTGGTGGTGAAATGCGGCACCGTT

ACGCTGAGCAAAAACATTAGTAAATCCGGTGAAGTCTCTGTGGAACTGAATGAT

ACCGACAGCTCTGCGGCCACCAAGAAAACCGCAGCTTGGAACTCAGGCACCTCG

ACGCTGACCATTACGGTTAATAGCAAGAAAACCAAAGATCTGGTCTTCACGAAA

GAAAACACCATCACGGTGCAGCAATATGACAGCAATGGTACCAAACTGGAAGGC

TCCGCTGTGGAAATCACGAAACTGGATGAAATCTGTAATGCACTGAAAGGTCTC

GAGCACCACCACCACCACCAC

S2D1-S1D4_aa
Heterodimer fusion protein of OspA serotype 2 with disulfide bond type 1 and OspA serotype 1 with disulfide bond type 4, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 119

FNEKGELSAKTMTRENGTKLEYTEMKSDGTGKAKEVLKNFTLEGKVANDKVTLEV

KCGTVTLSKEIAKSGEVTVALNDTNTTQATKKTGAWDSKTSTLTISVNSKKTTQLVF

TKQDTITVQKYDSAGTNLEGTAVEIKTLDELCNALKGTSDKNNGSGSKEKNKDGKY

SFNEKGEVSEKIITRACGTRLEYTGIKSDGSGKAKEVLKNFTLEGKVANDKTTLVVK

EGTVTLSKNISKSGEVSVELNDTDSSAATKKTAAWNSGTSTLTITVNSKKTKDLVFT

KECTITVQQYDSNGTKLEGSAVEITKLDEIKNALK

Lip-S2D1-S1D4_nt
Coding sequence for intermediate and final heterodimer fusion proteins of OspA serotype 2 with disulfide bond type 1 and OspA serotype 1 with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18)

SEQ ID NO: 120

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAAAACGGCACCAAACTGGAATATACGGAAATGAAAAGCGATGGCACCGGT

AAAGCGAAAGAAGTTCTGAAAAACTTTACCCTGGAAGGCAAAGTCGCCAATGAC

AAAGTCACCCTGGAAGTGAAATGCGGCACCGTTACGCTGTCAAAAGAAATTGCA

AAATCGGGTGAAGTGACCGTTGCTCTGAACGATACGAATACCACGCAAGCGACC

AAGAAAACCGGCGCCTGGGACAGCAAAACCTCTACGCTGACCATTAGTGTTAAT

AGCAAGAAAACCACGCAGCTGGTCTTCACCAAACAAGATACGATCACCGTGCAG

AAATACGACAGTGCGGGTACCAACCTGGAAGGCACGGCTGTTGAAATCAAAACC

CTGGACGAACTGTGTAACGCCCTGAAAGGCACTAGTGACAAAAACAATGGCTCT

GGTAGCAAAGAGAAAAACAAAGATGGCAAGTACTCATTCAACGAAAAAGGCGA

AGTCTCGGAAAAAATCATTACCCGTGCTTGCGGCACCCGTCTGGAATACACCGGC

ATTAAATCGGATGGCAGCGGCAAAGCGAAGGAAGTTCTGAAAAACTTTACCCTG

-continued

GAAGGCAAAGTCGCAAATGATAAGACCACCCTGGTGGTGAAAGAAGGCACCGTT

ACGCTGAGCAAAAACATTAGTAAGTCCGGTGAAGTCTCTGTGGAACTGAATGAT

ACCGACAGCTCTGCGGCCACCAAAAAGACGGCAGCTTGGAACTCAGGCACCTCG

ACGCTGACCATTACGGTTAATTCCAAAAAGACCAAAGATCTGGTCTTCACGAAA

GAATGCACCATCACGGTGCAGCAATATGACAGCAACGGTACCAAACTGGAAGGC

TCTGCGGTGGAAATCACGAAACTGGATGAAATCAAAAATGCACTGAAA

Lip-S2D1-S1D4_His_aa
Heterodimer fusion protein of OspA serotype 2 with disulfide bond type 1 and OspA serotype 1 with disulfide bond type 4, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation, C-terminal His tag (GLEHHHHHH) (SEQ ID NO: 214)

SEQ ID NO: 121

LipCSSFNEKGELSAKTMTRENGTKLEYTEMKSDGTGKAKEVLKNFTLEGKVANDK

VTLEVKCGTVTLSKEIAKSGEVTVALNDTNTTQATKKTGAWDSKTSTLTISVNSKKT

TQLVFTKQDTITVQKYDSAGTNLEGTAVEIKTLDELCNALKGTSDKNNGSGSKEKN

KDGKYSFNEKGEVSEKIITRACGTRLEYTGIKSDGSGKAKEVLKNFTLEGKVANDKT

TLVVKEGTVTLSKNISKSGEVSVELNDTDSSAATKKTAAWNSGTSTLTITVNSKKTK

DLVFTKECTITVQQYDSNGTKLEGSAVEITKLDEIKNALKGLEHHHHHH

Lip-S2D1-S1D4_His_nt
Coding sequence for heterodimer fusion protein of OspA serotype 2 with disulfide bond type 1 and OspA serotype 1 with disulfide bond type 4, *E. coli* lpp lipidation signal, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), C-terminal His tag (GLEHHHHHH) (SEQ ID NO: 214)

SEQ ID NO: 122

ATGAAAGCTACTAAACTGGTACTGGGCGCGGTAATCCTGGGTTCTACTCTGCTGG

CAGGTTGCTCAAGCTTCAACGAAAAAGGCGAACTGTCGGCGAAAACGATGACGC

GTGAAAACGGCACCAAACTGGAATATACGGAAATGAAAAGCGATGGCACCGGT

AAAGCGAAAGAAGTTCTGAAAAACTTTACCCTGGAAGGCAAAGTCGCCAATGAC

AAAGTCACCCTGGAAGTGAAATGCGGCACCGTTACGCTGTCAAAAGAAATTGCA

AAATCGGGTGAAGTGACCGTTGCTCTGAACGATACGAATACCACGCAAGCGACC

AAGAAAACCGGCGCCTGGGACAGCAAAACCTCTACGCTGACCATTAGTGTTAAT

AGCAAGAAAACCACGCAGCTGGTCTTCACCAAACAAGATACGATCACCGTGCAG

AAATACGACAGTGCGGGTACCAACCTGGAAGGCACGGCTGTTGAAATCAAAACC

CTGGACGAACTGTGTAACGCCCTGAAAGGCACTAGTGACAAAAACAATGGCTCT

GGTAGCAAAGAGAAAAACAAAGATGGCAAGTACTCATTCAACGAAAAAGGCGA

AGTCTCGGAAAAAATCATTACCCGTGCTTGCGGCACCCGTCTGGAATACACCGGC

ATTAAATCGGATGGCAGCGGCAAAGCGAAGGAAGTTCTGAAAAACTTTACCCTG

GAAGGCAAAGTCGCAAATGATAAGACCACCCTGGTGGTGAAAGAAGGCACCGTT

ACGCTGAGCAAAAACATTAGTAAGTCCGGTGAAGTCTCTGTGGAACTGAATGAT

ACCGACAGCTCTGCGGCCACCAAAAAGACGGCAGCTTGGAACTCAGGCACCTCG

ACGCTGACCATTACGGTTAATTCCAAAAAGACCAAAGATCTGGTCTTCACGAAA

GAATGCACCATCACGGTGCAGCAATATGACAGCAACGGTACCAAACTGGAAGGC

-continued

TCTGCGGTGGAAATCACGAAACTGGATGAAATCAAAAATGCACTGAAAGGTCTC

GAGCACCACCACCACCACCAC

S4D4-S3D1_aa
Heterodimer fusion protein of OspA serotype 4 with disulfide bond type 4 and OspA serotype 3 with disulfide bond type 1, LN1 peptide linker (SEQ ID NO: 184)

SEQ ID NO: 123

FNAKGELSEKTILRACGTRLEYTEIKSDGTGKAKEVLKDFALEGTLAADKTTLKVTE

GTVVLSKHIPNSGEITVELNDSNSTQATKKTGKWDSNTSTLTISVNSKKTKNIVFTKE

CTITVQKYDSAGTNLEGNAVEIKTLDELKNALKGTSDKNNGSGSKEKNKDGKYSFN

DKGKLSEKVVTRANGTRLEYTEIKNDGSGKAKEVLKGFALEGTLTDGGETKLTVTC

GTVTLSKNISKSGEITVALNDTETTPADKKTGEWKSDTSTLTISKNSQKPKQLVFTKE

NTITVQNYNRAGNALEGSPAEIKDLAELCAALK

Lip-S4D4-S3D1_nt
Coding sequence for intermediate and final heterodimer fusion proteins of OspA serotype 4 with disulfide bond type 4 and OspA serotype 3 with disulfide bond type 1, *E. coli* lpp lipidation signal, N-terminal CSS for addition of lipids, LN1 peptide linker (SEQ ID NO: 184)

SEQ ID NO: 124

ATGAAAGCTACTAAACTGGTACTGGGCGCGGTAATCCTGGGTTCTACTCTGCTGG

CAGGTTGCTCAAGCTTCAACGCTAAAGGTGAACTGTCGGAAAAAACCATCCTGC

GCGCCTGTGGCACCCGCCTGGAATACACGGAAATCAAGTCGGACGGCACGGGCA

AAGCAAAGGAAGTCCTGAAAGATTTTGCTCTGGAAGGTACCCTGGCGGCCGACA

AAACCACGCTGAAGGTGACGGAAGGCACCGTGGTTCTGAGCAAACATATTCCGA

ACTCTGGTGAAATCACCGTTGAACTGAACGATAGCAATTCTACGCAGGCGACCA

AAAAGACGGGCAAATGGGACAGTAATACCTCCACGCTGACCATTTCAGTCAACT

CGAAAAAGACCAAAAATATTGTGTTCACGAAGGAATGCACGATCACCGTTCAAA

AATATGATTCCGCAGGTACCAACCTGGAAGGCAACGCTGTGGAAATCAAAACCC

TGGACGAACTGAAAAACGCCCTGAAGGGTACTAGTGACAAAAACAATGGCTCTG

GTAGCAAAGAGAAAAACAAAGATGGCAAGTACTCATTTAACGATAAGGGCAAA

CTGTCGGAAAAAGTGGTCACCCGCGCAAATGGCACCCGCCTGGAATACACGGAA

ATCAAAAACGATGGTAGCGGCAAAGCGAAGGAAGTTCTGAAAGGCTTTGCCCTG

GAAGGTACCCTGACGGATGGCGGTGAAACCAAACTGACCGTGACGTGCGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAAAACACGATCACCGTGCAGAACTATAATCGTGCCGGTAATGCTCTGGAA

GGCTCACCGGCTGAAATCAAGGACCTGGCTGAACTGTGTGCGGCACTGAAA

Lip-S4D4-S3D1_His_aa
Heterodimer fusion protein of OspA serotype 4 with disulfide bond type 4 and OspA serotype 3 with disulfide bond type 1, N-terminal CSS for addition of lipids, LN1 peptide linker (SEQ ID NO: 184), N-terminal CSS for addition of lipids, N-terminal lipidation, C-terminal His tag (GLEHHHHHH) (SEQ ID NO: 214)

SEQ ID NO: 125

LipCSSFNAKGELSEKTILRACGTRLEYTEIKSDGTGKAKEVLKDFALEGTLAADKTT

LKVTEGTVVLSKHIPNSGEITVELNDSNSTQATKKTGKWDSNTSTLTISVNSKKTKNI

VFTKECTITVQKYDSAGTNLEGNAVEIKTLDELKNALKGTSDKNNGSGSKEKNKDG

-continued

KYSFNDKGKLSEKVVTRANGTRLEYTEIKNDGSGKAKEVLKGFALEGTLTDGGETK

LTVTCGTVTLSKNISKSGEITVALNDTETTPADKKTGEWKSDTSTLTISKNSQKPKQL

VFTKENTITVQNYNRAGNALEGSPAEIKDLAELCAALKGLEHHHHHH

Lip-S4D4-S3D1_His_nt
Coding sequence for heterodimer fusion protein of OspA serotype 4 with disulfide bond type 4 and OspA serotype 3 with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 126

ATGAAAGCTACTAAACTGGTACTGGGCGCGGTAATCCTGGGTTCTACTCTGCTGG

CAGGTTGCTCAAGCTTCAACGCTAAAGGTGAACTGTCGGAAAAAACCATCCTGC

GCGCCTGTGGCACCCGCCTGGAATACACGGAAATCAAGTCGGACGGCACGGGCA

AAGCAAAGGAAGTCCTGAAAGATTTTGCTCTGGAAGGTACCCTGGCGGCCGACA

AAACCACGCTGAAGGTGACGGAAGGCACCGTGGTTCTGAGCAAACATATTCCGA

ACTCTGGTGAAATCACCGTTGAACTGAACGATAGCAATTCTACGCAGGCGACCA

AAAAGACGGGCAAATGGGACAGTAATACCTCCACGCTGACCATTTCAGTCAACT

CGAAAAAGACCAAAAATATTGTGTTCACGAAGGAATGCACGATCACCGTTCAAA

AATATGATTCCGCAGGTACCAACCTGGAAGGCAACGCTGTGGAAATCAAAACCC

TGGACGAACTGAAAAACGCCCTGAAGGGTACTAGTGACAAAAACAATGGCTCTG

GTAGCAAAGAGAAAAACAAAGATGGCAAGTACTCATTTAACGATAAGGGCAAA

CTGTCGGAAAAAGTGGTCACCCGCGCAAATGGCACCCGCCTGGAATACACGGAA

ATCAAAAACGATGGTAGCGGCAAAGCGAAGGAAGTTCTGAAAGGCTTTGCCCTG

GAAGGTACCCTGACGGATGGCGGTGAAACCAAACTGACCGTGACGTGCGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAAAACACGATCACCGTGCAGAACTATAATCGTGCCGGTAATGCTCTGGAA

GGCTCACCGGCTGAAATCAAGGACCTGGCTGAACTGTGTGCGGCACTGAAAGGT

CTCGAGCACCACCACCACCACCAC

S4D1-S3D4_aa
Heterodimer fusion protein of OspA serotype 4 with disulfide bond type 1 and OspA serotype 3 with disulfide bond type 4, LN1 peptide linker (SEQ ID NO: 184)

SEQ ID NO: 127

FNAKGELSEKTILRANGTRLEYTEIKSDGTGKAKEVLKDFALEGTLAADKTTLKVTC

GTVVLSKHIPNSGEITVELNDSNSTQATKKTGKWDSNTSTLTISVNSKKTKNIVFTKE

DTITVQKYDSAGTNLEGNAVEIKTLDELCNALKGTSDKNNGSGSKEKNKDGKYSFN

DKGKLSEKVVTRACGTRLEYTEIKNDGSGKAKEVLKGFALEGTLTDGGETKLTVTE

GTVTLSKNISKSGEITVALNDTETTPADKKTGEWKSDTSTLTISKNSQKPKQLVFTKE

CTITVQNYNRAGNALEGSPAEIKDLAELKAALK

-continued

Lip-S4D1-S3D4_nt
Heterodimer fusion protein of OspA serotype 4 with disulfide bond type 1 and OspA serotype 3 with disulfide bond type 4, *E. coli* lpp lipidation signal, N-terminal CSS for addition of lipids, LN1 peptide linker (SEQ ID NO: 184)

SEQ ID NO: 128

ATGAAAGCTACTAAACTGGTACTGGGCGCGGTAATCCTGGGTTCTACTCTGCTGG

CAGGTTGCTCAAGCTTCAATGCTAAGGGCGAACTGAGCGAAAAAACGATCCTGC

GTGCGAATGGCACCCGTCTGGAATACACCGAAATCAAATCCGATGGTACGGGCA

AAGCAAAGGAAGTCCTGAAAGATTTTGCTCTGGAAGGTACCCTGGCGGCCGACA

AAACCACGCTGAAGGTGACGTGCGGCACCGTGGTTCTGAGCAAACATATTCCGA

ACTCTGGTGAAATCACCGTTGAACTGAACGATAGCAATTCTACGCAGGCAACCA

AAAAGACGGGCAAATGGGACAGTAATACCTCCACGCTGACCATTTCAGTCAACT

CGAAAAAGACCAAAAATATTGTGTTCACGAAGGAAGATACGATCACCGTTCAAA

AATATGACTCCGCGGGCACCAACCTGGAAGGCAATGCCGTCGAAATCAAAACCC

TGGATGAACTGTGTAACGCCCTGAAGGGTACTAGTGACAAAAACAATGGCTCTG

GTAGCAAAGAGAAAAACAAAGATGGCAAGTACTCATTTAACGATAAGGGCAAA

CTGTCAGAAAAAGTGGTCACCCGCGCTTGTGGCACCCGCCTGGAATACACCGAA

ATCAAAAACGACGGCTCGGGCAAAGCGAAGGAAGTTCTGAAAGGCTTTGCCCTG

GAAGGTACCCTGACGGATGGCGGTGAAACCAAACTGACCGTGACGGAAGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAATGCACGATCACCGTGCAGAACTATAATCGTGCCGGTAATGCTCTGGAA

GGCTCCCCGGCTGAAATCAAGGACCTGGCGGAACTGAAGGCGGCACTGAAA

Lip-S4D1-S3D4_His_aa
Heterodimer fusion protein of OspA serotype 4 with disulfide bond type 1 and OspA serotype 3 with disulfide bond type 4, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 129

LipCSSFNAKGELSEKTILRANGTRLEYTEIKSDGTGKAKEVLKDFALEGTLAADKTTL

KVTCGTVVLSKHIPNSGEITVELNDSNSTQATKKTGKWDSNTSTLTISVNSKKTKNIV

FTKEDTITVQKYDSAGTNLEGNAVEIKTLDELCNALKGTSDKNNGSGSKEKNKDGK

YSFNDKGKLSEKVVTRACGTRLEYTEIKNDGSGKAKEVLKGFALEGTLTDGGETKL

TVTEGTVTLSKNISKSGEITVALNDTETTPADKKTGEWKSDTSTLTISKNSQKPKQLV

FTKECTITVQNYNRAGNALEGSPAEIKDLAELKAALKGLEHHHHHH

Lip-S4D1-S3D4_His_nt
Coding sequence for heterodimer fusion protein of OspA serotype 4 with disulfide bond type 1 and OspA serotype 3 with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 130

ATGAAAGCTACTAAACTGGTACTGGGCGCGGTAATCCTGGGTTCTACTCTGCTGG

CAGGTTGCTCAAGCTTCAATGCTAAGGGCGAACTGAGCGAAAAAACGATCCTGC

GTGCGAATGGCACCCGTCTGGAATACACCGAAATCAAATCCGATGGTACGGGCA

AAGCAAAGGAAGTCCTGAAAGATTTTGCTCTGGAAGGTACCCTGGCGGCCGACA

-continued

AAACCACGCTGAAGGTGACGTGCGGCACCGTGGTTCTGAGCAAACATATTCCGA

ACTCTGGTGAAATCACCGTTGAACTGAACGATAGCAATTCTACGCAGGCAACCA

AAAAGACGGGCAAATGGGACAGTAATACCTCCACGCTGACCATTTCAGTCAACT

CGAAAAAGACCAAAAATATTGTGTTCACGAAGGAAGATACGATCACCGTTCAAA

AATATGACTCCGCGGGCACCAACCTGGAAGGCAATGCCGTCGAAATCAAAACCC

TGGATGAACTGTGTAACGCCCTGAAGGGTACTAGTGACAAAAACAATGGCTCTG

GTAGCAAAGAGAAAAACAAAGATGGCAAGTACTCATTTAACGATAAGGGCAAA

CTGTCAGAAAAAGTGGTCACCCGCGCTTGTGGCACCCGCCTGGAATACACCGAA

ATCAAAAACGACGGCTCGGGCAAAGCGAAGGAAGTTCTGAAAGGCTTTGCCCTG

GAAGGTACCCTGACGGATGGCGGTGAAACCAAACTGACCGTGACGGAAGGCACC

GTTACGCTGTCTAAAAACATTAGCAAGTCTGGTGAAATCACGGTCGCACTGAATG

ATACCGAAACCACGCCGGCTGACAAAAAGACCGGCGAATGGAAAAGTGACACC

TCCACGCTGACCATTTCAAAGAACTCGCAGAAACCGAAGCAACTGGTCTTCACC

AAAGAATGCACGATCACCGTGCAGAACTATAATCGTGCCGGTAATGCTCTGGAA

GGCTCCCCGGCTGAAATCAAGGACCTGGCGGAACTGAAGGCGGCACTGAAAGGT

CTCGAGCACCACCACCACCACCAC

S6D4-S5D1_aa
Heterodimer fusion protein of OspA serotype 6 with disulfide bond type 4 and OspA serotype 5 with disulfide bond type 1, LN1 peptide linker (SEQ ID NO: 184)

SEQ ID NO: 131

FNGKGETSEKTIVRACGTRLEYTDIKSDGSGKAKEVLKDFTLEGTLAADGKTTLKVT

EGTVVLSKNILKSGEITAALDDSDTTRATKKTGKWDSKTSTLTISVNSQKTKNLVFTK

ECTITVQRYDSAGTNLEGKAVEITTLKELKNALKGTSDKNNGSGSKEKNKDGKYSF

NEKGEISEKTIVRANGTRLEYTDIKSDKTGKAKEVLKDFTLEGTLAADGKTTLKVTC

GTVTLSKNISKSGEITVALDDTDSSGNKKSGTWDSGTSTLTISKNRTKTKQLVFTKED

TITVQNYDSAGTNLEGKAVEITTLKELCNALK

Lip-S6D4-S5D1_nt
Coding sequence for intermediate and final heterodimer fusion proteins of OspA serotype 6 with disulfide bond type 4 and OspA serotype 5 with disulfide bond type 1, *E. coli* lpp lipidation signal, N-terminal CSS for addition of lipids, LN1 peptide linker (SEQ ID NO: 184)

SEQ ID NO: 132

ATGAAAGCTACTAAACTGGTACTGGGCGCGGTAATCCTGGGTTCTACTCTGCTGG

CAGGTTGCTCAAGCTTCAACGGCAAAGGTGAAACGAGTGAAAAAACGATTGTTC

GCGCCTGTGGCACCCGCCTGGAATACACGGATATCAAGTCGGATGGTTCGGGCA

AAGCAAAGGAAGTCCTGAAAGATTTTACGCTGGAAGGTACCCTGGCAGCAGACG

GTAAAACCACGCTGAAGGTGACGGAAGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGACAGCAAGACCTCTACGCTGACCATTAGTGTCA

ACTCCCAGAAAACGAAGAATCTGGTGTTCACCAAAGAATGCACGATCACCGTTC

AACGCTATGATAGTGCGGGCACCAACCTGGAAGGCAAAGCCGTTGAAATTACCA

CGCTGAAAGAACTGAAGAATGCTCTGAAAGGTACTAGTGACAAAAACAATGGCT

CTGGTAGCAAAGAGAAAAACAAAGATGGCAAGTACTCATTCAACGAAAAAGGC

GAAATCTCAGAAAAAACCATCGTCCGCGCTAACGGCACCCGCCTGGAATACACC

-continued

GACATCAAATCAGACAAGACCGGTAAAGCGAAGGAAGTTCTGAAAGATTTTACG

CTGGAAGGTACCCTGGCAGCAGACGGTAAAACCACGCTGAAGGTGACCTGCGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGATTCAGGCACC

TCGACGCTGACCATTTCTAAAAATCGTACGAAAACCAAGCAGCTGGTCTTCACGA

AAGAAGATACGATCACCGTGCAAAACTATGACAGCGCAGGTACCAATCTGGAAG

GCAAAGCTGTGGAAATTACCACGCTGAAAGAACTGTGTAATGCTCTGAAA

Lip-S6D4-S5D1_His_aa
Heterodimer fusion protein of OspA serotype 6 with disulfide bond type 4 and OspA serotype 5 with disulfide bond type 1, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 133

LipCSSFNGKGETSEKTIVRACGTRLEYTDIKSDGSGKAKEVLKDFTLEGTLAADGKT

TLKVTEGTVVLSKNILKSGEITAALDDSDTTRATKKTGKWDSKTSTLTISVNSQKTK

NLVFTKECTITVQRYDSAGTNLEGKAVEITTLKELKNALKGTSDKNNGSGSKEKNKD

GKYSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGLEHHHHHH

Lip-S6D4-S5D1_His_nt
Coding sequence for heterodimer fusion protein of OspA serotype 6 with disulfide bond type 4 and OspA serotype 5 with disulfide bond type 1, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 134

ATGAAAGCTACTAAACTGGTACTGGGCGCGGTAATCCTGGGTTCTACTCTGCTGG

CAGGTTGCTCAAGCTTCAACGGCAAAGGTGAAACGAGTGAAAAAACGATTGTTC

GCGCCTGTGGCACCCGCCTGGAATACACGGATATCAAGTCGGATGGTTCGGGCA

AAGCAAAGGAAGTCCTGAAAGATTTTACGCTGGAAGGTACCCTGGCAGCAGACG

GTAAAACCACGCTGAAGGTGACGGAAGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGACAGCAAGACCTCTACGCTGACCATTAGTGTCA

ACTCCCAGAAAACGAAGAATCTGGTGTTCACCAAAGAATGCACGATCACCGTTC

AACGCTATGATAGTGCGGGCACCAACCTGGAAGGCAAAGCCGTTGAAATTACCA

CGCTGAAAGAACTGAAGAATGCTCTGAAAGGTACTAGTGACAAAAACAATGGCT

CTGGTAGCAAAGAGAAAAACAAAGATGGCAAGTACTCATTCAACGAAAAAGGC

GAAATCTCAGAAAAAACCATCGTCCGCGCTAACGGCACCCGCCTGGAATACACC

GACATCAAATCAGACAAGACCGGTAAAGCGAAGGAAGTTCTGAAAGATTTTACG

CTGGAAGGTACCCTGGCAGCAGACGGTAAAACCACGCTGAAGGTGACCTGCGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGATTCAGGCACC

TCGACGCTGACCATTTCTAAAAATCGTACGAAAACCAAGCAGCTGGTCTTCACGA

-continued

AAGAAGATACGATCACCGTGCAAAACTATGACAGCGCAGGTACCAATCTGGAAG

GCAAAGCTGTGGAAATTACCACGCTGAAAGAACTGTGTAATGCTCTGAAAGGTC

TCGAGCACCACCACCACCACCAC

S6D1-S5D4_aa
Heterodimer fusion protein of OspA serotype 6 with disulfide bond type 1 and OspA serotype 5 with disulfide bond type 4, LN1 peptide linker (SEQ ID NO: 184)

SEQ ID NO: 135

FNGKGETSEKTIVRANGTRLEYTDIKSDGSGKAKEVLKDFTLEGTLAADGKTTLKVT

CGTVVLSKNILKSGEITAALDDSDTTRATKKTGKWDSKTSTLTISVNSQKTKNLVFT

KEDTITVQRYDSAGTNLEGKAVEITTLKELCNALKGTSDKNNGSGSKEKNKDGKYS

FNEKGEISEKTIVRACGTRLEYTDIKSDKTGKAKEVLKDFTLEGTLAADGKTTLKVTE

GTVTLSKNISKSGEITVALDDTDSSGNKKSGTWDSGTSTLTISKNRTKTKQLVFTKEC

TITVQNYDSAGTNLEGKAVEITTLKELKNALK

Lip-S6D1-S5D4_nt
Coding sequence for intermediate and final heterodimer fusion proteins of OspA serotype 6 with disulfide bond type 1 and OspA serotype 5 with disulfide bond type 4, *E. coli* lpp lipidation signal, N-terminal CSS for addition of lipids, LN1 peptide linker (SEQ ID NO: 184)

SEQ ID NO: 136

ATGAAAGCTACTAAACTGGTACTGGGCGCGGTAATCCTGGGTTCTACTCTGCTGG

CAGGTTGCTCAAGCTTCAACGGCAAAGGTGAAACGAGCGAAAAGACCATCGTGC

GTGCGAACGGTACCCGCCTGGAATATACGGACATTAAATCGGACGGCAGCGGCA

AAGCAAAGGAAGTCCTGAAAGATTTTACGCTGGAAGGTACCCTGGCAGCAGACG

GTAAAACCACGCTGAAGGTGACGTGCGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGATAGCAAGACCTCTACGCTGACCATTAGTGTCA

ACTCCCAGAAAACGAAGAATCTGGTGTTCACCAAAGAAGATACGATCACCGTTC

AACGCTATGACAGTGCGGGCACCAACCTGGAAGGCAAAGCCGTTGAAATTACCA

CGCTGAAAGAACTGTGTAATGCTCTGAAAGGTACTAGTGACAAAAACAATGGCT

CTGGTAGCAAAGAGAAAAACAAAGATGGCAAGTACTCATTCAACGAAAAAGGC

GAAATCAGTGAAAAAACCATTGTGCGTGCGTGTGGCACCCGTCTGGAATATACC

GACATCAAGAGCGATAAAACGGGTAAAGCGAAGGAAGTTCTGAAAGATTTTACG

CTGGAAGGTACCCTGGCAGCAGACGGTAAAACCACGCTGAAGGTGACCGAAGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGACTCAGGCACC

TCGACGCTGACCATTTCTAAAAATCGTACGAAAACCAAGCAGCTGGTCTTCACGA

AAGAATGCACGATCACCGTGCAAAACTATGATAGCGCAGGTACCAATCTGGAAG

GCAAAGCTGTGGAAATTACCACGCTGAAAGAACTGAAGAATGCTCTGAAA

Lip-S6D1-S5D4_His_aa
Heterodimer fusion protein of OspA serotype 6 with disulfide bond type 1 and OspA serotype 5 with disulfide bond type 4, N-terminal CSS for addition of lipids, LN1 peptide linker (SEQ ID NO: 184), N-terminal lipidation, C-terminal His tag (GLEHHHHHH) (SEQ ID NO: 214)

SEQ ID NO: 137

LipCSSFNGKGETSEKTIVRANGTRLEYTDIKSDGSGKAKEVLKDFTLEGTLAADGKTT

LKVTCGTVVLSKNILKSGEITAALDDSDTTRATKKTGKWDSKTSTLTISVNSQKTKN

-continued

LVFTKEDTITVQRYDSAGTNLEGKAVEITTLKELCNALKGTSDKNNGSGSKEKNKDG

KYSFNEKGEISEKTIVRACGTRLEYTDIKSDKTGKAKEVLKDFTLEGTLAADGKTTL

KVTEGTVTLSKNISKSGEITVALDDTDSSGNKKSGTWDSGTSTLTISKNRTKTKQLVF

TKECTITVQNYDSAGTNLEGKAVEITTLKELKNALKGLEHHHHHH

Lip-S6D1-S5D4_His_nt
Coding sequence for heterodimer fusion protein of OspA serotype 6 with disulfide bond type 1 and OspA serotype 5 with disulfide bond type 4, *E. coli* lpp lipidation signal, N-terminal CSS for addition of lipids, LN1 peptide linker (SEQ ID NO: 184), C-terminal His tag (GLEHHHHHH) (SEQ ID NO: 214)

SEQ ID NO: 138

ATGAAAGCTACTAAACTGGTACTGGGCGCGGTAATCCTGGGTTCTACTCTGCTGG

CAGGTTGCTCAAGCTTCAACGGCAAAGGTGAAACGAGCGAAAAGACCATCGTGC

GTGCGAACGGTACCCGCCTGGAATATACGGACATTAAATCGGACGGCAGCGGCA

AAGCAAAGGAAGTCCTGAAAGATTTTACGCTGGAAGGTACCCTGGCAGCAGACG

GTAAAACCACGCTGAAGGTGACGTGCGGCACCGTGGTTCTGTCAAAAAACATTC

TGAAGTCGGGTGAAATCACCGCAGCTCTGGATGACAGCGATACCACGCGTGCTA

CGAAAAAGACCGGTAAATGGGATAGCAAGACCTCTACGCTGACCATTAGTGTCA

ACTCCCAGAAAACGAAGAATCTGGTGTTCACCAAAGAAGATACGATCACCGTTC

AACGCTATGACAGTGCGGGCACCAACCTGGAAGGCAAAGCCGTTGAAATTACCA

CGCTGAAAGAACTGTGTAATGCTCTGAAAGGTACTAGTGACAAAAACAATGGCT

CTGGTAGCAAAGAGAAAAACAAAGATGGCAAGTACTCATTCAACGAAAAAGGC

GAAATCAGTGAAAAAACCATTGTGCGTGCGTGTGGCACCCGTCTGGAATATACC

GACATCAAGAGCGATAAAACGGGTAAAGCGAAGGAAGTTCTGAAAGATTTTACG

CTGGAAGGTACCCTGGCAGCAGACGGTAAAACCACGCTGAAGGTGACCGAAGGT

ACCGTTACGCTGTCCAAAAACATTAGTAAGTCCGGCGAAATCACGGTCGCCCTG

GATGACACCGATAGCTCTGGCAACAAAAAGAGCGGTACCTGGGACTCAGGCACC

TCGACGCTGACCATTTCTAAAAATCGTACGAAAACCAAGCAGCTGGTCTTCACGA

AAGAATGCACGATCACCGTGCAAAACTATGATAGCGCAGGTACCAATCTGGAAG

GCAAAGCTGTGGAAATTACCACGCTGAAAGAACTGAAGAATGCTCTGAAAGGTC

TCGAGCACCACCACCACCACCAC

SEQ ID NO: 139

N-palmitoyl-S-(2RS)-2,3-bis-(palmitoyloxy)propyl cysteine
$Pam_3C$

Lip-S2D0-His
amino acids of positions 131-273 of *Borrelia afzelii* strain K78, OspA serotype 2, wild-type sequence, N-terminal CKQN for addition of lipids, C-terminal His tag (GLEHHHHHH) (SEQ ID NO: 214)

SEQ ID NO: 140

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTITVQKYDSAGTNLEGTAVEIKTLDELKNALKGLEHHHHHH

-continued

Lip-S2D1-His
aa 131-273 of *Borrelia afzelii* strain K78, OspA serotype 2 with disulfide bond type 1 (aa 182 and 269), N-terminal CKQN for addition of lipids, C-terminal His tag (GLEHHHHHH) (SEQ ID NO: 214)

SEQ ID NO: 141
LipCKQNELSAKTMTRENGTKLEYTEMKSDGTGKAKEVLKNFTLEGKVANDKVTLE

VKCGTVTLSKEIAKSGEVTVALNDTNTTQATKKTGAWDSKTSTLTISVNSKKTTQLV

FTKQDTITVQKYDSAGTNLEGTAVEIKTLDELCNALKGLEHHHHHH

Lip-S2D2-His
aa 131-273 of *Borrelia afzelii* strain K78, OspA serotype 2 with disulfide bond type 2 (aa 182 and 272), N-terminal CKQN for addition of lipids, C-terminal His tag (GLEHHHHHH) (SEQ ID NO: 214)

SEQ ID NO: 142
LipCKQNELSAKTMTRENGTKLEYTEMKSDGTGKAKEVLKNFTLEGKVANDKVTLE

VKCGTVTLSKEIAKSGEVTVALNDTNTTQATKKTGAWDSKTSTLTISVNSKKTTQLV

FTKQDTITVQKYDSAGTNLEGTAVEIKTLDELKNACKGLEHHHHHH

Lip-S2D3-His
aa 131-273 of *Borrelia afzelii* strain K78, OspA serotype 2 with disulfide bond type 3 (aa 244 and 259), N-terminal CKQN for addition of lipids, C-terminal His tag (GLEHHHHHH) (SEQ ID NO: 214)

SEQ ID NO: 143
LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTICVQKYDSAGTNLEGTCVEIKTLDELKNALKGLEHHHHHH

Lip-S2D4-His
aa 131-273 of *Borrelia afzelii* strain K78, OspA serotype 2 with disulfide bond type 4 (aa 141 and 241), N-terminal CKQN for addition of lipids, C-terminal His tag (GLEHHHHHH) (SEQ ID NO: 214)

SEQ ID NO: 144
LipCKQNELSAKTMTRECGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQCTITVQKYDSAGTNLEGTAVEIKTLDELKNALKGLEHHHHHH

Lip-S2D5-His
aa 131-273 of *Borrelia afzelii* strain K78, OspA serotype 2 with disulfide bond type 5 (aa 165 and 265), N-terminal CKQN for addition of lipids, C-terminal His tag (GLEHHHHHH) (SEQ ID NO: 214)

SEQ ID NO: 145
LipCKQNELSAKTMTRENGTKLEYTEMKSDGTGKAKEVLKNCTLEGKVANDKVTLE

VKEGTVTLSKEIAKSGEVTVALNDTNTTQATKKTGAWDSKTSTLTISVNSKKTTQLV

FTKQDTITVQKYDSAGTNLEGTAVEIKTCDELKNALKGLEHHHHHH

Lip-S2D6-His
aa 131-273 of *Borrelia afzelii* strain K78, OspA serotype 2 with disulfide bond type 6 (aa 185 and 272), N-terminal CKQN for addition of lipids, C-terminal His tag (GLEHHHHHH) (SEQ ID NO: 214)

SEQ ID NO: 146
LipCKQNELSAKTMTRENGTKLEYTEMKSDGTGKAKEVLKNFTLEGKVANDKVTLE

VKEGTCTLSKEIAKSGEVTVALNDTNTTQATKKTGAWDSKTSTLTISVNSKKTTQLV

FTKQDTITVQKYDSAGTNLEGTAVEIKTLDELKNACKGLEHHHHHH

-continued

Lip-S2D7-His
aa 131-273 of *Borrelia afzelii* strain K78, OspA sero-type 2 with disulfide bond type 7 (aa 199 and 223), N-terminal CKQN for addition of lipids, C-terminal His tag (GLEHHHHHH) (SEQ ID NO: 214)

SEQ ID NO: 147

LipCKQNELSAKTMTRENGTKLEYTEMKSDGTGKAKEVLKNFTLEGKVANDKVTLE

VKEGTVTLSKEIAKSGEVTCALNDTNTTQATKKTGAWDSKTSTCTISVNSKKTTQLV

FTKQDTITVQKYDSAGTNLEGTAVEIKTLDELKNALKGLEHHHHHH

Lip-S2D8-His
aa 131-273 of *Borrelia afzelii* strain K78, OspA sero-type 2 with disulfide bond type 8 (aa 243 and 262), N-terminal CKQN for addition of lipids, C-terminal His tag (GLEHHHHHH) (SEQ ID NO: 214)

SEQ ID NO: 148

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTCTVQKYDSAGTNLEGTAVECKTLDELKNALKGLEHHHHHH

Lip-S2D9-His
aa 131-273 of *Borrelia afzelii* strain K78, OspA sero-type 2 with disulfide bond type 9 (aa 184 and 204), N-terminal CKQN for addition of lipids, C-terminal His tag (GLEHHHHHH) (SEQ ID NO: 214)

SEQ ID NO: 149

LipCKQNELSAKTMTRENGTKLEYTEMKSDGTGKAKEVLKNFTLEGKVANDKVTLE

VKEGCVTLSKEIAKSGEVTVALNDCNTTQATKKTGAWDSKTSTLTISVNSKKTTQL

VFTKQDTITVQKYDSAGTNLEGTAVEIKTLDELKNALKGLEHHHHHH

Lip-S2D10-His
aa 131-273 of *Borrelia afzelii* strain K78, OspA sero-type 2 with disulfide bond type 10 (aa 201 and 214), N-terminal CKQN for addition of lipids, C-terminal His tag (GLEHHHHHH) (SEQ ID NO: 214)

SEQ ID NO: 150

LipCKQNELSAKTMTRENGTKLEYTEMKSDGTGKAKEVLKNFTLEGKVANDKVTLE

VKEGTVTLSKEIAKSGEVTVACNDTNTTQATKKTCAWDSKTSTLTISVNSKKTTQLV

FTKQDTITVQKYDSAGTNLEGTAVEIKTLDELKNALKGLEHHHHHH

Lip-S2D11-His
aa 131-273 of *Borrelia afzelii* strain K78, OspA sero-type 2 with disulfide bond type 11 (aa 246 and 259), N-terminal CKQN for addition of lipids, C-terminal His tag (GLEHHHHHH) (SEQ ID NO: 214)

SEQ ID NO: 151

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTITVCKYDSAGTNLEGTCVEIKTLDELKNALKGLEHHHHHH

Lip-S2D12-His
aa 131-273 of *Borrelia afzelii* strain K78, OspA sero-type 2 with disulfide bond type 12 (aa 167 and 178), N-terminal CKQN for addition of lipids, C-terminal His tag (GLEHHHHHH) (SEQ ID NO: 214)

SEQ ID NO: 152

LipCKQNELSAKTMTRENGTKLEYTEMKSDGTGKAKEVLKNFTCEGKVANDKVTCE

VKEGTVTLSKEIAKSGEVTVALNDTNTTQATKKTGAWDSKTSTLTISVNSKKTTQLV

FTKQDTITVQKYDSAGTNLEGTAVEIKTLDELKNALKGLEHHHHHH

-continued

Lip-S2D0
amino acids of positions 131-273 of *Borrelia afzelii* strain K78, OspA serotype 2, wild-type sequence, N-terminal CKQN for addition of lipids

SEQ ID NO: 153

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTITVQKYDSAGTNLEGTAVEIKTLDELKNALK

Lip-S2D1
aa 131-273 of *Borrelia afzelii* strain K78, OspA serotype 2 with disulfide bond type 1 (aa 182 and 269), N-terminal CKQN for addition of lipids

SEQ ID NO: 154

LipCKQNELSAKTMTRENGTKLEYTEMKSDGTGKAKEVLKNFTLEGKVANDKVTLE

VKCGTVTLSKEIAKSGEVTVALNDTNTTQATKKTGAWDSKTSTLTISVNSKKTTQLV

FTKQDTITVQKYDSAGTNLEGTAVEIKTLDELCNALK

Lip-S2D2
aa 131-273 of *Borrelia afzelii* strain K78, OspA serotype 2 with disulfide bond type 2 (aa 182 and 272), N-terminal CKQN for addition of lipids

SEQ ID NO: 155

LipCKQNELSAKTMTRENGTKLEYTEMKSDGTGKAKEVLKNFTLEGKVANDKVTLE

VKCGTVTLSKEIAKSGEVTVALNDTNTTQATKKTGAWDSKTSTLTISVNSKKTTQLV

FTKQDTITVQKYDSAGTNLEGTAVEIKTLDELKNACK

Lip-S2D3
aa 131-273 of *Borrelia afzelii* strain K78, OspA serotype 2 with disulfide bond type 3 (aa 244 and 259), N-terminal CKQN for addition of lipids

SEQ ID NO: 156

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTICVQKYDSAGTNLEGTCVEIKTLDELKNALK

Lip-S2D4
aa 131-273 of *Borrelia afzelii* strain K78, OspA serotype 2 with disulfide bond type 4 (aa 141 and 241), N-terminal CKQN for addition of lipids

SEQ ID NO: 157

LipCKQNELSAKTMTRECGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQCTITVQKYDSAGTNLEGTAVEIKTLDELKNALK

Lip-S2D5
aa 131-273 of *Borrelia afzelii* strain K78, OspA serotype 2 with disulfide bond type 5 (aa 165 and 265), N-terminal CKQN for addition of lipids

SEQ ID NO: 158

LipCKQNELSAKTMTRENGTKLEYTEMKSDGTGKAKEVLKNCTLEGKVANDKVTLE

VKEGTVTLSKEIAKSGEVTVALNDTNTTQATKKTGAWDSKTSTLTISVNSKKTTQLV

FTKQDTITVQKYDSAGTNLEGTAVEIKTCDELKNALK

Lip-S2D6
aa 131-273 of *Borrelia afzelii* strain K78, OspA serotype 2 with disulfide bond type 6 (aa 185 and 272), N-terminal CKQN for addition of lipids

SEQ ID NO: 159

LipCKQNELSAKTMTRENGTKLEYTEMKSDGTGKAKEVLKNFTLEGKVANDKVTLE

VKEGTCTLSKEIAKSGEVTVALNDTNTTQATKKTGAWDSKTSTLTISVNSKKTTQLV

FTKQDTITVQKYDSAGTNLEGTAVEIKTLDELKNACK

Lip-S2D7
aa 131-273 of *Borrelia afzelii* strain K78, OspA serotype 2 with disulfide bond type 7 (aa 199 and 223), N-terminal CKQN for addition of lipids

SEQ ID NO: 160

LipCKQNELSAKTMTRENGTKLEYTEMKSDGTGKAKEVLKNFTLEGKVANDKVTLE

VKEGTVTLSKEIAKSGEVTCALNDTNTTQATKKTGAWDSKTSTCTISVNSKKTTQLV

FTKQDTITVQKYDSAGTNLEGTAVEIKTLDELKNALK

Lip-S2D8
aa 131-273 of *Borrelia afzelii* strain K78, OspA serotype 2 with disulfide bond type 8 (aa 243 and 262), N-terminal CKQN for addition of lipids

SEQ ID NO: 161

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTCTVQKYDSAGTNLEGTAVECKTLDELKNALK

Lip-S2D9
aa 131-273 of *Borrelia afzelii* strain K78, OspA serotype 2 with disulfide bond type 9 (aa 184 and 204), N-terminal CKQN for addition of lipids

SEQ ID NO: 162

LipCKQNELSAKTMTRENGTKLEYTEMKSDGTGKAKEVLKNFTLEGKVANDKVTLE

VKEGCVTLSKEIAKSGEVTVALNDCNTTQATKKTGAWDSKTSTLTISVNSKKTTQL

VFTKQDTITVQKYDSAGTNLEGTAVEIKTLDELKNALK

Lip-S2D10
aa 131-273 of *Borrelia afzelii* strain K78, OspA serotype 2 with disulfide bond type 10 (aa 201 and 214), N-terminal CKQN for addition of lipids

SEQ ID NO: 163

LipCKQNELSAKTMTRENGTKLEYTEMKSDGTGKAKEVLKNFTLEGKVANDKVTLE

VKEGTVTLSKEIAKSGEVTVACNDTNTTQATKKTCAWDSKTSTLTISVNSKKTTQLV

FTKQDTITVQKYDSAGTNLEGTAVEIKTLDELKNALK

Lip-S2D11
aa 131-273 of *Borrelia afzelii* strain K78, OspA serotype 2 with disulfide bond type 11 (aa 246 and 259), N-terminal CKQN for addition of lipids

SEQ ID NO: 164

LipCKQNELSAKTMTRENGTKLEYTEMKSDGTGKAKEVLKNFTLEGKVANDKVTLE

VKEGTVTLSKEIAKSGEVTVALNDTNTTQATKKTGAWDSKTSTLTISVNSKKTTQLV

FTKQDTITVCKYDSAGTNLEGTCVEIKTLDELKNALK

Lip-S2D12
aa 131-273 of *Borrelia afzelii* strain K78, OspA serotype 2 with disulfide bond type 12 (aa 167 and 178), N-terminal CKQN for addition of lipids

SEQ ID NO: 165

LipCKQNELSAKTMTRENGTKLEYTEMKSDGTGKAKEVLKNFTCEGKVANDKVTCE

VKEGTVTLSKEIAKSGEVTVALNDTNTTQATKKTGAWDSKTSTLTISVNSKKTTQLV

FTKQDTITVQKYDSAGTNLEGTAVEIKTLDELKNALK

S2D0
amino acids of positions 131-273 of *Borrelia afzelii* strain K78, OspA serotype 2, wild-type sequence

SEQ ID NO: 166

ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

TVQKYDSAGTNLEGTAVEIKTLDELKNALK

-continued

S2D1
aa 131-273 of *Borrelia afzelii* strain K78, OspA sero-
type 2 with disulfide bond type 1 (aa 182 and 269)
SEQ ID NO: 167
ELSAKTMTRENGTKLEYTEMKSDGTGKAKEVLKNFTLEGKVANDKVTLEVKCGTV

TLSKEIAKSGEVTVALNDTNTTQATKKTGAWDSKTSTLTISVNSKKTTQLVFTKQDTI

TVQKYDSAGTNLEGTAVEIKTLDELCNALK

S2D2
aa 131-273 of *Borrelia afzelii* strain K78, OspA sero-
type 2 with disulfide bond type 2 (aa 182 and 272)
SEQ ID NO: 168
ELSAKTMTRENGTKLEYTEMKSDGTGKAKEVLKNFTLEGKVANDKVTLEVKCGTV

TLSKEIAKSGEVTVALNDTNTTQATKKTGAWDSKTSTLTISVNSKKTTQLVFTKQDTI

TVQKYDSAGTNLEGTAVEIKTLDELKNACK

S2D3
aa 131-273 of *Borrelia afzelii* strain K78, OspA sero-
type 2 with disulfide bond type 3 (aa 244 and 259)
SEQ ID NO: 169
ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

CVQKYDSAGTNLEGTCVEIKTLDELKNALK

S2D4
aa 131-273 of *Borrelia afzelii* strain K78, OspA sero-
type 2 with disulfide bond type 4 (aa 141 and 241)
SEQ ID NO: 170
ELSAKTMTRECGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQCTI

TVQKYDSAGTNLEGTAVEIKTLDELKNALK

S2D5
aa 131-273 of *Borrelia afzelii* strain K78, OspA sero-
type 2 with disulfide bond type 5 (aa 165 and 265)
SEQ ID NO: 171
ELSAKTMTRENGTKLEYTEMKSDGTGKAKEVLKNCTLEGKVANDKVTLEVKEGTV

TLSKEIAKSGEVTVALNDTNTTQATKKTGAWDSKTSTLTISVNSKKTTQLVFTKQDTI

TVQKYDSAGTNLEGTAVEIKTCDELKNALK

S2D6
aa 131-273 of *Borrelia afzelii* strain K78, OspA sero-
type 2 with disulfide bond type 6 (aa 185 and 272)
SEQ ID NO: 172
ELSAKTMTRENGTKLEYTEMKSDGTGKAKEVLKNFTLEGKVANDKVTLEVKEGTC

TLSKEIAKSGEVTVALNDTNTTQATKKTGAWDSKTSTLTISVNSKKTTQLVFTKQDTI

TVQKYDSAGTNLEGTAVEIKTLDELKNACK

S2D7
aa 131-273 of *Borrelia afzelii* strain K78, OspA sero-
type 2 with disulfide bond type 7 (aa 199 and 223)
SEQ ID NO: 173
ELSAKTMTRENGTKLEYTEMKSDGTGKAKEVLKNFTLEGKVANDKVTLEVKEGTV

TLSKEIAKSGEVTCALNDTNTTQATKKTGAWDSKTSTCTISVNSKKTTQLVFTKQDT

ITVQKYDSAGTNLEGTAVEIKTLDELKNALK

S2D8
aa 131-273 of *Borrelia afzelii* strain K78, OspA sero-
type 2 with disulfide bond type 8 (aa 243 and 262)
SEQ ID NO: 174
ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDT

CTVQKYDSAGTNLEGTAVECKTLDELKNALK

-continued

S2D9
aa 131-273 of *Borrelia afzelii* strain K78, OspA serotype 2 with disulfide bond type 9 (aa 184 and 204)

SEQ ID NO: 175

ELSAKTMTRENGTKLEYTEMKSDGTGKAKEVLKNFTLEGKVANDKVTLEVKEGCV

TLSKEIAKSGEVTVALNDCNTTQATKKTGAWDSKTSTLTISVNSKKTTQLVFTKQDT

ITVQKYDSAGTNLEGTAVEIKTLDELKNALK

S2D10
aa 131-273 of *Borrelia afzelii* strain K78, OspA serotype 2 with disulfide bond type 10 (aa 201 and 214)

SEQ ID NO: 176

ELSAKTMTRENGTKLEYTEMKSDGTGKAKEVLKNFTLEGKVANDKVTLEVKEGTV

TLSKEIAKSGEVTVACNDTNTTQATKKTCAWDSKTSTLTISVNSKKTTQLVFTKQDT

ITVQKYDSAGTNLEGTAVEIKTLDELKNALK

S2D11
aa 131-273 of *Borrelia afzelii* strain K78, OspA serotype 2 with disulfide bond type 11 (aa 246 and 259)

SEQ ID NO: 177

ELSAKTMTRENGTKLEYTEMKSDGTGKAKEVLKNFTLEGKVANDKVTLEVKEGTV

TLSKEIAKSGEVTVALNDTNTTQATKKTGAWDSKTSTLTISVNSKKTTQLVFTKQDTI

TVCKYDSAGTNLEGTCVEIKTLDELKNALK

S2D12
aa 131-273 of *Borrelia afzelii* strain K78, OspA serotype 2 with disulfide bond type 12 (aa 167 and 178)

SEQ ID NO: 178

ELSAKTMTRENGTKLEYTEMKSDGTGKAKEVLKNFTCEGKVANDKVTCEVKEGTV

TLSKEIAKSGEVTVALNDTNTTQATKKTGAWDSKTSTLTISVNSKKTTQLVFTKQDTI

TVQKYDSAGTNLEGTAVEIKTLDELKNALK

*B. burgdorferi* s.s. (strain B31, serotype 1), OspA_aa 126-273 with replaced hLFA-like sequence from serotype 1 OspA

SEQ ID NO: 179

FNEKGEVSEKIITRADGTRLEYTGIKSDGSGKAKEVLKNFTLEGKVANDKTTLVVKE

GTVTLSKNISKSGEVSVELNDTDSSAATKKTAAWNSGTSTLTITVNSKKTKDLVFTK

ENTITVQQYDSNGTKLEGSAVEITKLDEIKNALK

*B. garinii* (strain PBr, serotype 3), OspA_aa 126-274

SEQ ID NO: 180

FNDKGKLSEKVVTRANGTRLEYTEIKNDGSGKAKEVLKGFALEGTLTDGGETKLTV

TEGTVTLSKNISKSGEITVALNDTETTPADKKTGEWKSDTSTLTISKNSQKPKQLVFT

KENTITVQNYNRAGNALEGSPAEIKDLAELKAALK

*B. bavariensis* (strain PBi, serotype 4), OspA_aa 126-273

SEQ ID NO: 181

FNAKGELSEKTILRANGTRLEYTEIKSDGTGKAKEVLKDFALEGTLAADKTTLKVTE

GTVVLSKHIPNSGEITVELNDSNSTQATKKTGKWDSNTSTLTISVNSKKTKNIVFTKE

DTITVQKYDSAGTNLEGNAVEIKTLDELKNALK

*B. garinii* (strain PHei, serotype 5), OspA_aa 126-273

SEQ ID NO: 182

FNEKGEISEKTIVRANGTRLEYTDIKSDKTGKAKEVLKDFTLEGTLAADGKTTLKVT

EGTVTLSKNISKSGEITVALDDTDSSGNKKSGTWDSGTSTLTISKNRTKTKQLVFTKE

DTITVQNYDSAGTNLEGKAVEITTLKELKNALK

*B. garinii* (strain DK29, serotype 6), OspA_aa 126-274

SEQ ID NO: 183

FNGKGETSEKTIVRANGTRLEYTDIKSDGSGKAKEVLKDFTLEGTLAADGKTTLKVT

EGTVVLSKNILKSGEITAALDDSDTTRATKKTGKWDSKTSTLTISVNSQKTKNLVFTK

EDTITVQRYDSAGTNLEGKAVEITTLKELKNALK

LN1 peptide linker constructed from two separate
loop regions of the N-terminal half of OspA from
B. burgdorferi s.s. strain B31 (aa 65-74 and aa
42-53, amino acid exchange at position 53: D53S)
SEQ ID NO: 184
GTSDKNNGSGSKEKNKDGKYS Lip-S1D4-S2D4_aa
Heterodimer fusion protein of OspA serotypes 1 and 2
both with disulfide bond type 4, N-terminal CSS for
addition of lipids, LN1 peptide linker (SEQ ID NO:
184), aa 164-174 of OspA serotype 1 replaced by non-
hLFA-1-like sequence NFTLEGKVAND (SEQ ID NO: 18)
SEQ ID NO: 185
LipCSSFNEKGEVSEKIITRACGTRLEYTGIKSDGSGKAKEVLKNFTLEGKVANDKTTL

VVKEGTVTLSKNISKSGEVSVELNDTDSSAATKKTAAWNSGTSTLTITVNSKKTKDL

VFTKECTITVQQYDSNGTKLEGSAVEITKLDEIKNALKGTSDKNNGSGSKEKNKDGK

YSFNEKGELSAKTMTRECGTKLEYTEMKSDGTGKAKEVLKNFTLEGKVANDKVTL

EVKEGTVTLSKEIAKSGEVTVALNDTNTTQATKKTGAWDSKTSTLTISVNSKKTTQL

VFTKQCTITVQKYDSAGTNLEGTAVEIKTLDELKNALK

Lip-S1D1-S2D1_aa
Heterodimer fusion protein of OspA serotype 1 and OspA
serotype 2 with disulfide bond type 1, N-terminal CSS
for addition of lipids, LN1 peptide linker (SEQ ID NO:
184), aa 164-174 of OspA serotype 1 replaced by non-
hLFA-1-like sequence NFTLEGKVAND (SEQ ID NO: 18), N-
terminal lipidation
SEQ ID NO: 186
LipCSSFNEKGEVSEKIITRADGTRLEYTGIKSDGSGKAKEVLKNFTLEGKVANDKTTL

VVKCGTVTLSKNISKSGEVSVELNDTDSSAATKKTAAWNSGTSTLTITVNSKKTKDL

VFTKENTITVQQYDSNGTKLEGSAVEITKLDEICNALKGTSDKNNGSGSKEKNKDGK

YSFNEKGELSAKTMTRENGTKLEYTEMKSDGTGKAKEVLKNFTLEGKVANDKVTL

EVKCGTVTLSKEIAKSGEVTVALNDTNTTQATKKTGAWDSKTSTLTISVNSKKTTQL

VFTKQDTITVQKYDSAGTNLEGTAVEIKTLDELCNALK

Lip-S3D4-S4D4_aa
Heterodimer fusion protein of OspA serotype 3 and OspA
serotype 4 with disulfide bond type 4, N-terminal CSS
for addition of lipids, LN1 peptide linker (SEQ ID NO:
184), N-terminal lipidation
SEQ ID NO: 187
LipCSSFNEKGKLSEKVVTRACGTRLEYTEIKNDGSGKAKEVLKGFALEGTLTDGGET

KLTVTEGTVTLSKNISKSGEITVALNDTETTPADKKTGEWKSDTSTLTISKNSQKPKQ

LVFTKECTITVQNYNRAGNALEGSPAEIKDLAELKAALKGTSDKNNGSGSKEKNKD

GKYSFNAKGELSEKTILRACGTRLEYTEIKSDGTGKAKEVLKDFALEGTLAADKTTL

KVTEGTVVLSKHIPNSGEITVELNDSNSTQATKKTGKWDSNTSTLTISVNSKKTKNIV

FTKECTITVQKYDSAGTNLEGNAVEIKTLDELKNALK

Lip-S3D1-S4D1_aa
Heterodimer fusion protein of OspA serotypes 3 and 4
both with disulfide bond type 1, N-terminal CSS for
addition of lipids, LN1 peptide linker (SEQ ID NO:
184), N-terminal lipidation
SEQ ID NO: 188
LipCSSFNEKGKLSEKVVTRANGTRLEYTEIKNDGSGKAKEVLKGFALEGTLTDGGET

KLTVTCGTVTLSKNISKSGEITVALNDTETTPADKKTGEWKSDTSTLTISKNSQKPKQ

LVFTKENTITVQNYNRAGNALEGSPAEIKDLAELCAALKGTSDKNNGSGSKEKNKD

GKYSFNAKGELSEKTILRANGTRLEYTEIKSDGTGKAKEVLKDFALEGTLAADKTTL

-continued

KVTCGTVVLSKHIPNSGEITVELNDSNSTQATKKTGKWDSNTSTLTISVNSKKTKNIV

FTKEDTITVQKYDSAGTNLEGNAVEIKTLDELCNALK

Lip-S5D4-S6D4_aa
Heterodimer fusion protein OspA serotypes 5 and 6 both with disulfide bond type 4, N-terminal CSS for addition of lipids, LN1 peptide linker (SEQ ID NO: 184), N-terminal lipidation

SEQ ID NO: 189

LipCSSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALKGTSDKNNGSGSKEKNKDGK

YSFNGKGETSEKTIVRACGTRLEYTDIKSDGSGKAKEVLKDFTLEGTLAADGKTTLK

VTEGTVVLSKNILKSGEITAALDDSDTTRATKKTGKWDSKTSTLTISVNSQKTKNLVF

TKECTITVQRYDSAGTNLEGKAVEITTLKELKNALK

Lip-S5D1-S6D1_aa
Heterodimer fusion protein of OspA serotypes 6 both with disulfide bond type 1, N-terminal CSS for addition of lipids, LN1 peptide linker (SEQ ID NO: 184), N-terminal lipidation

SEQ ID NO: 190

LipCSSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGTSDKNNGSGSKEKNKDGK

YSFNGKGETSEKTIVRANGTRLEYTDIKSDGSGKAKEVLKDFTLEGTLAADGKTTLK

VTCGTVVLSKNILKSGEITAALDDSDTTRATKKTGKWDSKTSTLTISVNSQKTKNLV

FTKEDTITVQRYDSAGTNLEGKAVEITTLKELCNALK

Lip-S2D4-S1D4_aa
Heterodimer fusion protein of OspA serotypes 2 and 1 both with disulfide bond type 4, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 191

LipCSSFNEKGELSAKTMTRECGTKLEYTEMKSDGTGKAKEVLKNFTLEGKVANDK

VTLEVKEGTVTLSKEIAKSGEVTVALNDTNTTQATKKTGAWDSKTSTLTISVNSKKT

TQLVFTKQCTITVQKYDSAGTNLEGTAVEIKTLDELKNALKGTSDKNNGSGSKEKN

KDGKYSFNEKGEVSEKIITRACGTRLEYTGIKSDGSGKAKEVLKNFTLEGKVANDKT

TLVVKEGTVTLSKNISKSGEVSVELNDTDSSAATKKTAAWNSGTSTLTITVNSKKTK

DLVFTKECTITVQQYDSNGTKLEGSAVEITKLDEIKNALK

Lip-S2D1-S1D1_aa
Heterodimer fusion protein of OspA serotypes 2 and 1 both with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 192

LipCSSFNEKGELSAKTMTRENGTKLEYTEMKSDGTGKAKEVLKNFTLEGKVANDK

VTLEVKCGTVTLSKEIAKSGEVTVALNDTNTTQATKKTGAWDSKTSTLTISVNSKKT

TQLVFTKQDTITVQKYDSAGTNLEGTAVEIKTLDELCNALKGTSDKNNGSGSKEKN

KDGKYSFNEKGEVSEKIITRADGTRLEYTGIKSDGSGKAKEVLKNFTLEGKVANDKT

TLVVKCGTVTLSKNISKSGEVSVELNDTDSSAATKKTAAWNSGTSTLTITVNSKKTK

DLVFTKENTITVQQYDSNGTKLEGSAVEITKLDEICNALK

-continued

Lip-S4D4-S3D4_aa
Heterodimer fusion protein of OspA serotypes 4 and 3 both with disulfide bond type 4, N-terminal CSS for addition of lipids, LN1 peptide linker (SEQ ID NO: 184), N-terminal lipidation

SEQ ID NO: 193

LipCSSFNAKGELSEKTILRACGTRLEYTEIKSDGTGKAKEVLKDFALEGTLAADKTT

LKVTEGTVVLSKHIPNSGEITVELNDSNSTQATKKTGKWDSNTSTLTISVNSKKTKNI

VFTKECTITVQKYDSAGTNLEGNAVEIKTLDELKNALKGTSDKNNGSGSKEKNKDG

KYSFNDKGKLSEKVVTRACGTRLEYTEIKNDGSGKAKEVLKGFALEGTLTDGGETK

LTVTEGTVTLSKNISKSGEITVALNDTETTPADKKTGEWKSDTSTLTISKNSQKPKQL

VFTKECTITVQNYNRAGNALEGSPAEIKDLAELKAALK

Lip-S4D1-S3D1_aa
Heterodimer fusion protein of OspA serotypes 4 and 3 both with disulfide bond type 1, N-terminal CSS for addition of lipids, LN1 peptide linker (SEQ ID NO: 184), N-terminal lipidation

SEQ ID NO: 194

LipCSSFNAKGELSEKTILRANGTRLEYTEIKSDGTGKAKEVLKDFALEGTLAADKTT

LKVTCGTVVLSKHIPNSGEITVELNDSNSTQATKKTGKWDSNTSTLTISVNSKKTKNI

VFTKEDTITVQKYDSAGTNLEGNAVEIKTLDELCNALKGTSDKNNGSGSKEKNKDG

KYSFNDKGKLSEKVVTRANGTRLEYTEIKNDGSGKAKEVLKGFALEGTLTDGGETK

LTVTCGTVTLSKNISKSGEITVALNDTETTPADKKTGEWKSDTSTLTISKNSQKPKQL

VFTKENTITVQNYNRAGNALEGSPAEIKDLAELCAALK

Lip-S6D4-S5D4_aa
Heterodimer fusion protein of OspA serotypes 6 and 5 both with disulfide bond type 4, N-terminal CSS for addition of lipids, LN1 peptide linker (SEQ ID NO: 184), N-terminal lipidation

SEQ ID NO: 195

LipCSSFNGKGETSEKTIVRACGTRLEYTDIKSDGSGKAKEVLKDFTLEGTLAADGKT

TLKVTEGTVVLSKNILKSGEITAALDDSDTTRATKKTGKWDSKTSTLTISVNSQKTK

NLVFTKECTITVQRYDSAGTNLEGKAVEITTLKELKNALKGTSDKNNGSGSKEKNKD

GKYSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALK

Lip-S6D1-S5D1_aa
Heterodimer fusion protein of OspA serotypes 6 and 5 both with disulfide bond type 1, N-terminal CSS for addition of lipids, LN1 peptide linker (SEQ ID NO: 184), N-terminal lipidation

SEQ ID NO: 196

LipCSSFNGKGETSEKTIVRANGTRLEYTDIKSDGSGKAKEVLKDFTLEGTLAADGKT

TLKVTCGTVVLSKNILKSGEITAALDDSDTTRATKKTGKWDSKTSTLTISVNSQKTK

NLVFTKEDTITVQRYDSAGTNLEGKAVEITTLKELCNALKGTSDKNNGSGSKEKNKD

GKYSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALK

-continued

Lip-S1D4-S2D1_aa
Heterodimer fusion protein of OspA serotype 1 with disulfide bond type 4 and OspA serotype 2 with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 197

LipCSSFNEKGEVSEKIITRACGTRLEYTGIKSDGSGKAKEVLKNFTLEGKVANDKTTL

VVKEGTVTLSKNISKSGEVSVELNDTDSSAATKKTAAWNSGTSTLTITVNSKKTKDL

VFTKECTITVQQYDSNGTKLEGSAVEITKLDEIKNALKGTSDKNNGSGSKEKNKDGK

YSFNEKGELSAKTMTRENGTKLEYTEMKSDGTGKAKEVLKNFTLEGKVANDKVTL

EVKCGTVTLSKEIAKSGEVTVALNDTNTTQATKKTGAWDSKTSTLTISVNSKKTTQL

VFTKQDTITVQKYDSAGTNLEGTAVEIKTLDELCNALK

Lip-S1D1-S2D4_aa
Heterodimer fusion protein of OspA serotype 1 with disulfide bond type 1 and OspA serotype 2 with disulfide bond type 4, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 198

LipCSSFNEKGEVSEKIITRADGTRLEYTGIKSDGSGKAKEVLKNFTLEGKVANDKTTL

VVKCGTVTLSKNISKSGEVSVELNDTDSSAATKKTAAWNSGTSTLTITVNSKKTKDL

VFTKENTITVQQYDSNGTKLEGSAVEITKLDEICNALKGTSDKNNGSGSKEKNKDGK

YSFNEKGELSAKTMTRECGTKLEYTEMKSDGTGKAKEVLKNFTLEGKVANDKVTL

EVKEGTVTLSKEIAKSGEVTVALNDTNTTQATKKTGAWDSKTSTLTISVNSKKTTQL

VFTKQCTITVQKYDSAGTNLEGTAVEIKTLDELKNALK

Lip-S3D4-S4D1_aa
Heterodimer fusion protein of OspA serotype 3 with disulfide bond type 4 and OspA serotype 4 with disulfide bond type 1, N-terminal CSS for addition of lipids, LN1 peptide linker (SEQ ID NO: 184), N-terminal lipidation

SEQ ID NO: 199

LipCSSFNEKGKLSEKVVTRACGTRLEYTEIKNDGSGKAKEVLKGFALEGTLTDGGET

KLTVTEGTVTLSKNISKSGEITVALNDTETTPADKKTGEWKSDTSTLTISKNSQKPKQ

LVFTKECTITVQNYNRAGNALEGSPAEIKDLAELKAALKGTSDKNNGSGSKEKNKD

GKYSFNAKGELSEKTILRANGTRLEYTEIKSDGTGKAKEVLKDFALEGTLAADKTTL

KVTCGTVVLSKHIPNSGEITVELNDSNSTQATKKTGKWDSNTSTLTISVNSKKTKNIV

FTKEDTITVQKYDSAGTNLEGNAVEIKTLDELCNALK

Lip-S3D1-S4D4_aa
Heterodimer fusion protein of OspA serotype 3 with disulfide bond type 1 and OspA serotype 4 with disulfide bond type 1, N-terminal CSS for addition of lipids, LN1 peptide linker (SEQ ID NO: 184), N-terminal lipidation

SEQ ID NO: 200

LipCSSFNEKGKLSEKVVTRANGTRLEYTEIKNDGSGKAKEVLKGFALEGTLTDGGET

KLTVTCGTVTLSKNISKSGEITVALNDTETTPADKKTGEWKSDTSTLTISKNSQKPKQ

LVFTKENTITVQNYNRAGNALEGSPAEIKDLAELCAALKGTSDKNNGSGSKEKNKD

GKYSFNAKGELSEKTILRACGTRLEYTEIKSDGTGKAKEVLKDFALEGTLAADKTTL

KVTEGTVVLSKHIPNSGEITVELNDSNSTQATKKTGKWDSNTSTLTISVNSKKTKNIV

FTKECTITVQKYDSAGTNLEGNAVEIKTLDELKNALK

-continued

Lip-S5D4-S6D1_aa
Heterodimer fusion protein of OspA serotype 5 with disulfide bond type 4 and OspA serotype 6 with disulfide bond type 1, N-terminal CSS for addition of lipids, LN1 peptide linker (SEQ ID NO: 184), N-terminal lipidation

SEQ ID NO: 201

LipCSSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALKGTSDKNNGSGSKEKNKDGK

YSFNGKGETSEKTIVRANGTRLEYTDIKSDGSGKAKEVLKDFTLEGTLAADGKTTLK

VTCGTVVLSKNILKSGEITAALDDSDTTRATKKTGKWDSKTSTLTISVNSQKTKNLV

FTKEDTITVQRYDSAGTNLEGKAVEITTLKELCNALK

Lip-S5D1-S6D4_aa
Heterodimer fusion protein of OspA serotype 5 with disulfide bond type 1 and OspA serotype 6 with disulfide bond type 4, N-terminal CSS for addition of lipids, LN1 peptide linker (SEQ ID NO: 184), N-terminal lipidation

SEQ ID NO: 202

LipCSSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALKGTSDKNNGSGSKEKNKDGK

YSFNGKGETSEKTIVRACGTRLEYTDIKSDGSGKAKEVLKDFTLEGTLAADGKTTLK

VTEGTVVLSKNILKSGEITAALDDSDTTRATKKTGKWDSKTSTLTISVNSQKTKNLVF

TKECTITVQRYDSAGTNLEGKAVEITTLKELKNALK

Lip-S2D4-S1D1_aa
Heterodimer fusion protein of OspA serotype 2 with disulfide bond type 4 and OspA serotype 1 with disulfide bond type 1, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 203

LipCSSFNEKGELSAKTMTRECGTKLEYTEMKSDGTGKAKEVLKNFTLEGKVANDK

VTLEVKEGTVTLSKEIAKSGEVTVALNDTNTTQATKKTGAWDSKTSTLTISVNSKKT

TQLVFTKQCTITVQKYDSAGTNLEGTAVEIKTLDELKNALKGTSDKNNGSGSKEKN

KDGKYSFNEKGEVSEKIITRADGTRLEYTGIKSDGSGKAKEVLKNFTLEGKVANDKT

TLVVKCGTVTLSKNISKSGEVSVELNDTDSSAATKKTAAWNSGTSTLTITVNSKKTK

DLVFTKENTITVQQYDSNGTKLEGSAVEITKLDEICNALK

Lip-S2D1-S1D4_aa
Heterodimer fusion protein of OspA serotype 2 with disulfide bond type 1 and OspA serotype 1 with disulfide bond type 4, N-terminal CSS for addition of lipids, LN1 peptide linker (SEQ ID NO: 184), aa 164-174 of OspA serotype 1 replaced by non-hLFA-1-like sequence NFTLEGKVAND (SEQ ID NO: 18), N-terminal lipidation

SEQ ID NO: 204

LipCSSFNEKGELSAKTMTRENGTKLEYTEMKSDGTGKAKEVLKNFTLEGKVANDK

VTLEVKCGTVTLSKEIAKSGEVTVALNDTNTTQATKKTGAWDSKTSTLTISVNSKKT

TQLVFTKQDTITVQKYDSAGTNLEGTAVEIKTLDELCNALKGTSDKNNGSGSKEKN

KDGKYSFNEKGEVSEKIITRACGTRLEYTGIKSDGSGKAKEVLKNFTLEGKVANDKT

TLVVKEGTVTLSKNISKSGEVSVELNDTDSSAATKKTAAWNSGTSTLTITVNSKKTK

DLVFTKECTITVQQYDSNGTKLEGSAVEITKLDEIKNALK

-continued

Lip-S4D4-S3D1_aa
Heterodimer fusion protein of OspA serotype 4 with disulfide bond type 4 and OspA serotype 3 with disulfide bond type 1, N-terminal CSS for addition of lipids, LN1 peptide linker (SEQ ID NO: 184), N-terminal lipidation
SEQ ID NO: 205

LipCSSFNAKGELSEKTILRACGTRLEYTEIKSDGTGKAKEVLKDFALEGTLAADKTT

LKVTEGTVVLSKHIPNSGEITVELNDSNSTQATKKTGKWDSNTSTLTISVNSKKTKNI

VFTKECTITVQKYDSAGTNLEGNAVEIKTLDELKNALKGTSDKNNGSGSKEKNKDG

KYSFNDKGKLSEKVVTRANGTRLEYTEIKNDGSGKAKEVLKGFALEGTLTDGGETK

LTVTCGTVTLSKNISKSGEITVALNDTETTPADKKTGEWKSDTSTLTISKNSQKPKQL

VFTKENTITVQNYNRAGNALEGSPAEIKDLAELCAALK

Lip-S4D1-S3D4_aa
Coding sequence for intermediate and final heterodimer fusion proteins of OspA serotype 4 with disulfide bond type 1 and OspA serotype 3 with disulfide bond type 4, N-terminal CSS for addition of lipids, LN1 peptide linker (SEQ ID NO: 184), N-terminal lipidation
SEQ ID NO: 206

LipCSSFNAKGELSEKTILRANGTRLEYTEIKSDGTGKAKEVLKDFALEGTLAADKTT

LKVTCGTVVLSKHIPNSGEITVELNDSNSTQATKKTGKWDSNTSTLTISVNSKKTKNI

VFTKEDTITVQKYDSAGTNLEGNAVEIKTLDELCNALKGTSDKNNGSGSKEKNKDG

KYSFNDKGKLSEKVVTRACGTRLEYTEIKNDGSGKAKEVLKGFALEGTLTDGGETK

LTVTEGTVTLSKNISKSGEITVALNDTETTPADKKTGEWKSDTSTLTISKNSQKPKQL

VFTKECTITVQNYNRAGNALEGSPAEIKDLAELKAALK

Lip-S6D4-S5D1_aa
Heterodimer fusion protein of OspA serotype 6 with disulfide bond type 4 and OspA serotype 5 with disulfide bond type 1, N-terminal CSS for addition of lipids, LN1 peptide linker (SEQ ID NO: 184), N-terminal lipidation
SEQ ID NO: 207

LipCSSFNGKGETSEKTIVRACGTRLEYTDIKSDGSGKAKEVLKDFTLEGTLAADGKT

TLKVTEGTVVLSKNILKSGEITAALDDSDTTRATKKTGKWDSKTSTLTISVNSQKTK

NLVFTKECTITVQRYDSAGTNLEGKAVEITTLKELKNALKGTSDKNNGSGSKEKNKD

GKYSFNEKGEISEKTIVRANGTRLEYTDIKSDKTGKAKEVLKDFTLEGTLAADGKTT

LKVTCGTVTLSKNISKSGEITVALDDTDSSGNKKSGTWDSGTSTLTISKNRTKTKQLV

FTKEDTITVQNYDSAGTNLEGKAVEITTLKELCNALK

Lip-S6D1-S5D4_aa
Heterodimer fusion protein of OspA serotype 6 with disulfide bond type 1 and OspA serotype 5 with disulfide bond type 4, N-terminal CSS for addition of lipids, LN1 peptide linker (SEQ ID NO: 184), N-terminal lipidation
SEQ ID NO: 208

LipCSSFNGKGETSEKTIVRANGTRLEYTDIKSDGSGKAKEVLKDFTLEGTLAADGKT

TLKVTCGTVVLSKNILKSGEITAALDDSDTTRATKKTGKWDSKTSTLTISVNSQKTK

NLVFTKEDTITVQRYDSAGTNLEGKAVEITTLKELCNALKGTSDKNNGSGSKEKNKD

GKYSFNEKGEISEKTIVRACGTRLEYTDIKSDKTGKAKEVLKDFTLEGTLAADGKTT

LKVTEGTVTLSKNISKSGEITVALDDTDSSGNKKSGTWDSGTSTLTISKNRTKTKQLV

FTKECTITVQNYDSAGTNLEGKAVEITTLKELKNALK

-continued

*B. afzelii* (strain K78; OspA serotype 2) aa 17-273, lipidation signal sequence removed (aa 1-16: MKKYLLGIGLILALIA, (SEQ ID NO: 14)), C-terminal His tag (GLEHHHHHH) (SEQ ID NO: 214)

SEQ ID NO: 209

CKQNVSSLDEKNSASVDLPGEMKVLVSKEKDKDGKYSLKATVDKIELKGTSDKDN

GSGVLEGTKDDKSKAKLTIADDLSKTTFELFKEDGKTLVSRKVSSKDKTSTDEMFNE

KGELSAKTMTRENGTKLEYTEMKSDGTGKAKEVLKNFTLEGKVANDKVTLEVKEG

TVTLSKEIAKSGEVTVALNDTNTTQATKKTGAWDSKTSTLTISVNSKKTTQLVFTKQ

DTITVQKYDSAGTNLEGTAVEIKTLDELKNALKGLEHHHHHH

Cysteine-containing peptide from *E. coli*

SEQ ID NO: 210

CSS

Cysteine-containing peptide from OspA

SEQ ID NO: 211

CKQN amino acids of positions 126-274 of *B. garinii* strain T25, OspA serotype 7

SEQ ID NO: 212

FNDKGKLSEKVVTRANGTRLEYTEIQNDGSGKAKEVLKSLTLEGTLTADGETKLTVE

AGTVTLSKNISESGEITVELKDTETTPADKKSGTWDSKTSTLTISKNSQKTKQLVFTK

ENTITVQKYNTAGTKLEGSPAEIKDLEALKAALK

Forward oligonucleotide primer for the recA gene of all relevant *Borrelia* species causing Lyme borreliosis

SEQ ID NO: 213

CATGCTCTTGATCCTGTTTA

C-terminal His tag

SEQ ID NO: 214

GLEHHHHHH

Reverse oligonucleotide primer for the recA gene of all relevant *Borrelia* species causing Lyme borreliosis

SEQ ID NO: 215

CCCATTTCTCCATCTATCTC

The entire contents of all of the references (including literature references, issued patents, published patent applications, and co-pending patent applications) cited throughout this application are hereby expressly incorporated by reference.

What is claimed is:

1. A polypeptide comprising a mutant fragment of a *Borrelia* outer surface protein A (OspA), and wherein the mutant OspA fragment comprises a C-terminal domain of an OspA of *Borrelia afzelii, B. burgdorferi* s.s., *B. bavariensis*, or *B. garinii* which lacks at least the first 70 N-terminal amino acid residues; and wherein the mutant OspA fragment differs from the corresponding wild-type *B. afzelii, B. burgdorferi* s.s., *B. bavariensis*, or *B. garinii* OspA fragment sequence at least by the introduction of at least one disulfide bond that is formed by the introduction of i) one cysteine, which forms said disulfide bond with a cysteine residue present within the wild-type fragment; or ii) two cysteines, which together form said disulfide bond, wherein said two cysteines are substituted for amino acids at one amino acid at any of positions 182+/−3 and one amino acid at any of positions 269+/−3;

one amino acid at any of positions 182+/−3 and one amino acid at any of positions 272+/−3;

one amino acid at any of positions 244+/−3 and one amino acid at any of positions 259+/−3;

one amino acid at any of positions 141+/−3 and one amino acid at any of positions 241+/−3; and/or one amino acid at any of positions 165+/−3 and one amino acid at any of positions 265+/−3, wherein the numbering of the cysteine substitutions corresponds to amino acid positions in the full-length OspA of *B. afzelii*, K78 as defined by SEQ ID NO: 19 or the homologous amino acids of an OspA from a *Borrelia* other than *B. afzelii*.

2. The polypeptide of claim 1, wherein the mutant OspA fragment has a difference in protective capacity (Δpc) in a *Borrelia* Challenge Method of at least 50% compared to a placebo control.

3. The polypeptide of claim 1, wherein the mutant OspA fragment has a difference in protective capacity (Δpc) in a *Borrelia* Challenge Method of at least 60% compared to a placebo control.

4. The polypeptide of claim 1, wherein the mutant OspA fragment has a difference in protective capacity (Δpc) in a *Borrelia* Challenge Method of at least 70% compared to a placebo control.

5. The polypeptide of claim 1, wherein the mutant OspA fragment has a difference in protective capacity (Δpc) in a *Borrelia* Challenge Method of at least 80% compared to a placebo control.

6. The polypeptide of claim 1, wherein the mutant OspA fragment has a difference in protective capacity (Δpc) in a *Borrelia* Challenge Method of at least 90% compared to a placebo control.

7. The polypeptide of claim 1, wherein the introduction of the at least one disulfide bond in the OspA C-terminal domain increases the protective capacity (Δpc) of the polypeptide comprising the mutant OspA fragment relative to a polypeptide comprising the respective OspA C-terminal domain without a disulfide bond(s) by at least 10%, when measured in a *Borrelia* Challenge Method.

8. The polypeptide of claim 1, wherein said OspA C-terminal domain is from *B. burgdorferi* s.s., strain B31, OspA serotype 1; wherein the wild-type sequence of OspA from *B. burgdorferi* s.s., strain B31 is defined by SEQ ID NO: 20.

9. The polypeptide of claim 1, wherein said mutant OspA fragment is from the OspA C-terminal domain as defined by SEQ ID NO: 179, and comprises at least one introduced disulfide bond between a) the amino acid at position 182 and the amino acid at position 269;

b) the amino acid at position 182 and the amino acid at position 272;

c) the amino acid at position 244 and the amino acid at position 259;

d) the amino acid at position 141 and the amino acid at position 241; and/or e) the amino acid at position 165 and the amino acid at position 265;

wherein the numbering corresponds to amino acid positions in the full-length OspA protein as defined by SEQ ID NO: 20.

10. The polypeptide according to claim 1, wherein said polypeptide comprises one or more features of the group consisting of a) an *E. coli*-derived lpp lipidation signal as defined by MKATKLVLGAVILGSTLLAG (SEQ ID NO: 16);

b) absence of the amino acid sequence GYVLEGTLTAE (SEQ ID NO: 17);

c) a linker peptide led by an N-terminal cysteine residue as a site for lipidation;

d) presence of between 140 and 152 of the most C-terminal contiguous amino acids of the OspA protein; and e) absence of the N-terminal β-sheet of OspA.

11. The polypeptide of claim 1, wherein said mutant OspA fragment is from SEQ ID NO: 179 and comprises an introduced disulfide bond between the amino acid at position 182 and the amino acid at position 269, wherein the numbering corresponds to amino acid positions in the full-length OspA protein as defined by SEQ ID NO: 20.

12. A polypeptide comprising at least two mutant OspA fragments as defined in claim 1.

13. The polypeptide of claim 12, wherein the polypeptide comprises or consists of a heterodimer selected from the group consisting of Lip-S1D4-S2D4 (SEQ ID NO: 185), Lip-S1D1-S2D1 (SEQ ID NO: 186), Lip-S3D4-S4D4 (SEQ ID NO: 187), Lip-S3D1-S4D1 (SEQ ID NO: 188), Lip-S5D4-S6D4 (SEQ ID NO: 189), Lip-S5D1-S6D1 (SEQ ID NO: 190), Lip-S2D4-S1D4 (SEQ ID NO: 191), Lip-S2D1-S1D1 (SEQ ID NO: 192), Lip-S4D4-53D4 (SEQ ID NO:

193), Lip-S4D1-S3D1 (SEQ ID NO: 194), Lip-S6D4-S5D4 (SEQ ID NO: 195), Lip-S6D1-S5D1 (SEQ ID NO: 196), Lip-S1D4-S2D1 (SEQ ID NO: 197), Lip-S1D1-S2D4 (SEQ ID NO: 198), S3D4-S4D1 (SEQ ID NO: 199), S3D1-S4D4 (SEQ ID NO: 200), S5D4-S6D1 (SEQ ID NO: 201), S5D1-S6D4 (SEQ ID NO: 202), S2D4-S1D1 (SEQ ID NO: 203), S2D1-S1D4 (SEQ ID NO: 204), S4D4-S3D1 (SEQ ID NO: 205), S4D1-S3D4 (SEQ ID NO: 206), S6D4-S5D1 (SEQ ID NO: 207) and Lip-S6D1-S5D4 (SEQ ID NO: 208).

14. A pharmaceutical composition comprising a polypeptide according to claim 1 and optionally a pharmaceutically acceptable carrier or excipient.

15. A pharmaceutical composition comprising at least one of the polypeptides according to claim 13 and optionally a pharmaceutically acceptable carrier or excipient.

16. The pharmaceutical composition according to claim 14, wherein said pharmaceutically acceptable excipient is L-methionine.

17. The pharmaceutical composition according to claim 14, wherein said immunostimulatory substance is selected from the group consisting of polycationic polymers, polycationic peptides, immunostimulatory oligodeoxynucleotides (ODNs), oligo(dIdC)13 (SEQ ID NO: 32), peptides containing at least two LysLeuLys motifs, peptide KLKLLLLLKLK (SEQ ID NO: 33), a combination of KLKLLLLLKLK (SEQ ID NO: 33) and oligo(dIdC)13 (SEQ ID NO: 32), polyarginine, neuroactive compounds, human growth hormone, aluminium hydroxide, aluminium phosphate, Freund's complete adjuvant, and Freund's incomplete adjuvant.

18. The polypeptide of claim 1, wherein said OspA C-terminal domain comprises no more than 152 residues of the most C-terminal contiguous amino acid sequence of the OspA.

19. The polypeptide according to claim 8, wherein said OspA C-terminal domain further differs from the corresponding wild-type sequence by the replacement of the amino acid sequence provided by SEQ ID NO: 17 with the amino acid sequence provided by SEQ ID NO: 18.

* * * * *

UNITED STATES PATENT AND TRADEMARK OFFICE
CERTIFICATE OF CORRECTION

PATENT NO. : 11,208,439 B2
APPLICATION NO. : 15/906618
DATED : December 28, 2021
INVENTOR(S) : Pär Comstedt et al.

It is certified that error appears in the above-identified patent and that said Letters Patent is hereby corrected as shown below:

In the Claims

Claim 13, beginning at Column 436, Line 60, should read:
13. The polypeptide of claim 12, wherein the polypeptide comprises or consists of a heterodimer selected from the group consisting of Lip-S1D4-S2D4 (SEQ ID NO: 185), Lip-S1D1-S2D1 (SEQ ID NO: 186), Lip-S3D4-S4D4 (SEQ ID NO: 187), Lip-S3D1-S4D1 (SEQ ID NO: 188), Lip-S5D4-S6D4 (SEQ ID NO: 189), Lip-S5D1-S6D1 (SEQ ID NO: 190), Lip-S2D4-S1D4 (SEQ ID NO: 191), Lip-S2D1-S1D1 (SEQ ID NO: 192), Lip-S4D4-S3D4 (SEQ ID NO: 193), Lip-S4D1-S3D1 (SEQ ID NO: 194), Lip-S6D4-S5D4 (SEQ ID NO: 195), Lip-S6D1-S5D1 (SEQ ID NO: 196), Lip-S1D4-S2D1 (SEQ ID NO: 197), Lip-S1D1-S2D4 (SEQ ID NO: 198), S3D4-S4D1 (SEQ ID NO: 199), S3D1-S4D4 (SEQ ID NO: 200), S5D4-S6D1 (SEQ ID NO: 201), S5D1-S6D4 (SEQ ID NO: 202), S2D4-S1D1 (SEQ ID NO: 203), S2D1-S1D4 (SEQ ID NO: 204), S4D4-S3D1 (SEQ ID NO: 205), S4D1-S3D4 (SEQ ID NO: 206), S6D4-S5D1 (SEQ ID NO: 207) and Lip-S6D1-S5D4 (SEQ ID NO: 208).

Signed and Sealed this
Seventeenth Day of May, 2022

Katherine Kelly Vidal

Katherine Kelly Vidal
*Director of the United States Patent and Trademark Office*

SEQUENCE LISTING

```
<160> NUMBER OF SEQ ID NOS: 216

<210> SEQ ID NO 1
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 1

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60
```

```
Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 2
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 2

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Cys Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Cys Asn Ala Leu Lys Gly
    130                 135                 140

Leu Glu His His His His His His
145                 150


<210> SEQ ID NO 3
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 3

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Cys Gly Thr Val Thr Leu Ser Lys Glu Ile Ala Lys Ser
```

```
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys Gly
    130                 135                 140

Leu Glu His His His His His His
145                 150


<210> SEQ ID NO 4
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 4

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Cys Val Gln Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys Gly
    130                 135                 140

Leu Glu His His His His His His
145                 150


<210> SEQ ID NO 5
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 5

Glu Leu Ser Ala Lys Thr Met Thr Arg Glu Cys Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45
```

```
Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Cys Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 6
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 6

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Cys Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Cys Asp Glu Leu Lys Asn Ala Leu Lys Gly
    130                 135                 140

Leu Glu His His His His His His
145                 150


<210> SEQ ID NO 7
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 7

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45
```

```
Glu Val Lys Glu Gly Thr Cys Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys Gly
    130                 135                 140

Leu Glu His His His His His His
145                 150


<210> SEQ ID NO 8
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 8

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Cys Ala Leu Asn Asp Thr Asn Thr Thr Gln Ala Thr
65                  70                  75                  80

Lys Lys Thr Gly Ala Trp Asp Ser Lys Thr Ser Thr Cys Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 9
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 9

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
```

```
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Cys Thr Val Gln Lys Tyr Asp Ser Ala Gly Thr Asn Leu Glu Gly Thr
        115                 120                 125

Ala Val Glu Cys Lys Thr Leu Asp Glu Leu Lys Asn Ala Leu Lys Gly
    130                 135                 140

Leu Glu His His His His His His
145                 150


<210> SEQ ID NO 10
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 10

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Cys Val Thr Leu Ser Lys Glu Ile Ala Lys Ser
    50                  55                  60

Gly Glu Val Thr Val Ala Leu Asn Asp Cys Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 11
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 11

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30
```

```
Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Cys Asn Asp Thr Asn Thr Thr Gln Ala Thr
65                  70                  75                  80

Lys Lys Thr Cys Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 12
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 12

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Cys Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys Gly
    130                 135                 140

Leu Glu His His His His His His
145                 150


<210> SEQ ID NO 13
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 13

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30
```

```
Lys Asn Phe Thr Cys Glu Gly Lys Val Ala Asn Asp Lys Val Thr Cys
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys Gly
    130                 135                 140

Leu Glu His His His His His His
145                 150


<210> SEQ ID NO 14
<211> LENGTH: 16
<212> TYPE: PRT
<213> ORGANISM: Borrelia burgdorferi

<400> SEQUENCE: 14

Met Lys Lys Tyr Leu Leu Gly Ile Gly Leu Ile Leu Ala Leu Ile Ala
1               5                   10                  15


<210> SEQ ID NO 15
<211> LENGTH: 15
<212> TYPE: PRT
<213> ORGANISM: Borrelia burgdorferi

<400> SEQUENCE: 15

Met Arg Leu Leu Ile Gly Phe Ala Leu Ala Leu Ala Leu Ile Gly
1               5                   10                  15


<210> SEQ ID NO 16
<211> LENGTH: 20
<212> TYPE: PRT
<213> ORGANISM: Escherichia coli

<400> SEQUENCE: 16

Met Lys Ala Thr Lys Leu Val Leu Gly Ala Val Ile Leu Gly Ser Thr
1               5                   10                  15

Leu Leu Ala Gly
            20


<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 17

Gly Tyr Val Leu Glu Gly Thr Leu Thr Ala Glu
1               5                   10


<210> SEQ ID NO 18
<211> LENGTH: 11
<212> TYPE: PRT
<213> ORGANISM: Artificial Sequence
```

```
<220> FEATURE:
<223> OTHER INFORMATION: Synthetic Polypeptide

<400> SEQUENCE: 18

Asn Phe Thr Leu Glu Gly Lys Val Ala Asn Asp
1               5                   10


<210> SEQ ID NO 19
<211> LENGTH: 273
<212> TYPE: PRT
<213> ORGANISM: Borrelia afzelii

<400> SEQUENCE: 19

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys


<210> SEQ ID NO 20
<211> LENGTH: 273
<212> TYPE: PRT
<213> ORGANISM: Borrelia burgdorferi

<400> SEQUENCE: 20

Met Lys Lys Tyr Leu Leu Gly Ile Gly Leu Ile Leu Ala Leu Ile Ala
1               5                   10                  15
```

```
Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 21
<211> LENGTH: 274
<212> TYPE: PRT
<213> ORGANISM: Borrelia garinii

<400> SEQUENCE: 21

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
                85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
    130                 135                 140
```

```
                165                 170                 175

Thr Lys Leu Thr Val Thr Glu Gly Thr Val Thr Leu Ser Lys Asn Ile
            180                 185                 190

Ser Lys Ser Gly Glu Ile Thr Val Ala Leu Asn Asp Thr Glu Thr Thr
        195                 200                 205

Pro Ala Asp Lys Lys Thr Gly Glu Trp Lys Ser Asp Thr Ser Thr Leu
    210                 215                 220

Thr Ile Ser Lys Asn Ser Gln Lys Pro Lys Gln Leu Val Phe Thr Lys
225                 230                 235                 240

Glu Asn Thr Ile Thr Val Gln Asn Tyr Asn Arg Ala Gly Asn Ala Leu
                245                 250                 255

Glu Gly Ser Pro Ala Glu Ile Lys Asp Leu Ala Glu Leu Lys Ala Ala
            260                 265                 270

Leu Lys


<210> SEQ ID NO 22
<211> LENGTH: 273
<212> TYPE: PRT
<213> ORGANISM: Borrelia bavariensis

<400> SEQUENCE: 22

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Ser Asn Gly Ser Gly Thr Leu Glu Gly Glu Lys
65                  70                  75                  80

Ser Asp Lys Ser Lys Ala Lys Leu Thr Ile Ser Glu Asp Leu Ser Lys
                85                  90                  95

Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
        115                 120                 125

Lys Gly Glu Leu Ser Glu Lys Thr Ile Leu Arg Ala Asn Gly Thr Arg
    130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
                165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
        195                 200                 205

Ala Thr Lys Lys Thr Gly Lys Trp Asp Ser Asn Thr Ser Thr Leu Thr
    210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
                245                 250                 255

Gly Asn Ala Val Glu Ile Lys Thr Leu Asp Glu Leu Lys Asn Ala Leu
```

260 265 270

Lys

<210> SEQ ID NO 23
<211> LENGTH: 273
<212> TYPE: PRT
<213> ORGANISM: Borrelia garinii

<400> SEQUENCE: 23

Met Lys Lys Tyr Leu Leu Gly Ile Gly Leu Ile Leu Ala Leu Ile Ala
1 5 10 15

Cys Lys Gln Asn Val Ser Ser Leu Asp Glu Lys Asn Ser Val Ser Val
20 25 30

Asp Leu Pro Gly Gly Met Lys Val Leu Val Ser Lys Glu Lys Asp Lys
35 40 45

Asp Gly Lys Tyr Ser Leu Met Ala Thr Val Glu Lys Leu Glu Leu Lys
50 55 60

Gly Thr Ser Asp Lys Asn Asn Gly Ser Gly Thr Leu Glu Gly Glu Lys
65 70 75 80

Thr Asp Lys Ser Lys Val Lys Leu Thr Ile Ala Glu Asp Leu Ser Lys
85 90 95

Thr Thr Phe Glu Ile Phe Lys Glu Asp Gly Lys Thr Leu Val Ser Lys
100 105 110

Lys Val Thr Leu Lys Asp Lys Ser Ser Thr Glu Glu Lys Phe Asn Glu
115 120 125

Lys Gly Glu Ile Ser Glu Lys Thr Ile Val Arg Ala Asn Gly Thr Arg
130 135 140

Leu Glu Tyr Thr Asp Ile Lys Ser Asp Lys Thr Gly Lys Ala Lys Glu
145 150 155 160

Val Leu Lys Asp Phe Thr Leu Glu Gly Thr Leu Ala Ala Asp Gly Lys
165 170 175

Thr Thr Leu Lys Val Thr Glu Gly Thr Val Thr Leu Ser Lys Asn Ile
180 185 190

Ser Lys Ser Gly Glu Ile Thr Val Ala Leu Asp Asp Thr Asp Ser Ser
195 200 205

Gly Asn Lys Lys Ser Gly Thr Trp Asp Ser Gly Thr Ser Thr Leu Thr
210 215 220

Ile Ser Lys Asn Arg Thr Lys Thr Lys Gln Leu Val Phe Thr Lys Glu
225 230 235 240

Asp Thr Ile Thr Val Gln Asn Tyr Asp Ser Ala Gly Thr Asn Leu Glu
245 250 255

Gly Lys Ala Val Glu Ile Thr Thr Leu Lys Glu Leu Lys Asn Ala Leu
260 265 270

Lys

<210> SEQ ID NO 24
<211> LENGTH: 274
<212> TYPE: PRT
<213> ORGANISM: Borrelia garinii

<400> SEQUENCE: 24

Met Lys Lys Tyr Leu Leu Gly Ile Gly Leu Ile Leu Ala Leu Ile Ala
1 5 10 15

Cys Lys Gln Asn Val Ser Ser Leu Asp Glu Lys Asn Ser Val Ser Val
20 25 30

```
Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Ser Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Gly
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Ala Ala Leu Asp Asp Ser Asp Thr Thr
        195                 200                 205

Arg Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Arg Tyr Asp Ser Ala Gly Thr Asn Leu
                245                 250                 255

Glu Gly Lys Ala Val Glu Ile Thr Thr Leu Lys Glu Leu Lys Asn Ala
            260                 265                 270

Leu Lys


<210> SEQ ID NO 25
<211> LENGTH: 274
<212> TYPE: PRT
<213> ORGANISM: Borrelia garinii

<400> SEQUENCE: 25

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Ala Lys Ser Lys Ala Lys Leu Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Asp
        115                 120                 125
```

```
Lys Gly Lys Leu Ser Glu Lys Val Val Thr Arg Ala Asn Gly Thr Arg
130                 135                 140

Leu Glu Tyr Thr Glu Ile Gln Asn Asp Gly Ser Gly Lys Ala Lys Glu
145                 150                 155                 160

Val Leu Lys Ser Leu Thr Leu Glu Gly Thr Leu Thr Ala Asp Gly Glu
            165                 170                 175

Thr Lys Leu Thr Val Glu Ala Gly Thr Val Thr Leu Ser Lys Asn Ile
        180                 185                 190

Ser Glu Ser Gly Glu Ile Thr Val Glu Leu Lys Asp Thr Glu Thr Thr
    195                 200                 205

Pro Ala Asp Lys Lys Ser Gly Thr Trp Asp Ser Lys Thr Ser Thr Leu
210                 215                 220

Thr Ile Ser Lys Asn Ser Gln Lys Thr Lys Gln Leu Val Phe Thr Lys
225                 230                 235                 240

Glu Asn Thr Ile Thr Val Gln Lys Tyr Asn Thr Ala Gly Thr Lys Leu
                245                 250                 255

Glu Gly Ser Pro Ala Glu Ile Lys Asp Leu Glu Ala Leu Lys Ala Ala
            260                 265                 270

Leu Lys

<210> SEQ ID NO 26
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 26

gtatgtttag tgaggggggt g                                           21

<210> SEQ ID NO 27
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 27

ggatcatagc tcaggtggtt ag                                          22

<210> SEQ ID NO 28
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 28

agggggggtga agtcgtaaca ag                                         22

<210> SEQ ID NO 29
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 29

gtctgataaa cctgaggtcg ga                                          22

<210> SEQ ID NO 30
```

<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 30

Met Lys Lys Asp Asp Gln Ile Ala Ala Ala Met Val Leu Arg Gly Met
1 5 10 15

Ala Lys Asp Gly Gln Phe Ala Leu Lys
20 25

<210> SEQ ID NO 31
<211> LENGTH: 36
<212> TYPE: PRT
<213> ORGANISM: Mus musculus

<400> SEQUENCE: 31

Arg Leu Ala Gly Leu Leu Arg Lys Gly Gly Glu Lys Ile Gly Glu Lys
1 5 10 15

Leu Lys Lys Ile Gly Gln Lys Ile Lys Asn Phe Phe Gln Lys Leu Val
20 25 30

Pro Gln Pro Glu
35

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(26)
<223> OTHER INFORMATION: n=inosine

<400> SEQUENCE: 32
ncncncncnc ncncncncnc ncncnc 26

<210> SEQ ID NO 33
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 33

Lys Leu Lys Leu Leu Leu Leu Leu Lys Leu Lys
1 5 10

<210> SEQ ID NO 34
<211> LENGTH: 148
<212> TYPE: PRT
<213> ORGANISM: Borrelia afzelii

<400> SEQUENCE: 34

Phe Asn Glu Lys Gly Glu Leu Ser Ala Lys Thr Met Thr Arg Glu Asn
1 5 10 15

Gly Thr Lys Leu Glu Tyr Thr Glu Met Lys Ser Asp Gly Thr Gly Lys
20 25 30

Ala Lys Glu Val Leu Lys Asn Phe Thr Leu Glu Gly Lys Val Ala Asn
35 40 45

Asp Lys Val Thr Leu Glu Val Lys Glu Gly Thr Val Thr Leu Ser Lys
50 55 60

Glu Ile Ala Lys Ser Gly Glu Val Thr Val Ala Leu Asn Asp Thr Asn
65 70 75 80

Thr Thr Gln Ala Thr Lys Lys Thr Gly Ala Trp Asp Ser Lys Thr Ser
85 90 95

Thr Leu Thr Ile Ser Val Asn Ser Lys Lys Thr Thr Gln Leu Val Phe
100 105 110

Thr Lys Gln Asp Thr Ile Thr Val Gln Lys Tyr Asp Ser Ala Gly Thr
115 120 125

Asn Leu Glu Gly Thr Ala Val Glu Ile Lys Thr Leu Asp Glu Leu Lys
130 135 140

Asn Ala Leu Lys
145

<210> SEQ ID NO 35
<211> LENGTH: 143
<212> TYPE: PRT
<213> ORGANISM: Borrelia afzelii

<400> SEQUENCE: 35

Glu Leu Ser Ala Lys Thr Met Thr Arg Glu Asn Gly Thr Lys Leu Glu
1 5 10 15

Tyr Thr Glu Met Lys Ser Asp Gly Thr Gly Lys Ala Lys Glu Val Leu
20 25 30

Lys Asn Phe Thr Leu Glu Gly Lys Val Ala Asn Asp Lys Val Thr Leu
35 40 45

Glu Val Lys Glu Gly Thr Val Thr Leu Ser Lys Glu Ile Ala Lys Ser
50 55 60

Gly Glu Val Thr Val Ala Leu Asn Asp Thr Asn Thr Thr Gln Ala Thr
65 70 75 80

Lys Lys Thr Gly Ala Trp Asp Ser Lys Thr Ser Thr Leu Thr Ile Ser
85 90 95

Val Asn Ser Lys Lys Thr Thr Gln Leu Val Phe Thr Lys Gln Asp Thr
100 105 110

Ile Thr Val Gln Lys Tyr Asp Ser Ala Gly Thr Asn Leu Glu Gly Thr
115 120 125

Ala Val Glu Ile Lys Thr Leu Asp Glu Leu Lys Asn Ala Leu Lys
130 135 140

<210> SEQ ID NO 36
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 36

Gly Gly Gly Gly Gly Gly Gly Gly
1 5

<210> SEQ ID NO 37
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 37

Gly Gly Gly Gly Gly Gly Gly Gly Gly Gly Gly Gly
1 5 10

<210> SEQ ID NO 38
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 38

Gly Ala Gly Ala
1

<210> SEQ ID NO 39
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 39

Gly Ala Gly Ala Gly Ala Gly Ala
1 5

<210> SEQ ID NO 40
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 40

Gly Ala Gly Ala Gly Ala Gly Ala Gly Ala Gly Ala
1 5 10

<210> SEQ ID NO 41
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 41

Gly Gly Gly Ser Gly Gly Gly Ser
1 5

<210> SEQ ID NO 42
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 42

Gly Gly Gly Ser Gly Gly Gly Ser Gly Gly Gly Ser
1 5 10

<210> SEQ ID NO 43
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 43

Phe Asn Glu Lys Gly Glu Val Ser Glu Lys Ile Ile Thr Arg Ala Cys
1 5 10 15

Gly Thr Arg Leu Glu Tyr Thr Gly Ile Lys Ser Asp Gly Ser Gly Lys
20 25 30

Ala Lys Glu Val Leu Lys Asn Phe Thr Leu Glu Gly Lys Val Ala Asn
35 40 45

Asp Lys Thr Thr Leu Val Val Lys Glu Gly Thr Val Thr Leu Ser Lys
50 55 60

Asn Ile Ser Lys Ser Gly Glu Val Ser Val Glu Leu Asn Asp Thr Asp
65 70 75 80

Ser Ser Ala Ala Thr Lys Lys Thr Ala Ala Trp Asn Ser Gly Thr Ser
85 90 95

Thr Leu Thr Ile Thr Val Asn Ser Lys Lys Thr Lys Asp Leu Val Phe
100 105 110

Thr Lys Glu Cys Thr Ile Thr Val Gln Gln Tyr Asp Ser Asn Gly Thr
115 120 125

Lys Leu Glu Gly Ser Ala Val Glu Ile Thr Lys Leu Asp Glu Ile Lys
130 135 140

Asn Ala Leu Lys Gly Thr Ser Asp Lys Asn Asn Gly Ser Gly Ser Lys
145 150 155 160

Glu Lys Asn Lys Asp Gly Lys Tyr Ser Phe Asn Glu Lys Gly Glu Leu
165 170 175

Ser Ala Lys Thr Met Thr Arg Glu Cys Gly Thr Lys Leu Glu Tyr Thr
180 185 190

Glu Met Lys Ser Asp Gly Thr Gly Lys Ala Lys Glu Val Leu Lys Asn
195 200 205

Phe Thr Leu Glu Gly Lys Val Ala Asn Asp Lys Val Thr Leu Glu Val
210 215 220

Lys Glu Gly Thr Val Thr Leu Ser Lys Glu Ile Ala Lys Ser Gly Glu
225 230 235 240

Val Thr Val Ala Leu Asn Asp Thr Asn Thr Thr Gln Ala Thr Lys Lys
245 250 255

Thr Gly Ala Trp Asp Ser Lys Thr Ser Thr Leu Thr Ile Ser Val Asn
260 265 270

Ser Lys Lys Thr Thr Gln Leu Val Phe Thr Lys Gln Cys Thr Ile Thr
275 280 285

Val Gln Lys Tyr Asp Ser Ala Gly Thr Asn Leu Glu Gly Thr Ala Val
290 295 300

Glu Ile Lys Thr Leu Asp Glu Leu Lys Asn Ala Leu Lys
305 310 315

<210> SEQ ID NO 44
<211> LENGTH: 1020
<212> TYPE: PRT
<213> ORGANISM: Artificial Sequence
<220> FEATURE:
<223> OTHER INFORMATION: Synthetic Polypeptide

<400> SEQUENCE: 44

Ala Thr Gly Ala Ala Ala Gly Cys Thr Ala Cys Thr Ala Ala Ala Cys
1 5 10 15

Thr Gly Gly Thr Ala Cys Thr Gly Gly Gly Cys Gly Cys Gly Gly Thr
20 25 30

Ala Ala Thr Cys Cys Thr Gly Gly Gly Thr Thr Cys Thr Ala Cys Thr
35 40 45

Cys Thr Gly Cys Thr Gly Gly Cys Ala Gly Gly Thr Thr Gly Cys Thr
50 55 60

-continued

```
Cys Ala Ala Gly Cys Thr Thr Cys Ala Ala Cys Gly Ala Ala Ala Ala
65                  70                  75                  80

Gly Gly Gly Cys Gly Ala Ala Gly Thr Cys Thr Cys Gly Gly Ala Ala
                85                  90                  95

Ala Ala Ala Ala Thr Cys Ala Thr Thr Ala Cys Cys Cys Gly Thr Gly
            100                 105                 110

Cys Thr Thr Gly Cys Gly Gly Cys Ala Cys Cys Cys Gly Thr Cys Thr
        115                 120                 125

Gly Gly Ala Ala Thr Ala Cys Ala Cys Cys Gly Gly Cys Ala Thr Thr
    130                 135                 140

Ala Ala Ala Thr Cys Gly Gly Ala Thr Gly Gly Cys Ala Gly Cys Gly
145                 150                 155                 160

Gly Cys Ala Ala Ala Gly Cys Gly Ala Ala Gly Gly Ala Ala Gly Thr
                165                 170                 175

Thr Cys Thr Gly Ala Ala Ala Ala Ala Cys Thr Thr Thr Ala Cys Cys
            180                 185                 190

Cys Thr Gly Gly Ala Ala Gly Gly Cys Ala Ala Ala Gly Thr Cys Gly
        195                 200                 205

Cys Ala Ala Ala Thr Gly Ala Thr Ala Ala Gly Ala Cys Cys Ala Cys
    210                 215                 220

Cys Cys Thr Gly Gly Thr Gly Gly Thr Gly Ala Ala Ala Gly Ala Ala
225                 230                 235                 240

Gly Gly Cys Ala Cys Cys Gly Thr Thr Ala Cys Gly Cys Thr Gly Ala
                245                 250                 255

Gly Cys Ala Ala Ala Ala Ala Cys Ala Thr Thr Ala Gly Thr Ala Ala
            260                 265                 270

Gly Thr Cys Cys Gly Gly Thr Gly Ala Ala Gly Thr Cys Thr Cys Thr
        275                 280                 285

Gly Thr Gly Gly Ala Ala Cys Thr Gly Ala Ala Thr Gly Ala Thr Ala
    290                 295                 300

Cys Cys Gly Ala Cys Ala Gly Cys Thr Cys Thr Gly Cys Gly Gly Cys
305                 310                 315                 320

Cys Ala Cys Cys Ala Ala Ala Ala Ala Gly Ala Cys Gly Gly Cys Ala
                325                 330                 335

Gly Cys Thr Thr Gly Gly Ala Ala Cys Thr Cys Ala Gly Gly Cys Ala
            340                 345                 350

Cys Cys Thr Cys Gly Ala Cys Gly Cys Thr Gly Ala Cys Cys Ala Thr
        355                 360                 365

Thr Ala Cys Gly Gly Thr Thr Ala Ala Thr Thr Cys Cys Ala Ala Ala
    370                 375                 380

Ala Ala Gly Ala Cys Cys Ala Ala Ala Gly Ala Thr Cys Thr Gly Gly
385                 390                 395                 400

Thr Cys Thr Thr Cys Ala Cys Gly Ala Ala Ala Gly Ala Ala Thr Gly
                405                 410                 415

Cys Ala Cys Cys Ala Thr Cys Ala Cys Gly Gly Thr Gly Cys Ala Gly
            420                 425                 430

Cys Ala Ala Thr Ala Thr Gly Ala Cys Ala Gly Cys Ala Ala Cys Gly
        435                 440                 445

Gly Thr Ala Cys Cys Ala Ala Ala Cys Thr Gly Gly Ala Ala Gly Gly
    450                 455                 460

Cys Thr Cys Thr Gly Cys Gly Gly Thr Gly Gly Ala Ala Ala Thr Cys
465                 470                 475                 480

Ala Cys Gly Ala Ala Ala Cys Thr Gly Gly Ala Thr Gly Ala Ala Ala
                485                 490                 495

Thr Cys Ala Ala Ala Ala Ala Thr Gly Cys Thr Cys Thr Gly Ala Ala
            500                 505                 510

Ala Gly Gly Thr Ala Cys Thr Ala Gly Thr Gly Ala Cys Ala Ala Ala
        515                 520                 525
```

```
Gly Thr Gly Ala Ala Gly Thr Gly Ala Cys Cys Gly Thr Thr Gly Cys
785                 790                 795                 800

Thr Cys Thr Gly Ala Ala Cys Gly Ala Thr Ala Cys Gly Ala Ala Thr
                805                 810                 815

Ala Cys Cys Ala Cys Gly Cys Ala Ala Gly Cys Gly Ala Cys Cys Ala
            820                 825                 830

Ala Gly Ala Ala Ala Ala Cys Cys Gly Gly Cys Gly Cys Cys Thr Gly
        835                 840                 845

Gly Gly Ala Cys Ala Gly Cys Ala Ala Ala Ala Cys Cys Thr Cys Thr
    850                 855                 860

Ala Cys Gly Cys Thr Gly Ala Cys Cys Ala Thr Thr Ala Gly Thr Gly
865                 870                 875                 880

Thr Thr Ala Ala Cys Ala Gly Cys Ala Ala Gly Ala Ala Ala Ala Cys
                885                 890                 895

Cys Ala Cys Gly Cys Ala Gly Cys Thr Gly Gly Thr Cys Thr Thr Cys
            900                 905                 910

Ala Cys Cys Ala Ala Ala Cys Ala Ala Thr Gly Thr Ala Cys Gly Ala
        915                 920                 925

Thr Cys Ala Cys Cys Gly Thr Gly Cys Ala Gly Ala Ala Ala Thr Ala
    930                 935                 940

Cys Gly Ala Thr Ala Gly Thr Gly Cys Gly Gly Gly Thr Ala Cys Cys
945                 950                 955                 960

Ala Ala Cys Cys Thr Gly Gly Ala Ala Gly Gly Cys Ala Cys Cys Gly
                965                 970                 975

Cys Thr Gly Thr Thr Gly Ala Ala Ala Thr Cys Ala Ala Ala Ala Cys
            980                 985                 990

Cys Cys Thr Gly Gly Ala Cys Gly  Ala Ala Cys Thr Gly  Ala Ala Ala
        995                 1000                1005

Ala Ala  Cys Gly Cys Cys Cys  Thr Gly Ala Ala Ala
    1010                1015                1020
```

<210> SEQ ID NO 45
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 45

```
Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110
```

```
Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Cys
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Lys Asn Ala Leu Lys
305                 310                 315                 320

Gly Leu Glu His His His His His His
                325
```

<210> SEQ ID NO 46
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 46

```
atgaaagcta ctaaactggt actgggcgcg gtaatcctgg gttctactct gctggcaggt      60

tgctcaagct tcaacgaaaa gggcgaagtc tcggaaaaaa tcattacccg tgcttgcggc     120

acccgtctgg aatacaccgg cattaaatcg gatggcagcg gcaaagcgaa ggaagttctg     180

aaaaacttta ccctggaagg caaagtcgca aatgataaga ccaccctggt ggtgaaagaa     240

ggcaccgtta cgctgagcaa aaacattagt aagtccggtg aagtctctgt ggaactgaat     300

gataccgaca gctctgcggc caccaaaaag acggcagctt ggaactcagg cacctcgacg     360

ctgaccatta cggttaattc caaaaagacc aaagatctgg tcttcacgaa agaatgcacc     420

atcacggtgc agcaatatga cagcaacggt accaaactgg aaggctctgc ggtggaaatc     480

acgaaactgg atgaaatcaa aaatgctctg aaaggtacta gtgacaaaaa caatggctct     540

ggtagcaaag agaaaaacaa agatggcaag tactcattca acgaaaaagg cgaactgtcg     600

gcgaaaacga tgacgcgtga atgcggcacc aaactggaat atacggaaat gaaaagcgat     660

ggcaccggta aagcgaaaga agttctgaaa aactttaccc tggaaggcaa agtcgccaat     720

gacaaagtca ccctggaagt gaaagaaggc accgttacgc tgtcaaaaga aattgcaaaa     780
```

```
tcgggtgaag tgaccgttgc tctgaacgat acgaatacca cgcaagcgac caagaaaacc    840

ggcgcctggg acagcaaaac ctctacgctg accattagtg ttaacagcaa gaaaaccacg    900

cagctggtct tcaccaaaca atgtacgatc accgtgcaga aatacgatag tgcgggtacc    960

aacctggaag gcaccgctgt tgaaatcaaa accctggacg aactgaaaaa cgccctgaaa   1020

ggcctcgagc accaccacca ccaccac                                      1047
```

```
<210> SEQ ID NO 47
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 47

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175

Ser Ala Lys Thr Met Thr Arg Glu Asn Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Cys Gly Thr Val Thr Leu Ser Lys Glu Ile Ala Lys Ser Gly Glu
225                 230                 235                 240

Val Thr Val Ala Leu Asn Asp Thr Asn Thr Thr Gln Ala Thr Lys Lys
                245                 250                 255

Thr Gly Ala Trp Asp Ser Lys Thr Ser Thr Leu Thr Ile Ser Val Asn
            260                 265                 270

Ser Lys Lys Thr Thr Gln Leu Val Phe Thr Lys Gln Asp Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Cys Asn Ala Leu Lys
305                 310                 315
```

<210> SEQ ID NO 48
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 48
atgaaagcta ctaaactggt actgggcgcg gtaatcctgg gttctactct gctggcaggt 60
tgctcaagct tcaacgaaaa gggcgaagtc agcgaaaaaa tcattacccg cgcagacggc 120
acccgcctgg aatacaccgg catcaaatcg gacggcagcg gcaaagcgaa agaagttctg 180
aaaaacttta ccctggaagg caaagtcgca aatgataaaa ccaccctggt ggtgaaatgc 240
ggcaccgtta cgctgagcaa aaacattagt aaatccggtg aagtctctgt ggaactgaat 300
gataccgaca gctctgcggc caccaagaaa accgcagctt ggaactcagg cacctcgacg 360
ctgaccatta cggttaatag caagaaaacc aaagatctgg tcttcacgaa agaaaacacc 420
atcacggtgc agcaatatga cagcaatggt accaaactgg aaggctccgc tgtggaaatc 480
acgaaactgg atgaaatctg taatgctctg aaaggtacta gtgacaaaaa caatggctct 540
ggtagcaaag agaaaaacaa agatggcaag tactcattca acgaaaaagg cgaactgtcg 600
gcgaaaacga tgacgcgtga aaacggcacc aaactggaat atacggaaat gaaaagcgat 660
ggcaccggta aagcgaaaga agttctgaaa aactttaccc tggaaggcaa agtcgccaat 720
gacaaagtca ccctggaagt gaaatgcggc accgttacgc tgtcaaaaga aattgcaaaa 780
tcgggtgaag tgaccgttgc tctgaacgat acgaatacca cgcaagcgac caagaaaacc 840
ggcgcctggg acagcaaaac ctctacgctg accattagtg ttaatagcaa gaaaaccacg 900
cagctggtct tcaccaaaca agatacgatc accgtgcaga aatacgacag tgcgggtacc 960
aacctggaag gcacggctgt tgaaatcaaa accctggacg aactgtgtaa cgccctgaaa 1020

<210> SEQ ID NO 49
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 49

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

-continued

```
Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320

Gly Leu Glu His His His His His His
                325
```

```
<210> SEQ ID NO 50
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 50

atgaaagcta ctaaactggt actgggcgcg gtaatcctgg gttctactct gctggcaggt      60

tgctcaagct tcaacgaaaa gggcgaagtc agcgaaaaaa tcattacccg cgcagacggc     120

acccgcctgg aatacaccgg catcaaatcg gacggcagcg gcaaagcgaa agaagttctg     180

aaaaacttta ccctggaagg caaagtcgca aatgataaaa ccaccctggt ggtgaaatgc     240

ggcaccgtta cgctgagcaa aaacattagt aaatccggtg aagtctctgt ggaactgaat     300

gataccgaca gctctgcggc caccaagaaa accgcagctt ggaactcagg cacctcgacg     360

ctgaccatta cggttaatag caagaaaacc aaagatctgg tcttcacgaa agaaaacacc     420

atcacggtgc agcaatatga cagcaatggt accaaactgg aaggctccgc tgtggaaatc     480

acgaaactgg atgaaatctg taatgctctg aaaggtacta gtgacaaaaa caatggctct     540

ggtagcaaag agaaaaacaa agatggcaag tactcattca acgaaaaagg cgaactgtcg     600

gcgaaaacga tgacgcgtga aaacggcacc aaactggaat atacggaaat gaaaagcgat     660

ggcaccggta aagcgaaaga agttctgaaa aactttaccc tggaaggcaa agtcgccaat     720

gacaaagtca ccctggaagt gaaatgcggc accgttacgc tgtcaaaaga aattgcaaaa     780
```

-continued

```
tcgggtgaag tgaccgttgc tctgaacgat acgaatacca cgcaagcgac caagaaaacc    840

ggcgcctggg acagcaaaac ctctacgctg accattagtg ttaatagcaa gaaaaccacg    900

cagctggtct tcaccaaaca agatacgatc accgtgcaga aatacgacag tgcgggtacc    960

aacctggaag gcacggctgt tgaaatcaaa accctggacg aactgtgtaa cgccctgaaa   1020

ggcctcgagc accaccacca ccaccac                                       1047


<210> SEQ ID NO 51
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 51

Phe Asn Glu Lys Gly Lys Leu Ser Glu Lys Val Val Thr Arg Ala Cys
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Glu Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Cys Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Lys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Cys Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
    210                 215                 220

Val Thr Glu Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
                245                 250                 255

Lys Thr Gly Lys Trp Asp Ser Asn Thr Ser Thr Leu Thr Ile Ser Val
            260                 265                 270

Asn Ser Lys Lys Thr Lys Asn Ile Val Phe Thr Lys Glu Cys Thr Ile
        275                 280                 285

Thr Val Gln Lys Tyr Asp Ser Ala Gly Thr Asn Leu Glu Gly Asn Ala
    290                 295                 300

Val Glu Ile Lys Thr Leu Asp Glu Leu Lys Asn Ala Leu Lys
305                 310                 315
```

<210> SEQ ID NO 52
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 52
atgaaagcta ctaaactggt actgggcgcg gtaatcctgg gttctactct gctggcaggt 60
tgctcaagct tcaacgaaaa gggcaaactg tcagaaaaag tggtcacccg cgcttgtggc 120
acccgcctgg aatacaccga aatcaaaaac gacggctcgg gcaaagcgaa ggaagttctg 180
aaaggctttg ccctggaagg taccctgacg gatggcggtg aaaccaaact gaccgtgacg 240
gaaggcaccg ttacgctgtc taaaaacatt agcaagtctg gtgaaatcac ggtcgcactg 300
aatgataccg aaaccacgcc ggctgacaaa aagaccggcg aatggaaaag tgacacctcc 360
acgctgacca tttcaaagaa ctcgcagaaa ccgaagcaac tggtcttcac caaagaatgc 420
acgatcaccg tgcagaacta taatcgtgcc ggtaatgctc tggaaggctc cccggctgaa 480
atcaaggacc tggcggaact gaaggcggca ctgaaaggca ctagtgacaa aaacaatggc 540
tctggtagca aagagaaaaa caaagatggc aagtactcat tcaacgctaa aggtgaactg 600
tcggaaaaaa ccatcctgcg cgcctgtggc acccgcctgg aatacacgga aatcaagtcg 660
gacggcacgg gcaaagcaaa ggaagtcctg aaagattttg ctctggaagg taccctggcg 720
gccgacaaaa ccacgctgaa ggtgacggaa ggcaccgtgg ttctgagcaa acatattccg 780
aactctggtg aaatcaccgt tgaactgaac gatagcaatt ctacgcaggc gaccaaaaag 840
acgggcaaat gggacagtaa tacctccacg ctgaccattt cagtcaactc gaaaaagacc 900
aaaaatattg tgttcacgaa ggaatgcacg atcaccgttc aaaaatatga ttccgcaggt 960
accaacctgg aaggcaacgc tgtggaaatc aaaaccctgg acgaactgaa aaatgctctg 1020
aag 1023

<210> SEQ ID NO 53
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 53

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

-continued

```
Ser Asp Thr Ser Thr Leu Thr Ile Ser Lys Asn Ser Gln Lys Pro Lys
            100                 105                 110

Gln Leu Val Phe Thr Lys Glu Cys Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Lys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Cys Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Glu Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Cys Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Lys Asn Ala Leu
305                 310                 315                 320

Lys Gly Leu Glu His His His His His His
                325                 330
```

<210> SEQ ID NO 54
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 54

```
atgaaagcta ctaaactggt actgggcgcg gtaatcctgg gttctactct gctggcaggt      60

tgctcaagct tcaacgaaaa gggcaaactg tcagaaaaag tggtcacccg cgcttgtggc     120

acccgcctgg aatacaccga aatcaaaaac gacggctcgg gcaaagcgaa ggaagttctg     180

aaaggctttg ccctggaagg taccctgacg gatggcggtg aaaccaaact gaccgtgacg     240

gaaggcaccg ttacgctgtc taaaaacatt agcaagtctg gtgaaatcac ggtcgcactg     300

aatgataccg aaaccacgcc ggctgacaaa aagaccggcg aatggaaaag tgacacctcc     360

acgctgacca tttcaaagaa ctcgcagaaa ccgaagcaac tggtcttcac caaagaatgc     420

acgatcaccg tgcagaacta taatcgtgcc ggtaatgctc tggaaggctc cccggctgaa     480

atcaaggacc tggcggaact gaaggcggca ctgaaaggca ctagtgacaa aaacaatggc     540

tctggtagca aagagaaaaa caaagatggc aagtactcat tcaacgctaa aggtgaactg     600

tcggaaaaaa ccatcctgcg cgcctgtggc acccgcctgg aatacacgga aatcaagtcg     660

gacggcacgg gcaaagcaaa ggaagtcctg aaagattttg ctctggaagg taccctggcg     720
```

-continued

```
gccgacaaaa ccacgctgaa ggtgacggaa ggcaccgtgg ttctgagcaa acatattccg    780

aactctggtg aaatcaccgt tgaactgaac gatagcaatt ctacgcaggc gaccaaaaag    840

acgggcaaat gggacagtaa tacctccacg ctgaccattt cagtcaactc gaaaaagacc    900

aaaaatattg tgttcacgaa ggaatgcacg atcaccgttc aaaaatatga ttccgcaggt    960

accaacctgg aaggcaacgc tgtggaaatc aaaaccctgg acgaactgaa aaatgctctg   1020

aagggtctcg agcaccacca ccaccaccac                                    1050
```

<210> SEQ ID NO 55
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 55

```
Phe Asn Glu Lys Gly Lys Leu Ser Glu Lys Val Val Thr Arg Ala Asn
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Cys Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Cys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Asn Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
    210                 215                 220

Val Thr Cys Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
                245                 250                 255

Lys Thr Gly Lys Trp Asp Ser Asn Thr Ser Thr Leu Thr Ile Ser Val
            260                 265                 270

Asn Ser Lys Lys Thr Lys Asn Ile Val Phe Thr Lys Glu Asp Thr Ile
        275                 280                 285

Thr Val Gln Lys Tyr Asp Ser Ala Gly Thr Asn Leu Glu Gly Asn Ala
    290                 295                 300
```

Val Glu Ile Lys Thr Leu Asp Glu Leu Cys Asn Ala Leu Lys
305 310 315

<210> SEQ ID NO 56
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 56
atgaaagcta ctaaactggt actgggcgcg gtaatcctgg gttctactct gctggcaggt 60
tgctcaagct tcaacgaaaa gggcaaactg tcggaaaaag tggtcacccg cgcaaatggc 120
acccgcctgg aatacacgga aatcaaaaac gatggtagcg gcaaagcgaa ggaagttctg 180
aaaggctttg ccctggaagg taccctgacg gatggcggtg aaaccaaact gaccgtgacg 240
tgcggcaccg ttacgctgtc taaaaacatt agcaagtctg gtgaaatcac ggtcgcactg 300
aatgataccg aaaccacgcc ggctgacaaa aagaccggcg aatggaaaag tgacacctcc 360
acgctgacca tttcaaagaa ctcgcagaaa ccgaagcaac tggtcttcac caaagaaaac 420
acgatcaccg tgcagaacta taatcgtgcc ggtaatgctc tggaaggctc accggctgaa 480
atcaaggacc tggctgaact gtgtgcggca ctgaaaggca ctagtgacaa aaacaatggc 540
tctggtagca aagagaaaaa caaagatggc aagtactcat tcaacgctaa aggtgaactg 600
agcgaaaaaa cgatcctgcg tgcgaatggc acccgtctgg aatacaccga aatcaaatcc 660
gatggtacgg gcaaagcaaa ggaagtcctg aaagattttg ctctggaagg taccctggcg 720
gccgacaaaa ccacgctgaa ggtgacgtgc ggcaccgtgg ttctgagcaa acatattccg 780
aactctggtg aaatcaccgt tgaactgaac gatagcaatt ctacgcaggc aaccaaaaag 840
acgggcaaat gggacagtaa tacctccacg ctgaccattt cagtcaactc gaaaaagacc 900
aaaaatattg tgttcacgaa ggaagatacg atcaccgttc aaaaatatga ctccgcgggc 960
accaacctgg aaggcaatgc cgtcgaaatc aaaaccctgg atgaactgtg taatgctctg 1020
aag 1023

<210> SEQ ID NO 57
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 57

Cys Ser Ser Phe Asn Glu Lys Gly Lys Leu Ser Glu Lys Val Val Thr
1 5 10 15

Arg Ala Asn Gly Thr Arg Leu Glu Tyr Thr Glu Ile Lys Asn Asp Gly
20 25 30

Ser Gly Lys Ala Lys Glu Val Leu Lys Gly Phe Ala Leu Glu Gly Thr
35 40 45

Leu Thr Asp Gly Gly Glu Thr Lys Leu Thr Val Thr Cys Gly Thr Val
50 55 60

Thr Leu Ser Lys Asn Ile Ser Lys Ser Gly Glu Ile Thr Val Ala Leu
65 70 75 80

Asn Asp Thr Glu Thr Thr Pro Ala Asp Lys Lys Thr Gly Glu Trp Lys

```
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Cys Asn Ala Leu
305                 310                 315                 320

Lys Gly Leu Glu His His His His His His
                325                 330
```

<210> SEQ ID NO 58
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 58

```
atgaaagcta ctaaactggt actgggcgcg gtaatcctgg gttctactct gctggcaggt     60

tgctcaagct tcaacgaaaa gggcaaactg tcggaaaaag tggtcacccg cgcaaatggc    120

acccgcctgg aatacacgga aatcaaaaac gatggtagcg gcaaagcgaa ggaagttctg    180

aaaggctttg ccctggaagg taccctgacg gatggcggtg aaaccaaact gaccgtgacg    240

tgcggcaccg ttacgctgtc taaaaacatt agcaagtctg gtgaaatcac ggtcgcactg    300

aatgataccg aaaccacgcc ggctgacaaa aagaccggcg aatggaaaag tgacacctcc    360

acgctgacca tttcaaagaa ctcgcagaaa ccgaagcaac tggtcttcac caaagaaaac    420

acgatcaccg tgcagaacta taatcgtgcc ggtaatgctc tggaaggctc accggctgaa    480

atcaaggacc tggctgaact gtgtgcggca ctgaaaggca ctagtgacaa aaacaatggc    540

tctggtagca aagagaaaaa caaagatggc aagtactcat tcaacgctaa aggtgaactg    600

agcgaaaaaa cgatcctgcg tgcgaatggc acccgtctgg aatacaccga aatcaaatcc    660
```

```
gatggtacgg gcaaagcaaa ggaagtcctg aaagattttg ctctggaagg taccctggcg    720

gccgacaaaa ccacgctgaa ggtgacgtgc ggcaccgtgg ttctgagcaa acatattccg    780

aactctggtg aaatcaccgt tgaactgaac gatagcaatt ctacgcaggc aaccaaaaag    840

acgggcaaat gggacagtaa tacctccacg ctgaccattt cagtcaactc gaaaaagacc    900

aaaaatattg tgttcacgaa ggaagatacg atcaccgttc aaaaatatga ctccgcgggc    960

accaacctgg aaggcaatgc cgtcgaaatc aaaaccctgg atgaactgtg taatgctctg   1020

aagggtctcg agcaccacca ccaccaccac                                    1050
```

<210> SEQ ID NO 59
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 59

```
Phe Asn Glu Lys Gly Glu Ile Ser Glu Lys Thr Ile Val Arg Ala Cys
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Cys Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Cys Gly Thr Arg Leu Glu Tyr Thr
            180                 185                 190

Asp Ile Lys Ser Asp Gly Ser Gly Lys Ala Lys Glu Val Leu Lys Asp
        195                 200                 205

Phe Thr Leu Glu Gly Thr Leu Ala Ala Asp Gly Lys Thr Thr Leu Lys
    210                 215                 220

Val Thr Glu Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                245                 250                 255

Lys Thr Gly Lys Trp Asp Ser Lys Thr Ser Thr Leu Thr Ile Ser Val
            260                 265                 270

Asn Ser Gln Lys Thr Lys Asn Leu Val Phe Thr Lys Glu Cys Thr Ile
        275                 280                 285

Thr Val Gln Arg Tyr Asp Ser Ala Gly Thr Asn Leu Glu Gly Lys Ala
```

290 295 300

Val Glu Ile Thr Thr Leu Lys Glu Leu Lys Asn Ala Leu Lys
305 310 315

<210> SEQ ID NO 60
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 60
atgaaagcta ctaaactggt actgggcgcg gtaatcctgg gttctactct gctggcaggt 60
tgctcaagct tcaacgaaaa gggcgaaatc agtgaaaaaa ccattgtgcg tgcgtgtggc 120
acccgtctgg aatataccga catcaagagc gataaaacgg gtaaagcgaa ggaagttctg 180
aaagatttta cgctggaagg taccctggca gcagacggta aaaccacgct gaaggtgacc 240
gaaggtaccg ttacgctgtc caaaaacatt agtaagtccg gcgaaatcac ggtcgccctg 300
gatgacaccg atagctctgg caacaaaaag agcggtacct gggactcagg cacctcgacg 360
ctgaccattt ctaaaaatcg tacgaaaacc aagcagctgg tcttcacgaa agaatgcacg 420
atcaccgtgc aaaactatga tagcgcaggt accaatctgg aaggcaaagc tgtggaaatt 480
accacgctga aagaactgaa gaatgctctg aaaggtacta gtgacaaaaa caatggctct 540
ggtagcaaag agaaaaacaa agatggcaag tactcattca acggcaaagg tgaaacgagt 600
gaaaaaacga ttgttcgcgc ctgtggcacc cgcctggaat acacggatat caagtcggat 660
ggttcgggca aagcaaagga agtcctgaaa gattttacgc tggaaggtac cctggcagca 720
gacggtaaaa ccacgctgaa ggtgacggaa ggcaccgtgg ttctgtcaaa aaacattctg 780
aagtcgggtg aaatcaccgc agctctggat gacagcgata ccacgcgtgc tacgaaaaag 840
accggtaaat gggacagcaa gacctctacg ctgaccatta gtgtcaactc ccagaaaacg 900
aagaatctgg tgttcaccaa agaatgcacg atcaccgttc aacgctatga tagtgcgggc 960
accaacctgg aaggcaaagc cgttgaaatt accacgctga aagaactgaa gaatgctctg 1020
aaa 1023

<210> SEQ ID NO 61
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 61

Cys Ser Ser Phe Asn Glu Lys Gly Glu Ile Ser Glu Lys Thr Ile Val
1 5 10 15

Arg Ala Cys Gly Thr Arg Leu Glu Tyr Thr Asp Ile Lys Ser Asp Lys
20 25 30

Thr Gly Lys Ala Lys Glu Val Leu Lys Asp Phe Thr Leu Glu Gly Thr
35 40 45

Leu Ala Ala Asp Gly Lys Thr Thr Leu Lys Val Thr Glu Gly Thr Val
50 55 60

Thr Leu Ser Lys Asn Ile Ser Lys Ser Gly Glu Ile Thr Val Ala Leu
65 70 75 80

```
Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 62
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 62

```
atgaaagcta ctaaactggt actgggcgcg gtaatcctgg gttctactct gctggcaggt      60

tgctcaagct tcaacgaaaa gggcgaaatc agtgaaaaaa ccattgtgcg tgcgtgtggc     120

acccgtctgg aatataccga catcaagagc gataaaacgg gtaaagcgaa ggaagttctg     180

aaagatttta cgctggaagg taccctggca gcagacggta aaaccacgct gaaggtgacc     240

gaaggtaccg ttacgctgtc caaaaacatt agtaagtccg gcgaaatcac ggtcgccctg     300

gatgacaccg atagctctgg caacaaaaag agcggtacct gggactcagg cacctcgacg     360

ctgaccattt ctaaaaatcg tacgaaaacc aagcagctgg tcttcacgaa agaatgcacg     420

atcaccgtgc aaaactatga tagcgcaggt accaatctgg aaggcaaagc tgtggaaatt     480

accacgctga aagaactgaa gaatgctctg aaaggtacta gtgacaaaaa caatggctct     540

ggtagcaaag agaaaaacaa agatggcaag tactcattca acggcaaagg tgaaacgagt     600
```

-continued

```
gaaaaaacga ttgttcgcgc ctgtggcacc cgcctggaat acacggatat caagtcggat    660

ggttcgggca aagcaaagga agtcctgaaa gattttacgc tggaaggtac cctggcagca    720

gacggtaaaa ccacgctgaa ggtgacggaa ggcaccgtgg ttctgtcaaa aaacattctg    780

aagtcgggtg aaatcaccgc agctctggat gacagcgata ccacgcgtgc tacgaaaaag    840

accggtaaat gggacagcaa gacctctacg ctgaccatta gtgtcaactc ccagaaaacg    900

aagaatctgg tgttcaccaa agaatgcacg atcaccgttc aacgctatga tagtgcgggc    960

accaacctgg aaggcaaagc cgttgaaatt accacgctga aagaactgaa gaatgctctg   1020

aaaggtctcg agcaccacca ccaccaccac                                    1050
```

<210> SEQ ID NO 63
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 63

```
Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Asn Gly Thr Arg Leu Glu Tyr Thr
            180                 185                 190

Asp Ile Lys Ser Asp Gly Ser Gly Lys Ala Lys Glu Val Leu Lys Asp
        195                 200                 205

Phe Thr Leu Glu Gly Thr Leu Ala Ala Asp Gly Lys Thr Thr Leu Lys
    210                 215                 220

Val Thr Cys Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                245                 250                 255

Lys Thr Gly Lys Trp Asp Ser Lys Thr Ser Thr Leu Thr Ile Ser Val
            260                 265                 270

Asn Ser Gln Lys Thr Lys Asn Leu Val Phe Thr Lys Glu Asp Thr Ile
        275                 280                 285
```

Thr Val Gln Arg Tyr Asp Ser Ala Gly Thr Asn Leu Glu Gly Lys Ala
    290                 295                 300

Val Glu Ile Thr Thr Leu Lys Glu Leu Cys Asn Ala Leu Lys
305                 310                 315

<210> SEQ ID NO 64
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 64
atgaaagcta ctaaactggt actgggcgcg gtaatcctgg gttctactct gctggcaggt 60
tgctcaagct tcaacgaaaa gggcgaaatc tcagaaaaaa ccatcgtccg cgctaacggc 120
acccgcctgg aatacaccga catcaaatca gacaagaccg gtaaagcgaa ggaagttctg 180
aaagatttta cgctggaagg taccctggca gcagacggta aaaccacgct gaaggtgacc 240
tgcggtaccg ttacgctgtc caaaaacatt agtaagtccg gcgaaatcac ggtcgccctg 300
gatgacaccg atagctctgg caacaaaaag agcggtacct gggattcagg cacctcgacg 360
ctgaccattt ctaaaaatcg tacgaaaacc aagcagctgg tcttcacgaa agaagatacg 420
atcaccgtgc aaaactatga cagcgcaggt accaatctgg aaggcaaagc tgtggaaatt 480
accacgctga aagaactgtg taatgctctg aaaggtacta gtgacaaaaa caatggctct 540
ggtagcaaag agaaaaacaa agatggcaag tactcattca acggcaaagg tgaaacgagc 600
gaaaagacca tcgtgcgtgc gaacggtacc cgcctggaat atacggacat taaatcggac 660
ggcagcggca aagcaaagga agtcctgaaa gattttacgc tggaaggtac cctggcagca 720
gacggtaaaa ccacgctgaa ggtgacgtgc ggcaccgtgg ttctgtcaaa aaacattctg 780
aagtcgggtg aaatcaccgc agctctggat gacagcgata ccacgcgtgc tacgaaaaag 840
accggtaaat gggatagcaa gacctctacg ctgaccatta gtgtcaactc ccagaaaacg 900
aagaatctgg tgttcaccaa agaagatacg atcaccgttc aacgctatga cagtgcgggc 960
accaacctgg aaggcaaagc cgttgaaatt accacgctga aagaactgtg taatgctctg 1020
aaa 1023

<210> SEQ ID NO 65
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 65

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

-continued

```
Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330
```

<210> SEQ ID NO 66
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 66

```
atgaaagcta ctaaactggt actgggcgcg gtaatcctgg gttctactct gctggcaggt      60

tgctcaagct tcaacgaaaa gggcgaaatc tcagaaaaaa ccatcgtccg cgctaacggc     120

acccgcctgg aatacaccga catcaaatca gacaagaccg gtaaagcgaa ggaagttctg     180

aaagatttta cgctggaagg taccctggca gcagacggta aaaccacgct gaaggtgacc     240

tgcggtaccg ttacgctgtc caaaaacatt agtaagtccg gcgaaatcac ggtcgccctg     300

gatgacaccg atagctctgg caacaaaaag agcggtacct gggattcagg cacctcgacg     360

ctgaccattt ctaaaaatcg tacgaaaacc aagcagctgg tcttcacgaa agaagatacg     420

atcaccgtgc aaaactatga cagcgcaggt accaatctgg aaggcaaagc tgtggaaatt     480

accacgctga aagaactgtg taatgctctg aaaggtacta gtgacaaaaa caatggctct     540
```

```
ggtagcaaag agaaaaacaa agatggcaag tactcattca acggcaaagg tgaaacgagc    600

gaaaagacca tcgtgcgtgc gaacggtacc cgcctggaat atacggacat taaatcggac    660

ggcagcggca aagcaaagga agtcctgaaa gattttacgc tggaaggtac cctggcagca    720

gacggtaaaa ccacgctgaa ggtgacgtgc ggcaccgtgg ttctgtcaaa aaacattctg    780

aagtcgggtg aaatcaccgc agctctggat gacagcgata ccacgcgtgc tacgaaaaag    840

accggtaaat gggatagcaa gacctctacg ctgaccatta gtgtcaactc ccagaaaacg    900

aagaatctgg tgttcaccaa agaagatacg atcaccgttc aacgctatga cagtgcgggc    960

accaacctgg aaggcaaagc cgttgaaatt accacgctga aagaactgtg taatgctctg   1020

aaaggtctcg agcaccacca ccaccaccac                                    1050
```

```
<210> SEQ ID NO 67
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 67

Phe Asn Glu Lys Gly Glu Leu Ser Ala Lys Thr Met Thr Arg Glu Cys
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Glu Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Cys Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Val
                165                 170                 175

Ser Glu Lys Ile Ile Thr Arg Ala Cys Gly Thr Arg Leu Glu Tyr Thr
            180                 185                 190

Gly Ile Lys Ser Asp Gly Ser Gly Lys Ala Lys Glu Val Leu Lys Asn
        195                 200                 205

Phe Thr Leu Glu Gly Lys Val Ala Asn Asp Lys Thr Thr Leu Val Val
    210                 215                 220

Lys Glu Gly Thr Val Thr Leu Ser Lys Asn Ile Ser Lys Ser Gly Glu
225                 230                 235                 240

Val Ser Val Glu Leu Asn Asp Thr Asp Ser Ser Ala Ala Thr Lys Lys
                245                 250                 255

Thr Ala Ala Trp Asn Ser Gly Thr Ser Thr Leu Thr Ile Thr Val Asn
            260                 265                 270
```

Ser Lys Lys Thr Lys Asp Leu Val Phe Thr Lys Glu Cys Thr Ile Thr
        275                 280                 285

Val Gln Gln Tyr Asp Ser Asn Gly Thr Lys Leu Glu Gly Ser Ala Val
    290                 295                 300

Glu Ile Thr Lys Leu Asp Glu Ile Lys Asn Ala Leu Lys
305                 310                 315

<210> SEQ ID NO 68
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 68
atgaaagcta ctaaactggt actgggcgcg gtaatcctgg gttctactct gctggcaggt 60
tgctcaagct tcaacgaaaa aggcgaactg tcggcgaaaa cgatgacgcg tgaatgcggc 120
accaaactgg aatatacgga aatgaaaagc gatggcaccg gtaaagcgaa agaagttctg 180
aaaaacttta ccctggaagg caaagtcgcc aatgacaaag tcaccctgga agtgaaagaa 240
ggcaccgtta cgctgtcaaa agaaattgca aaatcgggtg aagtgaccgt tgctctgaac 300
gatacgaata ccacgcaagc gaccaagaaa accggcgcct gggacagcaa aacctctacg 360
ctgaccatta gtgttaacag caagaaaacc acgcagctgg tcttcaccaa acaatgtacg 420
atcaccgtgc agaaatacga tagtgcgggt accaacctgg aaggcaccgc tgttgaaatc 480
aaaaccctgg acgaactgaa aaacgccctg aaaggcacta gtgacaaaaa caatggctct 540
ggtagcaaag agaaaaacaa agatggcaag tactcattca acgaaaaagg cgaagtctcg 600
gaaaaaatca ttacccgtgc ttgcggcacc cgtctggaat acaccggcat taaatcggat 660
ggcagcggca aagcgaagga agttctgaaa aactttaccc tggaaggcaa agtcgcaaat 720
gataagacca ccctggtggt gaaagaaggc accgttacgc tgagcaaaaa cattagtaag 780
tccggtgaag tctctgtgga actgaatgat accgacagct ctgcggccac caaaaagacg 840
gcagcttgga actcaggcac ctcgacgctg accattacgg ttaattccaa aaagaccaaa 900
gatctggtct tcacgaaaga atgcaccatc acggtgcagc aatatgacag caacggtacc 960
aaactggaag gctctgcggt ggaaatcacg aaactggatg aaatcaaaaa tgcactgaaa 1020

<210> SEQ ID NO 69
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 69

Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Glu Gly Thr Val Thr
    50                  55                  60

```
Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Cys Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Lys Asn Ala Leu Lys
305                 310                 315                 320

Gly Leu Glu His His His His His His
                325
```

<210> SEQ ID NO 70
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 70

```
atgaaagcta ctaaactggt actgggcgcg gtaatcctgg gttctactct gctggcaggt      60

tgctcaagct tcaacgaaaa aggcgaactg tcggcgaaaa cgatgacgcg tgaatgcggc     120

accaaactgg aatatacgga aatgaaaagc gatggcaccg gtaaagcgaa agaagttctg     180

aaaaacttta ccctggaagg caaagtcgcc aatgacaaag tcaccctgga agtgaaagaa     240

ggcaccgtta cgctgtcaaa agaaattgca aaatcgggtg aagtgaccgt tgctctgaac     300

gatacgaata ccacgcaagc gaccaagaaa accggcgcct gggacagcaa aacctctacg     360

ctgaccatta gtgttaacag caagaaaacc acgcagctgg tcttcaccaa acaatgtacg     420

atcaccgtgc agaaatacga tagtgcgggt accaacctgg aaggcaccgc tgttgaaatc     480

aaaaccctgg acgaactgaa aaacgccctg aaaggcacta gtgacaaaaa caatggctct     540
```

```
ggtagcaaag agaaaaacaa agatggcaag tactcattca acgaaaaagg cgaagtctcg    600

gaaaaaatca ttacccgtgc ttgcggcacc cgtctggaat acaccggcat taaatcggat    660

ggcagcggca aagcgaagga agttctgaaa aactttaccc tggaaggcaa agtcgcaaat    720

gataagacca ccctggtggt gaaagaaggc accgttacgc tgagcaaaaa cattagtaag    780

tccggtgaag tctctgtgga actgaatgat accgacagct ctgcggccac caaaaagacg    840

gcagcttgga actcaggcac ctcgacgctg accattacgg ttaattccaa aaagaccaaa    900

gatctggtct tcacgaaaga atgcaccatc acggtgcagc aatatgacag caacggtacc    960

aaactggaag gctctgcggt ggaaatcacg aaactggatg aaatcaaaaa tgcactgaaa   1020

ggtctcgagc accaccacca ccaccac                                        1047


<210> SEQ ID NO 71
<211> LENGTH: 316
<212> TYPE: PRT
<213> ORGANISM: Artificial Sequence
<220> FEATURE:
<223> OTHER INFORMATION: Synthetic Polypeptide

<400> SEQUENCE: 71

Asn Glu Lys Gly Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Cys Asn
    130                 135                 140

Ala Leu Lys Gly Thr Ser Asp Lys Asn Asn Gly Ser Gly Ser Lys Glu
145                 150                 155                 160

Lys Asn Lys Asp Gly Lys Tyr Ser Phe Asn Glu Lys Gly Glu Val Ser
                165                 170                 175

Glu Lys Ile Ile Thr Arg Ala Asp Gly Thr Arg Leu Glu Tyr Thr Gly
            180                 185                 190

Ile Lys Ser Asp Gly Ser Gly Lys Ala Lys Glu Val Leu Lys Asn Phe
        195                 200                 205

Thr Leu Glu Gly Lys Val Ala Asn Asp Lys Thr Thr Leu Val Val Lys
    210                 215                 220

Cys Gly Thr Val Thr Leu Ser Lys Asn Ile Ser Lys Ser Gly Glu Val
225                 230                 235                 240

Ser Val Glu Leu Asn Asp Thr Asp Ser Ser Ala Ala Thr Lys Lys Thr
                245                 250                 255

Ala Ala Trp Asn Ser Gly Thr Ser Thr Leu Thr Ile Thr Val Asn Ser
            260                 265                 270
```

Lys Lys Thr Lys Asp Leu Val Phe Thr Lys Glu Asn Thr Ile Thr Val
275 280 285

Gln Gln Tyr Asp Ser Asn Gly Thr Lys Leu Glu Gly Ser Ala Val Glu
290 295 300

Ile Thr Lys Leu Asp Glu Ile Cys Asn Ala Leu Lys
305 310 315

<210> SEQ ID NO 72
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 72
atgaaagcta ctaaactggt actgggcgcg gtaatcctgg gttctactct gctggcaggt 60
tgctcaagct tcaacgaaaa aggcgaactg tcggcgaaaa cgatgacgcg tgaaaacggc 120
accaaactgg aatatacgga aatgaaaagc gatggcaccg gtaaagcgaa agaagttctg 180
aaaaacttta ccctggaagg caaagtcgcc aatgacaaag tcaccctgga agtgaaatgc 240
ggcaccgtta cgctgtcaaa agaaattgca aaatcgggtg aagtgaccgt tgctctgaac 300
gatacgaata ccacgcaagc gaccaagaaa accggcgcct gggacagcaa aacctctacg 360
ctgaccatta gtgttaatag caagaaaacc acgcagctgg tcttcaccaa acaagatacg 420
atcaccgtgc agaaatacga cagtgcgggt accaacctgg aaggcacggc tgttgaaatc 480
aaaaccctgg acgaactgtg taacgccctg aaaggcacta gtgacaaaaa caatggctct 540
ggtagcaaag agaaaaacaa agatggcaag tactcattca acgaaaaagg cgaagtcagc 600
gaaaaaatca ttacccgcgc agacggcacc cgcctggaat acaccggcat caaatcggac 660
ggcagcggca aagcgaaaga agttctgaaa aactttaccc tggaaggcaa agtcgcaaat 720
gataaaacca ccctggtggt gaaatgcggc accgttacgc tgagcaaaaa cattagtaaa 780
tccggtgaag tctctgtgga actgaatgat accgacagct ctgcggccac caagaaaacc 840
gcagcttgga actcaggcac ctcgacgctg accattacgg ttaatagcaa gaaaaccaaa 900
gatctggtct tcacgaaaga aaacaccatc acggtgcagc aatatgacag caatggtacc 960
aaactggaag gctccgctgt ggaaatcacg aaactggatg aaatctgtaa tgcactgaaa 1020

<210> SEQ ID NO 73
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 73

Cys Ser Ser Phe Asn Glu Lys Gly Glu Leu Ser Ala Lys Thr Met Thr
1 5 10 15

Arg Glu Asn Gly Thr Lys Leu Glu Tyr Thr Glu Met Lys Ser Asp Gly
20 25 30

Thr Gly Lys Ala Lys Glu Val Leu Lys Asn Phe Thr Leu Glu Gly Lys
35 40 45

Val Ala Asn Asp Lys Val Thr Leu Glu Val Lys Cys Gly Thr Val Thr
50 55 60

-continued

```
Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320

Gly Leu Glu His His His His His His
                325
```

<210> SEQ ID NO 74
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 74

```
atgaaagcta ctaaactggt actgggcgcg gtaatcctgg gttctactct gctggcaggt      60

tgctcaagct tcaacgaaaa aggcgaactg tcggcgaaaa cgatgacgcg tgaaaacggc     120

accaaactgg aatatacgga aatgaaaagc gatggcaccg gtaaagcgaa agaagttctg     180

aaaaacttta ccctggaagg caaagtcgcc aatgacaaag tcaccctgga agtgaaatgc     240

ggcaccgtta cgctgtcaaa agaaattgca aaatcgggtg aagtgaccgt tgctctgaac     300

gatacgaata ccacgcaagc gaccaagaaa accggcgcct gggacagcaa aacctctacg     360

ctgaccatta gtgttaatag caagaaaacc acgcagctgg tcttcaccaa acaagatacg     420

atcaccgtgc agaaatacga cagtgcgggt accaacctgg aaggcacggc tgttgaaatc     480

aaaaccctgg acgaactgtg taacgccctg aaaggcacta gtgacaaaaa caatggctct     540
```

-continued

```
ggtagcaaag agaaaaacaa agatggcaag tactcattca acgaaaaagg cgaagtcagc    600

gaaaaaatca ttacccgcgc agacggcacc cgcctggaat acaccggcat caaatcggac    660

ggcagcggca aagcgaaaga agttctgaaa aactttaccc tggaaggcaa agtcgcaaat    720

gataaaacca ccctggtggt gaaatgcggc accgttacgc tgagcaaaaa cattagtaaa    780

tccggtgaag tctctgtgga actgaatgat accgacagct ctgcggccac caagaaaacc    840

gcagcttgga actcaggcac ctcgacgctg accattacgg ttaatagcaa gaaaaccaaa    900

gatctggtct tcacgaaaga aaacaccatc acggtgcagc aatatgacag caatggtacc    960

aaactggaag gctccgctgt ggaaatcacg aaactggatg aaatctgtaa tgcactgaaa   1020

ggtctcgagc accaccacca ccaccac                                        1047
```

<210> SEQ ID NO 75
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 75

```
Phe Asn Ala Lys Gly Glu Leu Ser Glu Lys Thr Ile Leu Arg Ala Cys
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Glu Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Cys Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Cys Gly Thr Arg Leu Glu Tyr Thr
            180                 185                 190

Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
    210                 215                 220

Val Thr Glu Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
            260                 265                 270
```

```
Asn Ser Gln Lys Pro Lys Gln Leu Val Phe Thr Lys Glu Cys Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Lys Ala Ala Leu Lys
305                 310                 315


<210> SEQ ID NO 76
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 76

atgaaagcta ctaaactggt actgggcgcg gtaatcctgg gttctactct gctggcaggt     60

tgctcaagct tcaacgctaa aggtgaactg tcggaaaaaa ccatcctgcg cgcctgtggc    120

acccgcctgg aatacacgga aatcaagtcg gacggcacgg gcaaagcaaa ggaagtcctg    180

aaagattttg ctctggaagg taccctggcg gccgacaaaa ccacgctgaa ggtgacggaa    240

ggcaccgtgg ttctgagcaa acatattccg aactctggtg aaatcaccgt tgaactgaac    300

gatagcaatt ctacgcaggc gaccaaaaag acgggcaaat gggacagtaa tacctccacg    360

ctgaccattt cagtcaactc gaaaaagacc aaaaatattg tgttcacgaa ggaatgcacg    420

atcaccgttc aaaaatatga ttccgcaggt accaacctgg aaggcaacgc tgtggaaatc    480

aaaaccctgg acgaactgaa aaacgccctg aagggtacta gtgacaaaaa caatggctct    540

ggtagcaaag agaaaaacaa agatggcaag tactcattta acgataaggg caaactgtca    600

gaaaaagtgg tcacccgcgc ttgtggcacc cgcctggaat acaccgaaat caaaaacgac    660

ggctcgggca aagcgaagga agttctgaaa ggctttgccc tggaaggtac cctgacggat    720

ggcggtgaaa ccaaactgac cgtgacggaa ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaatgcacg atcaccgtgc agaactataa tcgtgccggt    960

aatgctctgg aaggctcccc ggctgaaatc aaggacctgg cggaactgaa ggcggcactg   1020

aaa                                                                 1023


<210> SEQ ID NO 77
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 77

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
```

```
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys Gly Leu Glu His His His His His His
                325                 330


<210> SEQ ID NO 78
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 78

atgaaagcta ctaaactggt actgggcgcg gtaatcctgg gttctactct gctggcaggt      60

tgctcaagct tcaacgctaa aggtgaactg tcggaaaaaa ccatcctgcg cgcctgtggc     120

acccgcctgg aatacacgga aatcaagtcg gacggcacgg gcaaagcaaa ggaagtcctg     180

aaagattttg ctctggaagg taccctggcg gccgacaaaa ccacgctgaa ggtgacggaa     240

ggcaccgtgg ttctgagcaa acatattccg aactctggtg aaatcaccgt tgaactgaac     300

gatagcaatt ctacgcaggc gaccaaaaag acgggcaaat gggacagtaa tacctccacg     360

ctgaccattt cagtcaactc gaaaaagacc aaaaatattg tgttcacgaa ggaatgcacg     420

atcaccgttc aaaaatatga ttccgcaggt accaacctgg aaggcaacgc tgtggaaatc     480
```

-continued

```
aaaaccctgg acgaactgaa aaacgccctg aagggtacta gtgacaaaaa caatggctct    540

ggtagcaaag agaaaaacaa agatggcaag tactcattta acgataaggg caaactgtca    600

gaaaaagtgg tcacccgcgc ttgtggcacc cgcctggaat acaccgaaat caaaaacgac    660

ggctcgggca aagcgaagga agttctgaaa ggctttgccc tggaaggtac cctgacggat    720

ggcggtgaaa ccaaactgac cgtgacggaa ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaatgcacg atcaccgtgc agaactataa tcgtgccggt    960

aatgctctgg aaggctcccc ggctgaaatc aaggacctgg cggaactgaa ggcggcactg   1020

aaaggtctcg agcaccacca ccaccaccac                                    1050
```

```
<210> SEQ ID NO 79
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 79

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Cys Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Asn Gly Thr Arg Leu Glu Tyr Thr
            180                 185                 190

Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
    210                 215                 220

Val Thr Cys Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
```

```
            260                 265                 270

Asn Ser Gln Lys Pro Lys Gln Leu Val Phe Thr Lys Glu Asn Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Cys Ala Ala Leu Lys
305                 310                 315


<210> SEQ ID NO 80
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 80

atgaaagcta ctaaactggt actgggcgcg gtaatcctgg gttctactct gctggcaggt      60

tgctcaagct tcaatgctaa gggcgaactg agcgaaaaaa cgatcctgcg tgcgaatggc     120

acccgtctgg aatacaccga aatcaaatcc gatggtacgg gcaaagcaaa ggaagtcctg     180

aaagattttg ctctggaagg taccctggcg gccgacaaaa ccacgctgaa ggtgacgtgc     240

ggcaccgtgg ttctgagcaa acatattccg aactctggtg aaatcaccgt tgaactgaac     300

gatagcaatt ctacgcaggc aaccaaaaag acgggcaaat gggacagtaa tacctccacg     360

ctgaccattt cagtcaactc gaaaaagacc aaaaatattg tgttcacgaa ggaagatacg     420

atcaccgttc aaaaatatga ctccgcgggc accaacctgg aaggcaatgc cgtcgaaatc     480

aaaaccctgg atgaactgtg taacgccctg aagggtacta gtgacaaaaa caatggctct     540

ggtagcaaag agaaaaacaa agatggcaag tactcattta acgataaggg caaactgtcg     600

gaaaaagtgg tcacccgcgc aaatggcacc cgcctggaat acacggaaat caaaaacgat     660

ggtagcggca aagcgaagga agttctgaaa ggctttgccc tggaaggtac cctgacggat     720

ggcggtgaaa ccaaactgac cgtgacgtgc ggcaccgtta cgctgtctaa aaacattagc     780

aagtctggtg aaatcacggt cgcactgaat gataccgaaa ccacgccggc tgacaaaaag     840

accggcgaat ggaaaagtga cacctccacg ctgaccattt caaagaactc gcagaaaccg     900

aagcaactgg tcttcaccaa agaaaacacg atcaccgtgc agaactataa tcgtgccggt     960

aatgctctgg aaggctcacc ggctgaaatc aaggacctgg ctgaactgtg tgcggcactg    1020

aaa                                                                 1023


<210> SEQ ID NO 81
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 81

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45
```

```
Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Asp Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys Gly Leu Glu His His His His His His
                325                 330
```

<210> SEQ ID NO 82
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 82

```
atgaaagcta ctaaactggt actgggcgcg gtaatcctgg gttctactct gctggcaggt     60

tgctcaagct tcaatgctaa gggcgaactg agcgaaaaaa cgatcctgcg tgcgaatggc    120

acccgtctgg aatacaccga aatcaaatcc gatggtacgg gcaaagcaaa ggaagtcctg    180

aaagattttg ctctggaagg taccctggcg gccgacaaaa ccacgctgaa ggtgacgtgc    240

ggcaccgtgg ttctgagcaa acatattccg aactctggtg aaatcaccgt tgaactgaac    300

gatagcaatt ctacgcaggc aaccaaaaag acgggcaaat gggacagtaa tacctccacg    360

ctgaccattt cagtcaactc gaaaaagacc aaaaatattg tgttcacgaa ggaagatacg    420
```

```
atcaccgttc aaaaatatga ctccgcgggc accaacctgg aaggcaatgc cgtcgaaatc    480

aaaaccctgg atgaactgtg taacgccctg aagggtacta gtgacaaaaa caatggctct    540

ggtagcaaag agaaaaacaa agatggcaag tactcattta acgataaggg caaactgtcg    600

gaaaaagtgg tcacccgcgc aaatggcacc cgcctggaat acacggaaat caaaaacgat    660

ggtagcggca aagcgaagga agttctgaaa ggctttgccc tggaaggtac cctgacggat    720

ggcggtgaaa ccaaactgac cgtgacgtgc ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaaaacacg atcaccgtgc agaactataa tcgtgccggt    960

aatgctctgg aaggctcacc ggctgaaatc aaggacctgg ctgaactgtg tgcggcactg   1020

aaaggtctcg agcaccacca ccaccaccac                                    1050


<210> SEQ ID NO 83
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 83

Phe Asn Gly Lys Gly Glu Thr Ser Glu Lys Thr Ile Val Arg Ala Cys
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Cys Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Lys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Cys Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Glu Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255
```

```
Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Cys Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Lys Asn Ala Leu Lys
305                 310                 315


<210> SEQ ID NO 84
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 84

atgaaagcta ctaaactggt actgggcgcg gtaatcctgg gttctactct gctggcaggt      60

tgctcaagct tcaacggcaa aggtgaaacg agtgaaaaaa cgattgttcg cgcctgtggc     120

acccgcctgg aatacacgga tatcaagtcg gatggttcgg gcaaagcaaa ggaagtcctg     180

aaagatttta cgctggaagg taccctggca gcagacggta aaaccacgct gaaggtgacg     240

gaaggcaccg tggttctgtc aaaaaacatt ctgaagtcgg gtgaaatcac cgcagctctg     300

gatgacagcg ataccacgcg tgctacgaaa aagaccggta aatgggacag caagacctct     360

acgctgacca ttagtgtcaa ctcccagaaa acgaagaatc tggtgttcac caaagaatgc     420

acgatcaccg ttcaacgcta tgatagtgcg ggcaccaacc tggaaggcaa agccgttgaa     480

attaccacgc tgaaagaact gaagaatgct ctgaaaggta ctagtgacaa aaacaatggc     540

tctggtagca aagagaaaaa caaagatggc aagtactcat tcaacgaaaa aggcgaaatc     600

agtgaaaaaa ccattgtgcg tgcgtgtggc acccgtctgg aatataccga catcaagagc     660

gataaaacgg gtaaagcgaa ggaagttctg aaagatttta cgctggaagg taccctggca     720

gcagacggta aaaccacgct gaaggtgacc gaaggtaccg ttacgctgtc caaaaacatt     780

agtaagtccg gcgaaatcac ggtcgccctg gatgacaccg atagctctgg caacaaaaag     840

agcggtacct gggactcagg cacctcgacg ctgaccattt ctaaaaatcg tacgaaaacc     900

aagcagctgg tcttcacgaa agaatgcacg atcaccgtgc aaaactatga tagcgcaggt     960

accaatctgg aaggcaaagc tgtggaaatt accacgctga aagaactgaa gaatgctctg    1020

aaa                                                                  1023


<210> SEQ ID NO 85
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 85

Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30
```

```
Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Cys Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 86
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 86

```
atgaaagcta ctaaactggt actgggcgcg gtaatcctgg gttctactct gctggcaggt      60

tgctcaagct tcaacggcaa aggtgaaacg agtgaaaaaa cgattgttcg cgcctgtggc     120

acccgcctgg aatacacgga tatcaagtcg gatggttcgg gcaaagcaaa ggaagtcctg     180

aaagatttta cgctggaagg taccctggca gcagacggta aaaccacgct gaaggtgacg     240

gaaggcaccg tggttctgtc aaaaaacatt ctgaagtcgg gtgaaatcac cgcagctctg     300

gatgacagcg ataccacgcg tgctacgaaa aagaccggta aatgggacag caagacctct     360
```

```
acgctgacca ttagtgtcaa ctcccagaaa acgaagaatc tggtgttcac caaagaatgc    420

acgatcaccg ttcaacgcta tgatagtgcg ggcaccaacc tggaaggcaa agccgttgaa    480

attaccacgc tgaaagaact gaagaatgct ctgaaaggta ctagtgacaa aaacaatggc    540

tctggtagca aagagaaaaa caaagatggc aagtactcat tcaacgaaaa aggcgaaatc    600

agtgaaaaaa ccattgtgcg tgcgtgtggc acccgtctgg aatataccga catcaagagc    660

gataaaacgg gtaaagcgaa ggaagttctg aaagatttta cgctggaagg taccctggca    720

gcagacggta aaaccacgct gaaggtgacc gaaggtaccg ttacgctgtc caaaaaacatt   780

agtaagtccg gcgaaatcac ggtcgccctg gatgacaccg atagctctgg caacaaaaag    840

agcggtacct gggactcagg cacctcgacg ctgaccattt ctaaaaatcg tacgaaaacc    900

aagcagctgg tcttcacgaa agaatgcacg atcaccgtgc aaaactatga tagcgcaggt    960

accaatctgg aaggcaaagc tgtggaaatt accacgctga aagaactgaa gaatgctctg   1020

aaaggtctcg agcaccacca ccaccaccac                                    1050
```

<210> SEQ ID NO 87
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 87

```
Phe Asn Gly Lys Gly Glu Thr Ser Glu Lys Thr Ile Val Arg Ala Asn
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Cys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
                165                 170                 175

Ile Ser Glu Lys Thr Ile Val Arg Ala Asn Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Cys Gly Thr Val Thr Leu Ser Lys Asn Ile Ser Lys Ser
225                 230                 235                 240
```

```
Gly Glu Ile Thr Val Ala Leu Asp Asp Thr Asp Ser Ser Gly Asn Lys
            245                 250                 255

Lys Ser Gly Thr Trp Asp Ser Gly Thr Ser Thr Leu Thr Ile Ser Lys
        260                 265                 270

Asn Arg Thr Lys Thr Lys Gln Leu Val Phe Thr Lys Glu Asp Thr Ile
    275                 280                 285

Thr Val Gln Asn Tyr Asp Ser Ala Gly Thr Asn Leu Glu Gly Lys Ala
290                 295                 300

Val Glu Ile Thr Thr Leu Lys Glu Leu Cys Asn Ala Leu Lys
305                 310                 315
```

<210> SEQ ID NO 88
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 88

```
atgaaagcta ctaaactggt actgggcgcg gtaatcctgg gttctactct gctggcaggt     60

tgctcaagct tcaacggcaa aggtgaaacg agcgaaaaga ccatcgtgcg tgcgaacggt    120

acccgcctgg aatatacgga cattaaatcg gacggcagcg gcaaagcaaa ggaagtcctg    180

aaagatttta cgctggaagg taccctggca gcagacggta aaaccacgct gaaggtgacg    240

tgcggcaccg tggttctgtc aaaaaacatt ctgaagtcgg gtgaaatcac cgcagctctg    300

gatgacagcg ataccacgcg tgctacgaaa aagaccggta aatgggatag caagacctct    360

acgctgacca ttagtgtcaa ctcccagaaa acgaagaatc tggtgttcac caaagaagat    420

acgatcaccg ttcaacgcta tgacagtgcg ggcaccaacc tggaaggcaa agccgttgaa    480

attaccacgc tgaaagaact gtgtaatgct ctgaaaggta ctagtgacaa aaacaatggc    540

tctggtagca aagagaaaaa caaagatggc aagtactcat tcaacgaaaa aggcgaaatc    600

tcagaaaaaa ccatcgtccg cgctaacggc acccgcctgg aatacaccga catcaaatca    660

gacaagaccg gtaaagcgaa ggaagttctg aaagatttta cgctggaagg taccctggca    720

gcagacggta aaaccacgct gaaggtgacc tgcggtaccg ttacgctgtc caaaaacatt    780

agtaagtccg gcgaaatcac ggtcgccctg gatgacaccg atagctctgg caacaaaaag    840

agcggtacct gggattcagg cacctcgacg ctgaccattt ctaaaaatcg tacgaaaacc    900

aagcagctgg tcttcacgaa agaagatacg atcaccgtgc aaaactatga cagcgcaggt    960

accaatctgg aaggcaaagc tgtggaaatt accacgctga aagaactgtg taatgctctg   1020

aaa                                                                 1023
```

<210> SEQ ID NO 89
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 89

```
Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
```

```
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Asp Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330
```

<210> SEQ ID NO 90
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 90

```
atgaaagcta ctaaactggt actgggcgcg gtaatcctgg gttctactct gctggcaggt      60

tgctcaagct tcaacggcaa aggtgaaacg agcgaaaaga ccatcgtgcg tgcgaacggt     120

acccgcctgg aatatacgga cattaaatcg gacggcagcg gcaaagcaaa ggaagtcctg     180

aaagatttta cgctggaagg taccctggca gcagacggta aaaccacgct gaaggtgacg     240

tgcggcaccg tggttctgtc aaaaaacatt ctgaagtcgg gtgaaatcac cgcagctctg     300
```

```
gatgacagcg ataccacgcg tgctacgaaa aagaccggta aatgggatag caagacctct    360

acgctgacca ttagtgtcaa ctcccagaaa acgaagaatc tggtgttcac caaagaagat    420

acgatcaccg ttcaacgcta tgacagtgcg ggcaccaacc tggaaggcaa agccgttgaa    480

attaccacgc tgaaagaact gtgtaatgct ctgaaaggta ctagtgacaa aaacaatggc    540

tctggtagca aagagaaaaa caaagatggc aagtactcat tcaacgaaaa aggcgaaatc    600

tcagaaaaaa ccatcgtccg cgctaacggc acccgcctgg aatacaccga catcaaatca    660

gacaagaccg gtaaagcgaa ggaagttctg aaagatttta cgctggaagg taccctggca    720

gcagacggta aaaccacgct gaaggtgacc tgcggtaccg ttacgctgtc caaaaacatt    780

agtaagtccg gcgaaatcac ggtcgccctg gatgacaccg atagctctgg caacaaaaag    840

agcggtacct gggattcagg cacctcgacg ctgaccattt ctaaaaatcg tacgaaaacc    900

aagcagctgg tcttcacgaa agaagatacg atcaccgtgc aaaactatga cagcgcaggt    960

accaatctgg aaggcaaagc tgtggaaatt accacgctga aagaactgtg taatgctctg   1020

aaaggtctcg agcaccacca ccaccaccac                                    1050
```

<210> SEQ ID NO 91
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 91

```
Phe Asn Glu Lys Gly Glu Val Ser Glu Lys Ile Ile Thr Arg Ala Cys
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Glu Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Cys Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175

Ser Ala Lys Thr Met Thr Arg Glu Asn Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Cys Gly Thr Val Thr Leu Ser Lys Glu Ile Ala Lys Ser Gly Glu
```

-continued

```
225                 230                 235                 240

Val Thr Val Ala Leu Asn Asp Thr Asn Thr Thr Gln Ala Thr Lys Lys
                245                 250                 255

Thr Gly Ala Trp Asp Ser Lys Thr Ser Thr Leu Thr Ile Ser Val Asn
            260                 265                 270

Ser Lys Lys Thr Thr Gln Leu Val Phe Thr Lys Gln Asp Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Cys Asn Ala Leu Lys
305                 310                 315


<210> SEQ ID NO 92
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 92

atgaaagcta ctaaactggt actgggcgcg gtaatcctgg gttctactct gctggcaggt     60

tgctcaagct tcaacgaaaa gggcgaagtc tcggaaaaaa tcattacccg tgcttgcggc    120

acccgtctgg aatacaccgg cattaaatcg gatggcagcg gcaaagcgaa ggaagttctg    180

aaaaacttta ccctggaagg caaagtcgca aatgataaga ccaccctggt ggtgaaagaa    240

ggcaccgtta cgctgagcaa aaacattagt aagtccggtg aagtctctgt ggaactgaat    300

gataccgaca gctctgcggc caccaaaaag acggcagctt ggaactcagg cacctcgacg    360

ctgaccatta cggttaattc caaaaagacc aaagatctgg tcttcacgaa agaatgcacc    420

atcacggtgc agcaatatga cagcaacggt accaaactgg aaggctctgc ggtggaaatc    480

acgaaactgg atgaaatcaa aaatgctctg aaaggtacta gtgacaaaaa caatggctct    540

ggtagcaaag agaaaaacaa agatggcaag tactcattca acgaaaaagg cgaactgtcg    600

gcgaaaacga tgacgcgtga aaacggcacc aaactggaat atacggaaat gaaaagcgat    660

ggcaccggta aagcgaaaga agttctgaaa aactttaccc tggaaggcaa agtcgccaat    720

gacaaagtca ccctggaagt gaaatgcggc accgttacgc tgtcaaaaga aattgcaaaa    780

tcgggtgaag tgaccgttgc tctgaacgat acgaatacca cgcaagcgac caagaaaacc    840

ggcgcctggg acagcaaaac ctctacgctg accattagtg ttaatagcaa gaaaaccacg    900

cagctggtct tcaccaaaca agatacgatc accgtgcaga aatacgacag tgcgggtacc    960

aacctggaag gcacggctgt tgaaatcaaa accctggacg aactgtgtaa cgccctgaaa   1020


<210> SEQ ID NO 93
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 93

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
```

```
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320

Gly Leu Glu His His His His His His
                325


<210> SEQ ID NO 94
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 94

atgaaagcta ctaaactggt actgggcgcg gtaatcctgg gttctactct gctggcaggt      60

tgctcaagct tcaacgaaaa gggcgaagtc tcggaaaaaa tcattacccg tgcttgcggc     120

acccgtctgg aatacaccgg cattaaatcg gatggcagcg gcaaagcgaa ggaagttctg     180

aaaaacttta ccctggaagg caaagtcgca aatgataaga ccaccctggt ggtgaaagaa     240

ggcaccgtta cgctgagcaa aaacattagt aagtccggtg aagtctctgt ggaactgaat     300
```

```
gataccgaca gctctgcggc caccaaaaag acggcagctt ggaactcagg cacctcgacg    360

ctgaccatta cggttaattc caaaaagacc aaagatctgg tcttcacgaa agaatgcacc    420

atcacggtgc agcaatatga cagcaacggt accaaactgg aaggctctgc ggtggaaatc    480

acgaaactgg atgaaatcaa aaatgctctg aaaggtacta gtgacaaaaa caatggctct    540

ggtagcaaag agaaaaacaa agatggcaag tactcattca acgaaaaagg cgaactgtcg    600

gcgaaaacga tgacgcgtga aaacggcacc aaactggaat atacggaaat gaaaagcgat    660

ggcaccggta aagcgaaaga agttctgaaa aactttaccc tggaaggcaa agtcgccaat    720

gacaaagtca ccctggaagt gaaatgcggc accgttacgc tgtcaaaaga aattgcaaaa    780

tcgggtgaag tgaccgttgc tctgaacgat acgaatacca cgcaagcgac caagaaaacc    840

ggcgcctggg acagcaaaac ctctacgctg accattagtg ttaatagcaa gaaaaccacg    900

cagctggtct tcaccaaaca agatacgatc accgtgcaga aatacgacag tgcgggtacc    960

aacctggaag gcacggctgt tgaaatcaaa accctggacg aactgtgtaa cgccctgaaa   1020

ggcctcgagc accaccacca ccaccac                                        1047


<210> SEQ ID NO 95
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 95

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Leu
                165                 170                 175

Ser Ala Lys Thr Met Thr Arg Glu Cys Gly Thr Lys Leu Glu Tyr Thr
            180                 185                 190

Glu Met Lys Ser Asp Gly Thr Gly Lys Ala Lys Glu Val Leu Lys Asn
        195                 200                 205

Phe Thr Leu Glu Gly Lys Val Ala Asn Asp Lys Val Thr Leu Glu Val
    210                 215                 220

Lys Glu Gly Thr Val Thr Leu Ser Lys Glu Ile Ala Lys Ser Gly Glu
```

```
225                 230                 235                 240

Val Thr Val Ala Leu Asn Asp Thr Asn Thr Thr Gln Ala Thr Lys Lys
                245                 250                 255

Thr Gly Ala Trp Asp Ser Lys Thr Ser Thr Leu Thr Ile Ser Val Asn
            260                 265                 270

Ser Lys Lys Thr Thr Gln Leu Val Phe Thr Lys Gln Cys Thr Ile Thr
        275                 280                 285

Val Gln Lys Tyr Asp Ser Ala Gly Thr Asn Leu Glu Gly Thr Ala Val
    290                 295                 300

Glu Ile Lys Thr Leu Asp Glu Leu Lys Asn Ala Leu Lys
305                 310                 315


<210> SEQ ID NO 96
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 96

atgaaagcta ctaaactggt actgggcgcg gtaatcctgg gttctactct gctggcaggt     60

tgctcaagct tcaacgaaaa gggcgaagtc agcgaaaaaa tcattacccg cgcagacggc    120

acccgcctgg aatacaccgg catcaaatcg gacggcagcg gcaaagcgaa agaagttctg    180

aaaaacttta ccctggaagg caaagtcgca aatgataaaa ccaccctggt ggtgaaatgc    240

ggcaccgtta cgctgagcaa aaacattagt aaatccggtg aagtctctgt ggaactgaat    300

gataccgaca gctctgcggc caccaagaaa accgcagctt ggaactcagg cacctcgacg    360

ctgaccatta cggttaatag caagaaaacc aaagatctgg tcttcacgaa agaaaacacc    420

atcacggtgc agcaatatga cagcaatggt accaaactgg aaggctccgc tgtggaaatc    480

acgaaactgg atgaaatctg taatgctctg aaaggtacta gtgacaaaaa caatggctct    540

ggtagcaaag agaaaaacaa agatggcaag tactcattca acgaaaaagg cgaactgtcg    600

gcgaaaacga tgacgcgtga atgcggcacc aaactggaat atacggaaat gaaaagcgat    660

ggcaccggta aagcgaaaga agttctgaaa aactttaccc tggaaggcaa agtcgccaat    720

gacaaagtca ccctggaagt gaaagaaggc accgttacgc tgtcaaaaga aattgcaaaa    780

tcgggtgaag tgaccgttgc tctgaacgat acgaatacca cgcaagcgac caagaaaacc    840

ggcgcctggg acagcaaaac ctctacgctg accattagtg ttaacagcaa gaaaaccacg    900

cagctggtct tcaccaaaca atgtacgatc accgtgcaga aatacgatag tgcgggtacc    960

aacctggaag gcaccgctgt tgaaatcaaa accctggacg aactgaaaaa cgccctgaaa   1020


<210> SEQ ID NO 97
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 97

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
```

```
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Cys
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Lys Asn Ala Leu Lys
305                 310                 315                 320

Gly Leu Glu His His His His His His
                325
```

<210> SEQ ID NO 98
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 98

```
atgaaagcta ctaaactggt actgggcgcg gtaatcctgg gttctactct gctggcaggt      60

tgctcaagct tcaacgaaaa gggcgaagtc agcgaaaaaa tcattacccg cgcagacggc     120

acccgcctgg aatacaccgg catcaaatcg gacggcagcg gcaaagcgaa agaagttctg     180

aaaaacttta ccctggaagg caaagtcgca aatgataaaa ccaccctggt ggtgaaatgc     240

ggcaccgtta cgctgagcaa aaacattagt aaatccggtg aagtctctgt ggaactgaat     300
```

```
gataccgaca gctctgcggc caccaagaaa accgcagctt ggaactcagg cacctcgacg    360

ctgaccatta cggttaatag caagaaaacc aaagatctgg tcttcacgaa agaaaacacc    420

atcacggtgc agcaatatga cagcaatggt accaaactgg aaggctccgc tgtggaaatc    480

acgaaactgg atgaaatctg taatgctctg aaaggtacta gtgacaaaaa caatggctct    540

ggtagcaaag agaaaaacaa agatggcaag tactcattca acgaaaaagg cgaactgtcg    600

gcgaaaacga tgacgcgtga atgcggcacc aaactggaat atacggaaat gaaaagcgat    660

ggcaccggta aagcgaaaga agttctgaaa aactttaccc tggaaggcaa agtcgccaat    720

gacaaagtca ccctggaagt gaaagaaggc accgttacgc tgtcaaaaga aattgcaaaa    780

tcgggtgaag tgaccgttgc tctgaacgat acgaatacca cgcaagcgac caagaaaacc    840

ggcgcctggg acagcaaaac ctctacgctg accattagtg ttaacagcaa gaaaaccacg    900

cagctggtct tcaccaaaca atgtacgatc accgtgcaga aatacgatag tgcgggtacc    960

aacctggaag gcaccgctgt tgaaatcaaa accctggacg aactgaaaaa cgccctgaaa   1020

ggcctcgagc accaccacca ccaccac                                      1047
```

<210> SEQ ID NO 99
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 99

```
Phe Asn Glu Lys Gly Lys Leu Ser Glu Lys Val Val Thr Arg Ala Cys
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Glu Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Cys Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Lys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Asn Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
    210                 215                 220

Val Thr Cys Gly Thr Val Val Leu Ser Lys His Ile Pro Asn Ser Gly
```

-continued 225 230 235 240

Glu Ile Thr Val Glu Leu Asn Asp Ser Asn Ser Thr Gln Ala Thr Lys
245 250 255

Lys Thr Gly Lys Trp Asp Ser Asn Thr Ser Thr Leu Thr Ile Ser Val
260 265 270

Asn Ser Lys Lys Thr Lys Asn Ile Val Phe Thr Lys Glu Asp Thr Ile
275 280 285

Thr Val Gln Lys Tyr Asp Ser Ala Gly Thr Asn Leu Glu Gly Asn Ala
290 295 300

Val Glu Ile Lys Thr Leu Asp Glu Leu Cys Asn Ala Leu Lys
305 310 315

<210> SEQ ID NO 100
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 100
atgaaagcta ctaaactggt actgggcgcg gtaatcctgg gttctactct gctggcaggt 60
tgctcaagct tcaacgaaaa gggcaaactg tcagaaaaag tggtcacccg cgcttgtggc 120
acccgcctgg aatacaccga aatcaaaaac gacggctcgg gcaaagcgaa ggaagttctg 180
aaaggctttg ccctggaagg taccctgacg gatggcggtg aaaccaaact gaccgtgacg 240
gaaggcaccg ttacgctgtc taaaaacatt agcaagtctg gtgaaatcac ggtcgcactg 300
aatgataccg aaaccacgcc ggctgacaaa aagaccggcg aatggaaaag tgacacctcc 360
acgctgacca tttcaaagaa ctcgcagaaa ccgaagcaac tggtcttcac caaagaatgc 420
acgatcaccg tgcagaacta taatcgtgcc ggtaatgctc tggaaggctc cccggctgaa 480
atcaaggacc tggcggaact gaaggcggca ctgaaaggca ctagtgacaa aaacaatggc 540
tctggtagca aagagaaaaa caaagatggc aagtactcat tcaacgctaa aggtgaactg 600
agcgaaaaaa cgatcctgcg tgcgaatggc acccgtctgg aatacaccga aatcaaatcc 660
gatggtacgg gcaaagcaaa ggaagtcctg aaagattttg ctctggaagg taccctggcg 720
gccgacaaaa ccacgctgaa ggtgacgtgc ggcaccgtgg ttctgagcaa acatattccg 780
aactctggtg aaatcaccgt tgaactgaac gatagcaatt ctacgcaggc aaccaaaaag 840
acgggcaaat gggacagtaa tacctccacg ctgaccattt cagtcaactc gaaaaagacc 900
aaaaatattg tgttcacgaa ggaagatacg atcaccgttc aaaaatatga ctccgcgggc 960
accaacctgg aaggcaatgc cgtcgaaatc aaaaccctgg atgaactgtg taatgctctg 1020
aag 1023

<210> SEQ ID NO 101
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 101

Cys Ser Ser Phe Asn Glu Lys Gly Lys Leu Ser Glu Lys Val Val Thr
1 5 10 15

```
Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Cys Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Lys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Cys Asn Ala Leu
305                 310                 315                 320

Lys Gly Leu Glu His His His His His His
                325                 330
```

<210> SEQ ID NO 102
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 102

```
atgaaagcta ctaaactggt actgggcgcg gtaatcctgg gttctactct gctggcaggt     60

tgctcaagct tcaacgaaaa gggcaaactg tcagaaaaag tggtcacccg cgcttgtggc    120

acccgcctgg aatacaccga aatcaaaaac gacggctcgg gcaaagcgaa ggaagttctg    180

aaaggctttg ccctggaagg taccctgacg gatggcggtg aaaccaaact gaccgtgacg    240
```

```
gaaggcaccg ttacgctgtc taaaaacatt agcaagtctg gtgaaatcac ggtcgcactg    300

aatgataccg aaaccacgcc ggctgacaaa aagaccggcg aatggaaaag tgacacctcc    360

acgctgacca tttcaaagaa ctcgcagaaa ccgaagcaac tggtcttcac caaagaatgc    420

acgatcaccg tgcagaacta taatcgtgcc ggtaatgctc tggaaggctc cccggctgaa    480

atcaaggacc tggcggaact gaaggcggca ctgaaaggca ctagtgacaa aaacaatggc    540

tctggtagca aagagaaaaa caaagatggc aagtactcat tcaacgctaa aggtgaactg    600

agcgaaaaaa cgatcctgcg tgcgaatggc acccgtctgg aatacaccga aatcaaatcc    660

gatggtacgg gcaaagcaaa ggaagtcctg aaagattttg ctctggaagg taccctggcg    720

gccgacaaaa ccacgctgaa ggtgacgtgc ggcaccgtgg ttctgagcaa acatattccg    780

aactctggtg aaatcaccgt tgaactgaac gatagcaatt ctacgcaggc aaccaaaaag    840

acgggcaaat gggacagtaa tacctccacg ctgaccattt cagtcaactc gaaaaagacc    900

aaaaatattg tgttcacgaa ggaagatacg atcaccgttc aaaaatatga ctccgcgggc    960

accaacctgg aaggcaatgc cgtcgaaatc aaaaccctgg atgaactgtg taatgctctg   1020

aagggtctcg agcaccacca ccaccaccac                                   1050
```

<210> SEQ ID NO 103
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 103

```
Phe Asn Glu Lys Gly Lys Leu Ser Glu Lys Val Val Thr Arg Ala Asn
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Cys Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Pro Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Cys Ala Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Ala Lys Gly Glu
                165                 170                 175

Leu Ser Glu Lys Thr Ile Leu Arg Ala Cys Gly Thr Arg Leu Glu Tyr
            180                 185                 190

Thr Glu Ile Lys Ser Asp Gly Thr Gly Lys Ala Lys Glu Val Leu Lys
        195                 200                 205

Asp Phe Ala Leu Glu Gly Thr Leu Ala Ala Asp Lys Thr Thr Leu Lys
    210                 215                 220
```

```
Val Thr Glu Gly Thr Val Val Leu Ser Lys His Ile Pro Asn Ser Gly
225                 230                 235                 240

Glu Ile Thr Val Glu Leu Asn Asp Ser Asn Ser Thr Gln Ala Thr Lys
                245                 250                 255

Lys Thr Gly Lys Trp Asp Ser Asn Thr Ser Thr Leu Thr Ile Ser Val
            260                 265                 270

Asn Ser Lys Lys Thr Lys Asn Ile Val Phe Thr Lys Glu Cys Thr Ile
        275                 280                 285

Thr Val Gln Lys Tyr Asp Ser Ala Gly Thr Asn Leu Glu Gly Asn Ala
    290                 295                 300

Val Glu Ile Lys Thr Leu Asp Glu Leu Lys Asn Ala Leu Lys
305                 310                 315


<210> SEQ ID NO 104
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 104

atgaaagcta ctaaactggt actgggcgcg gtaatcctgg gttctactct gctggcaggt     60

tgctcaagct tcaacgaaaa gggcaaactg tcggaaaaag tggtcacccg cgcaaatggc    120

acccgcctgg aatacacgga aatcaaaaac gatggtagcg gcaaagcgaa ggaagttctg    180

aaaggctttg ccctggaagg taccctgacg gatggcggtg aaaccaaact gaccgtgacg    240

tgcggcaccg ttacgctgtc taaaaacatt agcaagtctg gtgaaatcac ggtcgcactg    300

aatgataccg aaaccacgcc ggctgacaaa aagaccggcg aatggaaaag tgacacctcc    360

acgctgacca tttcaaagaa ctcgcagaaa ccgaagcaac tggtcttcac caaagaaaac    420

acgatcaccg tgcagaacta taatcgtgcc ggtaatgctc tggaaggctc accggctgaa    480

atcaaggacc tggctgaact gtgtgcggca ctgaaaggca ctagtgacaa aaacaatggc    540

tctggtagca aagagaaaaa caaagatggc aagtactcat tcaacgctaa aggtgaactg    600

tcggaaaaaa ccatcctgcg cgcctgtggc acccgcctgg aatacacgga aatcaagtcg    660

gacggcacgg gcaaagcaaa ggaagtcctg aaagattttg ctctggaagg taccctggcg    720

gccgacaaaa ccacgctgaa ggtgacggaa ggcaccgtgg ttctgagcaa acatattccg    780

aactctggtg aaatcaccgt tgaactgaac gatagcaatt ctacgcaggc gaccaaaaag    840

acgggcaaat gggacagtaa tacctccacg ctgaccattt cagtcaactc gaaaaagacc    900

aaaaatattg tgttcacgaa ggaatgcacg atcaccgttc aaaaatatga ttccgcaggt    960

accaacctgg aaggcaacgc tgtggaaatc aaaaccctgg acgaactgaa aaatgctctg   1020

aag                                                                  1023


<210> SEQ ID NO 105
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 105
```

```
Cys Ser Ser Phe Asn Glu Lys Gly Lys Leu Ser Glu Lys Val Val Thr
1               5                   10                  15

Arg Ala Asn Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Cys Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Cys Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Glu Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Cys Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Lys Asn Ala Leu
305                 310                 315                 320

Lys Gly Leu Glu His His His His His His
                325                 330
```

<210> SEQ ID NO 106
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 106

```
atgaaagcta ctaaactggt actgggcgcg gtaatcctgg gttctactct gctggcaggt     60

tgctcaagct tcaacgaaaa gggcaaactg tcggaaaaag tggtcacccg cgcaaatggc    120

acccgcctgg aatacacgga aatcaaaaac gatggtagcg gcaaagcgaa ggaagttctg    180
```

```
aaaggctttg ccctggaagg taccctgacg gatggcggtg aaaccaaact gaccgtgacg    240

tgcggcaccg ttacgctgtc taaaaacatt agcaagtctg gtgaaatcac ggtcgcactg    300

aatgataccg aaaccacgcc ggctgacaaa aagaccggcg aatggaaaag tgacacctcc    360

acgctgacca tttcaaagaa ctcgcagaaa ccgaagcaac tggtcttcac caaagaaaac    420

acgatcaccg tgcagaacta taatcgtgcc ggtaatgctc tggaaggctc accggctgaa    480

atcaaggacc tggctgaact gtgtgcggca ctgaaaggca ctagtgacaa aaacaatggc    540

tctggtagca aagagaaaaa caaagatggc aagtactcat tcaacgctaa aggtgaactg    600

tcggaaaaaa ccatcctgcg cgcctgtggc acccgcctgg aatacacgga aatcaagtcg    660

gacggcacgg gcaaagcaaa ggaagtcctg aaagattttg ctctggaagg taccctggcg    720

gccgacaaaa ccacgctgaa ggtgacggaa ggcaccgtgg ttctgagcaa acatattccg    780

aactctggtg aaatcaccgt tgaactgaac gatagcaatt ctacgcaggc gaccaaaaag    840

acgggcaaat gggacagtaa tacctccacg ctgaccattt cagtcaactc gaaaaagacc    900

aaaaatattg tgttcacgaa ggaatgcacg atcaccgttc aaaaatatga ttccgcaggt    960

accaacctgg aaggcaacgc tgtggaaatc aaaaccctgg acgaactgaa aaatgctctg   1020

aagggtctcg agcaccacca ccaccaccac                                    1050
```

```
<210> SEQ ID NO 107
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 107

Phe Asn Glu Lys Gly Glu Ile Ser Glu Lys Thr Ile Val Arg Ala Cys
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Cys Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Asn Gly Thr Arg Leu Glu Tyr Thr
            180                 185                 190

Asp Ile Lys Ser Asp Gly Ser Gly Lys Ala Lys Glu Val Leu Lys Asp
        195                 200                 205
```

-continued

```
Phe Thr Leu Glu Gly Thr Leu Ala Ala Asp Gly Lys Thr Thr Leu Lys
    210                 215                 220

Val Thr Cys Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                245                 250                 255

Lys Thr Gly Lys Trp Asp Ser Lys Thr Ser Thr Leu Thr Ile Ser Val
            260                 265                 270

Asn Ser Gln Lys Thr Lys Asn Leu Val Phe Thr Lys Glu Asp Thr Ile
        275                 280                 285

Thr Val Gln Arg Tyr Asp Ser Ala Gly Thr Asn Leu Glu Gly Lys Ala
    290                 295                 300

Val Glu Ile Thr Thr Leu Lys Glu Leu Cys Asn Ala Leu Lys
305                 310                 315


<210> SEQ ID NO 108
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 108

atgaaagcta ctaaactggt actgggcgcg gtaatcctgg gttctactct gctggcaggt     60

tgctcaagct tcaacgaaaa gggcgaaatc agtgaaaaaa ccattgtgcg tgcgtgtggc    120

acccgtctgg aatataccga catcaagagc gataaaacgg gtaaagcgaa ggaagttctg    180

aaagatttta cgctggaagg taccctggca gcagacggta aaaccacgct gaaggtgacc    240

gaaggtaccg ttacgctgtc caaaaacatt agtaagtccg gcgaaatcac ggtcgccctg    300

gatgacaccg atagctctgg caacaaaaag agcggtacct gggactcagg cacctcgacg    360

ctgaccattt ctaaaaatcg tacgaaaacc aagcagctgg tcttcacgaa agaatgcacg    420

atcaccgtgc aaaactatga tagcgcaggt accaatctgg aaggcaaagc tgtggaaatt    480

accacgctga aagaactgaa gaatgctctg aaaggtacta gtgacaaaaa caatggctct    540

ggtagcaaag agaaaaacaa agatggcaag tactcattca acggcaaagg tgaaacgagc    600

gaaaagacca tcgtgcgtgc gaacggtacc cgcctggaat atacggacat taaatcggac    660

ggcagcggca aagcaaagga agtcctgaaa gattttacgc tggaaggtac cctggcagca    720

gacggtaaaa ccacgctgaa ggtgacgtgc ggcaccgtgg ttctgtcaaa aaacattctg    780

aagtcgggtg aaatcaccgc agctctggat gacagcgata ccacgcgtgc tacgaaaaag    840

accggtaaat gggatagcaa gacctctacg ctgaccatta gtgtcaactc ccagaaaacg    900

aagaatctgg tgttcaccaa agaagatacg atcaccgttc aacgctatga cagtgcgggc    960

accaacctgg aaggcaaagc cgttgaaatt accacgctga aagaactgtg taatgctctg   1020

aaa                                                                 1023


<210> SEQ ID NO 109
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation
```

<400> SEQUENCE: 109

```
Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330
```

<210> SEQ ID NO 110
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 110

```
atgaaagcta ctaaactggt actgggcgcg gtaatcctgg gttctactct gctggcaggt      60

tgctcaagct tcaacgaaaa gggcgaaatc agtgaaaaaa ccattgtgcg tgcgtgtggc     120
```

-continued

```
acccgtctgg aatataccga catcaagagc gataaaacgg gtaaagcgaa ggaagttctg    180

aaagatttta cgctggaagg taccctggca gcagacggta aaaccacgct gaaggtgacc    240

gaaggtaccg ttacgctgtc caaaaacatt agtaagtccg gcgaaatcac ggtcgccctg    300

gatgacaccg atagctctgg caacaaaaag agcggtacct gggactcagg cacctcgacg    360

ctgaccattt ctaaaaatcg tacgaaaacc aagcagctgg tcttcacgaa agaatgcacg    420

atcaccgtgc aaaactatga tagcgcaggt accaatctgg aaggcaaagc tgtggaaatt    480

accacgctga aagaactgaa gaatgctctg aaaggtacta gtgacaaaaa caatggctct    540

ggtagcaaag agaaaaacaa agatggcaag tactcattca acggcaaagg tgaaacgagc    600

gaaaagacca tcgtgcgtgc gaacggtacc cgcctggaat atacggacat taaatcggac    660

ggcagcggca aagcaaagga agtcctgaaa gattttacgc tggaaggtac cctggcagca    720

gacggtaaaa ccacgctgaa ggtgacgtgc ggcaccgtgg ttctgtcaaa aaacattctg    780

aagtcgggtg aaatcaccgc agctctggat gacagcgata ccacgcgtgc tacgaaaaag    840

accggtaaat gggatagcaa gacctctacg ctgaccatta gtgtcaactc ccagaaaacg    900

aagaatctgg tgttcaccaa agaagatacg atcaccgttc aacgctatga cagtgcgggc    960

accaacctgg aaggcaaagc cgttgaaatt accacgctga aagaactgtg taatgctctg   1020

aaaggtctcg agcaccacca ccaccaccac                                    1050
```

```
<210> SEQ ID NO 111
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 111

Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Gly Lys Gly Glu Thr
                165                 170                 175

Ser Glu Lys Thr Ile Val Arg Ala Cys Gly Thr Arg Leu Glu Tyr Thr
            180                 185                 190

Asp Ile Lys Ser Asp Gly Ser Gly Lys Ala Lys Glu Val Leu Lys Asp
```

```
        195                 200                 205

Phe Thr Leu Glu Gly Thr Leu Ala Ala Asp Gly Lys Thr Thr Leu Lys
    210                 215                 220

Val Thr Glu Gly Thr Val Val Leu Ser Lys Asn Ile Leu Lys Ser Gly
225                 230                 235                 240

Glu Ile Thr Ala Ala Leu Asp Asp Ser Asp Thr Thr Arg Ala Thr Lys
                245                 250                 255

Lys Thr Gly Lys Trp Asp Ser Lys Thr Ser Thr Leu Thr Ile Ser Val
            260                 265                 270

Asn Ser Gln Lys Thr Lys Asn Leu Val Phe Thr Lys Glu Cys Thr Ile
        275                 280                 285

Thr Val Gln Arg Tyr Asp Ser Ala Gly Thr Asn Leu Glu Gly Lys Ala
    290                 295                 300

Val Glu Ile Thr Thr Leu Lys Glu Leu Lys Asn Ala Leu Lys
305                 310                 315
```

<210> SEQ ID NO 112
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 112

```
atgaaagcta ctaaactggt actgggcgcg gtaatcctgg gttctactct gctggcaggt     60

tgctcaagct tcaacgaaaa gggcgaaatc tcagaaaaaa ccatcgtccg cgctaacggc    120

acccgcctgg aatacaccga catcaaatca gacaagaccg gtaaagcgaa ggaagttctg    180

aaagatttta cgctggaagg taccctggca gcagacggta aaaccacgct gaaggtgacc    240

tgcggtaccg ttacgctgtc caaaaacatt agtaagtccg gcgaaatcac ggtcgccctg    300

gatgacaccg atagctctgg caacaaaaag agcggtacct gggattcagg cacctcgacg    360

ctgaccattt ctaaaaatcg tacgaaaacc aagcagctgg tcttcacgaa agaagatacg    420

atcaccgtgc aaaactatga cagcgcaggt accaatctgg aaggcaaagc tgtggaaatt    480

accacgctga aagaactgtg taatgctctg aaaggtacta gtgacaaaaa caatggctct    540

ggtagcaaag agaaaaacaa agatggcaag tactcattca acggcaaagg tgaaacgagt    600

gaaaaaacga ttgttcgcgc ctgtggcacc cgcctggaat acacggatat caagtcggat    660

ggttcgggca aagcaaagga agtcctgaaa gattttacgc tggaaggtac cctggcagca    720

gacggtaaaa ccacgctgaa ggtgacggaa ggcaccgtgg ttctgtcaaa aaacattctg    780

aagtcgggtg aaatcaccgc agctctggat gacagcgata ccacgcgtgc tacgaaaaag    840

accggtaaat gggacagcaa gacctctacg ctgaccatta gtgtcaactc ccagaaaacg    900

aagaatctgg tgttcaccaa agaatgcacg atcaccgttc aacgctatga tagtgcgggc    960

accaacctgg aaggcaaagc cgttgaaatt accacgctga aagaactgaa gaatgctctg   1020

aaa                                                                 1023
```

<210> SEQ ID NO 113
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<223> OTHER INFORMATION: Lipidation

<400> SEQUENCE: 113

```
Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330
```

<210> SEQ ID NO 114
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 114

```
atgaaagcta ctaaactggt actgggcgcg gtaatcctgg gttctactct gctggcaggt     60
```

```
tgctcaagct tcaacgaaaa gggcgaaatc tcagaaaaaa ccatcgtccg cgctaacggc    120

acccgcctgg aatacaccga catcaaatca gacaagaccg gtaaagcgaa ggaagttctg    180

aaagatttta cgctggaagg taccctggca gcagacggta aaccacgct gaaggtgacc    240

tgcggtaccg ttacgctgtc caaaaacatt agtaagtccg gcgaaatcac ggtcgccctg    300

gatgacaccg atagctctgg caacaaaaag agcggtacct gggattcagg cacctcgacg    360

ctgaccattt ctaaaaatcg tacgaaaacc aagcagctgg tcttcacgaa agaagatacg    420

atcaccgtgc aaaactatga cagcgcaggt accaatctgg aaggcaaagc tgtggaaatt    480

accacgctga aagaactgtg taatgctctg aaaggtacta gtgacaaaaa caatggctct    540

ggtagcaaag agaaaaacaa agatggcaag tactcattca acggcaaagg tgaaacgagt    600

gaaaaaacga ttgttcgcgc ctgtggcacc cgcctggaat acacggatat caagtcggat    660

ggttcgggca aagcaaagga agtcctgaaa gattttacgc tggaaggtac cctggcagca    720

gacggtaaaa ccacgctgaa ggtgacggaa ggcaccgtgg ttctgtcaaa aaacattctg    780

aagtcgggtg aaatcaccgc agctctggat gacagcgata ccacgcgtgc tacgaaaaag    840

accggtaaat gggacagcaa gacctctacg ctgaccatta gtgtcaactc ccagaaaacg    900

aagaatctgg tgttcaccaa agaatgcacg atcaccgttc aacgctatga tagtgcgggc    960

accaacctgg aaggcaaagc cgttgaaatt accacgctga aagaactgaa gaatgctctg   1020

aaaggtctcg agcaccacca ccaccaccac                                    1050
```

<210> SEQ ID NO 115
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 115

```
Phe Asn Glu Lys Gly Glu Leu Ser Ala Lys Thr Met Thr Arg Glu Cys
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Glu Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Cys Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Val
                165                 170                 175

Ser Glu Lys Ile Ile Thr Arg Ala Asp Gly Thr Arg Leu Glu Tyr Thr
            180                 185                 190
```

Gly Ile Lys Ser Asp Gly Ser Gly Lys Ala Lys Glu Val Leu Lys Asn
195 200 205

Phe Thr Leu Glu Gly Lys Val Ala Asn Asp Lys Thr Thr Leu Val Val
210 215 220

Lys Cys Gly Thr Val Thr Leu Ser Lys Asn Ile Ser Lys Ser Gly Glu
225 230 235 240

Val Ser Val Glu Leu Asn Asp Thr Asp Ser Ser Ala Ala Thr Lys Lys
245 250 255

Thr Ala Ala Trp Asn Ser Gly Thr Ser Thr Leu Thr Ile Thr Val Asn
260 265 270

Ser Lys Lys Thr Lys Asp Leu Val Phe Thr Lys Glu Asn Thr Ile Thr
275 280 285

Val Gln Gln Tyr Asp Ser Asn Gly Thr Lys Leu Glu Gly Ser Ala Val
290 295 300

Glu Ile Thr Lys Leu Asp Glu Ile Cys Asn Ala Leu Lys
305 310 315

<210> SEQ ID NO 116
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 116
atgaaagcta ctaaactggt actgggcgcg gtaatcctgg gttctactct gctggcaggt 60
tgctcaagct tcaacgaaaa aggcgaactg tcggcgaaaa cgatgacgcg tgaatgcggc 120
accaaactgg aatatacgga aatgaaaagc gatggcaccg gtaaagcgaa agaagttctg 180
aaaaacttta ccctggaagg caaagtcgcc aatgacaaag tcaccctgga agtgaaagaa 240
ggcaccgtta cgctgtcaaa agaaattgca aaatcgggtg aagtgaccgt tgctctgaac 300
gatacgaata ccacgcaagc gaccaagaaa accggcgcct gggacagcaa aacctctacg 360
ctgaccatta gtgttaacag caagaaaacc acgcagctgg tcttcaccaa acaatgtacg 420
atcaccgtgc agaaatacga tagtgcgggt accaacctgg aaggcaccgc tgttgaaatc 480
aaaaccctgg acgaactgaa aaacgccctg aaaggcacta gtgacaaaaa caatggctct 540
ggtagcaaag agaaaaacaa agatggcaag tactcattca acgaaaaagg cgaagtcagc 600
gaaaaaatca ttacccgcgc agacggcacc cgcctggaat acaccggcat caaatcggac 660
ggcagcggca aagcgaaaga agttctgaaa aactttaccc tggaaggcaa agtcgcaaat 720
gataaaacca ccctggtggt gaaatgcggc accgttacgc tgagcaaaaa cattagtaaa 780
tccggtgaag tctctgtgga actgaatgat accgacagct ctgcggccac caagaaaacc 840
gcagcttgga actcaggcac ctcgacgctg accattacgg ttaatagcaa gaaaaccaaa 900
gatctggtct tcacgaaaga aaacaccatc acggtgcagc aatatgacag caatggtacc 960
aaactggaag gctccgctgt ggaaatcacg aaactggatg aaatctgtaa tgcactgaaa 1020

<210> SEQ ID NO 117
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<223> OTHER INFORMATION: Lipidation

<400> SEQUENCE: 117

```
Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Glu Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Cys Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320

Gly Leu Glu His His His His His His
                325
```

<210> SEQ ID NO 118
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 118

```
atgaaagcta ctaaactggt actgggcgcg gtaatcctgg gttctactct gctggcaggt      60
```

```
tgctcaagct tcaacgaaaa aggcgaactg tcggcgaaaa cgatgacgcg tgaatgcggc    120

accaaactgg aatatacgga aatgaaaagc gatggcaccg gtaaagcgaa agaagttctg    180

aaaaacttta ccctggaagg caaagtcgcc aatgacaaag tcaccctgga agtgaaagaa    240

ggcaccgtta cgctgtcaaa agaaattgca aaatcgggtg aagtgaccgt tgctctgaac    300

gatacgaata ccacgcaagc gaccaagaaa accggcgcct gggacagcaa aacctctacg    360

ctgaccatta gtgttaacag caagaaaacc acgcagctgg tcttcaccaa acaatgtacg    420

atcaccgtgc agaaatacga tagtgcgggt accaacctgg aaggcaccgc tgttgaaatc    480

aaaaccctgg acgaactgaa aaacgccctg aaaggcacta gtgacaaaaa caatggctct    540

ggtagcaaag agaaaaacaa agatggcaag tactcattca acgaaaaagg cgaagtcagc    600

gaaaaaatca ttacccgcgc agacggcacc cgcctggaat acaccggcat caaatcggac    660

ggcagcggca aagcgaaaga agttctgaaa aactttaccc tggaaggcaa agtcgcaaat    720

gataaaacca ccctggtggt gaaatgcggc accgttacgc tgagcaaaaa cattagtaaa    780

tccggtgaag tctctgtgga actgaatgat accgacagct ctgcggccac caagaaaacc    840

gcagcttgga actcaggcac ctcgacgctg accattacgg ttaatagcaa gaaaaccaaa    900

gatctggtct tcacgaaaga aaacaccatc acggtgcagc aatatgacag caatggtacc    960

aaactggaag gctccgctgt ggaaatcacg aaactggatg aaatctgtaa tgcactgaaa   1020

ggtctcgagc accaccacca ccaccac                                        1047
```

```
<210> SEQ ID NO 119
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 119

Phe Asn Glu Lys Gly Glu Leu Ser Ala Lys Thr Met Thr Arg Glu Asn
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Cys Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Asp Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Glu Lys Gly Glu Val
                165                 170                 175

Ser Glu Lys Ile Ile Thr Arg Ala Cys Gly Thr Arg Leu Glu Tyr Thr
            180                 185                 190
```

```
Gly Ile Lys Ser Asp Gly Ser Gly Lys Ala Lys Glu Val Leu Lys Asn
        195                 200                 205

Phe Thr Leu Glu Gly Lys Val Ala Asn Asp Lys Thr Thr Leu Val Val
    210                 215                 220

Lys Glu Gly Thr Val Thr Leu Ser Lys Asn Ile Ser Lys Ser Gly Glu
225                 230                 235                 240

Val Ser Val Glu Leu Asn Asp Thr Asp Ser Ser Ala Ala Thr Lys Lys
                245                 250                 255

Thr Ala Ala Trp Asn Ser Gly Thr Ser Thr Leu Thr Ile Thr Val Asn
            260                 265                 270

Ser Lys Lys Thr Lys Asp Leu Val Phe Thr Lys Glu Cys Thr Ile Thr
        275                 280                 285

Val Gln Gln Tyr Asp Ser Asn Gly Thr Lys Leu Glu Gly Ser Ala Val
    290                 295                 300

Glu Ile Thr Lys Leu Asp Glu Ile Lys Asn Ala Leu Lys
305                 310                 315
```

<210> SEQ ID NO 120
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 120

```
atgaaagcta ctaaactggt actgggcgcg gtaatcctgg gttctactct gctggcaggt     60

tgctcaagct tcaacgaaaa aggcgaactg tcggcgaaaa cgatgacgcg tgaaaacggc    120

accaaactgg aatatacgga aatgaaaagc gatggcaccg gtaaagcgaa agaagttctg    180

aaaaacttta ccctggaagg caaagtcgcc aatgacaaag tcaccctgga agtgaaatgc    240

ggcaccgtta cgctgtcaaa agaaattgca aaatcgggtg aagtgaccgt tgctctgaac    300

gatacgaata ccacgcaagc gaccaagaaa accggcgcct gggacagcaa aacctctacg    360

ctgaccatta gtgttaatag caagaaaacc acgcagctgg tcttcaccaa acaagatacg    420

atcaccgtgc agaaatacga cagtgcgggt accaacctgg aaggcacggc tgttgaaatc    480

aaaaccctgg acgaactgtg taacgccctg aaaggcacta gtgacaaaaa caatggctct    540

ggtagcaaag agaaaaacaa agatggcaag tactcattca acgaaaaagg cgaagtctcg    600

gaaaaaatca ttacccgtgc ttgcggcacc cgtctggaat acaccggcat taaatcggat    660

ggcagcggca aagcgaagga agttctgaaa aactttaccc tggaaggcaa agtcgcaaat    720

gataagacca ccctggtggt gaaagaaggc accgttacgc tgagcaaaaa cattagtaag    780

tccggtgaag tctctgtgga actgaatgat accgacagct ctgcggccac caaaaagacg    840

gcagcttgga actcaggcac ctcgacgctg accattacgg ttaattccaa aaagaccaaa    900

gatctggtct tcacgaaaga atgcaccatc acggtgcagc aatatgacag caacggtacc    960

aaactggaag gctctgcggt ggaaatcacg aaactggatg aaatcaaaaa tgcactgaaa   1020
```

<210> SEQ ID NO 121
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<223> OTHER INFORMATION: Lipidation

<400> SEQUENCE: 121

```
Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Lys Asn Ala Leu Lys
305                 310                 315                 320

Gly Leu Glu His His His His His His
                325
```

<210> SEQ ID NO 122
<211> LENGTH: 1047
<212> TYPE: DNA
<213> ORGANISM: Artificial Sequence
<220> FEATURE:
<223> OTHER INFORMATION: Synthetic Polynucleotide

<400> SEQUENCE: 122

```
atgaaagcta ctaaactggt actgggcgcg gtaatcctgg gttctactct gctggcaggt     60
```

```
tgctcaagct tcaacgaaaa aggcgaactg tcggcgaaaa cgatgacgcg tgaaaacggc    120

accaaactgg aatatacgga aatgaaaagc gatggcaccg gtaaagcgaa agaagttctg    180

aaaaacttta ccctggaagg caaagtcgcc aatgacaaag tcaccctgga agtgaaatgc    240

ggcaccgtta cgctgtcaaa agaaattgca aaatcgggtg aagtgaccgt tgctctgaac    300

gatacgaata ccacgcaagc gaccaagaaa accggcgcct gggacagcaa aacctctacg    360

ctgaccatta gtgttaatag caagaaaacc acgcagctgg tcttcaccaa acaagatacg    420

atcaccgtgc agaaatacga cagtgcgggt accaacctgg aaggcacggc tgttgaaatc    480

aaaaccctgg acgaactgtg taacgccctg aaaggcacta gtgacaaaaa caatggctct    540

ggtagcaaag agaaaaacaa agatggcaag tactcattca acgaaaaagg cgaagtctcg    600

gaaaaaatca ttacccgtgc ttgcggcacc cgtctggaat acaccggcat taaatcggat    660

ggcagcggca aagcgaagga agttctgaaa aactttaccc tggaaggcaa agtcgcaaat    720

gataagacca ccctggtggt gaaagaaggc accgttacgc tgagcaaaaa cattagtaag    780

tccggtgaag tctctgtgga actgaatgat accgacagct ctgcggccac caaaaagacg    840

gcagcttgga actcaggcac ctcgacgctg accattacgg ttaattccaa aaagaccaaa    900

gatctggtct tcacgaaaga atgcaccatc acggtgcagc aatatgacag caacggtacc    960

aaactggaag gctctgcggt ggaaatcacg aaactggatg aaatcaaaaa tgcactgaaa   1020

ggtctcgagc accaccacca ccaccac                                       1047
```

<210> SEQ ID NO 123
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 123

```
Phe Asn Ala Lys Gly Glu Leu Ser Glu Lys Thr Ile Leu Arg Ala Cys
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Glu Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Cys Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Lys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175

Ser Glu Lys Val Val Thr Arg Ala Asn Gly Thr Arg Leu Glu Tyr Thr
            180                 185                 190
```

```
Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
    210                 215                 220

Val Thr Cys Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
            260                 265                 270

Asn Ser Gln Lys Pro Lys Gln Leu Val Phe Thr Lys Glu Asn Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Cys Ala Ala Leu Lys
305                 310                 315
```

<210> SEQ ID NO 124
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 124

```
atgaaagcta ctaaactggt actgggcgcg gtaatcctgg gttctactct gctggcaggt     60

tgctcaagct tcaacgctaa aggtgaactg tcggaaaaaa ccatcctgcg cgcctgtggc    120

acccgcctgg aatacacgga aatcaagtcg gacggcacgg gcaaagcaaa ggaagtcctg    180

aaagattttg ctctggaagg taccctggcg gccgacaaaa ccacgctgaa ggtgacggaa    240

ggcaccgtgg ttctgagcaa acatattccg aactctggtg aaatcaccgt tgaactgaac    300

gatagcaatt ctacgcaggc gaccaaaaag acgggcaaat gggacagtaa tacctccacg    360

ctgaccattt cagtcaactc gaaaaagacc aaaaatattg tgttcacgaa ggaatgcacg    420

atcaccgttc aaaaatatga ttccgcaggt accaacctgg aaggcaacgc tgtggaaatc    480

aaaaccctgg acgaactgaa aaacgccctg aagggtacta gtgacaaaaa caatggctct    540

ggtagcaaag agaaaaacaa agatggcaag tactcattta acgataaggg caaactgtcg    600

gaaaaagtgg tcacccgcgc aaatggcacc cgcctggaat acacggaaat caaaaacgat    660

ggtagcggca aagcgaagga agttctgaaa ggctttgccc tggaaggtac cctgacggat    720

ggcggtgaaa ccaaactgac cgtgacgtgc ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaaaacacg atcaccgtgc agaactataa tcgtgccggt    960

aatgctctgg aaggctcacc ggctgaaatc aaggacctgg ctgaactgtg tgcggcactg   1020

aaa                                                                 1023
```

<210> SEQ ID NO 125
<211> LENGTH: 330
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: LIPID
<222> LOCATION: (1)..(1)
<223> OTHER INFORMATION: Lipidation

<400> SEQUENCE: 125

Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys Gly Leu Glu His His His His His His
                325                 330


<210> SEQ ID NO 126
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 126
```

```
atgaaagcta ctaaactggt actgggcgcg gtaatcctgg gttctactct gctggcaggt     60

tgctcaagct tcaacgctaa aggtgaactg tcggaaaaaa ccatcctgcg cgcctgtggc    120

acccgcctgg aatacacgga aatcaagtcg gacggcacgg gcaaagcaaa ggaagtcctg    180

aaagattttg ctctggaagg taccctggcg gccgacaaaa ccacgctgaa ggtgacggaa    240

ggcaccgtgg ttctgagcaa acatattccg aactctggtg aaatcaccgt tgaactgaac    300

gatagcaatt ctacgcaggc gaccaaaaag acgggcaaat gggacagtaa tacctccacg    360

ctgaccattt cagtcaactc gaaaaagacc aaaaatattg tgttcacgaa ggaatgcacg    420

atcaccgttc aaaaatatga ttccgcaggt accaacctgg aaggcaacgc tgtggaaatc    480

aaaaccctgg acgaactgaa aaacgccctg aagggtacta gtgacaaaaa caatggctct    540

ggtagcaaag agaaaaacaa agatggcaag tactcattta acgataaggg caaactgtcg    600

gaaaaagtgg tcacccgcgc aaatggcacc cgcctggaat acacggaaat caaaaacgat    660

ggtagcggca aagcgaagga agttctgaaa ggctttgccc tggaaggtac cctgacggat    720

ggcggtgaaa ccaaactgac cgtgacgtgc ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaaaacacg atcaccgtgc agaactataa tcgtgccggt    960

aatgctctgg aaggctcacc ggctgaaatc aaggacctgg ctgaactgtg tgcggcactg   1020

aaaggtctcg agcaccacca ccaccaccac                                    1050
```

```
<210> SEQ ID NO 127
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 127

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Cys Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Cys
    130                 135                 140

Asn Ala Leu Lys Gly Thr Ser Asp Lys Asn Asn Gly Ser Gly Ser Lys
145                 150                 155                 160

Glu Lys Asn Lys Asp Gly Lys Tyr Ser Phe Asn Asp Lys Gly Lys Leu
                165                 170                 175
```

```
Ser Glu Lys Val Val Thr Arg Ala Cys Gly Thr Arg Leu Glu Tyr Thr
            180                 185                 190

Glu Ile Lys Asn Asp Gly Ser Gly Lys Ala Lys Glu Val Leu Lys Gly
        195                 200                 205

Phe Ala Leu Glu Gly Thr Leu Thr Asp Gly Gly Glu Thr Lys Leu Thr
    210                 215                 220

Val Thr Glu Gly Thr Val Thr Leu Ser Lys Asn Ile Ser Lys Ser Gly
225                 230                 235                 240

Glu Ile Thr Val Ala Leu Asn Asp Thr Glu Thr Thr Pro Ala Asp Lys
                245                 250                 255

Lys Thr Gly Glu Trp Lys Ser Asp Thr Ser Thr Leu Thr Ile Ser Lys
            260                 265                 270

Asn Ser Gln Lys Pro Lys Gln Leu Val Phe Thr Lys Glu Cys Thr Ile
        275                 280                 285

Thr Val Gln Asn Tyr Asn Arg Ala Gly Asn Ala Leu Glu Gly Ser Pro
    290                 295                 300

Ala Glu Ile Lys Asp Leu Ala Glu Leu Lys Ala Ala Leu Lys
305                 310                 315
```

<210> SEQ ID NO 128
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 128

```
atgaaagcta ctaaactggt actgggcgcg gtaatcctgg gttctactct gctggcaggt     60

tgctcaagct tcaatgctaa gggcgaactg agcgaaaaaa cgatcctgcg tgcgaatggc    120

acccgtctgg aatacaccga aatcaaatcc gatggtacgg gcaaagcaaa ggaagtcctg    180

aaagattttg ctctggaagg taccctggcg gccgacaaaa ccacgctgaa ggtgacgtgc    240

ggcaccgtgg ttctgagcaa acatattccg aactctggtg aaatcaccgt tgaactgaac    300

gatagcaatt ctacgcaggc aaccaaaaag acgggcaaat gggacagtaa tacctccacg    360

ctgaccattt cagtcaactc gaaaaagacc aaaaatattg tgttcacgaa ggaagatacg    420

atcaccgttc aaaaatatga ctccgcgggc accaacctgg aaggcaatgc cgtcgaaatc    480

aaaaccctgg atgaactgtg taacgccctg aagggtacta gtgacaaaaa caatggctct    540

ggtagcaaag agaaaaacaa agatggcaag tactcattta acgataaggg caaactgtca    600

gaaaaagtgg tcacccgcgc ttgtggcacc cgcctggaat acaccgaaat caaaaacgac    660

ggctcgggca aagcgaagga agttctgaaa ggctttgccc tggaaggtac cctgacggat    720

ggcggtgaaa ccaaactgac cgtgacggaa ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaatgcacg atcaccgtgc agaactataa tcgtgccggt    960

aatgctctgg aaggctcccc ggctgaaatc aaggacctgg cggaactgaa ggcggcactg   1020

aaa                                                                 1023
```

<210> SEQ ID NO 129
<211> LENGTH: 330
<212> TYPE: PRT
<213> ORGANISM: Artificial Sequence
<220> FEATURE:

<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 129

```
Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Asp Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys Gly Leu Glu His His His His His His
                325                 330
```

<210> SEQ ID NO 130
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 130

```
atgaaagcta ctaaactggt actgggcgcg gtaatcctgg gttctactct gctggcaggt     60

tgctcaagct tcaatgctaa gggcgaactg agcgaaaaaa cgatcctgcg tgcgaatggc    120

acccgtctgg aatacaccga aatcaaatcc gatggtacgg gcaaagcaaa ggaagtcctg    180

aaagatttg ctctggaagg taccctggcg gccgacaaaa ccacgctgaa ggtgacgtgc    240

ggcaccgtgg ttctgagcaa acatattccg aactctggtg aaatcaccgt tgaactgaac    300

gatagcaatt ctacgcaggc aaccaaaaag acgggcaaat gggacagtaa tacctccacg    360

ctgaccattt cagtcaactc gaaaaagacc aaaaatattg tgttcacgaa ggaagatacg    420

atcaccgttc aaaaatatga ctccgcgggc accaacctgg aaggcaatgc cgtcgaaatc    480

aaaaccctgg atgaactgtg taacgccctg aagggtacta gtgacaaaaa caatggctct    540

ggtagcaaag agaaaaacaa agatggcaag tactcattta acgataaggg caaactgtca    600

gaaaaagtgg tcacccgcgc ttgtggcacc cgcctggaat acaccgaaat caaaaacgac    660

ggctcgggca aagcgaagga agttctgaaa ggctttgccc tggaaggtac cctgacggat    720

ggcggtgaaa ccaaactgac cgtgacggaa ggcaccgtta cgctgtctaa aaacattagc    780

aagtctggtg aaatcacggt cgcactgaat gataccgaaa ccacgccggc tgacaaaaag    840

accggcgaat ggaaaagtga cacctccacg ctgaccattt caaagaactc gcagaaaccg    900

aagcaactgg tcttcaccaa agaatgcacg atcaccgtgc agaactataa tcgtgccggt    960

aatgctctgg aaggctcccc ggctgaaatc aaggacctgg cggaactgaa ggcggcactg   1020

aaaggtctcg agcaccacca ccaccaccac                                    1050
```

<210> SEQ ID NO 131
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 131

```
Phe Asn Gly Lys Gly Glu Thr Ser Glu Lys Thr Ile Val Arg Ala Cys
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Cys Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Lys Asn Ala Leu Lys Gly Thr Ser Asp Lys Asn Asn Gly Ser Gly Ser
145                 150                 155                 160

Lys Glu Lys Asn Lys Asp Gly Lys Tyr Ser Phe Asn Glu Lys Gly Glu
```

```
                165                 170                 175

Ile Ser Glu Lys Thr Ile Val Arg Ala Asn Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Cys Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Asp Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Cys Asn Ala Leu Lys
305                 310                 315


<210> SEQ ID NO 132
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 132

atgaaagcta ctaaactggt actgggcgcg gtaatcctgg gttctactct gctggcaggt      60

tgctcaagct tcaacggcaa aggtgaaacg agtgaaaaaa cgattgttcg cgcctgtggc     120

acccgcctgg aatacacgga tatcaagtcg gatggttcgg gcaaagcaaa ggaagtcctg     180

aaagatttta cgctggaagg taccctggca gcagacggta aaaccacgct gaaggtgacg     240

gaaggcaccg tggttctgtc aaaaaacatt ctgaagtcgg gtgaaatcac cgcagctctg     300

gatgacagcg ataccacgcg tgctacgaaa aagaccggta aatgggacag caagacctct     360

acgctgacca ttagtgtcaa ctcccagaaa acgaagaatc tggtgttcac caaagaatgc     420

acgatcaccg ttcaacgcta tgatagtgcg ggcaccaacc tggaaggcaa agccgttgaa     480

attaccacgc tgaaagaact gaagaatgct ctgaaaggta ctagtgacaa aaacaatggc     540

tctggtagca aagagaaaaa caaagatggc aagtactcat tcaacgaaaa aggcgaaatc     600

tcagaaaaaa ccatcgtccg cgctaacggc acccgcctgg aatacaccga catcaaatca     660

gacaagaccg gtaaagcgaa ggaagttctg aaagatttta cgctggaagg taccctggca     720

gcagacggta aaaccacgct gaaggtgacc tgcggtaccg ttacgctgtc caaaaacatt     780

agtaagtccg gcgaaatcac ggtcgccctg gatgacaccg atagctctgg caacaaaaag     840

agcggtacct gggattcagg cacctcgacg ctgaccattt ctaaaaatcg tacgaaaacc     900

aagcagctgg tcttcacgaa agaagatacg atcaccgtgc aaaactatga cagcgcaggt     960

accaatctgg aaggcaaagc tgtggaaatt accacgctga aagaactgtg taatgctctg    1020

aaa                                                                  1023


<210> SEQ ID NO 133
<211> LENGTH: 330
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 133

Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Cys Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Cys Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Asp Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys Gly Leu Glu His His His His His His
                325                 330


<210> SEQ ID NO 134
<211> LENGTH: 1050
<212> TYPE: DNA
<213> ORGANISM: Artificial Sequence
<220> FEATURE:
```

<223> OTHER INFORMATION: Synthetic Polynucleotide

<400> SEQUENCE: 134

```
atgaaagcta ctaaactggt actgggcgcg gtaatcctgg gttctactct gctggcaggt     60
tgctcaagct tcaacggcaa aggtgaaacg agtgaaaaaa cgattgttcg cgcctgtggc    120
acccgcctgg aatacacgga tatcaagtcg gatggttcgg gcaaagcaaa ggaagtcctg    180
aaagatttta cgctggaagg taccctggca gcagacggta aaaccacgct gaaggtgacg    240
gaaggcaccg tggttctgtc aaaaaacatt ctgaagtcgg gtgaaatcac cgcagctctg    300
gatgacagcg ataccacgcg tgctacgaaa aagaccggta aatgggacag caagacctct    360
acgctgacca ttagtgtcaa ctcccagaaa acgaagaatc tggtgttcac caaagaatgc    420
acgatcaccg ttcaacgcta tgatagtgcg ggcaccaacc tggaaggcaa agccgttgaa    480
attaccacgc tgaaagaact gaagaatgct ctgaaaggta ctagtgacaa aaacaatggc    540
tctggtagca aagagaaaaa caaagatggc aagtactcat tcaacgaaaa aggcgaaatc    600
tcagaaaaaa ccatcgtccg cgctaacggc acccgcctgg aatacaccga catcaaatca    660
gacaagaccg gtaaagcgaa ggaagttctg aaagatttta cgctggaagg taccctggca    720
gcagacggta aaaccacgct gaaggtgacc tgcggtaccg ttacgctgtc caaaaaacatt   780
agtaagtccg gcgaaatcac ggtcgccctg gatgacaccg atagctctgg caacaaaaag    840
agcggtacct gggattcagg cacctcgacg ctgaccattt ctaaaaatcg tacgaaaacc    900
aagcagctgg tcttcacgaa agaagatacg atcaccgtgc aaaactatga cagcgcaggt    960
accaatctgg aaggcaaagc tgtggaaatt accacgctga aagaactgtg taatgctctg   1020
aaaggtctcg agcaccacca ccaccaccac                                    1050
```

<210> SEQ ID NO 135
<211> LENGTH: 318
<212> TYPE: PRT
<213> ORGANISM: Artificial Sequence
<220> FEATURE:
<223> OTHER INFORMATION: Synthetic Polypeptide

<400> SEQUENCE: 135

```
Phe Asn Gly Lys Gly Glu Thr Ser Glu Lys Thr Ile Val Arg Ala Asn
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Cys Asn Ala Leu Lys Gly Thr Ser Asp Lys Asn Asn Gly Ser Gly Ser
145                 150                 155                 160
```

-continued

```
Lys Glu Lys Asn Lys Asp Gly Lys Tyr Ser Phe Asn Glu Lys Gly Glu
                165                 170                 175

Ile Ser Glu Lys Thr Ile Val Arg Ala Cys Gly Thr Arg Leu Glu Tyr
            180                 185                 190

Thr Asp Ile Lys Ser Asp Lys Thr Gly Lys Ala Lys Glu Val Leu Lys
        195                 200                 205

Asp Phe Thr Leu Glu Gly Thr Leu Ala Ala Asp Gly Lys Thr Thr Leu
    210                 215                 220

Lys Val Thr Glu Gly Thr Val Thr Leu Ser Lys Asn Ile Ser Lys Ser
225                 230                 235                 240

Gly Glu Ile Thr Val Ala Leu Asp Asp Thr Asp Ser Ser Gly Asn Lys
                245                 250                 255

Lys Ser Gly Thr Trp Asp Ser Gly Thr Ser Thr Leu Thr Ile Ser Lys
            260                 265                 270

Asn Arg Thr Lys Thr Lys Gln Leu Val Phe Thr Lys Glu Cys Thr Ile
        275                 280                 285

Thr Val Gln Asn Tyr Asp Ser Ala Gly Thr Asn Leu Glu Gly Lys Ala
    290                 295                 300

Val Glu Ile Thr Thr Leu Lys Glu Leu Lys Asn Ala Leu Lys
305                 310                 315
```

<210> SEQ ID NO 136
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 136

```
atgaaagcta ctaaactggt actgggcgcg gtaatcctgg gttctactct gctggcaggt     60

tgctcaagct tcaacggcaa aggtgaaacg agcgaaaaga ccatcgtgcg tgcgaacggt    120

acccgcctgg aatatacgga cattaaatcg gacggcagcg gcaaagcaaa ggaagtcctg    180

aaagatttta cgctggaagg taccctggca gcagacggta aaaccacgct gaaggtgacg    240

tgcggcaccg tggttctgtc aaaaaacatt ctgaagtcgg gtgaaatcac cgcagctctg    300

gatgacagcg ataccacgcg tgctacgaaa aagaccggta aatgggatag caagacctct    360

acgctgacca ttagtgtcaa ctcccagaaa acgaagaatc tggtgttcac caaagaagat    420

acgatcaccg ttcaacgcta tgacagtgcg ggcaccaacc tggaaggcaa agccgttgaa    480

attaccacgc tgaaagaact gtgtaatgct ctgaaaggta ctagtgacaa aaacaatggc    540

tctggtagca aagagaaaaa caaagatggc aagtactcat tcaacgaaaa aggcgaaatc    600

agtgaaaaaa ccattgtgcg tgcgtgtggc acccgtctgg aatataccga catcaagagc    660

gataaaacgg gtaaagcgaa ggaagttctg aaagatttta cgctggaagg taccctggca    720

gcagacggta aaaccacgct gaaggtgacc gaaggtaccg ttacgctgtc caaaaacatt    780

agtaagtccg gcgaaatcac ggtcgccctg gatgacaccg atagctctgg caacaaaaag    840

agcggtacct gggactcagg cacctcgacg ctgaccattt ctaaaaatcg tacgaaaacc    900

aagcagctgg tcttcacgaa agaatgcacg atcaccgtgc aaaactatga tagcgcaggt    960

accaatctgg aaggcaaagc tgtggaaatt accacgctga aagaactgaa gaatgctctg   1020

aaa                                                                 1023
```

<210> SEQ ID NO 137

```
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 137

Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys Gly Leu Glu His His His His His His
                325                 330


<210> SEQ ID NO 138
<211> LENGTH: 1050
<212> TYPE: DNA
```

<213> ORGANISM: Artificial Sequence
<220> FEATURE:
<223> OTHER INFORMATION: Synthetic Polynucleotide

<400> SEQUENCE: 138
atgaaagcta ctaaactggt actgggcgcg gtaatcctgg gttctactct gctggcaggt 60
tgctcaagct tcaacggcaa aggtgaaacg agcgaaaaga ccatcgtgcg tgcgaacggt 120
acccgcctgg aatatacgga cattaaatcg gacggcagcg gcaaagcaaa ggaagtcctg 180
aaagatttta cgctggaagg taccctggca gcagacggta aaaccacgct gaaggtgacg 240
tgcggcaccg tggttctgtc aaaaaacatt ctgaagtcgg gtgaaatcac cgcagctctg 300
gatgacagcg ataccacgcg tgctacgaaa aagaccggta aatgggatag caagacctct 360
acgctgacca ttagtgtcaa ctcccagaaa acgaagaatc tggtgttcac caaagaagat 420
acgatcaccg ttcaacgcta tgacagtgcg ggcaccaacc tggaaggcaa agccgttgaa 480
attaccacgc tgaaagaact gtgtaatgct ctgaaaggta ctagtgacaa aaacaatggc 540
tctggtagca aagagaaaaa caaagatggc aagtactcat tcaacgaaaa aggcgaaatc 600
agtgaaaaaa ccattgtgcg tgcgtgtggc acccgtctgg aatataccga catcaagagc 660
gataaaacgg gtaaagcgaa ggaagttctg aaagatttta cgctggaagg taccctggca 720
gcagacggta aaaccacgct gaaggtgacc gaaggtaccg ttacgctgtc caaaaacatt 780
agtaagtccg gcgaaatcac ggtcgccctg gatgacaccg atagctctgg caacaaaaag 840
agcggtacct gggactcagg cacctcgacg ctgaccattt ctaaaaatcg tacgaaaacc 900
aagcagctgg tcttcacgaa agaatgcacg atcaccgtgc aaaactatga tagcgcaggt 960
accaatctgg aaggcaaagc tgtggaaatt accacgctga aagaactgaa gaatgctctg 1020
aaaggtctcg agcaccacca ccaccaccac 1050

<210> SEQ ID NO 139

<400> SEQUENCE: 139

000

<210> SEQ ID NO 140
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 140

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Glu Gly Thr Val Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr

```
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys Gly Leu Glu His His His His His His
145                 150                 155


<210> SEQ ID NO 141
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 141

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Cys Asn
    130                 135                 140

Ala Leu Lys Gly Leu Glu His His His His His His
145                 150                 155


<210> SEQ ID NO 142
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 142

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
```

```
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Cys Lys Gly Leu Glu His His His His His His
145                 150                 155
```

<210> SEQ ID NO 143
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 143

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Cys Val Gln Lys Tyr Asp Ser Ala Gly Thr Asn
        115                 120                 125

Leu Glu Gly Thr Cys Val Glu Ile Lys Thr Leu Asp Glu Leu Lys Asn
    130                 135                 140

Ala Leu Lys Gly Leu Glu His His His His His His
145                 150                 155
```

<210> SEQ ID NO 144
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 144

Cys Lys Gln Asn Glu Leu Ser Ala Lys Thr Met Thr Arg Glu Cys Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Glu Gly Thr Val Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Cys Thr Ile Thr Val Gln Lys Tyr Asp Ser Ala Gly Thr Asn
115 120 125

Leu Glu Gly Thr Ala Val Glu Ile Lys Thr Leu Asp Glu Leu Lys Asn
130 135 140

Ala Leu Lys Gly Leu Glu His His His His His His
145 150 155

<210> SEQ ID NO 145
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 145

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Cys Thr Leu Glu Gly Lys Val Ala Asn Asp
35 40 45

Lys Val Thr Leu Glu Val Lys Glu Gly Thr Val Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Cys Asp Glu Leu Lys Asn
130 135 140

Ala Leu Lys Gly Leu Glu His His His His His His
145 150 155

<210> SEQ ID NO 146
<211> LENGTH: 156

<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 146

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Cys Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Cys Lys Gly Leu Glu His His His His His His
145                 150                 155
```

<210> SEQ ID NO 147
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 147

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Cys Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Cys Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125
```

```
Leu Glu Gly Thr Ala Val Glu Ile Lys Thr Leu Asp Glu Leu Lys Asn
    130                 135                 140

Ala Leu Lys Gly Leu Glu His His His His His His
145                 150                 155
```

<210> SEQ ID NO 148
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 148

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Cys Thr Val Gln Lys Tyr Asp Ser Ala Gly Thr Asn
        115                 120                 125

Leu Glu Gly Thr Ala Val Glu Cys Lys Thr Leu Asp Glu Leu Lys Asn
    130                 135                 140

Ala Leu Lys Gly Leu Glu His His His His His His
145                 150                 155
```

<210> SEQ ID NO 149
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 149

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Cys Val Thr Leu Ser Lys Glu
    50                  55                  60

Ile Ala Lys Ser Gly Glu Val Thr Val Ala Leu Asn Asp Cys Asn Thr
65                  70                  75                  80
```

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Leu Asp Glu Leu Lys Asn
130 135 140

Ala Leu Lys Gly Leu Glu His His His His His His
145 150 155

<210> SEQ ID NO 150
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 150

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Glu Gly Thr Val Thr Leu Ser Lys Glu
50 55 60

Ile Ala Lys Ser Gly Glu Val Thr Val Ala Cys Asn Asp Thr Asn Thr
65 70 75 80

Thr Gln Ala Thr Lys Lys Thr Cys Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Leu Asp Glu Leu Lys Asn
130 135 140

Ala Leu Lys Gly Leu Glu His His His His His His
145 150 155

<210> SEQ ID NO 151
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 151

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

```
Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Cys Lys Tyr Asp Ser Ala Gly Thr Asn
        115                 120                 125

Leu Glu Gly Thr Cys Val Glu Ile Lys Thr Leu Asp Glu Leu Lys Asn
    130                 135                 140

Ala Leu Lys Gly Leu Glu His His His His His His
145                 150                 155


<210> SEQ ID NO 152
<211> LENGTH: 156
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 152

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Cys Glu Gly Lys Val Ala Asn Asp
        35                  40                  45

Lys Val Thr Cys Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys Gly Leu Glu His His His His His His
145                 150                 155


<210> SEQ ID NO 153
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation
```

<400> SEQUENCE: 153

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Glu Gly Thr Val Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Leu Asp Glu Leu Lys Asn
130 135 140

Ala Leu Lys
145

<210> SEQ ID NO 154
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 154

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Cys Gly Thr Val Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Leu Asp Glu Leu Cys Asn
130 135 140

Ala Leu Lys
145

<210> SEQ ID NO 155

<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 155

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Cys Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Cys Lys
145

<210> SEQ ID NO 156
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 156

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Cys Val Gln Lys Tyr Asp Ser Ala Gly Thr Asn
        115                 120                 125

```
Leu Glu Gly Thr Cys Val Glu Ile Lys Thr Leu Asp Glu Leu Lys Asn
    130                 135                 140

Ala Leu Lys
145


<210> SEQ ID NO 157
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 157

Cys Lys Gln Asn Glu Leu Ser Ala Lys Thr Met Thr Arg Glu Cys Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Cys Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145


<210> SEQ ID NO 158
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 158

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Cys Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80
```

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Cys Asp Glu Leu Lys Asn
130 135 140

Ala Leu Lys
145

<210> SEQ ID NO 159
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 159

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

Lys Glu Val Leu Lys Asn Phe Thr Leu Glu Gly Lys Val Ala Asn Asp
35 40 45

Lys Val Thr Leu Glu Val Lys Glu Gly Thr Cys Thr Leu Ser Lys Glu
50 55 60

Ile Ala Lys Ser Gly Glu Val Thr Val Ala Leu Asn Asp Thr Asn Thr
65 70 75 80

Thr Gln Ala Thr Lys Lys Thr Gly Ala Trp Asp Ser Lys Thr Ser Thr
85 90 95

Leu Thr Ile Ser Val Asn Ser Lys Lys Thr Thr Gln Leu Val Phe Thr
100 105 110

Lys Gln Asp Thr Ile Thr Val Gln Lys Tyr Asp Ser Ala Gly Thr Asn
115 120 125

Leu Glu Gly Thr Ala Val Glu Ile Lys Thr Leu Asp Glu Leu Lys Asn
130 135 140

Ala Cys Lys
145

<210> SEQ ID NO 160
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 160

Cys Lys Gln Asn Glu Leu Ser Ala Lys Thr Met Thr Arg Glu Asn Gly
1 5 10 15

Thr Lys Leu Glu Tyr Thr Glu Met Lys Ser Asp Gly Thr Gly Lys Ala
20 25 30

```
Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Cys Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Cys Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145


<210> SEQ ID NO 161
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 161

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Cys Thr Val Gln Lys Tyr Asp Ser Ala Gly Thr Asn
        115                 120                 125

Leu Glu Gly Thr Ala Val Glu Cys Lys Thr Leu Asp Glu Leu Lys Asn
    130                 135                 140

Ala Leu Lys
145


<210> SEQ ID NO 162
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
```

```
<223> OTHER INFORMATION: Lipidation

<400> SEQUENCE: 162

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Cys Val Thr Leu Ser Lys Glu
    50                  55                  60

Ile Ala Lys Ser Gly Glu Val Thr Val Ala Leu Asn Asp Cys Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145


<210> SEQ ID NO 163
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 163

Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Cys Asn Asp Thr Asn Thr
65                  70                  75                  80

Thr Gln Ala Thr Lys Lys Thr Cys Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
        115                 120                 125

Leu Glu Gly Thr Ala Val Glu Ile Lys Thr Leu Asp Glu Leu Lys Asn
    130                 135                 140

Ala Leu Lys
145
```

<210> SEQ ID NO 164
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 164

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Leu Glu Gly Lys Val Ala Asn Asp
        35                  40                  45

Lys Val Thr Leu Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Cys Lys Tyr Asp Ser Ala Gly Thr Asn
        115                 120                 125

Leu Glu Gly Thr Cys Val Glu Ile Lys Thr Leu Asp Glu Leu Lys Asn
    130                 135                 140

Ala Leu Lys
145
```

<210> SEQ ID NO 165
<211> LENGTH: 147
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 165

```
Cys Lys Gln Asn Glu Leu Ser Ala Lys Thr Met Thr Arg Glu Asn Gly
1               5                   10                  15

Thr Lys Leu Glu Tyr Thr Glu Met Lys Ser Asp Gly Thr Gly Lys Ala
            20                  25                  30

Lys Glu Val Leu Lys Asn Phe Thr Cys Glu Gly Lys Val Ala Asn Asp
        35                  40                  45

Lys Val Thr Cys Glu Val Lys Glu Gly Thr Val Thr Leu Ser Lys Glu
    50                  55                  60

Ile Ala Lys Ser Gly Glu Val Thr Val Ala Leu Asn Asp Thr Asn Thr
65                  70                  75                  80

Thr Gln Ala Thr Lys Lys Thr Gly Ala Trp Asp Ser Lys Thr Ser Thr
                85                  90                  95

Leu Thr Ile Ser Val Asn Ser Lys Lys Thr Thr Gln Leu Val Phe Thr
            100                 105                 110

Lys Gln Asp Thr Ile Thr Val Gln Lys Tyr Asp Ser Ala Gly Thr Asn
```

115 120 125

Leu Glu Gly Thr Ala Val Glu Ile Lys Thr Leu Asp Glu Leu Lys Asn
130 135 140

Ala Leu Lys
145

<210> SEQ ID NO 166
<211> LENGTH: 143
<212> TYPE: PRT
<213> ORGANISM: Borrelia afzelii

<400> SEQUENCE: 166

Glu Leu Ser Ala Lys Thr Met Thr Arg Glu Asn Gly Thr Lys Leu Glu
1 5 10 15

Tyr Thr Glu Met Lys Ser Asp Gly Thr Gly Lys Ala Lys Glu Val Leu
20 25 30

Lys Asn Phe Thr Leu Glu Gly Lys Val Ala Asn Asp Lys Val Thr Leu
35 40 45

Glu Val Lys Glu Gly Thr Val Thr Leu Ser Lys Glu Ile Ala Lys Ser
50 55 60

Gly Glu Val Thr Val Ala Leu Asn Asp Thr Asn Thr Thr Gln Ala Thr
65 70 75 80

Lys Lys Thr Gly Ala Trp Asp Ser Lys Thr Ser Thr Leu Thr Ile Ser
85 90 95

Val Asn Ser Lys Lys Thr Thr Gln Leu Val Phe Thr Lys Gln Asp Thr
100 105 110

Ile Thr Val Gln Lys Tyr Asp Ser Ala Gly Thr Asn Leu Glu Gly Thr
115 120 125

Ala Val Glu Ile Lys Thr Leu Asp Glu Leu Lys Asn Ala Leu Lys
130 135 140

<210> SEQ ID NO 167
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 167

Glu Leu Ser Ala Lys Thr Met Thr Arg Glu Asn Gly Thr Lys Leu Glu
1 5 10 15

Tyr Thr Glu Met Lys Ser Asp Gly Thr Gly Lys Ala Lys Glu Val Leu
20 25 30

Lys Asn Phe Thr Leu Glu Gly Lys Val Ala Asn Asp Lys Val Thr Leu
35 40 45

Glu Val Lys Cys Gly Thr Val Thr Leu Ser Lys Glu Ile Ala Lys Ser
50 55 60

Gly Glu Val Thr Val Ala Leu Asn Asp Thr Asn Thr Thr Gln Ala Thr
65 70 75 80

Lys Lys Thr Gly Ala Trp Asp Ser Lys Thr Ser Thr Leu Thr Ile Ser
85 90 95

Val Asn Ser Lys Lys Thr Thr Gln Leu Val Phe Thr Lys Gln Asp Thr
100 105 110

Ile Thr Val Gln Lys Tyr Asp Ser Ala Gly Thr Asn Leu Glu Gly Thr
115 120 125

Ala Val Glu Ile Lys Thr Leu Asp Glu Leu Cys Asn Ala Leu Lys
130 135 140

<210> SEQ ID NO 168
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 168

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Cys Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys
    130                 135                 140
```

<210> SEQ ID NO 169
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 169

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Cys Val Gln Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys
    130                 135                 140
```

<210> SEQ ID NO 170
<211> LENGTH: 143
<212> TYPE: PRT

<213> ORGANISM: Artificial Sequence
<220> FEATURE:
<223> OTHER INFORMATION: Synthetic Polypeptide

<400> SEQUENCE: 170

```
Glu Leu Ser Ala Lys Thr Met Thr Arg Glu Cys Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Cys Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140
```

<210> SEQ ID NO 171
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 171

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Cys Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Cys Asp Glu Leu Lys Asn Ala Leu Lys
    130                 135                 140
```

<210> SEQ ID NO 172
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 172

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Cys Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Cys Lys
    130                 135                 140
```

<210> SEQ ID NO 173
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 173

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Cys Ala Leu Asn Asp Thr Asn Thr Thr Gln Ala Thr
65                  70                  75                  80

Lys Lys Thr Gly Ala Trp Asp Ser Lys Thr Ser Thr Cys Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140
```

<210> SEQ ID NO 174
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 174

```
Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
```

```
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Cys Thr Val Gln Lys Tyr Asp Ser Ala Gly Thr Asn Leu Glu Gly Thr
        115                 120                 125

Ala Val Glu Cys Lys Thr Leu Asp Glu Leu Lys Asn Ala Leu Lys
    130                 135                 140


<210> SEQ ID NO 175
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 175

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Cys Val Thr Leu Ser Lys Glu Ile Ala Lys Ser
    50                  55                  60

Gly Glu Val Thr Val Ala Leu Asn Asp Cys Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140


<210> SEQ ID NO 176
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 176

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45
```

```
Glu Val Lys Glu Gly Thr Val Thr Leu Ser Lys Glu Ile Ala Lys Ser
    50                  55                  60

Gly Glu Val Thr Val Ala Cys Asn Asp Thr Asn Thr Thr Gln Ala Thr
65                  70                  75                  80

Lys Lys Thr Cys Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Gln Lys Tyr Asp Ser Ala Gly Thr Asn Leu Glu Gly Thr
        115                 120                 125

Ala Val Glu Ile Lys Thr Leu Asp Glu Leu Lys Asn Ala Leu Lys
    130                 135                 140


<210> SEQ ID NO 177
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 177

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Leu Glu Gly Lys Val Ala Asn Asp Lys Val Thr Leu
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80

Lys Lys Thr Gly Ala Trp Asp Ser Lys Thr Ser Thr Leu Thr Ile Ser
                85                  90                  95

Val Asn Ser Lys Lys Thr Thr Gln Leu Val Phe Thr Lys Gln Asp Thr
            100                 105                 110

Ile Thr Val Cys Lys Tyr Asp Ser Ala Gly Thr Asn Leu Glu Gly Thr
        115                 120                 125

Cys Val Glu Ile Lys Thr Leu Asp Glu Leu Lys Asn Ala Leu Lys
    130                 135                 140


<210> SEQ ID NO 178
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 178

Glu Leu Ser Ala Lys Thr Met Thr Arg Glu Asn Gly Thr Lys Leu Glu
1               5                   10                  15

Tyr Thr Glu Met Lys Ser Asp Gly Thr Gly Lys Ala Lys Glu Val Leu
            20                  25                  30

Lys Asn Phe Thr Cys Glu Gly Lys Val Ala Asn Asp Lys Val Thr Cys
        35                  40                  45

Glu Val Lys Glu Gly Thr Val Thr Leu Ser Lys Glu Ile Ala Lys Ser
    50                  55                  60

Gly Glu Val Thr Val Ala Leu Asn Asp Thr Asn Thr Thr Gln Ala Thr
65                  70                  75                  80
```

Lys Lys Thr Gly Ala Trp Asp Ser Lys Thr Ser Thr Leu Thr Ile Ser
85 90 95

Val Asn Ser Lys Lys Thr Thr Gln Leu Val Phe Thr Lys Gln Asp Thr
100 105 110

Ile Thr Val Gln Lys Tyr Asp Ser Ala Gly Thr Asn Leu Glu Gly Thr
115 120 125

Ala Val Glu Ile Lys Thr Leu Asp Glu Leu Lys Asn Ala Leu Lys
130 135 140

<210> SEQ ID NO 179
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 179

Phe Asn Glu Lys Gly Glu Val Ser Glu Lys Ile Ile Thr Arg Ala Asp
1 5 10 15

Gly Thr Arg Leu Glu Tyr Thr Gly Ile Lys Ser Asp Gly Ser Gly Lys
20 25 30

Ala Lys Glu Val Leu Lys Asn Phe Thr Leu Glu Gly Lys Val Ala Asn
35 40 45

Asp Lys Thr Thr Leu Val Val Lys Glu Gly Thr Val Thr Leu Ser Lys
50 55 60

Asn Ile Ser Lys Ser Gly Glu Val Ser Val Glu Leu Asn Asp Thr Asp
65 70 75 80

Ser Ser Ala Ala Thr Lys Lys Thr Ala Ala Trp Asn Ser Gly Thr Ser
85 90 95

Thr Leu Thr Ile Thr Val Asn Ser Lys Lys Thr Lys Asp Leu Val Phe
100 105 110

Thr Lys Glu Asn Thr Ile Thr Val Gln Gln Tyr Asp Ser Asn Gly Thr
115 120 125

Lys Leu Glu Gly Ser Ala Val Glu Ile Thr Lys Leu Asp Glu Ile Lys
130 135 140

Asn Ala Leu Lys
145

<210> SEQ ID NO 180
<211> LENGTH: 149
<212> TYPE: PRT
<213> ORGANISM: Borrelia garinii

<400> SEQUENCE: 180

Phe Asn Asp Lys Gly Lys Leu Ser Glu Lys Val Val Thr Arg Ala Asn
1 5 10 15

Gly Thr Arg Leu Glu Tyr Thr Glu Ile Lys Asn Asp Gly Ser Gly Lys
20 25 30

Ala Lys Glu Val Leu Lys Gly Phe Ala Leu Glu Gly Thr Leu Thr Asp
35 40 45

Gly Gly Glu Thr Lys Leu Thr Val Thr Glu Gly Thr Val Thr Leu Ser
50 55 60

Lys Asn Ile Ser Lys Ser Gly Glu Ile Thr Val Ala Leu Asn Asp Thr
65 70 75 80

Glu Thr Thr Pro Ala Asp Lys Lys Thr Gly Glu Trp Lys Ser Asp Thr
85 90 95

```
Ser Thr Leu Thr Ile Ser Lys Asn Ser Gln Lys Pro Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Lys Ala Ala Leu Lys
145


<210> SEQ ID NO 181
<211> LENGTH: 148
<212> TYPE: PRT
<213> ORGANISM: Borrelia bavariensis

<400> SEQUENCE: 181

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Glu Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Lys
    130                 135                 140

Asn Ala Leu Lys
145


<210> SEQ ID NO 182
<211> LENGTH: 148
<212> TYPE: PRT
<213> ORGANISM: Borrelia garinii

<400> SEQUENCE: 182

Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Thr Trp Asp Ser Gly Thr Ser
                85                  90                  95

Thr Leu Thr Ile Ser Lys Asn Arg Thr Lys Thr Lys Gln Leu Val Phe
            100                 105                 110
```

```
Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Lys
    130                 135                 140

Asn Ala Leu Lys
145


<210> SEQ ID NO 183
<211> LENGTH: 149
<212> TYPE: PRT
<213> ORGANISM: Borrelia garinii

<400> SEQUENCE: 183

Phe Asn Gly Lys Gly Glu Thr Ser Glu Lys Thr Ile Val Arg Ala Asn
1               5                   10                  15

Gly Thr Arg Leu Glu Tyr Thr Asp Ile Lys Ser Asp Gly Ser Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Glu Gly Thr Val Val Leu Ser
    50                  55                  60

Lys Asn Ile Leu Lys Ser Gly Glu Ile Thr Ala Ala Leu Asp Asp Ser
65                  70                  75                  80

Asp Thr Thr Arg Ala Thr Lys Lys Thr Gly Lys Trp Asp Ser Lys Thr
                85                  90                  95

Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Lys Asn Ala Leu Lys
145


<210> SEQ ID NO 184
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 184

Gly Thr Ser Asp Lys Asn Asn Gly Ser Gly Ser Lys Glu Lys Asn Lys
1               5                   10                  15

Asp Gly Lys Tyr Ser
            20


<210> SEQ ID NO 185
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 185

Cys Ser Ser Phe Asn Glu Lys Gly Glu Val Ser Glu Lys Ile Ile Thr
1               5                   10                  15
```

```
Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Cys
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Lys Asn Ala Leu Lys
305                 310                 315                 320
```

<210> SEQ ID NO 186
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 186

```
Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
```

```
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320


<210> SEQ ID NO 187
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 187

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
    50                  55                  60
```

Thr Leu Ser Lys Asn Ile Ser Lys Ser Gly Glu Ile Thr Val Ala Leu
65 70 75 80

Asn Asp Thr Glu Thr Thr Pro Ala Asp Lys Lys Thr Gly Glu Trp Lys
85 90 95

Ser Asp Thr Ser Thr Leu Thr Ile Ser Lys Asn Ser Gln Lys Pro Lys
100 105 110

Gln Leu Val Phe Thr Lys Glu Cys Thr Ile Thr Val Gln Asn Tyr Asn
115 120 125

Arg Ala Gly Asn Ala Leu Glu Gly Ser Pro Ala Glu Ile Lys Asp Leu
130 135 140

Ala Glu Leu Lys Ala Ala Leu Lys Gly Thr Ser Asp Lys Asn Asn Gly
145 150 155 160

Ser Gly Ser Lys Glu Lys Asn Lys Asp Gly Lys Tyr Ser Phe Asn Ala
165 170 175

Lys Gly Glu Leu Ser Glu Lys Thr Ile Leu Arg Ala Cys Gly Thr Arg
180 185 190

Leu Glu Tyr Thr Glu Ile Lys Ser Asp Gly Thr Gly Lys Ala Lys Glu
195 200 205

Val Leu Lys Asp Phe Ala Leu Glu Gly Thr Leu Ala Ala Asp Lys Thr
210 215 220

Thr Leu Lys Val Thr Glu Gly Thr Val Val Leu Ser Lys His Ile Pro
225 230 235 240

Asn Ser Gly Glu Ile Thr Val Glu Leu Asn Asp Ser Asn Ser Thr Gln
245 250 255

Ala Thr Lys Lys Thr Gly Lys Trp Asp Ser Asn Thr Ser Thr Leu Thr
260 265 270

Ile Ser Val Asn Ser Lys Lys Thr Lys Asn Ile Val Phe Thr Lys Glu
275 280 285

Cys Thr Ile Thr Val Gln Lys Tyr Asp Ser Ala Gly Thr Asn Leu Glu
290 295 300

Gly Asn Ala Val Glu Ile Lys Thr Leu Asp Glu Leu Lys Asn Ala Leu
305 310 315 320

Lys

<210> SEQ ID NO 188
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 188

Cys Ser Ser Phe Asn Glu Lys Gly Lys Leu Ser Glu Lys Val Val Thr
1 5 10 15

Arg Ala Asn Gly Thr Arg Leu Glu Tyr Thr Glu Ile Lys Asn Asp Gly
20 25 30

Ser Gly Lys Ala Lys Glu Val Leu Lys Gly Phe Ala Leu Glu Gly Thr
35 40 45

Leu Thr Asp Gly Gly Glu Thr Lys Leu Thr Val Thr Cys Gly Thr Val
50 55 60

Thr Leu Ser Lys Asn Ile Ser Lys Ser Gly Glu Ile Thr Val Ala Leu
65 70 75 80

```
Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Cys Asn Ala Leu
305                 310                 315                 320

Lys


<210> SEQ ID NO 189
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 189

Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95
```

```
Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys


<210> SEQ ID NO 190
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 190

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110
```

```
Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys
```

<210> SEQ ID NO 191
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 191

```
Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Glu Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Cys Thr Ile Thr Val Gln Lys Tyr Asp Ser
        115                 120                 125
```

```
Ala Gly Thr Asn Leu Glu Gly Thr Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Lys Asn Ala Leu Lys
305                 310                 315                 320


<210> SEQ ID NO 192
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 192

Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160
```

```
Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320
```

<210> SEQ ID NO 193
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 193

```
Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
```

```
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys


<210> SEQ ID NO 194
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 194

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Asp Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
```

```
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys


<210> SEQ ID NO 195
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 195

Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Cys Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Lys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
```

```
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys


<210> SEQ ID NO 196
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 196

Cys Ser Ser Phe Asn Gly Lys Gly Glu Thr Ser Glu Lys Thr Ile Val
1               5                   10                  15

Arg Ala Asn Gly Thr Arg Leu Glu Tyr Thr Asp Ile Lys Ser Asp Gly
            20                  25                  30

Ser Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Asn Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Cys Gly Thr Val Thr Leu Ser Lys Asn Ile
```

```
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Asp Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys


<210> SEQ ID NO 197
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 197

Cys Ser Ser Phe Asn Glu Lys Gly Glu Val Ser Glu Lys Ile Ile Thr
1               5                   10                  15

Arg Ala Cys Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Glu Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Cys Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
```

```
                245                 250                 255

Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Cys Asn Ala Leu Lys
305                 310                 315                 320


<210> SEQ ID NO 198
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 198

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Cys Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Glu Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala
                245                 250                 255

Thr Lys Lys Thr Gly Ala Trp Asp Ser Lys Thr Ser Thr Leu Thr Ile
            260                 265                 270
```

```
Ser Val Asn Ser Lys Lys Thr Thr Gln Leu Val Phe Thr Lys Gln Cys
        275                 280                 285

Thr Ile Thr Val Gln Lys Tyr Asp Ser Ala Gly Thr Asn Leu Glu Gly
    290                 295                 300

Thr Ala Val Glu Ile Lys Thr Leu Asp Glu Leu Lys Asn Ala Leu Lys
305                 310                 315                 320


<210> SEQ ID NO 199
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 199

Cys Ser Ser Phe Asn Glu Lys Gly Lys Leu Ser Glu Lys Val Val Thr
1               5                   10                  15

Arg Ala Cys Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Glu Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Cys Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Lys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Asn Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Cys Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Asp Thr Ile Thr Val Gln Lys Tyr Asp Ser Ala Gly Thr Asn Leu Glu
    290                 295                 300
```

```
Gly Asn Ala Val Glu Ile Lys Thr Leu Asp Glu Leu Cys Asn Ala Leu
305                 310                 315                 320

Lys


<210> SEQ ID NO 200
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 200

Cys Ser Ser Phe Asn Glu Lys Gly Lys Leu Ser Glu Lys Val Val Thr
1               5                   10                  15

Arg Ala Asn Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Cys Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Ala
                165                 170                 175

Lys Gly Glu Leu Ser Glu Lys Thr Ile Leu Arg Ala Cys Gly Thr Arg
            180                 185                 190

Leu Glu Tyr Thr Glu Ile Lys Ser Asp Gly Thr Gly Lys Ala Lys Glu
        195                 200                 205

Val Leu Lys Asp Phe Ala Leu Glu Gly Thr Leu Ala Ala Asp Lys Thr
    210                 215                 220

Thr Leu Lys Val Thr Glu Gly Thr Val Val Leu Ser Lys His Ile Pro
225                 230                 235                 240

Asn Ser Gly Glu Ile Thr Val Glu Leu Asn Asp Ser Asn Ser Thr Gln
                245                 250                 255

Ala Thr Lys Lys Thr Gly Lys Trp Asp Ser Asn Thr Ser Thr Leu Thr
            260                 265                 270

Ile Ser Val Asn Ser Lys Lys Thr Lys Asn Ile Val Phe Thr Lys Glu
        275                 280                 285

Cys Thr Ile Thr Val Gln Lys Tyr Asp Ser Ala Gly Thr Asn Leu Glu
    290                 295                 300

Gly Asn Ala Val Glu Ile Lys Thr Leu Asp Glu Leu Lys Asn Ala Leu
305                 310                 315                 320
```

Lys

<210> SEQ ID NO 201
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 201

```
Cys Ser Ser Phe Asn Glu Lys Gly Glu Ile Ser Glu Lys Thr Ile Val
1               5                   10                  15

Arg Ala Cys Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Cys Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Asp Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Cys Asn Ala Leu
305                 310                 315                 320

Lys
```

<210> SEQ ID NO 202
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 202

```
Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Cys Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Glu Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
        275                 280                 285

Cys Thr Ile Thr Val Gln Arg Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys
```

<210> SEQ ID NO 203
<211> LENGTH: 320

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 203

Cys Ser Ser Phe Asn Glu Lys Gly Glu Leu Ser Ala Lys Thr Met Thr
1               5                   10                  15

Arg Glu Cys Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Glu Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Cys Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Asp Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Cys Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Asn
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Cys Asn Ala Leu Lys
305                 310                 315                 320


<210> SEQ ID NO 204
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
```

<221> NAME/KEY: LIPID
<222> LOCATION: (1)..(1)
<223> OTHER INFORMATION: Lipidation

<400> SEQUENCE: 204

Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Thr Gln
            100                 105                 110

Leu Val Phe Thr Lys Gln Asp Thr Ile Thr Val Gln Lys Tyr Asp Ser
        115                 120                 125

Ala Gly Thr Asn Leu Glu Gly Thr Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Val Ser Glu Lys Ile Ile Thr Arg Ala Cys Gly Thr Arg Leu
            180                 185                 190

Glu Tyr Thr Gly Ile Lys Ser Asp Gly Ser Gly Lys Ala Lys Glu Val
        195                 200                 205

Leu Lys Asn Phe Thr Leu Glu Gly Lys Val Ala Asn Asp Lys Thr Thr
    210                 215                 220

Leu Val Val Lys Glu Gly Thr Val Thr Leu Ser Lys Asn Ile Ser Lys
225                 230                 235                 240

Ser Gly Glu Val Ser Val Glu Leu Asn Asp Thr Asp Ser Ser Ala Ala
                245                 250                 255

Thr Lys Lys Thr Ala Ala Trp Asn Ser Gly Thr Ser Thr Leu Thr Ile
            260                 265                 270

Thr Val Asn Ser Lys Lys Thr Lys Asp Leu Val Phe Thr Lys Glu Cys
        275                 280                 285

Thr Ile Thr Val Gln Gln Tyr Asp Ser Asn Gly Thr Lys Leu Glu Gly
    290                 295                 300

Ser Ala Val Glu Ile Thr Lys Leu Asp Glu Ile Lys Asn Ala Leu Lys
305                 310                 315                 320

<210> SEQ ID NO 205
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 205

```
Cys Ser Ser Phe Asn Ala Lys Gly Glu Leu Ser Glu Lys Thr Ile Leu
1               5                   10                  15

Arg Ala Cys Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Glu Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Cys Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Lys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Asn Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Cys Ala Ala Leu
305                 310                 315                 320

Lys


<210> SEQ ID NO 206
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 206

Cys Ser Ser Phe Asn Ala Lys Gly Glu Leu Ser Glu Lys Thr Ile Leu
1               5                   10                  15
```

```
Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
            100                 105                 110

Ile Val Phe Thr Lys Glu Asp Thr Ile Thr Val Gln Lys Tyr Asp Ser
        115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Cys Gly Thr Arg Leu
            180                 185                 190

Glu Tyr Thr Glu Ile Lys Asn Asp Gly Ser Gly Lys Ala Lys Glu Val
        195                 200                 205

Leu Lys Gly Phe Ala Leu Glu Gly Thr Leu Thr Asp Gly Gly Glu Thr
    210                 215                 220

Lys Leu Thr Val Thr Glu Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
            260                 265                 270

Ile Ser Lys Asn Ser Gln Lys Pro Lys Gln Leu Val Phe Thr Lys Glu
        275                 280                 285

Cys Thr Ile Thr Val Gln Asn Tyr Asn Arg Ala Gly Asn Ala Leu Glu
    290                 295                 300

Gly Ser Pro Ala Glu Ile Lys Asp Leu Ala Glu Leu Lys Ala Ala Leu
305                 310                 315                 320

Lys
```

<210> SEQ ID NO 207
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 207

```
Cys Ser Ser Phe Asn Gly Lys Gly Glu Thr Ser Glu Lys Thr Ile Val
1               5                   10                  15

Arg Ala Cys Gly Thr Arg Leu Glu Tyr Thr Asp Ile Lys Ser Asp Gly
            20                  25                  30
```

Ser Gly Lys Ala Lys Glu Val Leu Lys Asp Phe Thr Leu Glu Gly Thr
35 40 45

Leu Ala Ala Asp Gly Lys Thr Thr Leu Lys Val Thr Glu Gly Thr Val
50 55 60

Val Leu Ser Lys Asn Ile Leu Lys Ser Gly Glu Ile Thr Ala Ala Leu
65 70 75 80

Asp Asp Ser Asp Thr Thr Arg Ala Thr Lys Lys Thr Gly Lys Trp Asp
85 90 95

Ser Lys Thr Ser Thr Leu Thr Ile Ser Val Asn Ser Gln Lys Thr Lys
100 105 110

Asn Leu Val Phe Thr Lys Glu Cys Thr Ile Thr Val Gln Arg Tyr Asp
115 120 125

Ser Ala Gly Thr Asn Leu Glu Gly Lys Ala Val Glu Ile Thr Thr Leu
130 135 140

Lys Glu Leu Lys Asn Ala Leu Lys Gly Thr Ser Asp Lys Asn Asn Gly
145 150 155 160

Ser Gly Ser Lys Glu Lys Asn Lys Asp Gly Lys Tyr Ser Phe Asn Glu
165 170 175

Lys Gly Glu Ile Ser Glu Lys Thr Ile Val Arg Ala Asn Gly Thr Arg
180 185 190

Leu Glu Tyr Thr Asp Ile Lys Ser Asp Lys Thr Gly Lys Ala Lys Glu
195 200 205

Val Leu Lys Asp Phe Thr Leu Glu Gly Thr Leu Ala Ala Asp Gly Lys
210 215 220

Thr Thr Leu Lys Val Thr Cys Gly Thr Val Thr Leu Ser Lys Asn Ile
225 230 235 240

Ser Lys Ser Gly Glu Ile Thr Val Ala Leu Asp Asp Thr Asp Ser Ser
245 250 255

Gly Asn Lys Lys Ser Gly Thr Trp Asp Ser Gly Thr Ser Thr Leu Thr
260 265 270

Ile Ser Lys Asn Arg Thr Lys Thr Lys Gln Leu Val Phe Thr Lys Glu
275 280 285

Asp Thr Ile Thr Val Gln Asn Tyr Asp Ser Ala Gly Thr Asn Leu Glu
290 295 300

Gly Lys Ala Val Glu Ile Thr Thr Leu Lys Glu Leu Cys Asn Ala Leu
305 310 315 320

Lys

<210> SEQ ID NO 208
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)
<223> OTHER INFORMATION: Lipidation

<400> SEQUENCE: 208

Cys Ser Ser Phe Asn Gly Lys Gly Glu Thr Ser Glu Lys Thr Ile Val
1 5 10 15

Arg Ala Asn Gly Thr Arg Leu Glu Tyr Thr Asp Ile Lys Ser Asp Gly
20 25 30

Ser Gly Lys Ala Lys Glu Val Leu Lys Asp Phe Thr Leu Glu Gly Thr
35 40 45

```
Leu Ala Ala Asp Gly Lys Thr Thr Leu Lys Val Thr Cys Gly Thr Val
    50                  55                  60

Val Leu Ser Lys Asn Ile Leu Lys Ser Gly Glu Ile Thr Ala Ala Leu
65                  70                  75                  80

Asp Asp Ser Asp Thr Thr Arg Ala Thr Lys Lys Thr Gly Lys Trp Asp
                85                  90                  95

Ser Lys Thr Ser Thr Leu Thr Ile Ser Val Asn Ser Gln Lys Thr Lys
            100                 105                 110

Asn Leu Val Phe Thr Lys Glu Asp Thr Ile Thr Val Gln Arg Tyr Asp
        115                 120                 125

Ser Ala Gly Thr Asn Leu Glu Gly Lys Ala Val Glu Ile Thr Thr Leu
    130                 135                 140

Lys Glu Leu Cys Asn Ala Leu Lys Gly Thr Ser Asp Lys Asn Asn Gly
145                 150                 155                 160

Ser Gly Ser Lys Glu Lys Asn Lys Asp Gly Lys Tyr Ser Phe Asn Glu
                165                 170                 175

Lys Gly Glu Ile Ser Glu Lys Thr Ile Val Arg Ala Cys Gly Thr Arg
            180                 185                 190

Leu Glu Tyr Thr Asp Ile Lys Ser Asp Lys Thr Gly Lys Ala Lys Glu
        195                 200                 205

Val Leu Lys Asp Phe Thr Leu Glu Gly Thr Leu Ala Ala Asp Gly Lys
    210                 215                 220

Thr Thr Leu Lys Val Thr Glu Gly Thr Val Thr Leu Ser Lys Asn Ile
225                 230                 235                 240

Ser Lys Ser Gly Glu Ile Thr Val Ala Leu Asp Asp Thr Asp Ser Ser
                245                 250                 255

Gly Asn Lys Lys Ser Gly Thr Trp Asp Ser Gly Thr Ser Thr Leu Thr
            260                 265                 270

Ile Ser Lys Asn Arg Thr Lys Thr Lys Gln Leu Val Phe Thr Lys Glu
        275                 280                 285

Cys Thr Ile Thr Val Gln Asn Tyr Asp Ser Ala Gly Thr Asn Leu Glu
    290                 295                 300

Gly Lys Ala Val Glu Ile Thr Thr Leu Lys Glu Leu Lys Asn Ala Leu
305                 310                 315                 320

Lys
```

<210> SEQ ID NO 209
<211> LENGTH: 266
<212> TYPE: PRT
<213> ORGANISM: Artificial Sequence
<220> FEATURE:
<223> OTHER INFORMATION: Synthetic Polypeptide

<400> SEQUENCE: 209

```
Cys Lys Gln Asn Val Ser Ser Leu Asp Glu Lys Asn Ser Ala Ser Val
1               5                   10                  15

Asp Leu Pro Gly Glu Met Lys Val Leu Val Ser Lys Glu Lys Asp Lys
            20                  25                  30

Asp Gly Lys Tyr Ser Leu Lys Ala Thr Val Asp Lys Ile Glu Leu Lys
        35                  40                  45

Gly Thr Ser Asp Lys Asp Asn Gly Ser Gly Val Leu Glu Gly Thr Lys
    50                  55                  60

Asp Asp Lys Ser Lys Ala Lys Leu Thr Ile Ala Asp Asp Leu Ser Lys
65                  70                  75                  80
```

```
Thr Thr Phe Glu Leu Phe Lys Glu Asp Gly Lys Thr Leu Val Ser Arg
                85                  90                  95

Lys Val Ser Ser Lys Asp Lys Thr Ser Thr Asp Glu Met Phe Asn Glu
            100                 105                 110

Lys Gly Glu Leu Ser Ala Lys Thr Met Thr Arg Glu Asn Gly Thr Lys
        115                 120                 125

Leu Glu Tyr Thr Glu Met Lys Ser Asp Gly Thr Gly Lys Ala Lys Glu
    130                 135                 140

Val Leu Lys Asn Phe Thr Leu Glu Gly Lys Val Ala Asn Asp Lys Val
145                 150                 155                 160

Thr Leu Glu Val Lys Glu Gly Thr Val Thr Leu Ser Lys Glu Ile Ala
                165                 170                 175

Lys Ser Gly Glu Val Thr Val Ala Leu Asn Asp Thr Asn Thr Thr Gln
            180                 185                 190

Ala Thr Lys Lys Thr Gly Ala Trp Asp Ser Lys Thr Ser Thr Leu Thr
        195                 200                 205

Ile Ser Val Asn Ser Lys Lys Thr Thr Gln Leu Val Phe Thr Lys Gln
    210                 215                 220

Asp Thr Ile Thr Val Gln Lys Tyr Asp Ser Ala Gly Thr Asn Leu Glu
225                 230                 235                 240

Gly Thr Ala Val Glu Ile Lys Thr Leu Asp Glu Leu Lys Asn Ala Leu
                245                 250                 255

Lys Gly Leu Glu His His His His His His
            260                 265
```

<210> SEQ ID NO 210

<400> SEQUENCE: 210

000

<210> SEQ ID NO 211
<211> LENGTH: 4
<212> TYPE: PRT
<213> ORGANISM: Borrelia afzelii

<400> SEQUENCE: 211

```
Cys Lys Gln Asn
1
```

<210> SEQ ID NO 212
<211> LENGTH: 149
<212> TYPE: PRT
<213> ORGANISM: Borrelia garinii

<400> SEQUENCE: 212

```
Phe Asn Asp Lys Gly Lys Leu Ser Glu Lys Val Val Thr Arg Ala Asn
1               5                   10                  15

Gly Thr Arg Leu Glu Tyr Thr Glu Ile Gln Asn Asp Gly Ser Gly Lys
            20                  25                  30

Ala Lys Glu Val Leu Lys Ser Leu Thr Leu Glu Gly Thr Leu Thr Ala
        35                  40                  45

Asp Gly Glu Thr Lys Leu Thr Val Glu Ala Gly Thr Val Thr Leu Ser
    50                  55                  60

Lys Asn Ile Ser Glu Ser Gly Glu Ile Thr Val Glu Leu Lys Asp Thr
65                  70                  75                  80

Glu Thr Thr Pro Ala Asp Lys Lys Ser Gly Thr Trp Asp Ser Lys Thr
                85                  90                  95
```

Ser Thr Leu Thr Ile Ser Lys Asn Ser Gln Lys Thr Lys Gln Leu Val
100 105 110

Phe Thr Lys Glu Asn Thr Ile Thr Val Gln Lys Tyr Asn Thr Ala Gly
115 120 125

Thr Lys Leu Glu Gly Ser Pro Ala Glu Ile Lys Asp Leu Glu Ala Leu
130 135 140

Lys Ala Ala Leu Lys
145

<210> SEQ ID NO 213
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 213
catgctcttg atcctgttta 20

<210> SEQ ID NO 214
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 214

Gly Leu Glu His His His His His His
1 5

<210> SEQ ID NO 215
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 215
cccatttctc catctatctc 20

<210> SEQ ID NO 216
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 216

Phe Asn Glu Lys Gly Glu Val Ser Glu Lys Ile Ile Thr Arg Ala Asp
1 5 10 15

Gly Thr Arg Leu Glu Tyr Thr Gly Ile Lys Ser Asp Gly Ser Gly Lys
20 25 30

Ala Lys Glu Val Leu Lys Asn Phe Thr Leu Glu Gly Lys Val Ala Asn
35 40 45

Asp Lys Thr Thr Leu Val Val Lys Cys Gly Thr Val Thr Leu Ser Lys
50 55 60

Asn Ile Ser Lys Ser Gly Glu Val Ser Val Glu Leu Asn Asp Thr Asp
65 70 75 80

Ser Ser Ala Ala Thr Lys Lys Thr Ala Ala Trp Asn Ser Gly Thr Ser
85 90 95

Thr Leu Thr Ile Thr Val Asn Ser Lys Lys Thr Lys Asp Leu Val Phe

-continued

```
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Cys
    130                 135                 140

Asn Ala Leu Lys
145
```